US012213688B2

(12) United States Patent
Chou et al.

(10) Patent No.: US 12,213,688 B2
(45) Date of Patent: Feb. 4, 2025

(54) ANCHORING DELIVERY SYSTEM AND METHODS

(71) Applicant: Route 92 Medical, Inc., San Mateo, CA (US)

(72) Inventors: Tony M. Chou, San Mateo, CA (US); Joey English, San Mateo, CA (US); Randolf Von Oepen, San Mateo, CA (US); Scott D. Wilson, San Mateo, CA (US); Kirsten Valley, San Mateo, CA (US); Philip Evard, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 273 days.

(21) Appl. No.: 17/545,885

(22) Filed: Dec. 8, 2021

(65) Prior Publication Data
US 2022/0096103 A1    Mar. 31, 2022

Related U.S. Application Data

(63) Continuation of application No. 15/727,373, filed on Oct. 6, 2017, now Pat. No. 11,224,449, which is a
(Continued)

(51) Int. Cl.
*A61B 17/22*    (2006.01)
*A61B 17/221*    (2006.01)
(Continued)

(52) U.S. Cl.
CPC ............ *A61B 17/22* (2013.01); *A61B 17/221* (2013.01); *A61M 25/01* (2013.01); *A61M 25/04* (2013.01);
(Continued)

(58) Field of Classification Search
CPC .................. A61B 17/22; A61B 17/221; A61B 2017/00986; A61B 2017/22047;
(Continued)

(56) References Cited

U.S. PATENT DOCUMENTS

| 2,623,520 A | 12/1952 | Bamford, Jr. et al. |
| 2,730,101 A | 1/1956 | Hoffman |

(Continued)

FOREIGN PATENT DOCUMENTS

| CN | 101121055 A | 2/2008 |
| CN | 101588835 A | 11/2009 |
| CN | 103260689 A | 8/2013 |
| CN | 103284775 A | 9/2013 |
| CN | 103648574 A | 3/2014 |
| CN | 104394785 A | 3/2015 |
| CN | 104739486 A | 7/2015 |
| CN | 105920720 A | 9/2016 |
| CN | 106039526 A | 10/2016 |
| DE | 102006039236 A1 | 2/2008 |
| EP | 117940 A2 | 9/1984 |

(Continued)

OTHER PUBLICATIONS

2007 International Stroke Conference: Abstracts. Stroke, vol. 38, No. 2, 2007, pp. 454-607. Web. Downloaded Jun. 13, 2017.
(Continued)

*Primary Examiner* — Richard G Louis
(74) *Attorney, Agent, or Firm* — Mintz Levin Cohn Ferris Glovsky and Popeo, P.C.

(57) ABSTRACT

An anchoring delivery system for use in an intracranial artery is provided including a tethering device having an elongated tether and an anchor coupled to a distal end of the tether. The anchor is deployable from a low profile configuration to a higher profile configuration to fix the distal end of the tether at an anchoring site in an anchoring vessel. The tethering device is configured to be used with a guide-sheath having a lumen configured to receive the tether. Related devices, systems, and methods are also described.

52 Claims, 51 Drawing Sheets

Related U.S. Application Data continuation of application No. 15/217,810, filed on Jul. 22, 2016, now Pat. No. 10,426,497.

(60) Provisional application No. 62/301,857, filed on Mar. 1, 2016, provisional application No. 62/275,939, filed on Jan. 7, 2016, provisional application No. 62/196,613, filed on Jul. 24, 2015.

(51) Int. Cl.
| | |
|---|---|
| A61M 25/01 | (2006.01) |
| A61M 25/04 | (2006.01) |
| A61M 25/06 | (2006.01) |
| A61B 17/00 | (2006.01) |
| A61M 25/09 | (2006.01) |

(52) U.S. Cl.
CPC .............. A61M 25/0662 (2013.01); A61B 2017/00986 (2013.01); A61B 2017/22047 (2013.01); A61B 2017/22049 (2013.01); A61B 2017/22069 (2013.01); A61M 2025/0681 (2013.01); A61M 2025/09125 (2013.01)

(58) Field of Classification Search
CPC ........... A61B 2017/22049; A61B 2017/22069; A61M 25/01; A61M 25/04; A61M 25/0662; A61M 2025/0681; A61M 2025/09125
See application file for complete search history.

(56) References Cited

U.S. PATENT DOCUMENTS

| | | |
|---|---|---|
| 3,612,050 A | 10/1971 | Sheridan |
| 3,631,848 A | 1/1972 | Muller |
| 3,949,757 A | 4/1976 | Sabel |
| 3,996,938 A | 12/1976 | Clark, III |
| 4,013,080 A | 3/1977 | Froning |
| 4,020,829 A | 5/1977 | Willson et al. |
| 4,033,331 A | 7/1977 | Guss et al. |
| 4,174,715 A | 11/1979 | Hasson |
| 4,319,580 A | 3/1982 | Colley et al. |
| 4,323,071 A | 4/1982 | Simpson et al. |
| 4,406,656 A | 9/1983 | Hattler et al. |
| 4,571,240 A | 2/1986 | Samson et al. |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,762,128 A | 8/1988 | Rosenbluth |
| 4,771,777 A | 9/1988 | Horzewski et al. |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,840,690 A | 6/1989 | Melinyshyn et al. |
| 4,863,431 A | 9/1989 | Vaillancourt |
| 4,865,581 A | 9/1989 | Lundquist et al. |
| 4,873,978 A | 10/1989 | Ginsburg |
| 4,873,979 A | 10/1989 | Hanna |
| 4,883,460 A | 11/1989 | Zanetti |
| 4,887,613 A | 12/1989 | Farr et al. |
| 4,898,575 A | 2/1990 | Fischell et al. |
| 4,900,303 A | 2/1990 | Lemelson |
| 4,921,478 A | 5/1990 | Solano et al. |
| 4,921,479 A | 5/1990 | Grayzel |
| 4,921,484 A | 5/1990 | Hillstead |
| 4,923,462 A | 5/1990 | Stevens |
| 4,946,440 A | 8/1990 | Hall |
| 4,946,443 A | 8/1990 | Hauser et al. |
| 4,994,033 A | 2/1991 | Shockey et al. |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,103,827 A | 4/1992 | Smith |
| 5,108,419 A | 4/1992 | Reger et al. |
| 5,135,484 A | 8/1992 | Wright |
| 5,152,277 A | 10/1992 | Honda et al. |
| 5,161,534 A | 11/1992 | Berthiaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,207,648 A | 5/1993 | Gross |
| 5,211,651 A | 5/1993 | Reger et al. |
| 5,217,705 A | 6/1993 | Reno et al. |
| 5,219,332 A | 6/1993 | Nelson et al. |
| 5,243,997 A | 9/1993 | Uflacker et al. |
| 5,250,060 A | 10/1993 | Carbo et al. |
| 5,257,979 A | 11/1993 | Jagpal |
| 5,267,960 A | 12/1993 | Hayman et al. |
| 5,269,297 A | 12/1993 | Weng et al. |
| 5,303,714 A | 4/1994 | Abele et al. |
| 5,308,318 A | 5/1994 | Plassche, Jr. |
| 5,312,338 A | 5/1994 | Nelson et al. |
| 5,312,356 A | 5/1994 | Engelson et al. |
| RE34,633 E | 6/1994 | Sos et al. |
| 5,318,032 A | 6/1994 | Lonsbury et al. |
| 5,324,262 A | 6/1994 | Fischell et al. |
| 5,325,868 A | 7/1994 | Kimmelstiel |
| 5,328,471 A | 7/1994 | Slepian |
| 5,338,300 A | 8/1994 | Cox |
| 5,352,197 A | 10/1994 | Hammersmark et al. |
| 5,364,358 A | 11/1994 | Hewitt et al. |
| 5,370,623 A | 12/1994 | Kreamer |
| 5,380,284 A | 1/1995 | Don Michael |
| 5,385,562 A | 1/1995 | Adams et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,429,605 A | 7/1995 | Richling; Bernd et al. |
| 5,437,632 A | 8/1995 | Engelson |
| 5,438,993 A | 8/1995 | Lynch et al. |
| 5,441,051 A | 8/1995 | Hileman et al. |
| 5,443,454 A | 8/1995 | Tanabe et al. |
| 5,454,795 A | 10/1995 | Samson |
| 5,464,023 A | 11/1995 | Viera |
| 5,465,716 A | 11/1995 | Avitall |
| 5,466,222 A | 11/1995 | Ressemann et al. |
| 5,476,450 A | 12/1995 | Ruggio |
| 5,484,407 A | 1/1996 | Osypka |
| 5,484,412 A | 1/1996 | Pierpont |
| 5,484,418 A | 1/1996 | Quiachon et al. |
| 5,485,667 A | 1/1996 | Kleshinski |
| 5,490,859 A | 2/1996 | Mische et al. |
| 5,492,530 A | 2/1996 | Fischell et al. |
| 5,496,294 A | 3/1996 | Hergenrother et al. |
| 5,501,694 A | 3/1996 | Ressemann et al. |
| 5,522,836 A | 6/1996 | Palermo |
| 5,527,292 A | 6/1996 | Adams et al. |
| 5,533,967 A | 7/1996 | Imran |
| 5,538,512 A | 7/1996 | Zenzon et al. |
| 5,542,936 A | 8/1996 | Razi |
| 5,542,937 A | 8/1996 | Chee et al. |
| 5,546,958 A | 8/1996 | Thorud et al. |
| 5,549,119 A | 8/1996 | Solar |
| 5,549,601 A | 8/1996 | Mcintyre et al. |
| 5,549,626 A | 8/1996 | Miller et al. |
| 5,558,635 A | 9/1996 | Cannon |
| 5,571,122 A | 11/1996 | Kelly et al. |
| 5,573,520 A | 11/1996 | Schwartz et al. |
| 5,578,009 A | 11/1996 | Kraus et al. |
| 5,591,194 A | 1/1997 | Berthiaume |
| 5,599,307 A | 2/1997 | Bacher et al. |

(56) References Cited

U.S. PATENT DOCUMENTS

| | | |
|---|---|---|
| 5,599,326 A | 2/1997 | Carter |
| 5,603,698 A * | 2/1997 | Roberts ............... A61F 2/95 606/198 |
| 5,628,754 A | 5/1997 | Shevlin et al. |
| 5,643,254 A | 7/1997 | Scheldrup et al. |
| 5,658,263 A | 8/1997 | Dang et al. |
| 5,658,264 A | 8/1997 | Samson |
| 5,658,309 A | 8/1997 | Berthiaume et al. |
| 5,662,622 A | 9/1997 | Gore et al. |
| 5,667,499 A | 9/1997 | Welch et al. |
| 5,676,659 A | 10/1997 | McGurk |
| 5,682,894 A | 11/1997 | Orr et al. |
| 5,693,029 A | 12/1997 | Leonhardt |
| 5,695,483 A | 12/1997 | Samson |
| 5,702,373 A | 12/1997 | Samson |
| 5,702,439 A | 12/1997 | Keith et al. |
| 5,707,376 A | 1/1998 | Kavteladze et al. |
| 5,720,764 A | 2/1998 | Naderlinger |
| 5,730,734 A | 3/1998 | Adams et al. |
| 5,749,849 A | 5/1998 | Engelson |
| 5,749,858 A | 5/1998 | Cramer |
| 5,766,191 A | 6/1998 | Trerotola |
| 5,776,141 A | 7/1998 | Klein et al. |
| 5,776,142 A | 7/1998 | Gunderson |
| 5,794,629 A | 8/1998 | Frazee |
| 5,795,341 A | 8/1998 | Samson |
| 5,810,869 A | 9/1998 | Kaplan et al. |
| 5,810,874 A | 9/1998 | Lefebvre |
| 5,814,064 A | 9/1998 | Daniel et al. |
| 5,817,101 A | 10/1998 | Fiedler |
| 5,827,229 A | 10/1998 | Auth et al. |
| 5,827,242 A | 10/1998 | Follmer et al. |
| 5,833,650 A | 11/1998 | Imran |
| 5,836,868 A | 11/1998 | Ressemann et al. |
| 5,836,926 A | 11/1998 | Peterson et al. |
| 5,836,955 A | 11/1998 | Buelna et al. |
| 5,843,002 A | 12/1998 | Pecor et al. |
| 5,843,051 A | 12/1998 | Adams et al. |
| 5,843,103 A | 12/1998 | Wulfman |
| 5,846,251 A | 12/1998 | Hart |
| 5,851,189 A | 12/1998 | Forber |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,329 A | 3/1999 | Patterson et al. |
| 5,882,334 A | 3/1999 | Sepetka et al. |
| 5,885,209 A | 3/1999 | Green |
| 5,891,114 A | 4/1999 | Chien et al. |
| 5,895,399 A | 4/1999 | Barbut et al. |
| 5,897,567 A | 4/1999 | Ressemann et al. |
| 5,899,890 A | 5/1999 | Chiang et al. |
| 5,899,892 A | 5/1999 | Mortier et al. |
| 5,908,407 A | 6/1999 | Frazee et al. |
| 5,910,154 A | 6/1999 | Tsugita et al. |
| 5,911,725 A | 6/1999 | Boury |
| 5,911,734 A | 6/1999 | Tsugita et al. |
| 5,913,848 A | 6/1999 | Luther et al. |
| 5,916,192 A | 6/1999 | Nita et al. |
| 5,916,208 A | 6/1999 | Luther et al. |
| 5,921,952 A | 7/1999 | Desmond, III et al. |
| 5,928,192 A | 7/1999 | Maahs |
| 5,928,260 A | 7/1999 | Chin et al. |
| 5,935,122 A | 8/1999 | Fourkas et al. |
| 5,935,139 A | 8/1999 | Bates |
| 5,938,645 A | 8/1999 | Gordon |
| 5,941,869 A | 8/1999 | Patterson et al. |
| 5,957,882 A | 9/1999 | Nita et al. |
| 5,972,019 A | 10/1999 | Engelson et al. |
| 5,976,093 A | 11/1999 | Jang |
| 5,976,178 A | 11/1999 | Goldsteen et al. |
| 5,997,508 A | 12/1999 | Lunn et al. |
| 5,997,523 A | 12/1999 | Jang |
| 5,997,557 A | 12/1999 | Barbut et al. |
| 6,004,310 A | 12/1999 | Bardsley et al. |
| 6,007,530 A | 12/1999 | Dornhofer et al. |
| 6,010,522 A | 1/2000 | Barbut et al. |
| 6,013,085 A | 1/2000 | Howard |
| 6,022,336 A | 2/2000 | Zadno-Azizi et al. |
| 6,022,340 A | 2/2000 | Sepetka et al. |
| 6,030,349 A | 2/2000 | Wilson et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,066,149 A | 5/2000 | Samson et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,090,118 A | 7/2000 | McGuckin, Jr. |
| 6,106,530 A | 8/2000 | Harada |
| 6,110,139 A | 8/2000 | Loubser |
| 6,117,141 A | 9/2000 | Ouchi |
| 6,120,480 A | 9/2000 | Zhang et al. |
| 6,135,991 A | 10/2000 | Muni et al. |
| 6,139,524 A | 10/2000 | Killion |
| 6,142,958 A | 11/2000 | Hammarstrom et al. |
| 6,142,987 A | 11/2000 | Tsugita |
| 6,146,370 A | 11/2000 | Barbut |
| 6,146,373 A | 11/2000 | Cragg et al. |
| 6,146,396 A | 11/2000 | Konya et al. |
| 6,146,415 A | 11/2000 | Fitz |
| 6,152,909 A | 11/2000 | Bagaoisan et al. |
| 6,152,912 A | 11/2000 | Jansen et al. |
| 6,156,005 A | 12/2000 | Theron |
| 6,159,195 A | 12/2000 | Ha et al. |
| 6,159,230 A | 12/2000 | Samuels |
| 6,161,547 A | 12/2000 | Barbut |
| 6,165,163 A | 12/2000 | Chien et al. |
| 6,165,167 A | 12/2000 | Delaloye |
| 6,165,199 A | 12/2000 | Barbut |
| 6,168,579 B1 | 1/2001 | Tsugita |
| 6,171,295 B1 | 1/2001 | Garabedian et al. |
| 6,176,844 B1 | 1/2001 | Lee |
| 6,197,016 B1 | 3/2001 | Fourkas et al. |
| 6,203,561 B1 | 3/2001 | Ramee et al. |
| 6,206,868 B1 | 3/2001 | Parodi |
| 6,210,370 B1 | 4/2001 | Chi-Sing et al. |
| 6,221,038 B1 | 4/2001 | Brisken |
| 6,221,049 B1 | 4/2001 | Selmon et al. |
| 6,228,046 B1 | 5/2001 | Brisken |
| 6,228,052 B1 | 5/2001 | Pohndorf |
| 6,234,971 B1 | 5/2001 | Jang |
| 6,238,402 B1 | 5/2001 | Sullivan, III et al. |
| 6,238,412 B1 | 5/2001 | Dubrul et al. |
| 6,238,430 B1 | 5/2001 | Klumb et al. |
| 6,240,231 B1 | 5/2001 | Ferrera et al. |
| 6,254,628 B1 | 7/2001 | Wallace et al. |
| 6,258,052 B1 | 7/2001 | Milo |
| 6,258,080 B1 | 7/2001 | Samson |
| 6,258,115 B1 | 7/2001 | Dubrul |
| 6,270,477 B1 | 8/2001 | Bagaoisan et al. |
| 6,277,115 B1 | 8/2001 | Saadat |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,309,379 B1 | 10/2001 | Willard et al. |
| 6,346,116 B1 | 2/2002 | Brooks et al. |
| 6,355,027 B1 | 3/2002 | Le et al. |
| 6,361,545 B1 | 3/2002 | Macoviak et al. |
| 6,364,894 B1 | 4/2002 | Healy et al. |
| 6,364,900 B1 | 4/2002 | Heuser |
| 6,368,316 B1 | 4/2002 | Jansen et al. |
| 6,368,338 B1 | 4/2002 | Konya et al. |
| 6,368,344 B1 | 4/2002 | Fitz |
| 6,368,355 B1 | 4/2002 | Uflacker |
| 6,379,325 B1 | 4/2002 | Benett et al. |
| 6,383,172 B1 | 5/2002 | Barbut |
| 6,391,044 B1 | 5/2002 | Yadav et al. |

(56) References Cited

U.S. PATENT DOCUMENTS

| | | |
|---|---|---|
| 6,394,976 B1 | 5/2002 | Winston et al. |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,451,005 B1 | 9/2002 | Saitou et al. |
| 6,454,741 B1 | 9/2002 | Muni et al. |
| 6,454,775 B1 | 9/2002 | Demarais et al. |
| 6,458,151 B1 | 10/2002 | Saltiel |
| 6,464,664 B1 | 10/2002 | Jonkman et al. |
| 6,468,219 B1 | 10/2002 | Njemanze |
| 6,475,195 B1 | 11/2002 | Voda |
| 6,475,244 B2 | 11/2002 | Herweck et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,485,466 B2 | 11/2002 | Hamilton |
| 6,485,500 B1 | 11/2002 | Kokish et al. |
| 6,485,501 B1 | 11/2002 | Green |
| 6,508,824 B1 | 1/2003 | Flaherty et al. |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,517,520 B2 | 2/2003 | Chang et al. |
| 6,524,303 B1 | 2/2003 | Garibaldi |
| 6,527,746 B1 | 3/2003 | Oslund et al. |
| 6,533,800 B1 | 3/2003 | Barbut |
| 6,537,241 B1 | 3/2003 | Odland |
| 6,537,295 B2 | 3/2003 | Petersen |
| 6,540,712 B1 | 4/2003 | Parodi et al. |
| 6,540,768 B1 | 4/2003 | Diaz et al. |
| 6,544,276 B1 | 4/2003 | Azizi |
| 6,549,800 B1 | 4/2003 | Atalar et al. |
| 6,551,268 B1 | 4/2003 | Kaganov et al. |
| 6,551,273 B1 | 4/2003 | Olson et al. |
| 6,551,302 B1 | 4/2003 | Rosinko et al. |
| 6,554,820 B1 | 4/2003 | Wendlandt et al. |
| 6,554,827 B2 | 4/2003 | Chandrasekaran et al. |
| 6,554,849 B1 | 4/2003 | Jones et al. |
| 6,555,057 B1 | 4/2003 | Barbut et al. |
| 6,558,377 B2 | 5/2003 | Lee et al. |
| 6,558,405 B1 | 5/2003 | McInnes |
| 6,562,049 B1 | 5/2003 | Norlander et al. |
| 6,562,052 B2 | 5/2003 | Nobles et al. |
| 6,569,148 B2 | 5/2003 | Bagaoisan et al. |
| 6,579,246 B2 | 6/2003 | Jacobsen et al. |
| 6,579,260 B2 | 6/2003 | Maki et al. |
| 6,579,264 B1 | 6/2003 | Rossi |
| 6,579,484 B1 | 6/2003 | Tiernan et al. |
| 6,582,390 B1 | 6/2003 | Sanderson |
| 6,582,396 B1 | 6/2003 | Parodi |
| 6,582,440 B1 | 6/2003 | Brumbach |
| 6,582,448 B1 | 6/2003 | Boyle et al. |
| 6,589,262 B1 | 7/2003 | Honebrink et al. |
| 6,592,616 B1 | 7/2003 | Stack et al. |
| 6,595,953 B1 | 7/2003 | Coppi et al. |
| 6,595,980 B1 | 7/2003 | Barbut |
| 6,596,011 B2 | 7/2003 | Johnson et al. |
| 6,605,074 B2 | 8/2003 | Zadno-Azizi et al. |
| 6,610,077 B1 | 8/2003 | Hancock et al. |
| 6,612,999 B2 | 9/2003 | Brennan et al. |
| 6,616,681 B2 | 9/2003 | Hanson et al. |
| 6,620,148 B1 | 9/2003 | Tsugita |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,673,025 B1 | 1/2004 | Richardson et al. |
| 6,676,637 B1 | 1/2004 | Bonnette et al. |
| 6,679,893 B1 | 1/2004 | Tran |
| 6,682,505 B2 | 1/2004 | Bates et al. |
| 6,685,672 B1 | 2/2004 | Forman |
| 6,685,722 B1 | 2/2004 | Rosenbluth et al. |
| 6,689,144 B2 | 2/2004 | Gerberding |
| 6,692,473 B2 | 2/2004 | St. Cyr et al. |
| 6,695,858 B1 | 2/2004 | Dubrul et al. |
| 6,695,865 B2 | 2/2004 | Boyle et al. |
| 6,702,782 B2 | 3/2004 | Miller et al. |
| 6,702,834 B1 | 3/2004 | Boylan et al. |
| 6,706,055 B2 | 3/2004 | Douk et al. |
| 6,711,436 B1 | 3/2004 | Duhaylongsod |
| 6,716,183 B2 | 4/2004 | Clayman et al. |
| 6,719,717 B1 | 4/2004 | Johnson et al. |
| 6,723,064 B2 | 4/2004 | Babaev |
| 6,726,675 B1 | 4/2004 | Beyar |
| 6,730,104 B1 | 5/2004 | Sepetka et al. |
| 6,733,517 B1 | 5/2004 | Collins |
| 6,740,104 B1 | 5/2004 | Solar et al. |
| 6,749,627 B2 | 6/2004 | Thompson et al. |
| 6,755,803 B1 | 6/2004 | Le et al. |
| 6,755,812 B2 | 6/2004 | Peterson et al. |
| 6,755,847 B2 | 6/2004 | Eskuri |
| 6,758,854 B1 | 7/2004 | Butler et al. |
| 6,761,708 B1 | 7/2004 | Chiu et al. |
| 6,764,464 B2 | 7/2004 | McGuckin, Jr. et al. |
| 6,773,448 B2 | 8/2004 | Kusleika et al. |
| 6,790,204 B2 | 9/2004 | Zadno-Azizi et al. |
| 6,805,684 B2 | 10/2004 | Bonnette et al. |
| 6,805,692 B2 | 10/2004 | Muni et al. |
| 6,824,545 B2 | 11/2004 | Sepetka et al. |
| 6,824,550 B1 | 11/2004 | Noriega et al. |
| 6,824,553 B1 | 11/2004 | Samson et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,911,036 B2 | 6/2005 | Douk et al. |
| 6,926,658 B2 | 8/2005 | Farnan |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zadno-Azizi |
| 6,960,189 B2 | 11/2005 | Bates et al. |
| 6,969,395 B2 | 11/2005 | Eskuri |
| 6,972,030 B2 | 12/2005 | Lee et al. |
| 6,977,068 B1 | 12/2005 | Nair et al. |
| 6,991,642 B2 | 1/2006 | Petersen |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,325 B1 | 4/2006 | Sullivan |
| 7,033,336 B2 | 4/2006 | Hogendijk |
| 7,033,344 B2 | 4/2006 | Imran |
| 7,037,267 B1 | 5/2006 | Lipson et al. |
| 7,048,758 B2 | 5/2006 | Boyle et al. |

(56) References Cited

U.S. PATENT DOCUMENTS

| | | |
|---|---|---|
| 7,052,500 B2 | 5/2006 | Bashiri et al. |
| 7,056,328 B2 | 6/2006 | Arnott |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,115,134 B2 | 10/2006 | Chambers |
| 7,115,138 B2 | 10/2006 | Renati et al. |
| 7,118,539 B2 | 10/2006 | Vrba et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,166,120 B2 | 1/2007 | Kusleika |
| 7,169,165 B2 | 1/2007 | Belef et al. |
| 7,172,621 B2 | 2/2007 | Theron |
| 7,220,271 B2 | 5/2007 | Clubb et al. |
| 7,223,253 B2 | 5/2007 | Hogendijk |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,235,061 B2 | 6/2007 | Tsugita |
| 7,242,977 B2 | 7/2007 | Partridge et al. |
| 7,250,042 B2 | 7/2007 | Kataishi et al. |
| 7,285,126 B2 | 10/2007 | Sepetka et al. |
| 7,306,585 B2 | 12/2007 | Ross |
| 7,309,334 B2 | 12/2007 | von Hoffmann |
| 7,316,678 B2 | 1/2008 | Nash et al. |
| 7,329,278 B2 | 2/2008 | Seguin et al. |
| 7,367,982 B2 | 5/2008 | Nash et al. |
| 7,374,560 B2 | 5/2008 | Ressemann et al. |
| 7,374,561 B2 | 5/2008 | Barbut |
| 7,374,564 B2 | 5/2008 | Brown |
| 7,381,200 B2 | 6/2008 | Katoh et al. |
| 7,384,412 B2 | 6/2008 | Coppi |
| 7,402,151 B2 | 7/2008 | Rosenman et al. |
| 7,422,579 B2 | 9/2008 | Wahr et al. |
| 7,449,010 B1 | 11/2008 | Hayase et al. |
| 7,458,980 B2 | 12/2008 | Barbut |
| 7,476,232 B2 | 1/2009 | Deal |
| 7,497,844 B2 | 3/2009 | Spear et al. |
| 7,507,229 B2 | 3/2009 | Hewitt et al. |
| 7,524,303 B1 | 4/2009 | Don Michael et al. |
| 7,534,250 B2 | 5/2009 | Schaeffer et al. |
| 7,537,568 B2 | 5/2009 | Moehring |
| 7,549,974 B2 | 6/2009 | Nayak |
| 7,558,622 B2 | 7/2009 | Tran |
| 7,604,612 B2 | 10/2009 | Ressemann et al. |
| 7,615,042 B2 | 11/2009 | Beyar et al. |
| 7,625,207 B2 | 12/2009 | Hershey et al. |
| 7,691,121 B2 | 4/2010 | Rosenbluth et al. |
| 7,717,934 B2 | 5/2010 | Kusleika |
| 7,731,683 B2 | 6/2010 | Jang et al. |
| 7,736,355 B2 | 6/2010 | Itou et al. |
| 7,766,049 B2 | 8/2010 | Miller et al. |
| 7,766,820 B2 | 8/2010 | Core |
| 7,771,358 B2 | 8/2010 | Moehring et al. |
| 7,785,286 B2 | 8/2010 | Magnin et al. |
| 7,803,136 B2 | 9/2010 | Schatz |
| 7,806,906 B2 | 10/2010 | Don Michael |
| 7,815,626 B1 | 10/2010 | McFadden et al. |
| 7,837,692 B2 | 11/2010 | Mulholland et al. |
| 7,842,055 B2 | 11/2010 | Pintor et al. |
| 7,842,065 B2 | 11/2010 | Belef et al. |
| 7,850,642 B2 | 12/2010 | Moll et al. |
| 7,850,654 B2 | 12/2010 | Belhe et al. |
| 7,854,746 B2 | 12/2010 | Dorn et al. |
| 7,867,216 B2 | 1/2011 | Wahr et al. |
| 7,879,062 B2 | 2/2011 | Galdonik et al. |
| 7,905,856 B2 | 3/2011 | McGuckin, Jr. et al. |
| 7,905,877 B1 | 3/2011 | Jimenez et al. |
| 7,905,891 B2 | 3/2011 | Self |
| 7,909,812 B2 | 3/2011 | Jansen et al. |
| 7,927,309 B2 | 4/2011 | Palm |
| 7,927,347 B2 | 4/2011 | Hogendijk et al. |
| 7,931,659 B2 | 4/2011 | Bose et al. |
| 7,938,820 B2 | 5/2011 | Webster et al. |
| 7,967,789 B2 | 6/2011 | Solar et al. |
| 7,972,294 B2 | 7/2011 | Nash et al. |
| 7,972,298 B2 | 7/2011 | Wallace et al. |
| 7,972,308 B2 | 7/2011 | Putz |
| 7,988,646 B2 | 8/2011 | Taber |
| 7,998,104 B2 | 8/2011 | Chang |
| 8,021,351 B2 | 9/2011 | Boldenow et al. |
| 8,029,533 B2 | 10/2011 | Bagaoisan et al. |
| 8,043,279 B2 | 10/2011 | Hisamatsu et al. |
| 8,048,032 B2 | 11/2011 | Root et al. |
| 8,052,636 B2 | 11/2011 | Moll et al. |
| 8,052,640 B2 | 11/2011 | Fiorella et al. |
| 8,066,757 B2 | 11/2011 | Ferrera et al. |
| 8,070,694 B2 | 12/2011 | Galdonik et al. |
| 8,084,246 B2 | 12/2011 | Hoon et al. |
| 8,092,483 B2 | 1/2012 | Galdonik et al. |
| 8,114,032 B2 | 2/2012 | Ferry et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,172,831 B2 | 5/2012 | Webler, Jr. |
| 8,181,324 B2 | 5/2012 | McFadden et al. |
| 8,211,023 B2 | 7/2012 | Swan et al. |
| 8,221,348 B2 | 7/2012 | Hackett et al. |
| 8,231,600 B2 | 7/2012 | von Hoffmann |
| 8,235,968 B2 | 8/2012 | Tremaglio |
| 8,251,978 B2 | 8/2012 | Nash et al. |
| 8,252,010 B1 | 8/2012 | Raju et al. |
| 8,252,014 B2 | 8/2012 | Fisher |
| 8,257,302 B2 | 9/2012 | Beyar et al. |
| 8,292,850 B2 | 10/2012 | Root et al. |
| 8,308,712 B2 | 11/2012 | Provost et al. |
| 8,343,089 B2 | 1/2013 | Chang |
| 8,361,105 B2 | 1/2013 | Adams et al. |
| 8,366,735 B2 | 2/2013 | Bose et al. |
| 8,414,516 B2 | 4/2013 | Chang |
| 8,419,786 B2 | 4/2013 | Cottone, Jr. et al. |
| 8,425,549 B2 | 4/2013 | Lenker et al. |
| 8,460,312 B2 | 6/2013 | Bose et al. |
| 8,465,456 B2 | 6/2013 | Stivland |
| 8,523,801 B2 | 9/2013 | Nash et al. |
| 8,535,272 B2 | 9/2013 | Wang et al. |
| 8,540,759 B2 | 9/2013 | Porter |
| 8,545,552 B2 | 10/2013 | Garrison et al. |
| 8,574,245 B2 | 11/2013 | Garrison et al. |
| 8,600,477 B2 | 12/2013 | Beyar et al. |
| 8,609,426 B2 | 12/2013 | Silver |
| 8,636,714 B2 | 1/2014 | McFerran |
| 8,663,259 B2 | 3/2014 | Levine et al. |
| 8,682,411 B2 | 3/2014 | Kassab et al. |
| 8,690,907 B1 | 4/2014 | Janardhan et al. |
| 8,702,680 B2 | 4/2014 | Jimenez et al. |
| 8,708,954 B2 | 4/2014 | Webler |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,764,813 B2 | 7/2014 | Jantzen et al. |
| 8,795,305 B2 | 8/2014 | Martin et al. |
| 8,801,670 B2 | 8/2014 | Drontle et al. |
| 8,801,749 B2 | 8/2014 | Adams et al. |
| 8,814,892 B2 | 8/2014 | Galdonik et al. |
| 8,870,805 B2 | 10/2014 | Chang |
| 8,876,776 B2 | 11/2014 | Kassab et al. |
| 8,932,286 B2 | 1/2015 | Terry et al. |
| 8,932,320 B1 | 1/2015 | Janardhan et al. |
| RE45,380 E | 2/2015 | Root et al. |
| 8,961,533 B2 | 2/2015 | Stahler et al. |
| 8,961,549 B2 | 2/2015 | Conn |
| 8,974,411 B2 | 3/2015 | McKinnon |
| 8,996,095 B2 | 3/2015 | Anderson et al. |
| 9,014,786 B2 | 4/2015 | Carmeli et al. |
| 9,023,070 B2 | 5/2015 | Levine et al. |
| 9,034,007 B2 | 5/2015 | Janardhan |
| 9,107,691 B2 | 8/2015 | Fojtik |

(56) References Cited

U.S. PATENT DOCUMENTS

| | | | |
|---|---|---|---|
| 9,119,656 B2 | 9/2015 | Bose et al. | |
| 9,126,018 B1 | 9/2015 | Garrison | |
| 9,144,383 B2 | 9/2015 | Zharov | |
| 9,144,662 B2 | 9/2015 | Di Caprio et al. | |
| RE45,760 E | 10/2015 | Root et al. | |
| RE45,776 E | 10/2015 | Root et al. | |
| 9,199,057 B2 | 12/2015 | Nielser | |
| 9,211,132 B2 | 12/2015 | Bowman | |
| 9,220,562 B2 | 12/2015 | Brannan et al. | |
| 9,233,230 B2 | 1/2016 | Puhasmagi et al. | |
| 9,241,699 B1 * | 1/2016 | Kume | A61M 39/24 |
| 9,259,215 B2 | 2/2016 | Chou et al. | |
| 9,259,228 B2 | 2/2016 | Cruise et al. | |
| 9,265,512 B2 | 2/2016 | Garrison et al. | |
| 9,278,201 B2 | 3/2016 | Rapaport et al. | |
| 9,282,992 B2 | 3/2016 | Levine et al. | |
| 9,295,817 B2 | 3/2016 | Chang | |
| 9,314,268 B2 | 4/2016 | Cahill | |
| 9,351,993 B2 | 5/2016 | Cruise et al. | |
| 9,352,123 B2 | 5/2016 | Zhou et al. | |
| 9,370,639 B2 | 6/2016 | Plassman et al. | |
| 9,375,223 B2 | 6/2016 | Wallace | |
| 9,381,278 B2 | 7/2016 | Constant et al. | |
| 9,399,118 B2 | 7/2016 | Kume et al. | |
| RE46,116 E | 8/2016 | Root et al. | |
| 9,408,916 B2 | 8/2016 | Cruise et al. | |
| 9,414,819 B2 | 8/2016 | Fitz et al. | |
| 9,433,427 B2 | 9/2016 | Look et al. | |
| 9,439,791 B2 | 9/2016 | Vong et al. | |
| 9,445,828 B2 | 9/2016 | Turjman et al. | |
| 9,451,884 B2 | 9/2016 | Zharov et al. | |
| 9,451,963 B2 | 9/2016 | Cruise et al. | |
| 9,486,221 B2 | 11/2016 | Cruise et al. | |
| 9,486,611 B2 | 11/2016 | Petersen et al. | |
| 9,492,637 B2 | 11/2016 | Garrison et al. | |
| 9,504,476 B2 | 11/2016 | Gulachenski | |
| 9,510,855 B2 | 12/2016 | Rapaport et al. | |
| 9,526,504 B2 | 12/2016 | Chang | |
| 9,526,505 B2 | 12/2016 | Marks et al. | |
| 9,532,792 B2 | 1/2017 | Galdonik et al. | |
| 9,533,344 B2 | 1/2017 | Monetti et al. | |
| 9,539,022 B2 | 1/2017 | Bowman | |
| 9,539,122 B2 | 1/2017 | Burke et al. | |
| 9,546,236 B2 | 1/2017 | Cruise et al. | |
| 9,561,121 B2 | 2/2017 | Sudin et al. | |
| 9,561,125 B2 | 2/2017 | Bowman et al. | |
| 9,561,345 B2 | 2/2017 | Garrison et al. | |
| 9,597,101 B2 | 3/2017 | Galdonik et al. | |
| 9,615,832 B2 | 4/2017 | Bose et al. | |
| 9,622,753 B2 | 4/2017 | Cox | |
| 9,623,228 B2 | 4/2017 | Ryan et al. | |
| 9,655,633 B2 | 5/2017 | Leynov et al. | |
| 9,655,755 B2 | 5/2017 | Chou et al. | |
| 9,655,989 B2 | 5/2017 | Cruise et al. | |
| 9,662,118 B2 | 5/2017 | Chang | |
| 9,662,129 B2 | 5/2017 | Galdonik et al. | |
| 9,662,480 B2 | 5/2017 | Kume et al. | |
| 9,669,183 B2 | 6/2017 | Chang | |
| 9,669,191 B2 | 6/2017 | Chou et al. | |
| 9,681,882 B2 | 6/2017 | Garrison et al. | |
| 9,688,788 B2 | 6/2017 | Plotkin et al. | |
| 9,693,789 B2 | 7/2017 | Garrison et al. | |
| 9,693,852 B2 | 7/2017 | Lam et al. | |
| 9,717,500 B2 | 8/2017 | Tieu et al. | |
| 9,724,103 B2 | 8/2017 | Cruise et al. | |
| 9,764,111 B2 | 9/2017 | Gulachenski | |
| 9,770,251 B2 | 9/2017 | Bowman et al. | |
| 9,789,242 B2 | 10/2017 | Criado et al. | |
| 9,803,043 B2 | 10/2017 | Cruise et al. | |
| 9,820,761 B2 | 11/2017 | Garrison et al. | |
| 9,827,047 B2 | 11/2017 | Fudaba et al. | |
| 9,861,783 B2 | 1/2018 | Garrison et al. | |
| 9,877,731 B2 | 1/2018 | Cruise et al. | |
| 9,883,885 B2 | 2/2018 | Hendrick et al. | |
| 9,907,880 B2 | 3/2018 | Cruise et al. | |
| 10,183,146 B2 | 1/2019 | Yang et al. | |
| 10,192,230 B2 | 1/2019 | Look et al. | |
| 10,213,582 B2 | 2/2019 | Garrison et al. | |
| 10,441,301 B2 | 10/2019 | Vale et al. | |
| 10,456,552 B2 | 10/2019 | Goyal | |
| 10,485,956 B2 | 11/2019 | O'Donovan | |
| 10,667,871 B2 | 6/2020 | Romo et al. | |
| 2001/0014790 A1 | 8/2001 | Heller et al. | |
| 2001/0027310 A1 | 10/2001 | Parisi et al. | |
| 2001/0031980 A1 | 10/2001 | Wensel et al. | |
| 2001/0044598 A1 | 11/2001 | Parodi | |
| 2001/0044600 A1 | 11/2001 | Elkins | |
| 2001/0044632 A1 | 11/2001 | Daniel et al. | |
| 2001/0049486 A1 | 12/2001 | Evans et al. | |
| 2001/0049517 A1 | 12/2001 | Zadno-Azizi et al. | |
| 2001/0051811 A1 | 12/2001 | Bonnette et al. | |
| 2002/0016565 A1 | 2/2002 | Zadno-Azizi et al. | |
| 2002/0026145 A1 | 2/2002 | Bagaoisan et al. | |
| 2002/0035347 A1 | 3/2002 | Bagaoisan et al. | |
| 2002/0055747 A1 | 5/2002 | Cano et al. | |
| 2002/0062133 A1 | 5/2002 | Gilson et al. | |
| 2002/0072705 A1 | 6/2002 | Vrba et al. | |
| 2002/0077600 A1 * | 6/2002 | Sirimanne | A61M 25/0606 606/198 |
| 2002/0087076 A1 | 7/2002 | Meguro et al. | |
| 2002/0087119 A1 | 7/2002 | Parodi | |
| 2002/0091407 A1 | 7/2002 | Zadno-Azizi et al. | |
| 2002/0095174 A1 | 7/2002 | Tsugita et al. | |
| 2002/0111648 A1 | 8/2002 | Kusleika et al. | |
| 2002/0111666 A1 | 8/2002 | Hart et al. | |
| 2002/0123765 A1 | 9/2002 | Sepetka et al. | |
| 2002/0128679 A1 | 9/2002 | Turovskiy et al. | |
| 2002/0133111 A1 | 9/2002 | Shadduck | |
| 2002/0138094 A1 | 9/2002 | Borillo et al. | |
| 2002/0143362 A1 | 10/2002 | Macoviak et al. | |
| 2002/0151922 A1 | 10/2002 | Hogendijk et al. | |
| 2002/0151927 A1 | 10/2002 | Douk et al. | |
| 2002/0156455 A1 | 10/2002 | Barbut | |
| 2002/0156460 A1 | 10/2002 | Ye et al. | |
| 2002/0165571 A1 | 11/2002 | Hebert et al. | |
| 2002/0165574 A1 | 11/2002 | Ressemann et al. | |
| 2002/0165598 A1 | 11/2002 | Wahr et al. | |
| 2002/0169472 A1 | 11/2002 | Douk et al. | |
| 2002/0173785 A1 | 11/2002 | Spear et al. | |
| 2002/0173815 A1 | 11/2002 | Hogendijk et al. | |
| 2002/0177869 A1 * | 11/2002 | Eidenschink | A61M 25/09041 606/194 |
| 2002/0177899 A1 | 11/2002 | Eum et al. | |
| 2002/0183782 A1 | 12/2002 | Tsugita et al. | |
| 2002/0183783 A1 | 12/2002 | Shadduck | |
| 2003/0023263 A1 | 1/2003 | Krolik et al. | |
| 2003/0040762 A1 | 2/2003 | Dorros et al. | |
| 2003/0050600 A1 | 3/2003 | Ressemann et al. | |
| 2003/0065353 A1 | 4/2003 | Horzewski et al. | |
| 2003/0065356 A1 | 4/2003 | Tsugita et al. | |
| 2003/0069468 A1 | 4/2003 | Bolling et al. | |
| 2003/0078562 A1 | 4/2003 | Makower et al. | |
| 2003/0120208 A1 | 6/2003 | Houser et al. | |
| 2003/0130577 A1 | 7/2003 | Purdy et al. | |
| 2003/0135193 A1 | 7/2003 | Hilgers et al. | |
| 2003/0135198 A1 | 7/2003 | Berhow et al. | |
| 2003/0135232 A1 | 7/2003 | Douk et al. | |
| 2003/0153942 A1 | 8/2003 | Wang et al. | |
| 2003/0186203 A1 | 10/2003 | Aboud | |
| 2003/0191492 A1 | 10/2003 | Gellman et al. | |
| 2003/0212304 A1 | 11/2003 | Lattouf | |
| 2003/0212384 A1 | 11/2003 | Hayden | |
| 2003/0233038 A1 | 12/2003 | Hassett | |
| 2004/0006344 A1 | 1/2004 | Nguyen et al. | |
| 2004/0006365 A1 | 1/2004 | Brady et al. | |
| 2004/0015151 A1 | 1/2004 | Chambers | |
| 2004/0019322 A1 | 1/2004 | Hoffmann | |
| 2004/0059243 A1 | 3/2004 | Flores et al. | |
| 2004/0116878 A1 | 6/2004 | Byrd et al. | |
| 2004/0122360 A1 | 6/2004 | Waldhauser et al. | |
| 2004/0133232 A1 | 7/2004 | Rosenbluth et al. | |
| 2004/0138608 A1 | 7/2004 | Barbut et al. | |
| 2004/0153049 A1 | 8/2004 | Hewitt et al. | |
| 2004/0153118 A1 | 8/2004 | Clubb et al. | |

(56) References Cited

U.S. PATENT DOCUMENTS

| | | |
|---|---|---|
| 2004/0193177 A1 | 9/2004 | Houghton et al. |
| 2004/0210194 A1 | 10/2004 | Bonnette et al. |
| 2004/0220611 A1 | 11/2004 | Ogle |
| 2004/0230285 A1 | 11/2004 | Gifford, III et al. |
| 2004/0236215 A1 | 11/2004 | Mihara et al. |
| 2004/0243102 A1 | 12/2004 | Berg et al. |
| 2004/0254602 A1 | 12/2004 | Lehe et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0021075 A1 | 1/2005 | Bonnette et al. |
| 2005/0021152 A1 | 1/2005 | Ogle et al. |
| 2005/0027236 A1 | 2/2005 | Douk |
| 2005/0049574 A1 | 3/2005 | Petrick et al. |
| 2005/0059957 A1 | 3/2005 | Campbell et al. |
| 2005/0065467 A1 | 3/2005 | Pudelko et al. |
| 2005/0065498 A1 | 3/2005 | McFerran |
| 2005/0085746 A1 | 4/2005 | Adams et al. |
| 2005/0085847 A1 | 4/2005 | Galdonik et al. |
| 2005/0090802 A1 | 4/2005 | Connors et al. |
| 2005/0103332 A1 | 5/2005 | Gingles et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0182386 A1 | 8/2005 | Aggerholm |
| 2005/0209559 A1 | 9/2005 | Thornton et al. |
| 2005/0209631 A1 | 9/2005 | Galdonik et al. |
| 2005/0209674 A1 | 9/2005 | Kutscher et al. |
| 2005/0209675 A1 | 9/2005 | Ton et al. |
| 2005/0228479 A1 | 10/2005 | Pavcnik et al. |
| 2005/0245892 A1 | 11/2005 | Elkins et al. |
| 2005/0251206 A1 | 11/2005 | Maahs et al. |
| 2005/0273051 A1 | 12/2005 | Coppi |
| 2005/0277976 A1 | 12/2005 | Galdonik et al. |
| 2006/0020165 A1 | 1/2006 | Adams |
| 2006/0030835 A1 | 2/2006 | Sherman et al. |
| 2006/0030876 A1 | 2/2006 | Peacock et al. |
| 2006/0047301 A1 | 3/2006 | Ogle |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064036 A1 | 3/2006 | Osborne et al. |
| 2006/0079787 A1 | 4/2006 | Whiting et al. |
| 2006/0089618 A1 | 4/2006 | McFerran et al. |
| 2006/0095062 A1 | 5/2006 | Stephens |
| 2006/0100530 A1 | 5/2006 | Kliot et al. |
| 2006/0129091 A1 | 6/2006 | Bonnette et al. |
| 2006/0135961 A1 | 6/2006 | Rosenman et al. |
| 2006/0173440 A1 | 8/2006 | Lamson et al. |
| 2006/0195137 A1 | 8/2006 | Sepetka et al. |
| 2006/0200047 A1 | 9/2006 | Galdonik et al. |
| 2006/0200191 A1 | 9/2006 | Zadno-Azizi |
| 2006/0217664 A1 | 9/2006 | Hattler et al. |
| 2006/0247755 A1 | 11/2006 | Pal et al. |
| 2006/0258987 A1 | 11/2006 | Lentz et al. |
| 2006/0259063 A1 | 11/2006 | Bates et al. |
| 2006/0264759 A1 | 11/2006 | Moehring et al. |
| 2006/0271098 A1 | 11/2006 | Peacock |
| 2007/0005084 A1 | 1/2007 | Clague et al. |
| 2007/0016132 A1 | 1/2007 | Oepen et al. |
| 2007/0021778 A1 | 1/2007 | Carly |
| 2007/0043333 A1 | 2/2007 | Kampa et al. |
| 2007/0060888 A1 | 3/2007 | Goff et al. |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0073264 A1 | 3/2007 | Stedman et al. |
| 2007/0106211 A1 | 5/2007 | Provost-Tine et al. |
| 2007/0135733 A1 | 6/2007 | Soukup et al. |
| 2007/0173784 A1 | 7/2007 | Johansson et al. |
| 2007/0185501 A1 | 8/2007 | Martin et al. |
| 2007/0185521 A1 | 8/2007 | Bui et al. |
| 2007/0185522 A1 | 8/2007 | Davies et al. |
| 2007/0191820 A1 | 8/2007 | Maksimovich |
| 2007/0197956 A1 | 8/2007 | Le et al. |
| 2007/0198028 A1 | 8/2007 | Miloslavski et al. |
| 2007/0198049 A1 | 8/2007 | Barbut |
| 2007/0208302 A1 | 9/2007 | Webster et al. |
| 2007/0227543 A1 | 10/2007 | Peichel |
| 2007/0239261 A1 | 10/2007 | Bose et al. |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2008/0027379 A1 | 1/2008 | Wilkins |
| 2008/0033525 A1 | 2/2008 | Shaked et al. |
| 2008/0058839 A1 | 3/2008 | Nobles et al. |
| 2008/0082107 A1 | 4/2008 | Miller et al. |
| 2008/0082109 A1 | 4/2008 | Moll et al. |
| 2008/0086110 A1 | 4/2008 | Galdonik et al. |
| 2008/0097251 A1 | 4/2008 | Babaev |
| 2008/0109088 A1 | 5/2008 | Galdonik et al. |
| 2008/0119890 A1 | 5/2008 | Adams et al. |
| 2008/0140010 A1 | 6/2008 | Kennedy et al. |
| 2008/0167678 A1 | 7/2008 | Morsi |
| 2008/0172066 A9 | 7/2008 | Galdonik et al. |
| 2008/0177245 A1 | 7/2008 | Mesallum |
| 2008/0183128 A1 | 7/2008 | Morriss et al. |
| 2008/0188888 A1 | 8/2008 | Adams et al. |
| 2008/0195140 A1 | 8/2008 | Myla et al. |
| 2008/0200946 A1 | 8/2008 | Braun et al. |
| 2008/0234723 A1 | 9/2008 | Buiser et al. |
| 2008/0243222 A1 | 10/2008 | Schafersman et al. |
| 2008/0262350 A1 | 10/2008 | Unger |
| 2008/0262472 A1 | 10/2008 | Lunn et al. |
| 2008/0262506 A1 | 10/2008 | Griffin et al. |
| 2008/0281248 A1 | 11/2008 | Angheloiu et al. |
| 2008/0294111 A1 | 11/2008 | Tal et al. |
| 2008/0312639 A1 | 12/2008 | Weber |
| 2009/0018455 A1 | 1/2009 | Chang |
| 2009/0018525 A1 | 1/2009 | Waite et al. |
| 2009/0024072 A1 | 1/2009 | Criado et al. |
| 2009/0024089 A1 | 1/2009 | Levine et al. |
| 2009/0030400 A1 | 1/2009 | Bose et al. |
| 2009/0082800 A1 | 3/2009 | Janardhan |
| 2009/0124956 A1 | 5/2009 | Swetlin et al. |
| 2009/0163891 A1 | 6/2009 | Ewing et al. |
| 2009/0165881 A1 | 7/2009 | Tegg et al. |
| 2009/0198172 A1 | 8/2009 | Garrison et al. |
| 2009/0209857 A1 | 8/2009 | Secretain et al. |
| 2009/0227992 A1 | 9/2009 | Nir et al. |
| 2009/0234321 A1 | 9/2009 | Shapland et al. |
| 2009/0247987 A1 | 10/2009 | Chevalier, Jr. et al. |
| 2009/0254166 A1 | 10/2009 | Chou et al. |
| 2009/0264865 A1 | 10/2009 | Kawai |
| 2009/0270800 A1* | 10/2009 | Spurchise ......... A61M 25/0074 604/95.04 |
| 2009/0281379 A1 | 11/2009 | Binmoeller et al. |
| 2009/0299393 A1 | 12/2009 | Martin et al. |
| 2009/0312699 A1 | 12/2009 | Pudelko et al. |
| 2009/0312786 A1 | 12/2009 | Trask et al. |
| 2010/0004607 A1 | 1/2010 | Wilson et al. |
| 2010/0022948 A1 | 1/2010 | Wilson et al. |
| 2010/0030141 A1 | 2/2010 | Chermoni |
| 2010/0042118 A1 | 2/2010 | Garrison et al. |
| 2010/0049168 A1 | 2/2010 | Parker et al. |
| 2010/0057051 A1 | 3/2010 | Howat et al. |
| 2010/0063479 A1 | 3/2010 | Merdan et al. |
| 2010/0063480 A1 | 3/2010 | Shireman |
| 2010/0094330 A1 | 4/2010 | Barbut |
| 2010/0114017 A1 | 5/2010 | Lenker et al. |
| 2010/0125322 A1* | 5/2010 | Fitzgerald ................ A61F 2/95 623/1.11 |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0211050 A1 | 8/2010 | Luther |
| 2010/0217235 A1 | 8/2010 | Thorstenson et al. |
| 2010/0217276 A1 | 8/2010 | Garrison et al. |
| 2010/0228269 A1 | 9/2010 | Garrison et al. |
| 2010/0256600 A1 | 10/2010 | Ferrera |
| 2010/0268029 A1 | 10/2010 | Phan et al. |
| 2010/0312141 A1 | 12/2010 | Keast et al. |
| 2010/0318097 A1 | 12/2010 | Ferrera et al. |

(56) References Cited

U.S. PATENT DOCUMENTS

| | | |
|---|---|---|
| 2011/0009875 A1 | 1/2011 | Grandfield et al. |
| 2011/0015482 A1 | 1/2011 | Carrillo, Jr. |
| 2011/0034986 A1 | 2/2011 | Chou et al. |
| 2011/0046709 A1* | 2/2011 | Coffey ................ A61F 2/97 623/1.11 |
| 2011/0082373 A1 | 4/2011 | Gurley et al. |
| 2011/0087147 A1 | 4/2011 | Garrison et al. |
| 2011/0106200 A1 | 5/2011 | Ziegler |
| 2011/0112567 A1 | 5/2011 | Lenker et al. |
| 2011/0125181 A1 | 5/2011 | Brady et al. |
| 2011/0152760 A1 | 6/2011 | Parker |
| 2011/0172678 A1 | 7/2011 | Behl et al. |
| 2011/0172700 A1 | 7/2011 | Bose et al. |
| 2011/0230859 A1 | 9/2011 | Galdonik et al. |
| 2011/0238041 A1 | 9/2011 | Lim et al. |
| 2011/0238083 A1 | 9/2011 | Moll et al. |
| 2011/0245751 A1 | 10/2011 | Hofmann |
| 2011/0264133 A1 | 10/2011 | Hanlon et al. |
| 2012/0040858 A1 | 2/2012 | Ford et al. |
| 2012/0065479 A1 | 3/2012 | Lahiji et al. |
| 2012/0065490 A1 | 3/2012 | Zharov et al. |
| 2012/0071838 A1 | 3/2012 | Fojtik |
| 2012/0071856 A1 | 3/2012 | Goldfarb et al. |
| 2012/0078140 A1 | 3/2012 | Nita |
| 2012/0095485 A1 | 4/2012 | Cully et al. |
| 2012/0101561 A1 | 4/2012 | Porter |
| 2012/0109044 A1 | 5/2012 | Santamore et al. |
| 2012/0116350 A1 | 5/2012 | Strauss et al. |
| 2012/0123466 A1 | 5/2012 | Porter et al. |
| 2012/0148175 A1 | 6/2012 | Wesselmann |
| 2012/0150147 A1 | 6/2012 | Leynov et al. |
| 2012/0165756 A1 | 6/2012 | Root et al. |
| 2012/0172918 A1 | 7/2012 | Fifer et al. |
| 2012/0179097 A1 | 7/2012 | Cully et al. |
| 2012/0253313 A1 | 10/2012 | Galdonik et al. |
| 2012/0271281 A1 | 10/2012 | Schertiger |
| 2012/0277671 A1 | 11/2012 | Fuentes |
| 2012/0296275 A1 | 11/2012 | Martin et al. |
| 2012/0310212 A1 | 12/2012 | Fischell et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |
| 2013/0053792 A1 | 2/2013 | Fischell et al. |
| 2013/0116701 A1 | 5/2013 | Wang et al. |
| 2013/0158507 A1 | 6/2013 | Browr |
| 2013/0158578 A1 | 6/2013 | Ghodke et al. |
| 2013/0165873 A1 | 6/2013 | Morriss et al. |
| 2013/0172851 A1 | 7/2013 | Shimada et al. |
| 2013/0184735 A1 | 7/2013 | Fischell et al. |
| 2013/0197621 A1 | 8/2013 | Ryan et al. |
| 2013/0226276 A1 | 8/2013 | Newell et al. |
| 2013/0274783 A1 | 10/2013 | Wynberg |
| 2013/0281788 A1 | 10/2013 | Garrison |
| 2014/0012281 A1* | 1/2014 | Wang ................ A61M 25/0023 606/108 |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0046297 A1 | 2/2014 | Shimada et al. |
| 2014/0081243 A1 | 3/2014 | Zhou et al. |
| 2014/0088510 A1 | 3/2014 | Nimkar et al. |
| 2014/0114287 A1 | 4/2014 | Beasley et al. |
| 2014/0155783 A1 | 6/2014 | Starksen et al. |
| 2014/0155908 A1 | 6/2014 | Rosenbluth et al. |
| 2014/0155932 A1 | 6/2014 | Weishaupt et al. |
| 2014/0180246 A1 | 6/2014 | Comerota et al. |
| 2014/0207043 A1 | 7/2014 | Anand et al. |
| 2014/0228808 A1 | 8/2014 | Webster et al. |
| 2014/0236120 A1 | 8/2014 | Tsai et al. |
| 2014/0249508 A1 | 9/2014 | Wang et al. |
| 2014/0257018 A1 | 9/2014 | Farnan |
| 2014/0257186 A1 | 9/2014 | Kerr |
| 2014/0273920 A1 | 9/2014 | Smith |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296769 A1 | 10/2014 | Hyde et al. |
| 2014/0296868 A1 | 10/2014 | Garrison et al. |
| 2014/0296889 A1 | 10/2014 | Avneri et al. |
| 2014/0343537 A1 | 11/2014 | Eversull et al. |
| 2014/0358123 A1 | 12/2014 | Ueda et al. |
| 2014/0358178 A1 | 12/2014 | Hewitt et al. |
| 2014/0371709 A1 | 12/2014 | Allen et al. |
| 2015/0025562 A1 | 1/2015 | Dinh et al. |
| 2015/0080939 A1 | 3/2015 | Adams et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0151090 A1 | 6/2015 | Sutton et al. |
| 2015/0165160 A1 | 6/2015 | Thungana et al. |
| 2015/0173782 A1* | 6/2015 | Garrison ............ A61M 25/0043 606/127 |
| 2015/0174368 A1 | 6/2015 | Garrison et al. |
| 2015/0196210 A1 | 7/2015 | McCaffrey et al. |
| 2015/0245848 A1 | 9/2015 | Shimon |
| 2015/0265802 A1 | 9/2015 | Fukuoka et al. |
| 2015/0282821 A1 | 10/2015 | Look et al. |
| 2015/0327843 A1 | 11/2015 | Garrison |
| 2015/0327919 A1 | 11/2015 | Clopp et al. |
| 2015/0335857 A1 | 11/2015 | Ishikawa |
| 2015/0352330 A1 | 12/2015 | Wasdyke et al. |
| 2016/0008025 A1 | 1/2016 | Gupta et al. |
| 2016/0008572 A1 | 1/2016 | Di Caprio et al. |
| 2016/0015935 A1 | 1/2016 | Chan et al. |
| 2016/0022964 A1 | 1/2016 | Goyal |
| 2016/0058459 A1 | 3/2016 | Bowman |
| 2016/0066931 A1 | 3/2016 | Kugler et al. |
| 2016/0081825 A1 | 3/2016 | Sudin et al. |
| 2016/0096002 A1 | 4/2016 | Di Caprio et al. |
| 2016/0100819 A1 | 4/2016 | Tieu |
| 2016/0121081 A1 | 5/2016 | Iwano et al. |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0136398 A1 | 5/2016 | Heilman et al. |
| 2016/0143661 A1* | 5/2016 | Wood ................ A61B 17/00234 606/129 |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206322 A1 | 7/2016 | Fitz et al. |
| 2016/0220396 A1 | 8/2016 | Zhou et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346502 A1 | 12/2016 | Fuller et al. |
| 2016/0346508 A1 | 12/2016 | Williams et al. |
| 2016/0346509 A1 | 12/2016 | Anderson et al. |
| 2016/0361180 A1 | 12/2016 | Vong et al. |
| 2016/0361459 A1 | 12/2016 | Baldwin |
| 2016/0367272 A1 | 12/2016 | Garrison et al. |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |

(56) References Cited

U.S. PATENT DOCUMENTS

| | | |
|---|---|---|
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0231647 A1 | 8/2017 | Saunders et al. |
| 2017/0239440 A1 | 8/2017 | Yang et al. |
| 2017/0246014 A1 | 8/2017 | Rapaport et al. |
| 2017/0252043 A1 | 9/2017 | Fuller et al. |
| 2017/0252536 A1 | 9/2017 | Yang et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0333060 A1 | 11/2017 | Panian |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Greene, Jr. et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Panian |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Baldwin et al. |
| 2018/0064453 A1 | 3/2018 | Garrison et al. |
| 2018/0116684 A1 | 5/2018 | Garrison et al. |
| 2018/0133436 A1 | 5/2018 | Garrison et al. |
| 2018/0242978 A1 | 8/2018 | Chou et al. |
| 2019/0008534 A1 | 1/2019 | Garrison et al. |
| 2019/0046218 A1 | 2/2019 | Garrison et al. |
| 2019/0133744 A1 | 5/2019 | Janardhan et al. |
| 2019/0269538 A1 | 9/2019 | Chou et al. |
| 2019/0366042 A1 | 12/2019 | Garrison et al. |
| 2019/0366043 A1 | 12/2019 | Garrison et al. |
| 2020/0016369 A1 | 1/2020 | Garrison et al. |
| 2020/0046939 A1 | 2/2020 | Garrison et al. |
| 2020/0046940 A1 | 2/2020 | Garrison et al. |
| 2020/0164178 A1 | 5/2020 | Garrison et al. |
| 2020/0187965 A1 | 6/2020 | Garrison et al. |
| 2020/0215306 A1 | 7/2020 | Garrison et al. |
| 2020/0337716 A1 | 10/2020 | Garrison et al. |
| 2020/0345981 A1 | 11/2020 | Garrison et al. |
| 2021/0212707 A1 | 7/2021 | Chou et al. |
| 2021/0330332 A1 | 10/2021 | Chou et al. |
| 2021/0338256 A1 | 11/2021 | Chou et al. |
| 2022/0047285 A1 | 2/2022 | Chou et al. |

FOREIGN PATENT DOCUMENTS

| | | |
|---|---|---|
| EP | 0427429 A2 | 5/1991 |
| EP | 1226795 A2 | 7/2002 |
| EP | 1440663 A1 | 7/2004 |
| EP | 1639951 A1 | 3/2006 |
| EP | 2 069 528 B1 | 3/2013 |
| EP | 2821094 A1 | 1/2015 |
| GB | 2020557 A | 11/1979 |
| JP | 3026200 U | 7/1996 |
| JP | H11-146883 A | 6/1999 |
| JP | 2002-291756 A | 10/2002 |
| JP | 2003-521286 A | 7/2003 |
| JP | 2003-522560 A | 7/2003 |
| JP | 2005-500138 A | 1/2005 |
| JP | 2005-523123 A | 8/2005 |
| JP | 2008-503249 A | 2/2008 |
| JP | 2008-517652 A | 5/2008 |
| JP | 3142466 U | 6/2008 |
| JP | 2012143558 A | 8/2012 |
| JP | 2014-138756 A | 7/2014 |
| WO | WO-93/17750 A1 | 9/1993 |
| WO | WO-94/02194 A1 | 2/1994 |
| WO | WO-95/05209 A1 | 2/1995 |
| WO | WO-98/38930 A1 | 9/1998 |
| WO | WO-99/45835 A2 | 9/1999 |
| WO | WO-00/16705 A1 | 3/2000 |
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-02/055146 A1 | 7/2002 |
| WO | WO-02/085092 A2 | 10/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2005/084130 A2 | 9/2005 |
| WO | WO-2006/111944 A1 | 10/2006 |
| WO | WO-2006/127929 A2 | 11/2006 |
| WO | WO-2006/132434 A1 | 12/2006 |
| WO | WO-2007/098494 A1 | 8/2007 |
| WO | WO-2008/006111 A2 | 1/2008 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |
| WO | WO-2010/039456 A1 | 4/2010 |
| WO | WO-2011/011493 A1 | 1/2011 |
| WO | WO-2012/009518 A1 | 1/2012 |
| WO | WO-2012/035633 A1 | 3/2012 |
| WO | WO-2012/047803 A2 | 4/2012 |
| WO | WO-2014/008489 A1 | 1/2014 |
| WO | WO-2014/203336 A1 | 12/2014 |
| WO | WO-2015/042368 A2 | 3/2015 |
| WO | WO-2015/100178 A1 | 7/2015 |
| WO | WO-2015/157330 A1 | 10/2015 |
| WO | WO-2017/118818 A1 | 7/2017 |
| WO | PCT/US21/35387 | 6/2021 |
| WO | PCT/US21/54280 | 10/2021 |

OTHER PUBLICATIONS

Farooq, Vasim et al. "Forward and Back Aspiration during ST-Elevation Myocardial Infarction: a Feasibility Study." EuroIntervention, vol. 11, No. 14, 2016, pp. 1639-1648.

Farooq, Vasim et al. "The Use of a Guide Catheter Extension System as an Aid During Transradial Percutaneous Coronary Intervention of Coronary Artery Bypass Grafts." Catheterization and Cardiovascular Interventions, vol. 78, No. 6, 2011, pp. 847-863.

Feldman, "Transcatheter Aspiration of a Thrombus in an Aortocoronary Saphenous Vein Graft," *American Journal of Cardiology*, 60(4):379-380. (1987).

(56) References Cited

OTHER PUBLICATIONS

Guidezilla Guide Extension Catheter, Boston Scientific 510k Submission, Feb. 20, 2017, 5 pages. Web. Accessed Oct. 23, 2017.
Heart and Stroke Foundation of Canada. "Vacuum cleaner sucks up strokes." ScienceDaily, Jun. 8, 2010, 4 pages, www.sciencedaily.com/releases/2010/06/100608162240.htm.
Hopf-Jensen, S. (Nov. 2016, e-published Jul. 1, 2016) "Impact and Effectiveness of Dual Aspiration Technique in Stent-Assisted Mechanical Thrombectomy: Recent Improvements in Acute Stroke Management," Cardiovasc Intervent Radiol, 39:1620-1628.
Kopeck, Rachel. "Penumbra, Inc. Launches 5MAX™ ACE—The Newest Clot Extraction Device to Treat Acute Ischemic Stroke Patients." Penumbra Inc., Jul. 8, 2013, 3 pages, http://www.penumbrainc.com/news/penumbra-inc-launches-5max-ace-the-newest-clot-extraction-device-to-treat-acute-ischemic-stroke-patients/.
Merit Medical Systems Acquired Distal Access's SPINR Platform, Jul. 15, 2015, Digital Access, LLC; Merit Medical Systems, 5 pages. Web. Accessed Oct. 23, 2017.
Patel, Tejas et al. (2014) "Balloon-Assisted Tracking: A Must-Know Technique to Overcome Difficult Anatomy During Transradial Approach," Catheter Cardiovasc. Interv. 83(2):211-220.
Penumbra, Inc., "Penumbra, Inc. Completes Pivotal Stroke Trial of Intracranial Revascularization," Press Release, (2007). Web. Accessed Jun. 14, 2017. 2 pages.
Penumbra, Inc., "The Penumbra Pivotal Stroke Trial: Safety and Effectiveness of a New Generation of Mechanical Devices for Clot Removal in Intracranial Large Vessel Occlusive Disease," Stroke 2009, 40:2761-2768. Web. Downloaded Jun. 15, 2017.
Reeder et al., "Aspiration Thrombectomy for Removal of Coronary Thrombus," American Journal of Cardiology. (Jul. 1, 1992) 70:107-110 (Abstract only).
Request for Ex Parte Reexamination Transmittal Form and Request for Ex Parte Reexamination pursuant to 37 CFR 1.150 of U.S. Pat. No. 9,820,761 issued Nov. 21, 2017. Request filed May 11, 2018 and assigned U.S. Appl. No. 90/014, 136. 35 pages.
Simon et al., Exploring the efficacy of cyclic vs. static aspiration in a cerebral thrombectomy model: an initial proof of concept study, J. Neuro Intervent Surg 2014, 6, pp. 677-683. Web. Downloaded Oct. 18, 2017.
Simon et al., Hydrodynamic comparison of the Penumbra system and commonly available syringes in forced—suction thrombectomy, J. Neuro Intervent Surg 2014, 6, pp. 205-211. Web. Downloaded Oct. 18, 2017.
Spiotta et al., Evolution of thrombectomy approaches and devices for acute stroke: a technical review, J. Neuro Intervent Surg 2015, 7, pp. 2-7. Web. Downloaded Oct. 18, 2017.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).
Turk, Aquilla S, et al. (2014) "Initial clinical experience with the ADAPT technique: A direct aspiration first pass technique for stroke thrombectomy." J NeuroIntervent Surg 2014:6:231-237. doi:10.1136/neurintsurg-2013-010713. Web. Accessed Sep. 26, 2018.
Webb et al., "Retrieval and Analysis of Particulate Debris After Saphenous Vein Graft Intervention," *Journal of the American College of Cardiology*, 34(2):468-475 (1999).
Yoo et al., "The Penumbra Stroke System: a technical review." Journal of NeuroInterventional Surgery. 4:199-205 (2012). Web. Downloaded Jun. 15, 2017.
U.S. Appl. No. 16/414,532, filed May 16, 2019.
U.S. Appl. No. 16/584,351, filed Sep. 26, 2019.
U.S. Appl. No. 16/596,535, filed Oct. 8, 2019.
U.S. Appl. No. 16/775,105, filed Jan. 28, 2020.
U.S. Appl. No. 16/821,804, filed Mar. 17, 2020.
U.S. Appl. No. 16/890,962, filed Jun. 2, 2020.
U.S. Appl. No. 16/925,708, filed Jul. 10, 2020.
U.S. Appl. No. 17/011,448, filed Sep. 3, 2020.
U.S. Appl. No. 17/089,495, filed Nov. 4, 2020.
U.S. Appl. No. 17/093,401, filed Nov. 9, 2020.
U.S. Appl. No. 17/152,581, filed Jan. 19, 2021.
U.S. Appl. No. 17/319,943, filed May 13, 2021.
U.S. Appl. No. 17/481,639, filed Sep. 22, 2021.
U.S. Appl. No. 17/497,713, filed Oct. 8, 2021.
U.S. Appl. No. 17/516,540, filed Nov. 1, 2021.
U.S. Appl. No. 17/849,379, filed Jun. 24, 2022.
U.S. Appl. No. 17/859,955, filed Jul. 7, 2022.
U.S. Appl. No. 17/883,295, filed Aug. 8, 2022.
U.S. Appl. No. 17/883,430, filed Aug. 8, 2022.
U.S. Appl. No. 15/699,401, filed Sep. 8, 2017.
U.S. Appl. No. 16/319,038, filed Jul. 21, 2017.
U.S. Appl. No. 16/543,215, filed Aug. 16, 2019.
U.S. Appl. No. 16/596,531, filed Oct. 8, 2019.
U.S. Appl. No. 17/152,575, filed Jan. 19, 2021.
"2012 Buyer's Guide: Microcatheters." Endovascular Today, 2012, pp. 48-51.
"2017 Buyer's Guide: Microcatheters." Endovascular Today, http://evtoday.com/buyers-guide/chart.asp?id=25. Accessed on Oct. 10, 2017. 11 pages.
"Asahi Fubuki Catheter Dilator Kit." Asahi-Intecc USA Medical. 2017. Web. Accessed Oct. 2, 2017. 3 pages. www.asahi-inteccusa-medical.com/medical-product/fubuki-dilator-kit/. Accessed Oct. 2, 2017.
Adami, M.D., et al., (2002). "Use of the Parodi Anti-Embolism System in Carotid Stenting: Italian Trial Results" J Endovasc Ther 9:147-154.
Alexandrescu et al. (2006). "Filter-protected carotid stenting via a minimal cervical access with transitory aspirated reversed flow during initial passage of the target lesion" J. Endovasc. Ther. 13(2):196-204.
Alvarez et al. (2008). "Transcervical carotid stenting with flow reversal is safe in octogenarians: A preliminary safety study" J. Vasc. Surg. 47:96-100.
Bates M.D., et al. (2003). "Reversal of the Direction of Internal Carotid Artery Blood Flow by Occlusion of the Common and External Carotid Arteries in a Swine Model" Catherization and Cardiovascular Intervention 60:270-275.
Bates, M.D., et al. (2004). "Internal Carotid Artery Flow Arrest/Reversal Cerebral Protection Techniques" The West Virginal Medical Journal, vol. 99:60-63.
Bergeron et al. (1999). "Percutaneous stenting of the internal carotid artery: the European Cast I Study" J. Endovasc. Surg. 6:155-159.
Bergeron et al. (2008). MEET Presentation, Cannes, French Riviera "Why I do not use routine femoral access for CAS".
Bergeron P. et al. (1996). "Recurrent Carotid Disease: Will Stents be an alternative to surgery?" J Endovasc Surg; 3: 76-79.
Bourekas, E. C., A. P. Slivka, et al. (2004). "Intraarterial thrombolytic therapy within 3 hours of the onset of stroke." Neurosurgery 54(1): 39-44; discussion 44-6.
Chang, D.W., et al., "A new approach to carotid angioplasty and stenting with transcervical occlusion and protective shunting: Why it may be a better carotid artery intervention" (J Vasc Surg 2004; 39:994-1002.).
Chang, M.D., "Carotid Angioplasty And Stenting Using Transcervical Occlusion and Protective Shunting Via A Mini Incision in the Neck: A New Technique for Difficult Femoral Access or Filter Placement May Be the Better Carotid Artery Intervention" 30th Global: Vascular and Endovascular Issues, Techniques and Horizons Symposium, New York, NY, Nov. 20-23, 2003; XXVII 6.1-XXVII 6.2.
Cohen et al. (2012). "A reappraisal of the common carotid artery as an access site in interventional procedures for acute stroke therapies", Case Reports, Journal of Clinical Neuroscience 19, pp. 323-326.
Coppi et al. (2005). "PRIAMUS Proximal flow blockage cerebral protection during carotid stenting: Results from a multicenter Italian registry" J. Cardiovasc. Surg. 46:219-227.
Criado et al. (1997). "Evolving indications for and early results of carotid artery stenting" Am. J. Surg.; 174:111-114.
Criado et al. (2004). "Transcervical carotid artery angioplasty and stenting with carotid flow reversal: Surgical technique" J. Vasc. Surg. 18:257-261.

(56) References Cited

OTHER PUBLICATIONS

Criado et al. (2004). "Transcervical carotid stenting with internal carotid artery flow reversal: Feasibility and preliminary results" J. Vasc. Surg. 40:476-483.
Criado, et al. (2007). "Transcervical carotid stenting with carotid artery flow reversal: 3-year follow-up of 103 stents." J Vasc Surg 46(5): 864-9.
Criado, F.J., et al. (2000). "Access strategies for carotid artery intervention." J Invasive Cardiol, 12(1): p. 61-8.
Criado, M.D., et al. (2004) "Carotid angioplasty with internal carotid artery flow reversal is well tolerated in the awake patient" Journal of Vascular Surgery, 40(1):92-7.
Delgado Almandoz, Josser E., et al. "Comparison of clinical outcomes in patients with acute ischemic strokes treated with mechanical thrombectomy using either Solumbra or ADAPT techniques." *Journal of NeuroInterventional Surgery*, vol. 8, 2016, pp. 1123-1128.
Diederich et al. (2004) "First Clinical experiences with an endovascular clamping system for neuroprotection during carotid stenting" *Eur. J. Vasc. Endovasc. Surg.* 28:629-633.
Diethrich et al., (1996). "Percutaneous techniques for endoluminal carotid interventions" J. Endovasc. Surg. 3:182-202.
Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.
Feldtman, R. W., C. J. Buckley, et al. (2006). "How I do it: cervical access for carotid artery stenting." Am J Surg 192(6): 779-81.
Fiorella, D., M. Kelly, et al. (2008). "Endovascular Treatment of Cerebral Aneurysms." Endovascular Today Jun. 2008. pp. 53-64.
Frazee, J. G. and X. Luo (1999). "Retrograde transvenous perfusion." Crit Care Clin 15(4): 777-88, vii.
Frazee, J. G., X. Luo, et al. (1998). "Retrograde transvenous neuroperfusion: a back door treatment for stroke." Stroke 29(9): 1912-6.
Friedrich, Benjamin, et al. "Distance to Thrombus in Acute Middle Cerebral Artery Occlusion." *Stroke*, vol. 46, No. 3, 2015, pp. 692-696.
Frölich AM, et al. (2020, Epub Sep. 3, 2020). "The novel Tenzing 7 delivery catheter designed to deliver intermediate catheters to the face of embolus without crossing: clinical performance predicted in anatomically challenging model." J NeuroIntervent Surg, 5 pages. doi: 10.1136/ neurintsurg-2020-016412.
Goldstein (2007). "Acute Ischemic Stroke Treatment in 2007" *Circ* 116:1504-1514.
Goyal, M. et al. (Mar. 12, 2015, e-published Feb. 11, 2015). "Randomized Assessment of Rapid Endovascular Treatment of Ischemic Stroke." *N Engl J Med*, 372(11):1019-1030.
Gray et al. (2007). "The CAPTURE registry: Results of carotid stenting with embolic protection in the post approval setting" *Cath. Cardovasc. Interven.* 69:341-348.
Henry, et al. (1999). "Carotid Stenting With Cerebral Protection: First Clinical Experience Using the PercuSurge GuardWire System" J. Endovasc. Surg. 6:321-331.
Hoffer et al. (2003). "Percutaneous Arterial Closure Devices" J. Vasc. Interv. Radiol. 14:865-885.
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Jankowitz, Brian, et al. (2012). "Manual Aspiration Thrombectomy Adjunctive Endovascular Recanalization Technique in Acute Stroke Interventions." *Stroke*. 2012;43:1408-1411. Web. Accessed Sep. 26, 2018.
Koebbe, C. J., E. Veznedaroglu, et al. (2006). "Endovascular management of intracranial aneurysms: current experience and future advances." Neurosurgery 59(5 Suppl 3): S93-102; discussion S3-13.

Lin et al. (2005). "Protected carotid artery stenting and angioplasty via transfemoral versus transcervical approaches" Vasc. Endovasc. Surg. 39(6):499-503.
Lo et al. (2005). "Advantages and indications of transcervical carotid artery stenting with carotid flow reversal" J. Cardovasc. Surg (Torino). 46(3):229-239.
Luebke, T et al. (2007). "Meta-analysis of randomized trials comparing carotid endarterectomy and endovascular treatment" Eur. J. Vasc. Endovasc. Surg. 34:470-479.
Macdonald, S. (2006). "Is there any evidence that cerebral protection is beneficial?" *J. Cardiovasc. Surg.* 47:127-36.
Mas et al. (2006). "Endarterectomy versus stenting in patients with symptomatic severe carotid stenosis" *NEJM* 355:1660-71.
Matas et al. (2007). "Transcervical carotid stenting with flow reversal protection: Experience in high-risk patients" J. Vasc. Surg. 46:49-54.
Mokin, Maxim, et al. (2015). "Primary stentriever versus combined stentriever plus aspiration thrombectomy approaches: in vitro stroke model comparison." Journal of NeuroInterventional Surgery, vol. 7, pp. 453-457.
MomaPresn (AET). Biamino, G. MO.MA as a distal protective device, University of Leipzig, Heart Center Department of Clinical and Interventional, Angiology Leipzig, Germany, 2002. 37 pages.
Nesbit, G. M., G. Luh, et al. (2004). "New and future endovascular treatment strategies for acute ischemic stroke." J Vasc Interv Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ohki, M.D., et al. (2001)."Efficacy of a proximal occlusion catheter with reversal of flow in the prevention of embolic events during carotid artery stenting: An experimental analysis." J Vasc Surg; 33:504-9.
Ouriel, K., R. K. Greenberg, et al. (2001). "Hemodynamic conditions at the carotid bifurcation during protective common carotid occlusion." J Vasc Surg 34(4): 577-80.
Parodi (2005). "Is flow reversal the best method of protection during carotid stenting?" J Endovasc. Ther. 12:166-170.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Paullus WS, Pait TG, Rhoton Al Jr. Microsurgical exposure of the petrous portion of the carotid artery. J Neurosurg. 1977;47(5):713-726. (Year: 1977).
Pena, Carlos. "Letter to Sequent Medical Inc Re: K150894, Trade/ Device Name: VIA™ 21 Microcatheter." Department of Health & Human Services, Aug. 28, 2015, 14 pages.
Perez-Arjona, E. A., Z. DelProsto, et al. (2004). "Direct percutaneous carotid artery stenting with distal protection: technical case report." Neurol Res 26(3): 338-41.
Pipinos et al. (2005). "Transcervical approach with protective flow reversal for carotid angioplasty and stenting" J. Endovasc. Ther. 12:446-453.
Pipinos et al. (2006). "Transcervical carotid stenting with flow reversal for neuroprotection: Technique, results, advantages, and limitations" 14(5):245-255.
Powers, W.J., et al. (2015, e-published online before print Jun. 29, 2015). "2015 AHA/ASA Focused Update of the 2013 Guidelines for the Early Management of Patients With Acute Ischemic Stroke Regarding Endovascular Treatment: A Guideline for Healthcare Professionals From the American Heart Association/American Stroke Association Powers et al. on behalf of the American Heart Association Stroke Council Stroke." *Stroke*. 46:3020-3035.
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results froma prospective multicenter registry" J. Endovasc. Ther. 12:156-165.

(56) References Cited

OTHER PUBLICATIONS

Ribo et al. (2006). "Transcranial doppler monitoring of transcervical carotid stenting with flow reversal protection: a novel carotid revascularization technique" 27:2846-2849. (originally published online Sep. 28, 2006).

Ribo, M., C. Molina, et al. (2008). "Buying Time for Recanalization in Acute Stroke: Arterial Blood Infusion Beyond the Occluding Clot as a Neuroprotective Strategy." J Neuroimaging. 4 pages.

Ross, I. B. and G. D. Luzardo (2006). "Direct access to the carotid circulation by cut down for endovascular neuro-interventions." Surg Neurol 65(2): 207-11; discussion 211.

Saver, J.L. et al. (Jun. 11, 2015, e-published Apr. 17, 2015). "Stent-Retriever Thrombectomy after Intravenous t-PA vs. t-PA Alone in Stroke." *N Engl J Med*, 372(24):2285-2295.

Seidel, A. et al. (2005). "Relationship between the diameter of great saphenous vein and body mass index," J Vasc Bras, vol. 4, No. 3, p. 265-269.

Spinnaker® Elite ™ Flow Directed Catheters Go with the Flow. Indications for Use. 2 pages. Web. Aug. 27, 2019.

Spinnaker® Elite ™ Flow Directed Catheters *Go with the Flow*. Promotional Brochure. 1 page. Web. Aug. 27, 2019.

Stecker et al., (2002). "Stent placement in common carotid and internal carotid artery stenoses with use of an open transcervical approach in a patient with previous endarterectomy" J. Vasc. Interv. Radiol. 13:413-417.

Stejskal, et al. "Experience of 500 Cases of Neurophysiological Monitoring in Carotid Endarterectomy", Acta Neurochir, 2007, 149:681-689.

Theron, et al. "New Triple Coaxial Catheter System for Carotid Angioplasty with Cerebral Protection" AJNR 11:869-874, Sep./Oct. 1990 0195-6108/90/1106-0869 @ American Society of Neurology.

Vijaywargiya et al."Anatomical study of petrous and cavernous parts of internal carotid artery". Anatomy and Cell Biology 2017;50: 163-170. (Year: 2017).

Zuckerman, Bram. "Letter to Cathera Inc: Re K151638, Trade/ Device Name: Phenom™ Catheters." Department of Health & Human Services, Nov. 13, 2015, 6 pages.

\* cited by examiner

Detail A

A-A

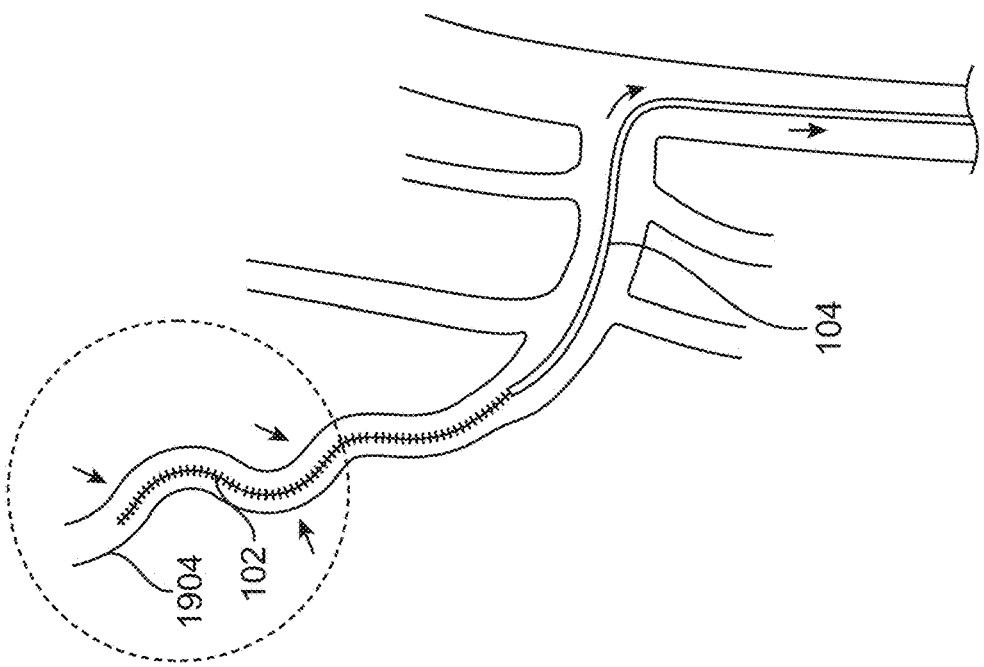
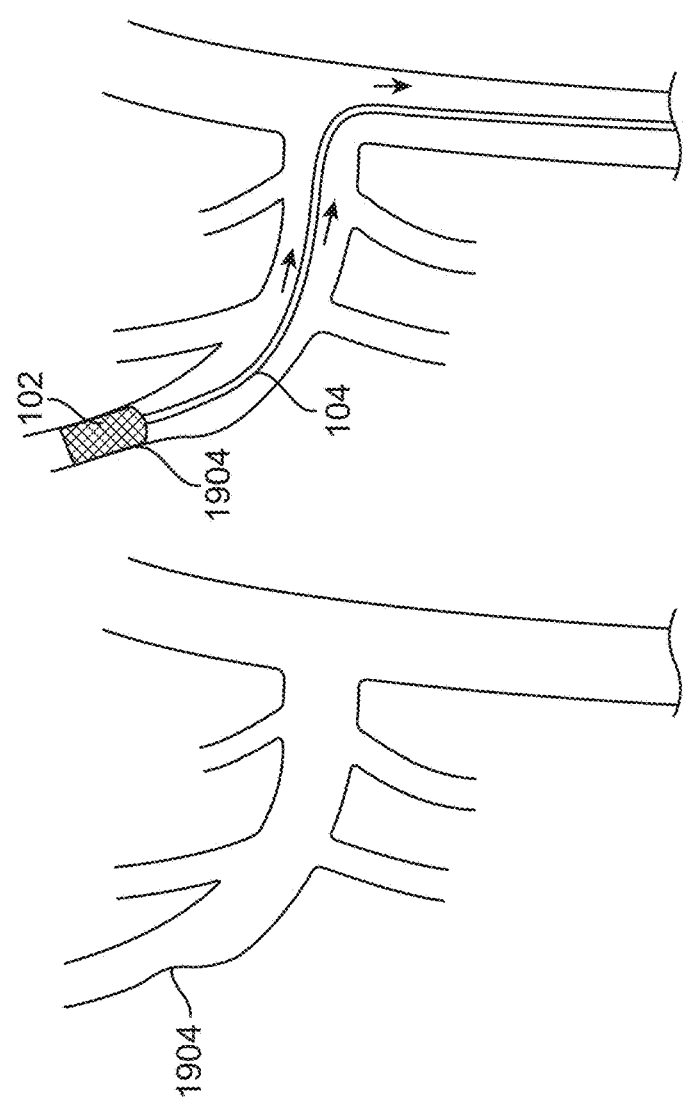

Detail B

Detail B

Detail B

Detail B

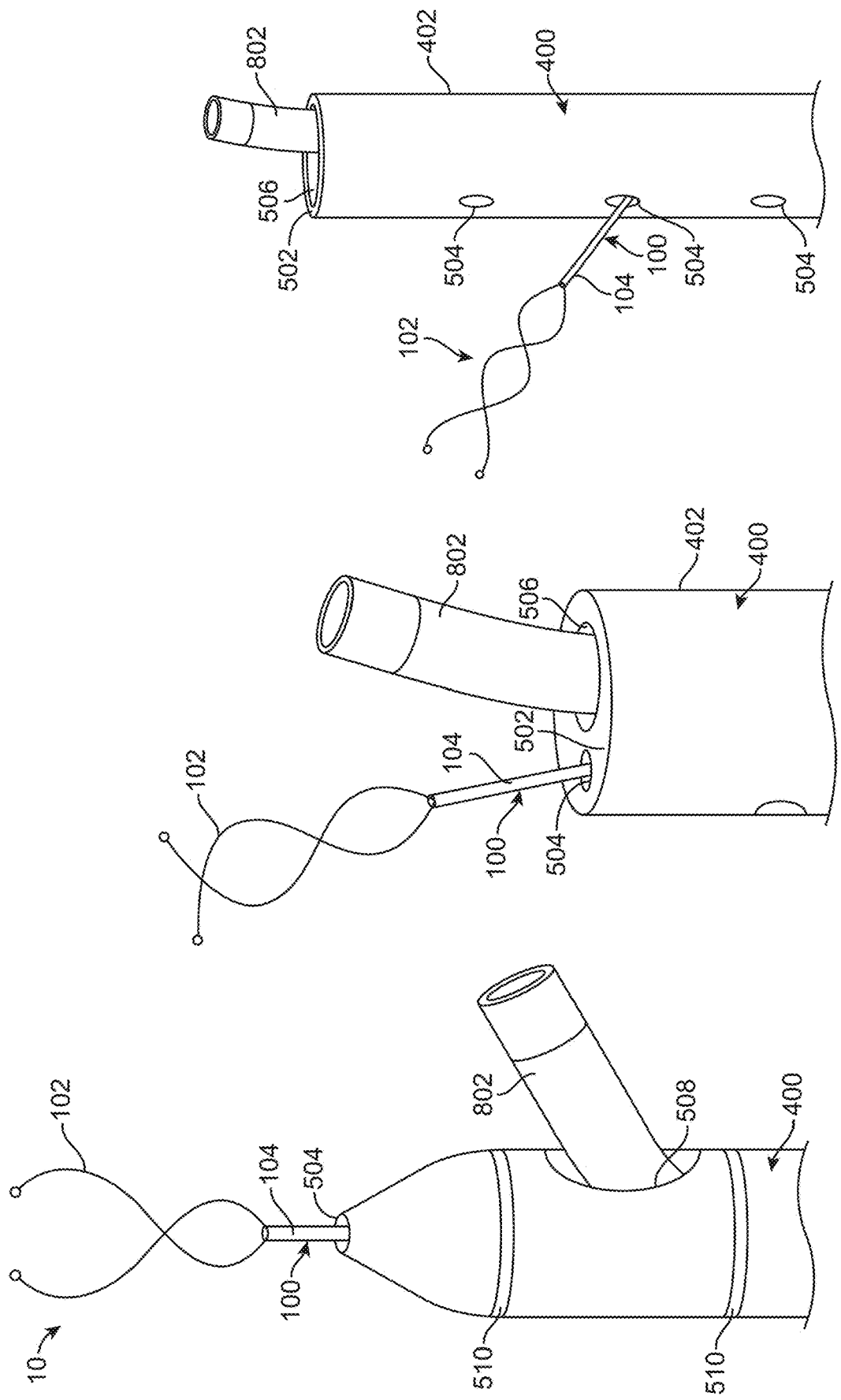

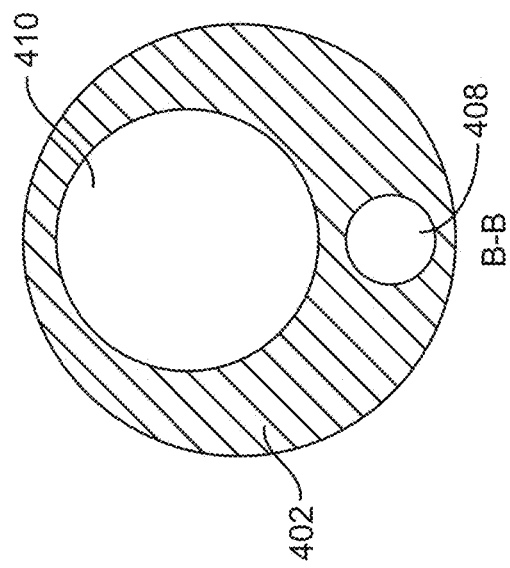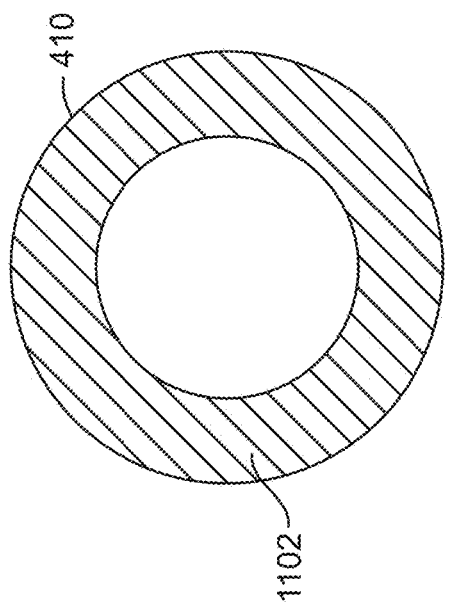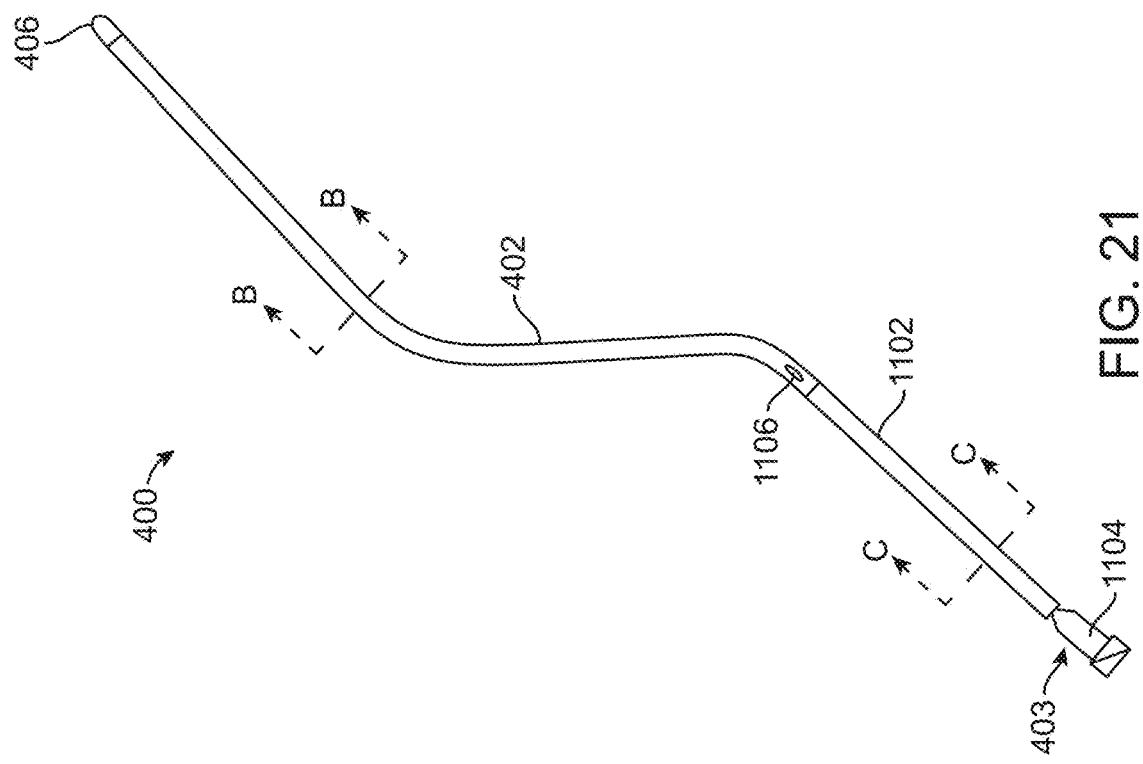

ANCHORING DELIVERY SYSTEM AND METHODS

CROSS-REFERENCE TO RELATED APPLICATIONS

This application claims priority to U.S. application Ser. No. 15/727,373, filed Oct. 6, 2017, which is a continuation of U.S. application Ser. No. 15/217,810, filed Jul. 22, 2016, entitled "Anchoring Delivery System and Methods," now U.S. Pat. No. 10,426,497, which claims the benefit of priority to U.S. Provisional Application Nos. 62/196,613, filed Jul. 24, 2015, entitled "Anchoring Guide System;" and 62/275,939, filed Jan. 7, 2016, entitled "Anchoring Delivery system;" and 62/301,857, filed Mar. 1, 2016, entitled "Anchoring Delivery System." The entire contents of each are hereby incorporated by reference herein in their entireties.

FIELD

The present technology relates generally to medical devices and methods, and more particularly, to delivery systems and methods for delivering medical devices to a target anatomy.

BACKGROUND INFORMATION

Acute ischemic stroke (AIS) usually occurs when an artery to the brain is occluded, preventing delivery of fresh oxygenated blood from the heart and lungs to the brain. These occlusions are typically caused by a thrombus or an embolus lodging in the artery and blocking the artery that feeds a territory of brain tissue. If an artery is blocked, ischemia follows, and brain cells may stop working. Furthermore, if the artery remains blocked for more than a few minutes, the brain cells may die, leading to permanent neurological deficit or death. Therefore, immediate treatment is critical.

Two principal therapies are employed for treating ischemic stroke: thrombolytic therapy and endovascular treatment. The most common treatment used to reestablish flow or re-perfuse the stroke territory is the use of intravenous (IV) thrombolytic therapy. The timeframe to enact thrombolytic therapy is within 3 hours of symptom onset for IV infusion (4.5 hours in selected patients) or within 6 hours for site-directed intra-arterial infusion. Instituting therapy at later times has no proven benefit and may expose the patient to greater risk of bleeding due to the thrombolytic effect. Endovascular treatment most commonly uses a set of tools to mechanically remove the embolus, with our without the use of thrombolytic therapy.

The gamut of endovascular treatments include mechanical embolectomy, which utilizes a retrievable structure, e.g., a coil-tipped retrievable stent (also known as a "Stentriever"), a woven wire stent, or a laser cut stent with struts that can be opened within a clot in the cerebral anatomy to engage the clot with the stent struts, create a channel in the emboli to restore a certain amount of blood flow, and to subsequently retrieve the retrievable structure by pulling it out of the anatomy, along with aspiration techniques. Other endovascular techniques to mechanically remove AIS-associated embolus include Manual Aspiration Thrombectomy (MAT) (also known as the "ADAPT" technique). MAT is an endovascular procedure where large bore catheters are inserted through the transfemoral artery and maneuvered through complex anatomy to the level of the embolus, which may be in the extracranial carotids, vertebral arteries, or intracranial arteries. Aspiration techniques may be used to remove the embolus through the large bore catheters. Another endovascular procedure is Stentriever-Mediated Manual Aspiration Thrombectomy (SMAT) (similar to the Stentriever-assisted "Solumbra" technique). SMAT, like MAT, involves accessing the embolus through the transfemoral artery. After access is achieved, however, a retrievable structure is utilized to pull the embolus back into a large bore catheter.

SUMMARY

The endovascular treatments for AIS described above face the same challenge: navigating complex anatomy leading to the cerebrovascular area. The anatomy leading to the lesion can be tortuous and diseased, which may complicate device delivery. To access the cerebral anatomy, guide catheters or guide sheaths are used to direct interventional devices such as retrievable structures, guidewires, microcatheters, and intermediate access catheters to the target site from the access site, typically the femoral artery. It can often be very challenging to establish guide or sheath position in a fashion that is stable and provides support for device delivery. To maneuver the catheters into position, coaxial, triaxial, or quadraxial systems are often used in which a guidewire/microcatheter system is first deployed and coaxial larger catheters are subsequently delivered. The clinical challenge, especially in the octogenarian population, is the elongation of the aortic arch against the fixed thoracic descending aorta, leading to a shifting of all great vessels, especially the brachiocephalic takeoff. Such shifting makes it more challenging to access the anatomy during treatment of, e.g., stroke, aneurysm, and other distally located vascular diseases. As catheters, wires, balloons, stents, or retrievable structures are advanced through the great vessels, they have a tendency to prolapse into the ascending aorta when pushed into a highly angulated and/or tortuous anatomy.

It would be advantageous, and even necessary in cases where it might be impossible to advance a catheter deep into the vasculature, to provide an anchoring delivery system to provide support during endovascular treatment of AIS (or during any other procedures employing the advancement of sheaths or catheters). For example, an anchoring delivery system may be beneficial during vascular procedures like the treatment of chronic total occlusions during coronary intervention. Essentially, any tortuous or complex target anatomy may be more easily accessed with the benefit of increased stabilization of a medical device being delivered to the target site.

It should be apparent from the foregoing that there is a need to provide systems and methods for providing an anchoring delivery system for procedures that include the advancement of catheters and sheaths into a target anatomy like, but not limited to, AIS procedures.

In a first implementation, an anchoring delivery system for use in an intracranial artery is describing. The system includes a tethering device having an elongated tether and an anchor coupled to a distal end of the tether. The anchor is deployable from a low profile configuration to a higher profile configuration to fix the distal end of the tether at an anchoring site in an anchoring vessel. The tethering device is configured to be used with a guide-sheath having a lumen configured to receive the tether.

The anchoring delivery system can further include the guide-sheath. The lumen of the guide-sheath can be a working lumen configured to deliver at least one working device into a target vessel. The lumen of the guide-sheath can be a tether lumen separate from the working lumen. The guide-sheath can be reversibly attachable to the tether at a point of fixation proximal to the anchoring site. The anchor can be deployed at the anchoring site and the guide-sheath can be attached to the tether at the point of fixation. The tether between the anchoring site and the point of fixation can be tensioned, for example, upon delivery of a working device. One or both of the tethering device and the guide-sheath can include a tether gripper at the point of fixation to attach the guide-sheath to the tether of the tethering device. The tether lumen can extend from a tether port near a distal end of the guide-sheath to the tether gripper. The working lumen can extend from a mouth at or near the distal end of the guide-sheath to a proximal end of the guide-sheath. The guide-sheath can include a deflecting surface between the working lumen and the tether lumen. The deflecting surface can be oblique to the working lumen.

The anchor in the higher profile configuration can engage an anchoring anatomy and resist a proximal pull on the tether. The tether can be an elongated member extending from a proximal end to a distal joint that attaches to the anchor. The distal joint can removably attach the tether to the anchor. The distal joint can fixedly attach the tether to the anchor. The tether can have a cross-sectional diameter that varies along a length of the tether. The anchor can automatically self-expand from the low profile configuration to a higher profile configuration when the anchor is unconstrained. The anchor need not automatically self-expand from the low profile configuration to a higher profile configuration when the anchor is unconstrained. The tether can include an anchor wire extending through a runner tube such that a withdrawal load applied to the anchor wire causes the anchor wire to move relative to the runner tube and the anchor to transition to the low profile configuration. The anchor can include several convoluted struts. The anchor can be a coiled wire. The anchor can be a curved wire.

The system can further include a pusher tube slidably positioned over the tether. The pusher tube can be gripped and advanced to push the anchor forward for delivery to an anchoring site in a target anatomy. The system can further include a delivery element positioned over the anchor to collapse or constrain the anchor in the low profile state. The anchoring device can lock to at least a portion of the guide-sheath. The tether can be a flexible wire, rod, ribbon, or hypotube. The tether and the anchor can be formed from a single and same wire. The tether and the anchor can be formed from separate wires.

The tether can include an outer running tube positioned over an inner anchor wire, the inner anchor wire being attached at a distal end to the anchor. The inner anchor wire and outer running tube can be slidably positioned relative to one another. A first locking element can be attached to a proximal end of the anchor wire and a second locking element can be attached to a proximal end of the runner tube. The first locking element and second locking element can be actuated relative to one another to transition the anchor between the low profile configuration and the higher profile configuration.

The system can further include the guide-sheath having an elongated body extending from a proximal furcation at a proximal end region to a distal tip at a distal end. The distal tip can be configured to bluntly dissect through and dilate narrowed sections of a diseased vessel. The elongated body of the guide-sheath can include a tether lumen and a working lumen. A segment of the tether lumen can bifurcate away from a segment of the working lumen. The distal tip of the guide-sheath can have a same or similar outer diameter as a section of the body of the guide-sheath leading up to the distal tip. The distal tip can have a distal face orthogonal to a longitudinal axis passing through the body of the guide-sheath. The distal tip can be an elongated tubular portion extending distal to a region of the body having a uniform outer diameter such that the elongated tubular portion has a reduced diameter compared to the uniform outer diameter of the body. The tether lumen can have a distal end. The tether lumen can form a tether entry port in a distal face of the guide-sheath and the working lumen can have a distal end forming a working port in the distal face. The tether lumen can form a tether entry port along a side of at least a distal region of the body. The guide-sheath can include a distal tip that tapers from a section of the body leading up to the distal end. An outer surface of the body of the guide-sheath can have a diameter that reduces from a larger dimension to a smaller dimension at a distal end of the tether lumen. The distal tip can taper from an outer diameter of approximately 0.114" to about 0.035". The distal tip can taper from 0.110" to 0.035" over a length of approximately 50 mm. The tip can be concentrically disposed around a tether port formed by the tether lumen. The working lumen can extend parallel to the tether lumen through the body to a mouth located proximal to a tether port near the distal end of the guide-sheath. The working port can be an elongated mouth disposed in a side surface of the body. The mouth can have a dimension in at least one direction that is larger than a diameter of the working lumen. The tether lumen can form multiple tether ports in a distal region of the guide-sheath. The working lumen can extend along a deflecting surface that directs a working device passing distally through the body of the guide-sheath outward through a mouth and a distal region of the guide-sheath. The deflecting surface can be oblique to the working lumen. The tether lumen can have a diameter large enough to receive the tether, but not large enough to receive the anchor of the tethering device. The tether lumen can have a diameter large enough to receive the anchor over at least a portion of a length of the tether lumen. The guide-sheath can include a chamber located proximal to tether entry port in the distal tip of the guide-sheath. The chamber can be sized to receive the anchor of the tethering device.

The systems described herein can further include at least one working device that fits through a working lumen of the guide sheath. The working device can be a catheter system. The catheter system can include a catheter having a flexible distal luminal portion having a proximal end, a proximal end region, a distal end, and a lumen extending between the proximal end and the distal end. The catheter can include a proximal spine extending proximally from the proximal end region. The proximal spine can be less flexible than the distal luminal portion and is configured to control movement of the catheter. The catheter system can further include a catheter advancement element. The catheter advancement element can include a flexible elongate body having a proximal end region, a distal tip, a single lumen that terminates at a distal opening in fluid communication with the vessel, and an outer diameter. The outer diameter can be sized to be received within the lumen of the luminal portion of the catheter. The single lumen can extend longitudinally through the elongate body to the distal opening and can be sized to accommodate a guidewire therethrough. The catheter advancement element can include a proximal portion extending from the proximal end region of the elongate body and extending proximally outside of the vessel of the patient. The proximal portion can have a single lumen that communicates with the single lumen of the flexible elongate body. The catheter can be sized to fit within the working lumen.

In an interrelated aspect, described herein is an anchoring delivery system. The system includes a tethering device having an elongated tether and an anchor coupled to a distal end of the tether. The anchor is deployable from a low profile configuration to a higher profile configuration to fix the distal end of the tether at an anchoring site in an anchoring vessel. The tethering device is configured to be used with a guide-sheath having a lumen configured to receive the tether. The anchoring delivery system includes the guide-sheath. The lumen of the guide-sheath is a working lumen configured to deliver a working device into a target vessel.

The guide sheath can include a working lumen and a tether lumen. The system can further include a working device that fits through the working lumen. When the anchor is deployed at the anchoring site and the guide-sheath is attached to the tether at the point of fixation, the tether between the anchoring site and the point of fixation is tensioned, for example, upon delivery of the working device. One or both of the tethering device and the guide-sheath can include a tether gripper at the point of fixation to attach the guide-sheath to the tether of the tethering device.

In an interrelated aspect, disclosed is an anchoring delivery system having a tethering device and a guide-sheath. The tethering device has an elongated tether and an anchor coupled to a distal end of the tether. The anchor is deployable from a low profile configuration to a higher profile configuration to fix the distal end of the tether at an anchoring site in an anchoring vessel. The tethering device is configured to be used with the guide-sheath having a lumen configured to receive the tether. The lumen of the guide-sheath is a working lumen configured to deliver at least one working device into a target vessel. When the anchor is deployed at the anchoring site and the guide-sheath is attached to the tether at the point of fixation. The tether is tensioned between the anchoring site and the point of fixation, for example, upon delivery of a working device.

In an interrelated aspect, described is an anchoring delivery system for use in an intracranial artery having a tethering device, a guide-sheath, and at least one working device. The tethering device has an elongated tether and an anchor coupled to a distal end of the tether. The anchor is deployable from a low profile configuration to a higher profile configuration to fix the distal end of the tether at an anchoring site in an anchoring vessel. The tethering device is configured to be used with a guide-sheath having a lumen configured to receive the tether. The guide-sheath has a working lumen configured to deliver a working device into a target vessel. When the anchor is deployed at the anchoring site and the guide-sheath is attached to the tether at the point of fixation. The tether is tensioned between the anchoring site and the point of fixation, for example, upon delivery of a working device.

In an interrelated aspect, described is a method including delivering a tethering device to an anchoring vessel. The tethering device includes an anchor coupled to a distal end of a tether. The method includes deploying the anchor of the tethering device in the anchoring vessel. The method includes advancing a guide-sheath over the tether of the tethering device to position an opening from the guide-sheath near an entrance of a target vessel.

The method can further include attaching the guide-sheath to the tether of the tethering device. The tethering device can fix and support the guide-sheath for advancing at least one working tool through the guide-sheath. The anchor can be deployed at an anchoring site in the anchoring vessel distal to the entrance of the target vessel. The guide-sheath can include a tether lumen to receive the tether. The guide-sheath can be attached to the tether by a tether gripper at a point of fixation proximal to the entrance of the target vessel.

The method can include delivering at least one working device through a working lumen of the guide-sheath into the entrance of the target vessel. Delivering the working device can tension the tether between the anchoring site and the point of fixation. The tether lumen and the working lumen can be the same lumen. The method can include advancing a second tethering device through a working lumen of the guide-sheath into the target vessel. The second tethering device can include a second anchor coupled to a second distal end of a second tether. The method can include deploying the second anchor of the second tethering device in the target vessel. The method can include removing the guide-sheath from the tether of the tethering device. The method can include advancing the guide-sheath over the second tether of the second tethering device to position the opening from the guide-sheath near a second entrance of a second target vessel. The method can include advancing the second tethering device through the deployed anchor of the first tethering device. The method can include advancing the guide-sheath over the tether to capture the anchor and removing the guide-sheath and the captured anchor from the target anatomy.

In an interrelated aspect, disclosed is a method including advancing a catheter over a guidewire into an anchoring vessel and exchanging the guidewire for a tethering device. The tethering device includes an anchor coupled to a distal end of a tether. The method includes deploying the anchor of the tethering device in the anchoring vessel; advancing a guide-sheath over the catheter to position a mouth of the guide-sheath near an entrance of a target vessel; removing the catheter from the guide-sheath; and attaching the guide-sheath to the tether of the tethering device.

The anchor can be deployed at an anchoring site in the anchoring vessel distal to the entrance of the target vessel. The guide-sheath can include a tether lumen to receive the catheter and the tether. The guide-sheath can be attached to the tether by a tether gripper at a point of fixation proximal to the entrance of the target vessel. The method can further include advancing a working device through a working lumen of the guide-sheath into the entrance of the target vessel. Tensioning the tether between the anchoring site and the point of fixation. The tether lumen and the working lumen can be the same lumen.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIGS. 5M-5O illustrate schematic views of an anchoring vessel and an anchor;

FIG. 18 illustrates a distal end of an anchoring delivery system having a tethering device in a tether lumen of a tetherable guide-sheath and a working device in a working lumen of the tetherable guide-sheath, in accordance with an implementation;

FIG. 19 illustrates a distal end of an anchoring delivery system having a tethering device in a tether lumen of a tetherable guide-sheath and a working device in a working lumen of the tetherable guide-sheath, in accordance with an implementation;

FIG. 20 illustrates a distal end of an anchoring delivery system having a tethering device and a working device in a same lumen of a tetherable guide-sheath, in accordance with an implementation;

FIG. 21 illustrates a perspective view of a tetherable guide-sheath, in accordance with an implementation;

FIG. 22 illustrates a sectional view, taken about line B-B of FIG. 21, of a tetherable guide-sheath, in accordance with an implementation;

FIG. 23 illustrates a sectional view, taken about line C-C of FIG. 21, of a tetherable guide-sheath, in accordance with an implementation;

It should be appreciated that the drawings are for example only and are not meant to be to scale. It is to be understood that devices described herein may include features not necessarily depicted in each figure.

DETAILED DESCRIPTION

Described herein are anchoring delivery systems that include a tethering device and a tetherable guide-sheath to support and guide devices to a target anatomy, in particular tortuous anatomy of the cerebral vasculature. The tethering device may include an anchor to be placed in an anchoring anatomy, e.g., a carotid, subclavian or vertebral arterial circulation, and the tetherable guide-sheath may be tethered to a tether of the tethering device, the tether being attached to the anchor. Thus, the tether may constrain the tetherable guide-sheath, and a subsequent working device may be delivered through a lumen of the tetherable guide-sheath without concomitant prolapse of the tetherable guide-sheath or the working device when the working device, e.g., an advanced catheter, wire, balloon, and/or retrievable structure, is advanced to a target anatomy, e.g., a distal neurovasculature. The stability provided by the constrained tetherable guide-sheath will allow some AIS approaches to be performed successfully, accurately and more safely when they otherwise could not be completed due to tortuosity or angulation at the great vessels or at the intracranial vasculature. Additionally, the anchoring delivery system can be used empirically or as a reaction to encountering challenging anatomy when attempting to place a guide catheter in the internal carotid artery (ICA) or common carotid artery (CCA) during AIS procedures. The anchoring delivery system has single-operator ease of use.

Figure 1A:
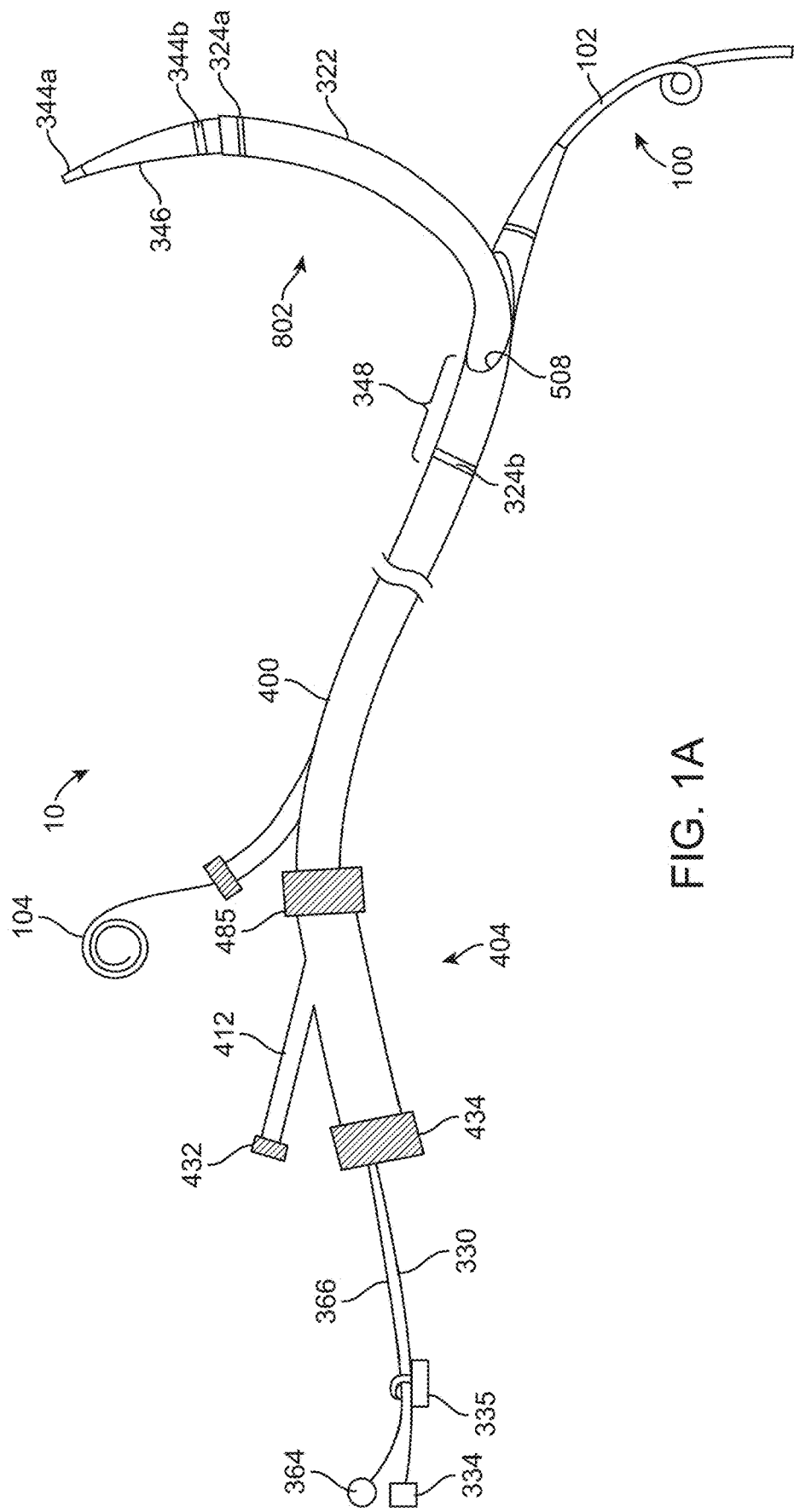
FIG. 1A illustrates a perspective view of an anchoring delivery system having a tethering device, a tetherable guide-sheath, and an implementation of a working device extending therethrough.
Figure 1B:
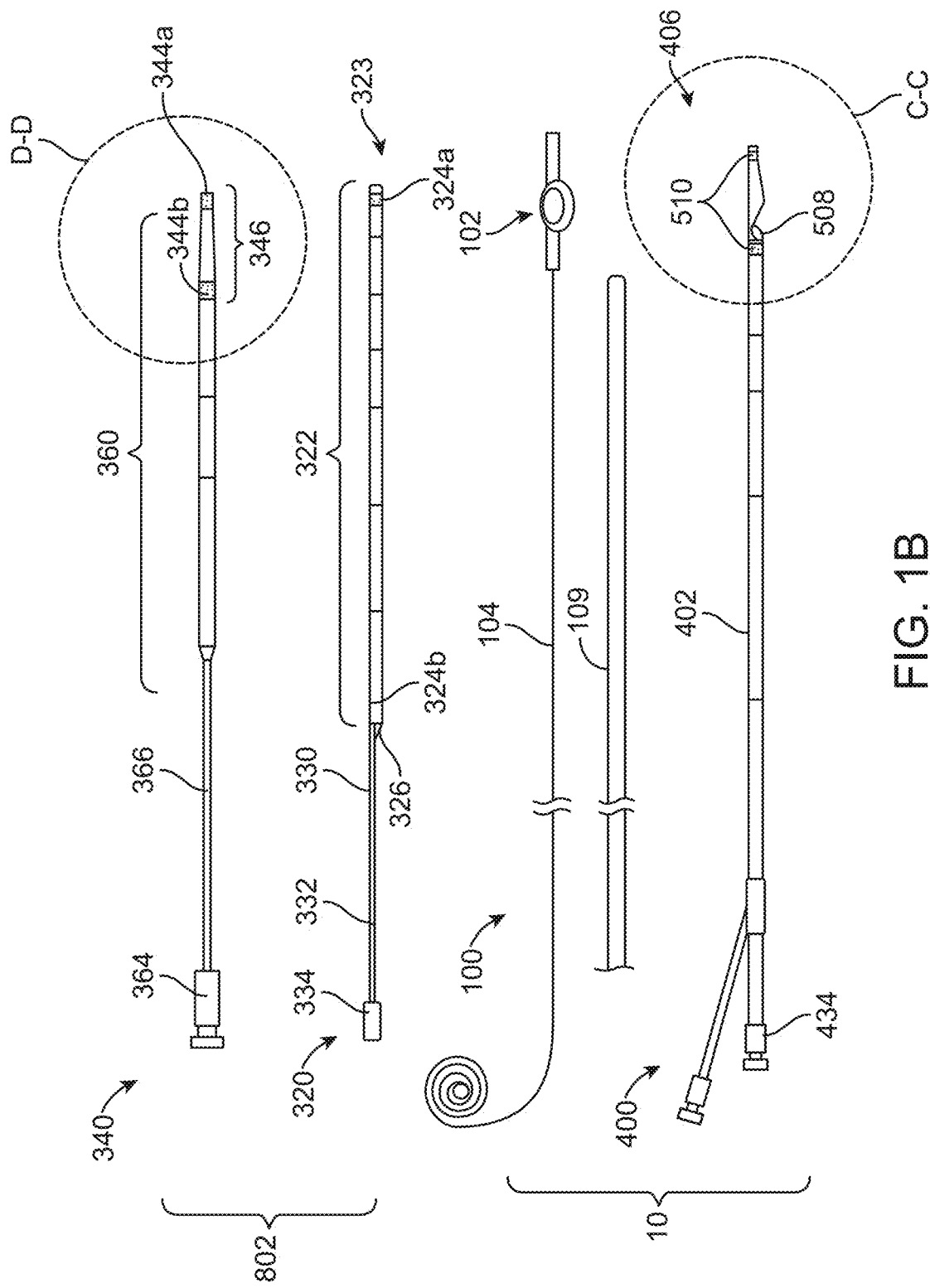
FIG. 1B illustrates an exploded view of the anchoring delivery system and the working device of FIG. 1A.
Figure 1C:
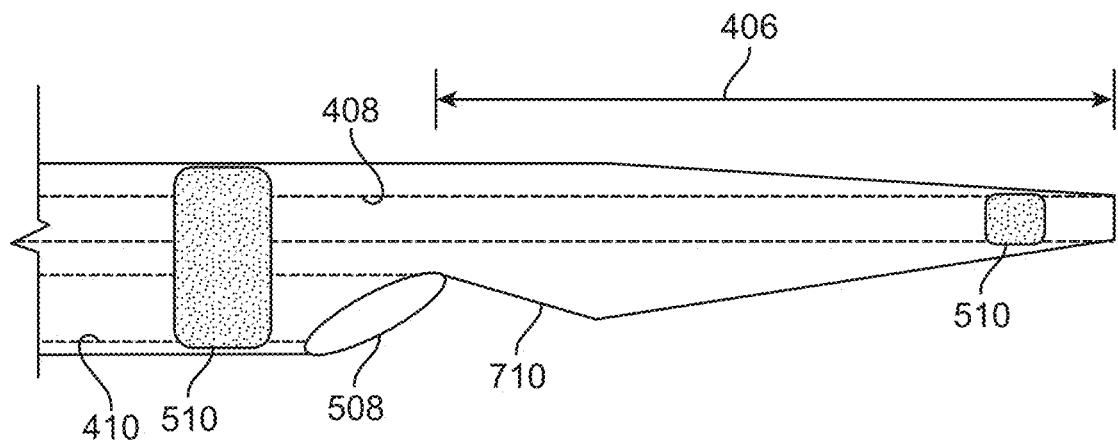
FIG. 1C illustrates a detail view of a distal end of the tetherable guide-sheath of FIG. 1A taken along circle C-C.

Referring now to the drawings, FIG. 1A illustrates a perspective view of an anchoring delivery system 10 supporting the advancement of an implementation of a working device 802 therethrough. FIG. 1B illustrates an exploded view of the anchoring delivery system 10 and an exploded view of the working device 802 of FIG. 1A. The anchoring delivery system 10 includes an implementation of a tethering device 100 and a tetherable guide-sheath 400 configured to receive and support the advancement of the working device 802 therethrough, each of which will be described in more detail herein.

It should be appreciated that the configuration of the tethering device 100 can vary as described elsewhere herein. The tethering device 100 does not necessarily need to be used with the tetherable guide-sheath 400 as described. It should be appreciated that the tethering device 100 can be used with any of a variety of comparable commercially available guide-sheath to form an anchoring delivery system 10. For example, the tethering devices described herein can be used with guiding sheaths having an ID between 0.087"-0.089" such as the Cook SHUTTLE 6F (Cook Medical, Inc., Bloomington, IN), Terumo DESTINATION 6F (Terumo Europe NV), Cordis VISTA BRITE TIP (Cordis Corp., Hialeah, FL), and Penumbra NEURON MAX 088 (Penumbra, Inc., Alameda, CA), or comparable commercially available guiding sheath. Further, it should be appreciated that the working devices for advancing through the guiding sheath can vary and need not be limited to the implementation shown in the figures. The guiding sheath, whether the tetherable guide sheath 400 or another commercially-available guiding sheath, can be used to deliver any of a variety of working devices configured to provide thrombotic treatments such as large-bore catheters, aspiration thrombectomy, advanced catheters, wires, balloons, retrievable structures such as coil-tipped retrievable stents "Stentriever". The working devices can include various embolectomy devices known in the art as well as those described herein.

Tethering Devices

Figure 2A:
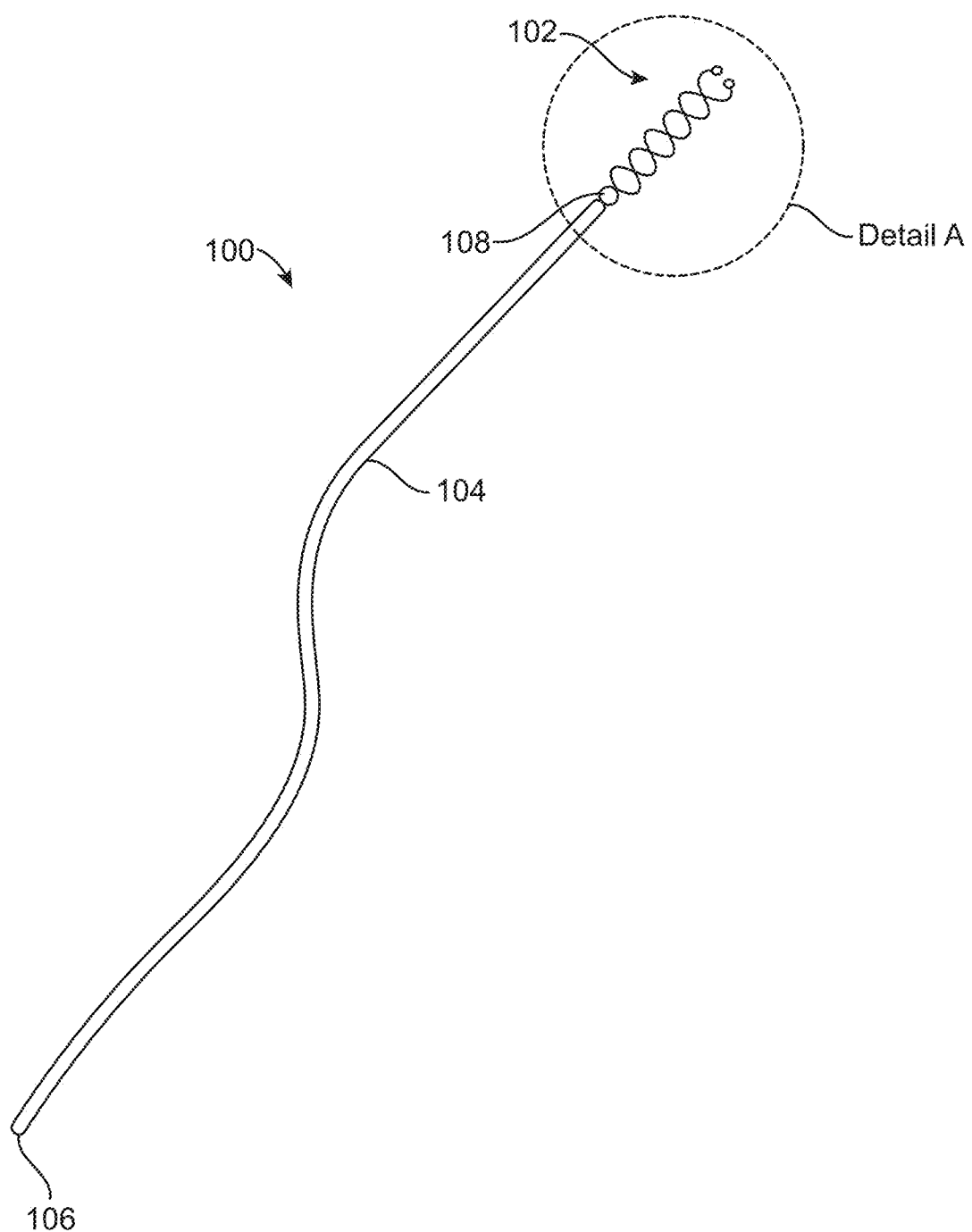
FIG. 2A illustrates a perspective view of a tethering device, in accordance with an implementation.

The anchoring delivery system 10 can include a tethering device 100. FIG. 2A shows a perspective view of a tethering device 100 in accordance with an implementation. The tethering device 100 can include a distal anchor 102 coupled to a proximal tether 104, for example, by a distal and/or a proximal joint 108. The tether 104 can be an elongate element extending proximally from the distal anchor 102 such as a filamentous element having an outer diameter that is small and flexible enough to curve through the tortuous vessels of the cerebral vasculature without kinking. Keeping the tether 104 to a small diameter also allows the diameter of a tethered guide-sheath sized to receive the tether 104 to be as small as possible minimizing the access arteriotomy size. In at least some implementations, the tether 104 has a relatively low "pushability" such that it is generally not useful for advancing the anchor 102 through the vasculature without the assistance of a delivery tool. However, upon application of a proximal pulling force on the tether 104, for example when the tethering device 100 is anchored in a vessel by the anchor 102, the tether 104 is strong enough to maintain the tethering device 100 in a tensioned or taut state, as will be described in more detail below. The anchor 102 can have any of a variety of configurations as will be described in more detail below. Generally, the anchor 102 has a first, low-profile (unexpanded or constrained) configuration such that the anchor 102 may be delivered to the anchoring anatomy. The anchor 102 also has a second, higher-profile (expanded or unconstrained) configuration after delivery to and deployment within the target location such that the anchor 102 anchors (itself and the tethering device 100) within the target anatomy. It should be appreciated that use of the terms "expanded" and "unexpanded" as used herein refer generally to an overall shape or profile of the anchor 102 that is, in the case of an "expanded" anchor, greater than the overall shape or profile of the anchor 102 during delivery to the target anatomy or, in the case of an "unexpanded" anchor, less than the overall shape or profile of the anchor 102 during anchoring in the target anatomy, respectively. "Expanded" and "unexpanded" as used herein are not intended to require any particular type of change in profile of the anchor 102.

The anchor 102 can be deployable from the unexpanded state to the expanded state to fix a distal end of the tether 104 at an anchoring site in an anchoring vessel of a target anatomy, as described below. Thus, the anchor 102 may have enough radial strength in the expanded configuration to grip the anchoring anatomy and resist a proximal pull on the tether 104. The anchor 102 is generally configured to anchor within the anchoring vessel, as opposed to dilating a stenosis or scaffold the vessel such as with stents. However, it should be appreciated that the anchors 102 described herein can anchor in a manner that also dilates, scaffolds, embeds, and/or distorts the anchoring vessel within which the anchor 102 is anchored. The anchors 102 described herein can also facilitate anchoring of the tethering device 100 by other features that do not necessarily involve a change in shape, such as by externalizing a portion of the wire and/or incorporating superficial magnetic features in order to clamp outside the body, as will be described in more detail below.

Still with respect to FIG. 2A, the tether 104 of the tethering device 100 can be an elongated member extending from a proximal end 106 of the tethering device 100 to a distal joint 108 and having an outer surface extending along a longitudinal axis. The tether 104 can be stiffer and/or less prone to bending than the wires typically attached to retrievable structures, such as a Merci retriever or a Stentriever device, such that upon anchoring of the distal anchor 102 into a vessel the tether 104 can serve a supportive function to support a tetherable guide-sheath 400 against buckling or prolapse, which will be described in more detail below. The tether 104 can also be formed by a combination of elements providing the proper supportive function. The tether 104 can have various dimensions and/or material configurations. The dimensions and/or material configurations of the tether 104 can be selected to achieve a desired tensile strength, flexibility, and trackability. In some implementations, a diameter of the tether 104 ranges from 0.005 inches to 0.025 inches, e.g., 0.008 inches, or 0.009 inches, or 0.010 inches, or 0.035 inches, depending on the degree of support that the tether 104 provides. The tether 104 can be a solid wire rod, a ribbon, or a hypotube of stainless steel or NiTi. In some implementations, the tether 104 can be a stainless steel rod, ribbon or hypotube. In other implementations, the tether 104 can be Drawn Filled Tubing (DFT) with a radiopaque core, such as an outer sheath of a composite to provide strength and a core material to provide superelasticity, conductivity, radiopacity, resiliency, etc. In some implementations, the tether 104 can be DFT of Nickel titanium with a radiopaque core such as platinum or tantalum.

The tether 104 can have several different cross-sectional areas at locations along its longitudinal axis between the proximal end 106 of the tether 104 to where it couples with the anchor 102. For example, a proximal section near the proximal end 106 of the tether 104 can have a first cross-sectional diameter. The first cross-sectional diameter may be sized, for example, to favor support over trackability. Similarly, the tether 104 can include a distal section distal to the proximal section that has a different cross-sectional diameter compared to the first cross-sectional diameter. For example, the distal section can include a second cross-sectional diameter that is smaller than the first cross-sectional diameter of the proximal section. As such, the distal section of the tether 104 can be configured to favor trackability over support.

The anchor 102 of the tethering device 100 can be sized to engage a range of vessel diameters, i.e., covering the lumen diameters to provide solid apposition against target anchor 102 sites such as the proximal CCA, proximal and mid-subclavian, and the external carotid artery (ECA). For example, the anchor 102 of the tethering device 100 can engage arteries of about 1 mm inside diameter to arteries with 40 mm inside diameters. For AIS procedures, it may be more common to anchor in arteries ranging from 2 mm inside diameter to 10 mm inside diameter. In other implementations, the anchor 102 of the tethering device 100 may be sized to be able to engage smaller arteries such as side branches. In comparison to conventional retrievable structures used in SMAT procedures, which are typically rather flimsy and unable to anchor against an artery wall, the anchors described herein are specifically designed to anchor within a target anatomy. For example, the anchors described herein can be sized to anchor within internal carotid artery (ICA), middle cerebral arteries at the M1 segment, Vertebral, Basilar vessels, or vessels generally larger than 3 mm. The anchors described herein can also be sized to anchor within vessels in the insular segment arteries at the M2 segment, P1 or vessels which are generally within the 2 mm-3 mm range. The anchors described herein can also be sized to anchor within vessels that are at the M3 segment or within vessels that are generally less than 2 mm.

The anchor 102 of the tethering device 100 can have any of a variety of configurations as described herein. For example, the anchor 102 can include an expandable structure configured to self-expand upon release of a constraint and/or expand when a force is applied. In some implementations (e.g., FIGS. 2B and 2D), the anchor 102 of the tethering device 100 can include a self-expanding material, such as nitinol, to expand to an understood diameter in the air and exert a controllable and consistent radial outward pressure when expanded and constrained within a vessel. In an implementation, the anchor 102 can include a closed-cell stent like structure, e.g., made of self-expanding material like nitinol that may be set to a desired shape, for example, by a heat set process. In other implementations, the anchor 102 of the tethering device 100 can include a non-self-expanding material (e.g., FIG. 2C) such that the anchor 102 expands when a force is applied.

The anchor 102 can be collapsed to a first configuration for delivery into the target vessel, expanded to a second configuration upon deployment in the target vessel and subsequently collapsed to or towards the first configuration for removal from the vessel. The anchor 102 of the tethering device 100 can collapse or be constrained to a small dimension such that it can be delivered through the lumen of a delivery catheter, e.g., a microcatheter or finder catheter as described below. In some implementations, the anchor 102 of the tethering device 100 can be actively collapsed using one or more additional features or components. The anchor 102 can additionally or optionally be malleable such that it can be pulled into the small dimension. The anchor 102 of the tethering device 100 can be deployed by unsleeving the anchor 102, e.g., advancing the anchor 102 from the lumen of the delivery catheter, retracting the delivery catheter to expose the anchor 102 from the lumen, or a combination or the two.

Figure 2B:
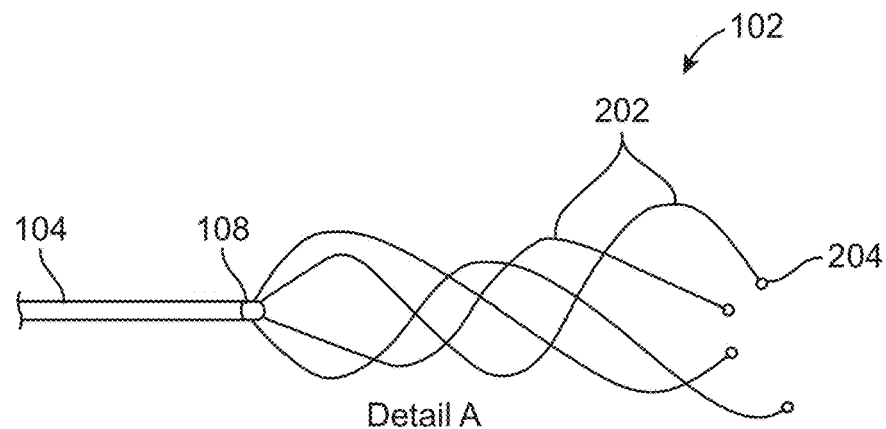
FIGS. 2B-2D illustrate detail views, taken from Detail A of FIG. 2A, of an anchor coupled to a tether of a tethering device.

FIG. 2B is a detail view taken from Detail A of FIG. 2A of an anchor 102 coupled to a tether 104 of a tethering device 100. As described above, the tether 104 can terminate at a distal joint 108 between the proximal end 106 and the anchor 102. The anchor 102 can be physically connected or attached to the tether 104 by one or more joints. The joint 108 may be a permanent attachment between the tether 104 and the anchor 102, such as a welding joint or other attachment joint. Alternatively, the anchor 102 can be detachably connected to the tether 104 at the joint 108. For example, the tether 104 can terminate at the distal joint 108, and the distal joint 108 may be severable at the discretion of an operator to decouple the anchor 102 from the tether 104. The decoupling between the anchor 102 and the tether 104 can be a permanent or reversible decoupling. For example, the distal joint 108 between the tether 104 and the anchor 102 may be an adhesive joint having a predetermined breaking stress, such that when sufficient pulling force is applied to the tether 104, the distal joint 108 breaks to detach the tether 104 from the anchor 102. In another implementation, the distal joint 108 can be a threaded joint. For example, the tether 104 can include an external thread at the distal joint 108 that engages with an internal thread of a tube section located at a proximal end or a distal joint 108 of the anchor 102. Thus, the operator can rotate the tether 104 around the longitudinal axis of the tethering device 100 when the anchor 102 is anchored in the anchoring anatomy to unscrew the tether 104 from the anchor 102. It should be appreciated that other mechanisms of detachment between the tether 104 and the anchor 102 are considered herein. Detachment of the anchor 102 from the tether 104 can be useful where re-sheathing of the anchor 102 by a delivery catheter or a tetherable guide-sheath, which will be described in more detail below, is not possible or may cause rupture or damage to a vessel. Thus, the anchor 102 can be left behind in the vessel and the tether 104 may be safely removed from a patient.

Figure 5A:
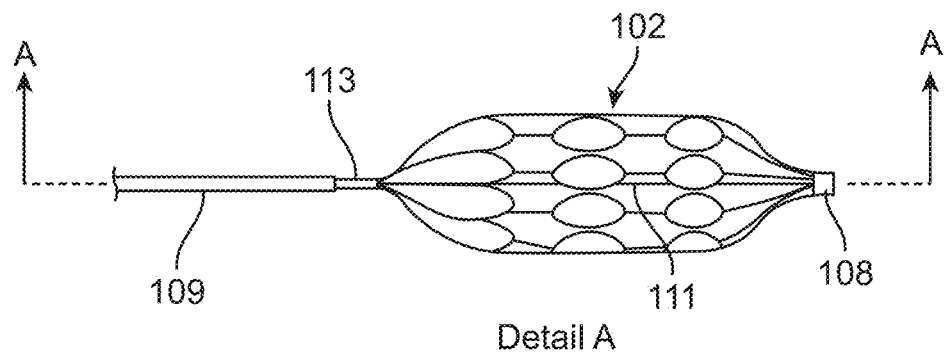
FIG. 5A illustrates a detail view, taken from Detail A of FIG. 4, of a distal portion of a tethering device.

As shown in FIG. 2B, the anchor 102 can include several convoluted struts 202 extending from the distal joint 108 to respective distal strut ends 204. The convoluted struts 202 can follow any path from the distal joint 108 to the distal strut ends 204. In an implementation, the convoluted struts 202 can extend in a generally longitudinal direction when the anchor 102 is in the unexpanded or constrained state, and the convoluted struts 202 can expand to extend in a generally spiral direction when the anchor 102 is in the expanded state. Thus, a transverse dimension of the convoluted struts 202 can be less in the unexpanded state than in the expanded state, and a longitudinal length of the convoluted struts 202 can be greater in the unexpanded, constrained state than in the expanded state. As shown in FIG. 2B, when the convoluted struts 202 expand together they can form a weaved structure that can engage an inner surface of the anchoring vessel. The respective proximal ends of the convoluted struts 202 can be attached to the distal joint 108 and the distal strut ends 204 can be freely suspended. More particularly, the distal strut ends 204 may not be attached to each other such that the struts 202 are individually cantilevered from the distal joint 108. However, the distal strut ends 204 can be coupled to each other, e.g., by being commonly connected to a second joint of the anchor 102, for example as shown in FIG. 5A, which will be described in more detail below. The struts 202 can also incorporate one or more barbs or cleats to improve their anchoring strength within the vessel and prevent slippage of the anchor 102 in a proximal direction, for example, upon a pulling force being applied during use.

Figure 2C:
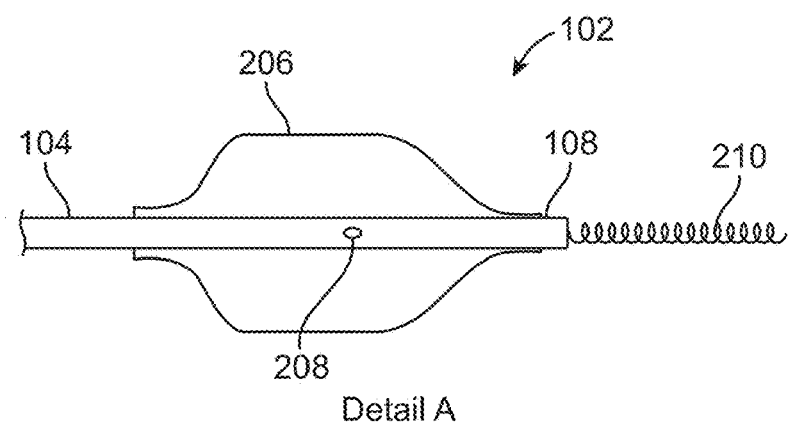

FIG. 2C is a detail view taken from Detail A of FIG. 2A of an additional implementation of an anchor 102 coupled to a tether 104 of a tethering device 100. The anchor 102 can include a balloon 206 having an outer surface containing an internal volume. The tether 104 can include a tubular structure, such as a hypotube, extending from the proximal end 106 to a distal joint 108. An inner lumen of the tether 104 can be in fluid communication with the internal volume of the balloon 206 through an inflation port 208 formed in a sidewall of the tether 104 hypotube. To facilitate tracking of the anchor 102, the distal joint 108 of the tether 104 can be connected to a soft, distal tip 210. The distal tip 210 can be a spiral wire coil or other configuration tip that is flexible and atraumatic to the anchoring anatomy.

Figure 2D:
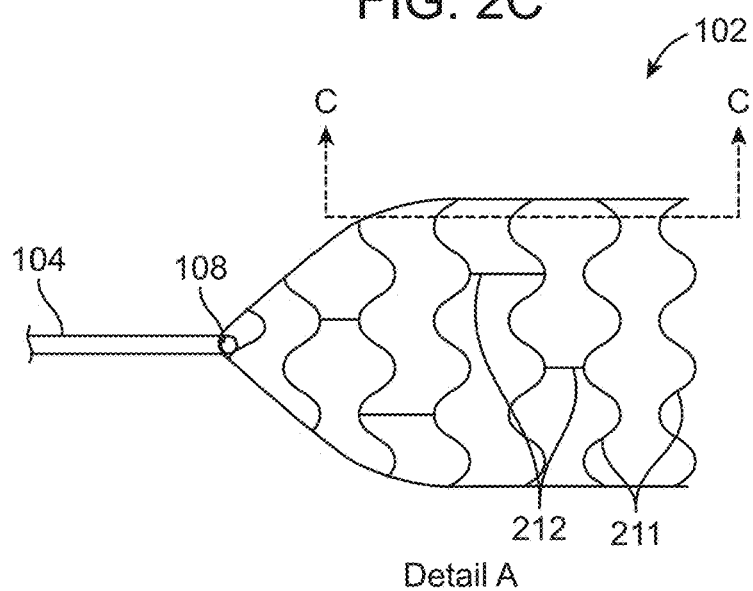

FIG. 2D is a detail view taken from Detail A of FIG. 2A of an additional implementation of an anchor 102 coupled to a tether 104 of a tethering device 100. The anchor 102 can include a self-expandable structure capable of self-expanding from a first, collapsed state to a second, expanded state. The tether 104 can connect to the anchor 102 at a distal joint 108 and an outer diameter of the anchor 102 can enlarge from the distal joint 108 towards the distal-most terminus of the anchor 102. Thus, when the self-expandable structure is expanded, an outer dimension of the structure from the distal joint 108 towards a distal-most terminus of the anchor can gradually widen to a maximum dimension. The self-expandable structure of the anchor 102 can include a sequence of anchor rings 211 disposed longitudinally relative to each other. The anchor rings 211 can be connected by one or more ring connectors 212, such that the anchor rings 211 transmit longitudinal force between each other. The self-expandable structure can have an open cell or a closed cell configuration, as is known in the art, depending on the number of ring connectors 212 used between adjacent anchor rings 211.

Figure 3:
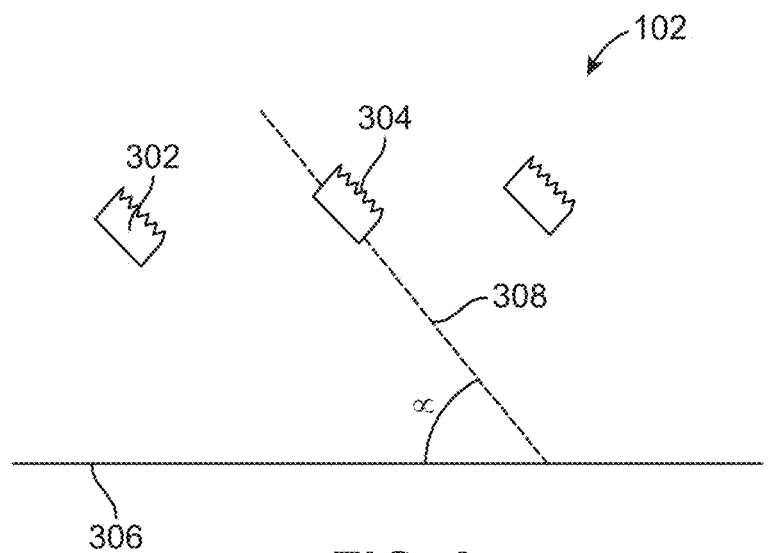
FIG. 3 illustrates a detail view of an anchor of a tethering device.

As mentioned above, the anchor 102 may have enough radial strength in the expanded configuration to grip the anchoring anatomy and resist a proximal pull on the tether 104. FIG. 3 is a detail view of an implementation of an anchor 102 of a tethering device 100 that includes one or more ribs or struts 302 making up the expandable anchor 102. The configuration of the struts 302, for example, their orientation and/or how they provide a shape to the anchor 102 as a whole, as well as by incorporating features such as barbs, hooks, cleats, surface textures, etc. can be designed such that they aid to resist longitudinal movement of the anchor 102 once engaged with the anchoring anatomy. For example, the struts 302 can be configured to resist being pulled proximally when the strut 302 is engaged with tissue. In some implementations, the strut 302 can be specifically designed to resist proximal movement within the anchoring anatomy, but may still be pushed in a distal direction through the anchoring anatomy. Thus, the anchor 102 can provide directionally biased resistance to movement within the anchoring anatomy. As shown in FIG. 3, the struts 302 can include respective strut surfaces 304, which may face generally outward relative to a longitudinal axis 306 passing through the tether 104. The struts 302 can be oriented, e.g., by design or shape setting, such that a strut plane 308 passing through the strut 302 parallel to the strut surface 304 is directed at an angle α to the longitudinal axis 306. This may be referred to as "fish scaling". More particularly, the struts 302 or the cells of the anchor 102 can bend outward during deployment such that a longitudinal plane passing through the struts 302 becomes angled relative to the longitudinal direction. For example, the angle can be proximally directed such that the strut 302 will tend to dig into a tissue at the anchoring anatomy when the anchor 102 is pulled proximally. Thus, the "fish-scaled" struts 302 can resist a proximal pull applied to the tether 104. By contrast, the angle of the strut plane 308 can allow the struts 302 to be pushed distally without the struts 302 digging into the tissue. Thus, the anchor 102 can be configured to grip the anchoring anatomy in one direction (e.g. proximally) but not in another direction (e.g. distally). "Fish-scaling" in stent design is often deemed to be undesirable for certain indications. However, "fish-scaling" of the anchor 102 in this context can be beneficial.

In addition to shaping the anchor 102 as a whole in a manner that facilitates gripping of the anchoring anatomy by the struts 302 can be individually modified to facilitate such gripping. For example, the strut surface 304 can be ribbed or roughened, e.g., by bead blasting or chemical etching, to increase friction between the tissue at the anchoring anatomy and the anchor 102. In an implementation, rather than roughening the strut surface 304 by a secondary manufacturing process, the strut surface 304 can be manufactured by a process that does not include a polishing process that is otherwise applied to the remainder of the anchor 102. For example, the anchor 102 may be electropolished during manufacturing, but strut surface 304 may be masked during the electropolishing process to avoid smoothing the strut surface 304. In another implementation, surface treatments such as applying an adhesive to the outer surface of the struts 302 (or any other structural feature of the anchor 102) can be used to permanently or temporarily bond the anchor 102 with the tissue at the anchoring anatomy. The adhesive can be activated upon contact with the tissue such that it does not cause the anchor 102 to stick to an inner surface of the tetherable guide-sheath or another catheter, e.g., a finder catheter, that the tethering device 100 is delivered through.

As mentioned above, the anchor 102 of the tethering device 100 can also be designed to enhance anchoring by providing traction due to incorporation of one or more features that protrude from the anchor 102 to anchor to the surrounding anatomy. For example, the anchor 102 can include features having a predetermined shape and size, such as one or more barbs or hooks that protrude from the sides of the anchor 102 to imbed into surrounding vascular tissue and grip the vessel when a proximal pull force is exerted on the tether 104. These gripping features of the anchor 102, however, can be configured to collapse such that the anchor 102 can be removed from the vessel. In some implementations, the features can be configured to yield and/or collapsed when a distal tip of tetherable guide-sheath 400 is advanced over them, as will be described in more detail below. For example, the struts 202 shown in FIG. 2B can incorporate one or more cleats or barbs on their distal ends to improve their grip within the anatomy. The cleats can protrude outward toward the vessel wall such that upon expansion or release of the struts 202 from their constrained configuration the pointed ends of the cleats engage with the vessel wall. The cleats can be configured to undergo flexure upon re-sheathing such that they can be removed from the anatomy. For example, the cleats in the unconstrained configuration can bend outward such that their pointed ends extend towards the vessel wall and/or bend back towards the proximal direction to improve engagement with the vessel wall, for example, upon proximal pull force on the tethering device. Their pointed ends can be urged away from the vessel wall during re-sheathing, for example, such that they flex back in the distal direction upon distal advancement of a sheath or tubular structure to once again constrain the struts 202 in a low profile configuration.

It should be appreciated that reference to one implementation of an anchor as having a particular feature, such as a surface treatment, anchoring feature, cleat, barb, etc., may be incorporated into any of the various anchors described herein.

Figure 4:
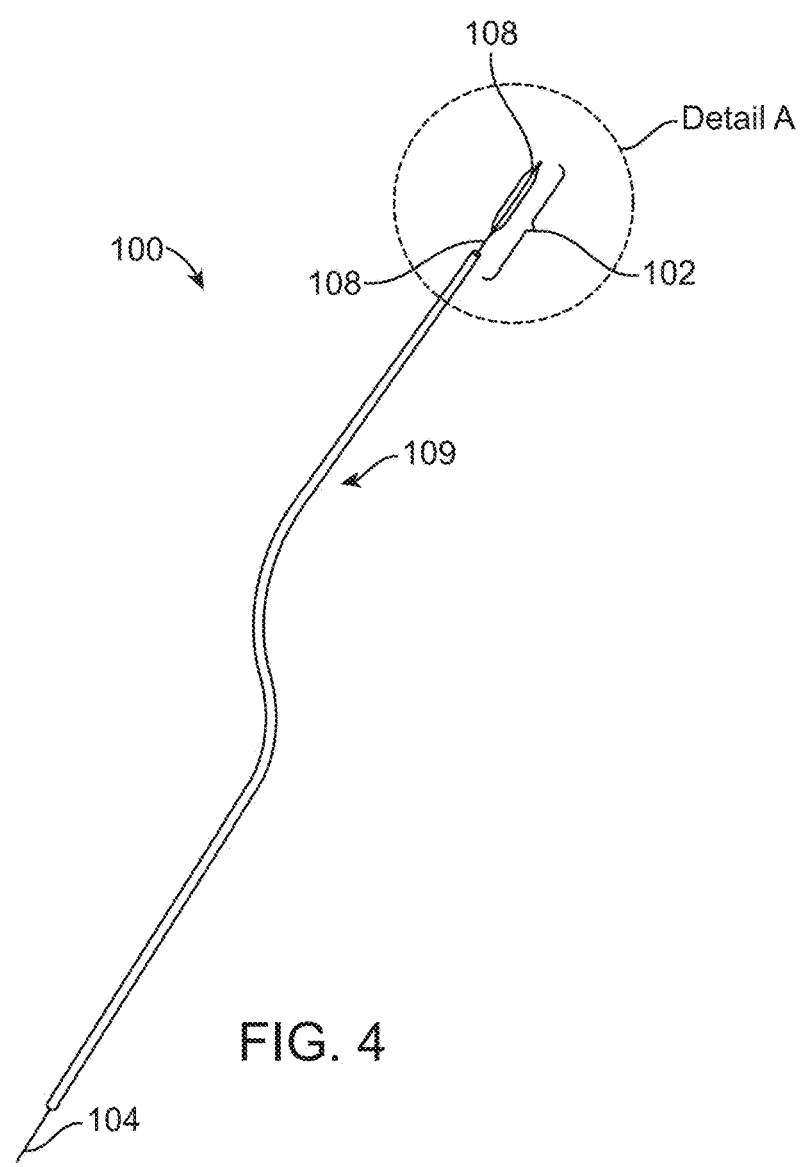
FIG. 4 illustrates a perspective view of a tethering device, in accordance with an interrelated implementation.

FIG. 4 shows a perspective view of another tethering device in accordance with an implementation having an anchor 102 physically connected to a tether 104 and further including a pusher tube 109. The tether 104 can be attached to the anchor 102 at one or more joints 108, such as a first joint 108 distal to the anchor 102 and/or a second joint 108 proximal to the anchor 102. The pusher tube 109 can slide distally and proximally relative to the tether 104, and may be removed prior to delivery of a tetherable guide-sheath 400 over the tether 104. The tether 104 and/or pusher tube 109 can be gripped and advanced to push the anchor 102 forward for delivery to an anchoring site in a target anatomy. Similarly, the pusher tube 109 can be retracted over the tether 104 to remove the pusher tube 109 from the target anatomy, while keeping the anchor 102 and the tether 104 in place to receive a tetherable guide-sheath, as will be described in more detail below. In some implementations, the anchor 102 is collapsed or constrained inside the pusher tube 109 and the pusher tube 109 is used to provide some heft and pushability such that the pusher tube 109 is used to advance an otherwise flexible wire of the tether 104, for example through a microcatheter, finder catheter, or diagnostic catheter. The size of the pusher tube 109 can remain small enough such that a tetherable guide-sheath 400 can be thread onto it, as will be discussed in more detail below.

Referring to FIG. 5A, a detail view, taken from Detail A of FIG. 4, of a distal portion of a tethering device is illustrated in accordance with an implementation. The anchor 102 can be configured to expand when a force is applied. The anchor 102 can include a closed-cell stent like structure, e.g., made of self-expanding material like nitinol. The anchor 102 can include a slit tube structure, for example, a structure that includes a tube made of a self-expanding material like nitinol, and having several longitudinal slits or slots that allow the tube to be expanded from an unexpanded, tubular shape, to an expanded shape. Accordingly, the anchor 102 may be set to a desired shape, for example, by a heat set process. Alternatively, the anchor 102 can be formed from spring steel, alloys, or even polymeric material. Furthermore, the tether 104 can include an anchor wire 111 extending through a runner tube 113. The anchor wire 111 can be seen in FIG. 5A although is hidden behind a middle rib 115 of the slit tube in FIG. 5D. The anchor wire 111 can connect to the anchor 102 at the distal joint 108. Similarly, the runner tube 113 may be connected to the anchor 102 at the proximal joint 108. Thus, a withdrawal or pulling load applied to the anchor wire 111 can lead to compression of the anchor 102 between the distal joint 108 and the proximal joint 108. The compression may cause outward bowing and expansion of the ribs 115 of the anchor 102. Accordingly, when actuated within an anchoring vessel, the anchor 102 may secure the tethering device 100 within the target anatomy.

Figure 5B:
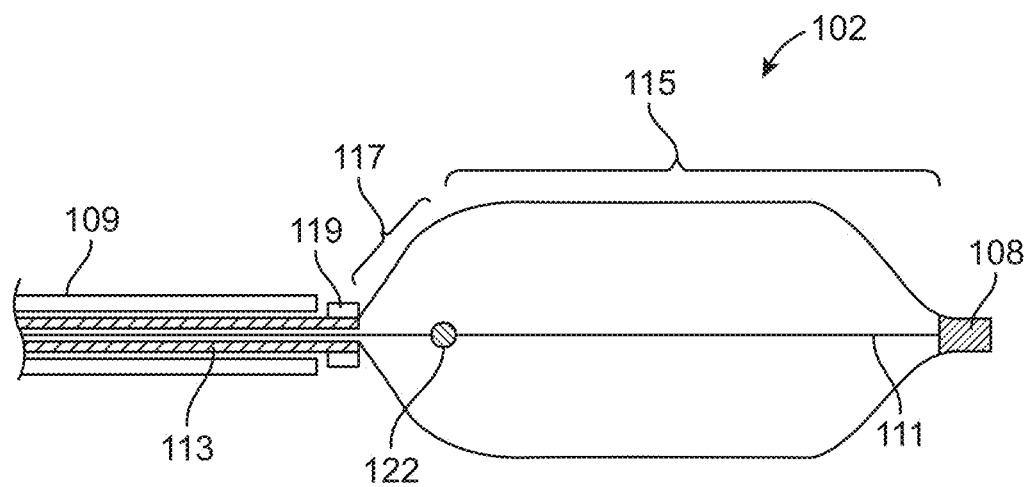
FIG. 5B illustrates a sectional view, taken about line A-A of FIG. 5A, of a distal portion of a tethering device.

FIG. 5B is a sectional view of FIG. 5A taken about line A-A, of a distal portion of the tethering device 100 shown in FIG. 4. The anchor 102 can be a self-expanding structure having one or more rib segments 115 interconnected with one or more spreader segments 117. The anchor 102 can also include a slit tube structure having one or more rib segments 115 extending longitudinally between a proximal joint 108 and a distal joint 108 as shown in FIGS. 5D-5G. Each rib segment 115 can have a distal end attached to the distal joint 108 and a proximal end attached to a distal end of a corresponding spreader segment 117. Similarly, each spreader segment 117 can have a proximal end connected to the proximal joint 108 of the anchor 102. In an implementation, the proximal joint 108 includes a tether collar 119, such as a band that is swaged, glued, or otherwise affixed to one or more of the anchor 102 or the runner tube 113 of the tether 104.

Still with respect to FIGS. 5A-5B, the anchor wire 111 can include a rigid member designed to transmit longitudinal force to the distal joint 108. Thus, the anchor wire 111 can be fixed to the distal joint 108, and can impart an expansion force to the anchor 102 when pulled. More particularly, when a compressive load is applied to the anchor 102 between the distal joint 108 and the tether collar 119, the rib segments 115 may tend to bow outward, and the spreader segments 117 may maintain a lateral separation between the proximal ends of the rib segments 115 and the anchor wire 111. Accordingly, the anchor 102 may expand from an unexpanded state, e.g. a tubular shape, to an expanded state, e.g. a bulbous shape. The anchor wire 111 may have an outer diameter of 0.006 inch, the runner tube 113 may have an outer diameter of 0.011 inch, and the pusher tube 109 may have an outer diameter of 0.020 inch. The wall thicknesses of the runner tube 113 and the pusher tube 109 may be minimized for their respective materials, which may be a medically acceptable material such as nitinol or stainless steel.

Figure 5C:
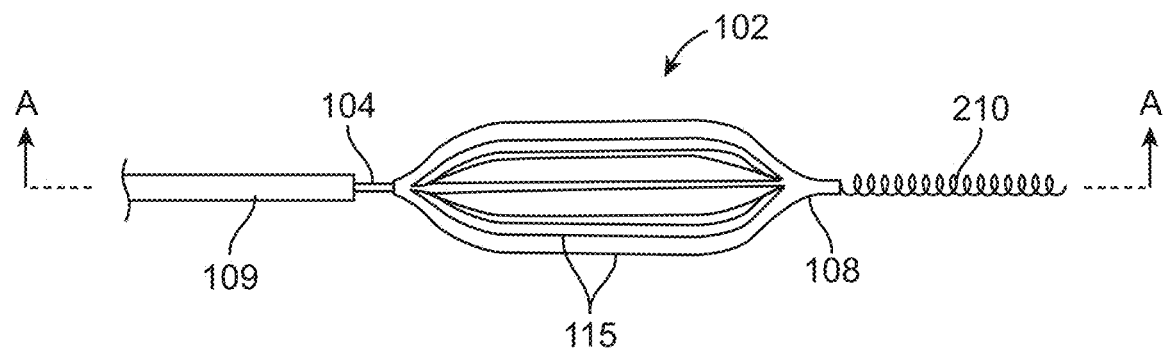
FIG. 5C illustrates a detail view, taken from Detail A of FIG. 4, of a distal portion of a tethering device.

FIG. 5C is a detail view of a distal portion of a tethering device. As with other implementations, the anchor 102 can be configured to self-expand and/or expand when a force is applied to it. The anchor 102 can include a slit tube structure, for example a tube made of a self-expanding material like nitinol, and the tube can include several longitudinal slits or slots that allow the tube to be expanded from an unexpanded, tubular shape, to an expanded shape as shown. Accordingly, the slit tube structure can be set to a desired shape, for example the illustrated expanded shape, by a heat set process. Alternatively the anchor can be formed from spring steel, alloys, or polymeric materials as described elsewhere herein. The tether 104 can include an anchor wire 111 (hidden behind a middle rib of the slit tube structure in FIG. 5C) extending through a runner tube 113. The anchor wire 111 can connect to the anchor 102 at the distal joint 108. Similarly, the runner tube 113 can connect to the anchor 102 at the proximal joint 108. Thus, a withdrawal or pulling load applied to the anchor wire 111 can lead to compression of the anchor 102 between the distal joint 108 and the proximal joint 108. The compression can cause outward bowing and expansion of the ribs 115 of the anchor 102. Accordingly, when actuated within the anchoring vessel, the anchor 102 can secure the tethering device 100 within the target anatomy.

Figure 5D:
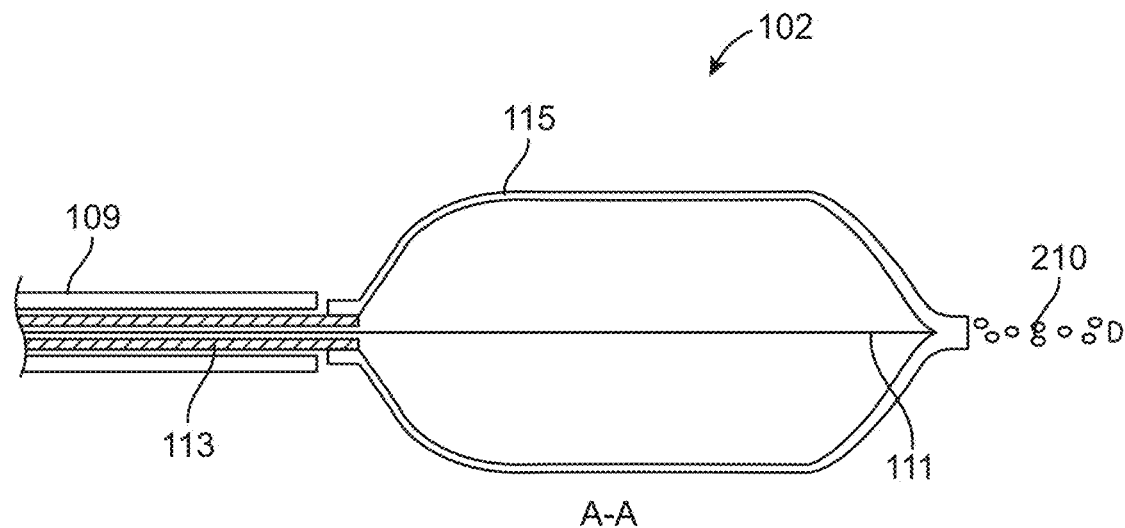
FIG. 5D illustrates a sectional view, taken about line A-A of FIG. 5C, of a distal portion of a tethering device.

FIG. 5D is a sectional view taken about line A-A of FIG. 5C of a distal portion of a tethering device. The anchor 102 can be a slit tube structure having one or more rib segments extending longitudinally between the proximal joint 108 and the distal point 108. Each rib segment 115 may have a distal end attached to the distal joint 108 and a proximal end attached to the proximal joint 108. In an implementation, the proximal joint 108 includes a tether collar 119, such as a band that is swaged, glued, or otherwise affixed to one or more of the anchor 102 or the runner tube 113 of the tether 104. The distal end of the anchor 102 in any of the various implementations described herein can include an atraumatic distal tip 210 (see FIGS. 5C-5E).

Figure 5E:
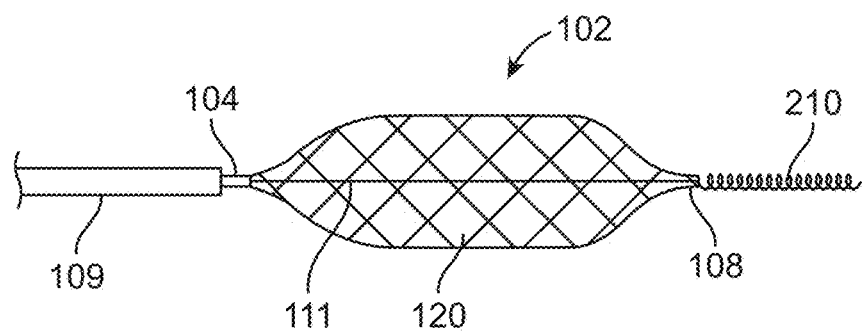
FIG. 5E illustrates a detail view, taken from Detail A of FIG. 4, of a distal portion of a tethering device.

FIG. 5E illustrates an interrelated implementation in which the anchor 102 includes a braid or overlapping wire structure. The anchor 102 can include a braided mesh 120 made of self-expanding material such as nitinol such that the mesh structure can be set to a desired shape by, for example, a heat set process. As with other implementations, the tether 104 can include an anchor wire 111 extending through a runner tube 113 such that a withdrawal or pulling load applied to the anchor wire 111 can lead to compression of the anchor 102 between the distal joint 108 and the proximal joint 108. The compression can cause outward bowing and expansion of the braided mesh 120 to secure the tethering device in the target anatomy.

The runner tube 113 can be large enough to provide a slip fit with the anchor wire 111, such that the anchor wire 111 is able to easily slide along an entire length of the runner tube 113. Nonetheless, the runner tube 113 may be small enough to minimize a diameter of a tether lumen in the tetherable guide-sheath 400, as will be described below. The runner tube 113 can be fixed to the proximal joint 108 of the anchor 102, and can be longer than a distance between the anchoring site and an exit port in the tetherable guide-sheath, but shorter than an overall length of the anchor wire 111 and the anchor lengths. Accordingly, the anchor wire 111 can exit a proximal end of the runner tube 113. The runner tube 113 can have a similar length to the pusher tube 109, or the runner tube 113 can be shorter than the pusher tube 109, for example, to minimize an overall length of the anchoring delivery system 10.

The pusher tube 109 can be large enough to provide a slip fit with the runner tube 113, such that the runner tube 113 is able to easily slide along a length of the pusher tube 109. The pusher tube 109, however, may be small enough to abut the tether collar 119 or a proximal end of the anchor 102. Accordingly, the pusher tube 109 can be pressed forward (and/or the anchor 102 withdrawn) such that a distal face of the pusher tube 109 presses against the tether collar 119 (or proximal end of the anchor 102) to exert a forward load on the anchor 102. The pusher tube 109 can be longer than an overall length of a delivery catheter, which may typically be 100 cm in length. Accordingly, the pusher tube 109 can be grasped and pulled back after delivery of the anchor 102 to the anchoring site to remove the pusher tube 109 from the anchor 102, the tether 104 and the patient anatomy.

Figure 5F:
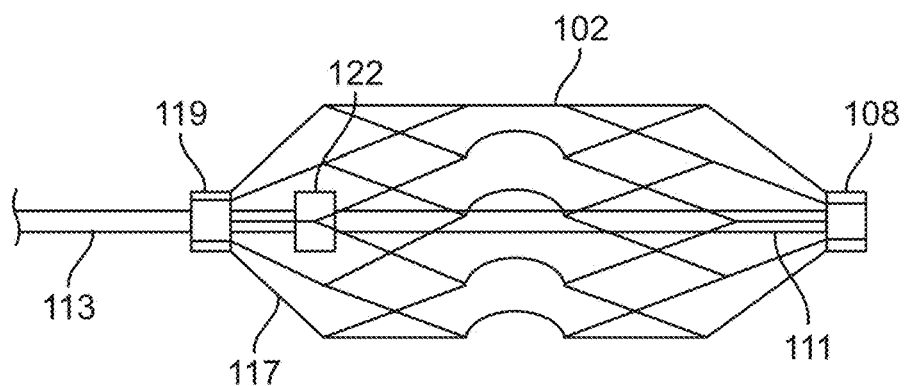
FIG. 5F illustrates a detail view, taken from Detail A of FIG. 4, of a distal portion of a tethering device.
Figure 5G:
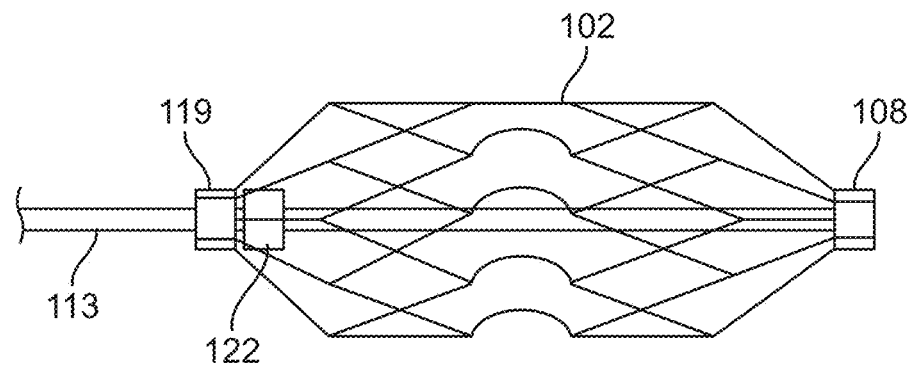
FIG. 5G illustrates the tethering device of FIG. 5F after further expansion of the anchor.

FIGS. 5F-5G illustrate a distal portion of an implementation of the tethering device 100. As previously described, a distal end of an elongated member such as the anchor wire 111 may be connected to a distal end of the anchor 102 at a distal joint 108. The connection can be either permanent or temporary, e.g., like the transition described above. For example, the anchor wire 111 can be threaded into the distal joint 108 of the anchor 102 such that it may be rotated to detach from the anchor 102. The anchor wire 111 can also be connected permanently to the anchor 102 such as by soldering, welding, gluing, crimping or other fasteners. The anchor 102 can be preloaded into a pusher tube 109 or constricting sheath. The anchor 102 can be loaded during the procedure into a catheter, which might have already been placed into the vasculature of a patient. The distal attachment point or joint 108 between the anchor wire 111 allows the push force to be transmitted to the distal portion of the anchor 102 such that the anchor 102 can be "pulled" into the pusher tube 109, which can significantly simplify loading. When the anchor 102 is constricted by the pusher tube 109, or is inside a catheter, the distal end of the pusher tube 109 or the distal end of the catheter can be positioned at the location where the anchor 102 is to be deployed. During deployment, the pusher tube 109 or the catheter can remain stable and the anchor 102 can be pushed out, e.g. by applying a distal load to the runner tube 113. After the distal part of the anchor 102 is in contact with an inner surface of the anchoring anatomy, the pusher tube 109 may be pulled back to allow the anchor 102 to expand into contact with the anchoring anatomy. In some implementations, the anchor 102 has a closed cell structure and the anchoring structure will be constricted in its diameter as long as the anchor 102 is not fully released. This feature can significantly simplify the release of the anchor 102 into the target anatomy.

As best shown in FIGS. 5F and 5G, the tethering device 100 can include a stopper 122 attached to the anchor wire 111. The stopper 122 can limit an amount of expansion of the anchor 102. For example, when the anchor wire 111 is pulled back within the runner tube 113, the stopper 122 may eventually contact a proximal end of the anchor 102 and/or the tether collar 119, to prevent additional bowing of the rib segments 115. At that point, the anchor 102 can grip the anchoring vessel with sufficient friction to resist being pulled proximally by the tether 104. Accordingly, the expansion of the anchor 102 may stop. A distance between the stopper 122 and the proximal end of the anchor 102 can define the maximum expansion dimension of the anchor 102. Furthermore, the distance can correlate with a radial force applied to the anchoring anatomy by the anchor 102. Thus, the stopper 122 can be located to tune the radial force and the corresponding fictional force applied to the tissue by the anchor 102. More particularly, the anchor 102 can be configured to apply sufficient frictional force to the tissue to resist a pull force applied by an operator to the tether 104, or a reaction load applied to the tether 104 by a working device being advanced to a target anatomy, as described below.

The anchors described herein are designed to stay fixed in a vessel when deployed, but may slide through a catheter for delivery to the anchoring site by pushing on the tether 104 and/or pusher tube 109 of the system. Additionally, the anchor 102 may be withdrawn into a capturing element, such as a tetherable guide-sheath 400, a micro catheter, etc., for removal from the anatomy. Accordingly, pulling the anchor 102 into the capturing element may retract and collapse the expandable structure rather than expand the expandable structure. Furthermore, the elongated section of the tethering device 100, i.e., the combination of the tether 104 and the pusher tube 109, may be larger during delivery of the anchor 102 to the anchoring site than after delivery. More particularly, after delivering the anchor 102, the pusher tube 109 may be removed from the anatomy to make the remaining portion of the elongated section, i.e., the tether 104, as thin as possible such that the tetherable guide-sheath may be advanced over the tether 104 and fixed to the tether 104 while maintaining a sufficiently large working lumen to advance a working device through the tetherable guide-sheath to a target vessel.

The anchors described herein can include a structure configured to anchor within an anchoring vessel that relies upon apposition of a plurality of struts or rings with the underlying vessel. The anchors described herein can also include a structure configured to anchor within an anchoring vessel without relying upon apposition. For example, the anchors can incorporate a coiled wire having one or more loops configured to be constrained to a straighter, low profile configuration during delivery and upon release of the constraint take on a higher profile configuration that is helical, spiral, twisted, bent, curved, or double-curved etc. such that the anchor anchors within the vessel, for example, as shown in FIGS. 5H-5L, and as will be described in more detail below.

Figure 5H:
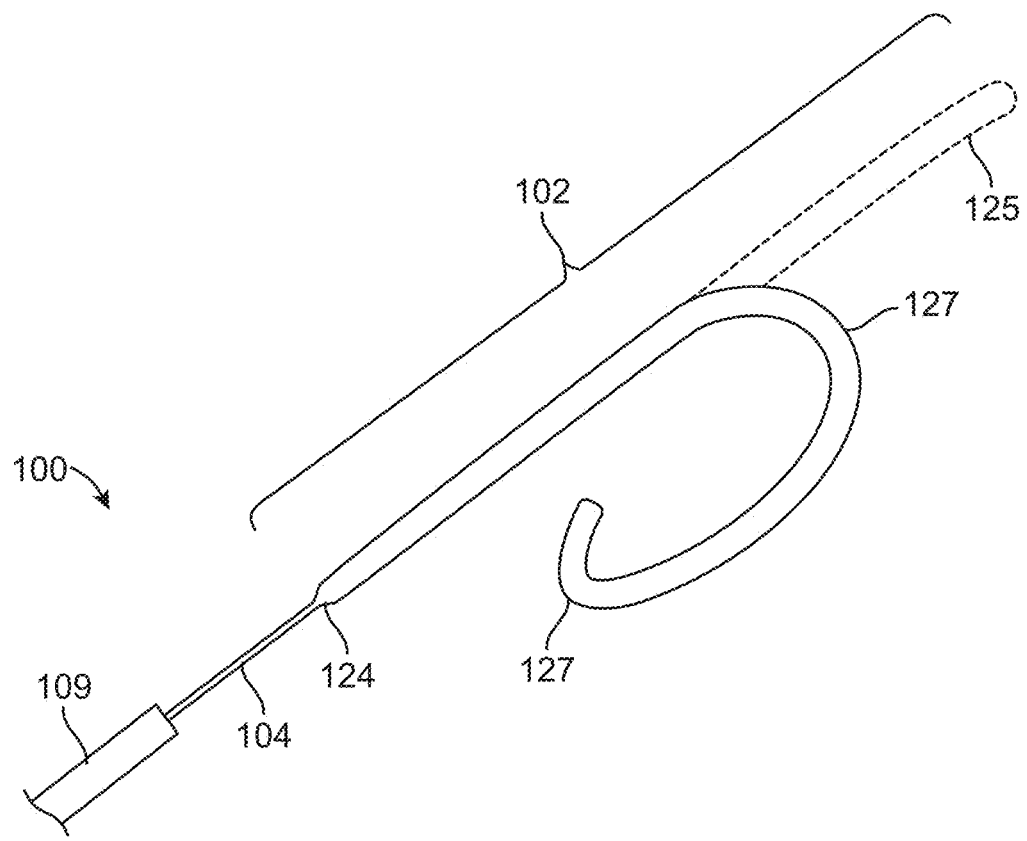
FIG. 5H illustrates a detail view, taken from Detail A of FIG. 4, of a distal portion of a tethering device, in accordance with an interrelated implementation.

FIG. 5H shows a detail view of a distal portion of a tethering device in accordance with an implementation. The tethering device 100 can include an anchor 102 configured to deform or distort the vessel as opposed to vessel apposition devices, such as a stent-type anchor, which rely upon high radial force. Such anchors provide excellent holding force even if deployed in straight vessels. The anchor 102 provides simplicity in manufacture, deliverability, anchoring even in relatively straight vessels, and speed of execution that is appealing from a clinical standpoint. The tethering device 100 can include an anchor 102 having a shape memory wire that passively changes (e.g. self-expands) from a smaller profile configuration to a larger profile configuration. The tethering device 100 including the anchor 102 can be configured to be inserted into a vessel through a diagnostic catheter that accepts 0.038-inch (0.97 mm) guide wires. As such, the anchor 102 may include a wire segment, e.g., a segment of wire having a diameter of, e.g., 0.038-inch, that is formed from a shape memory wire, e.g., nitinol wire. The shape memory wire may be pre-formed into a heat set shape having one or more primary and/or secondary curves, bends, coils, or turns. The shape memory wire can include a heat set shape that includes, but is not limited to, a J-shape, a hook-shape or other profile having one or more bends, curves, coils, etc. Furthermore, the shape memory wire may be elastically deflected into a substantially straightened or elongated shape for delivery through a lumen of a catheter. Thus, the anchor 102 may be delivered in the smaller profile configuration when the shape memory wire is straightened (as shown by dotted lines 125 in FIG. 5H), and the anchor 102 may change into the larger profile configuration when the wire returns towards the pre-set hook-shape 127 within the anchoring vessel. When the anchor 102 returns towards the resting shape inside the vessel, the vessel itself can undergo an amount of distortion and in turn engage the anatomy surrounding the vessel. Thus, the vessel distortion and resistance provided by the anatomy adjacent the vessel can contribute to the level of holding force provided by the anchor 102 upon deployment in the anchoring vessel, as is described in more detail below.

Figure 5I:
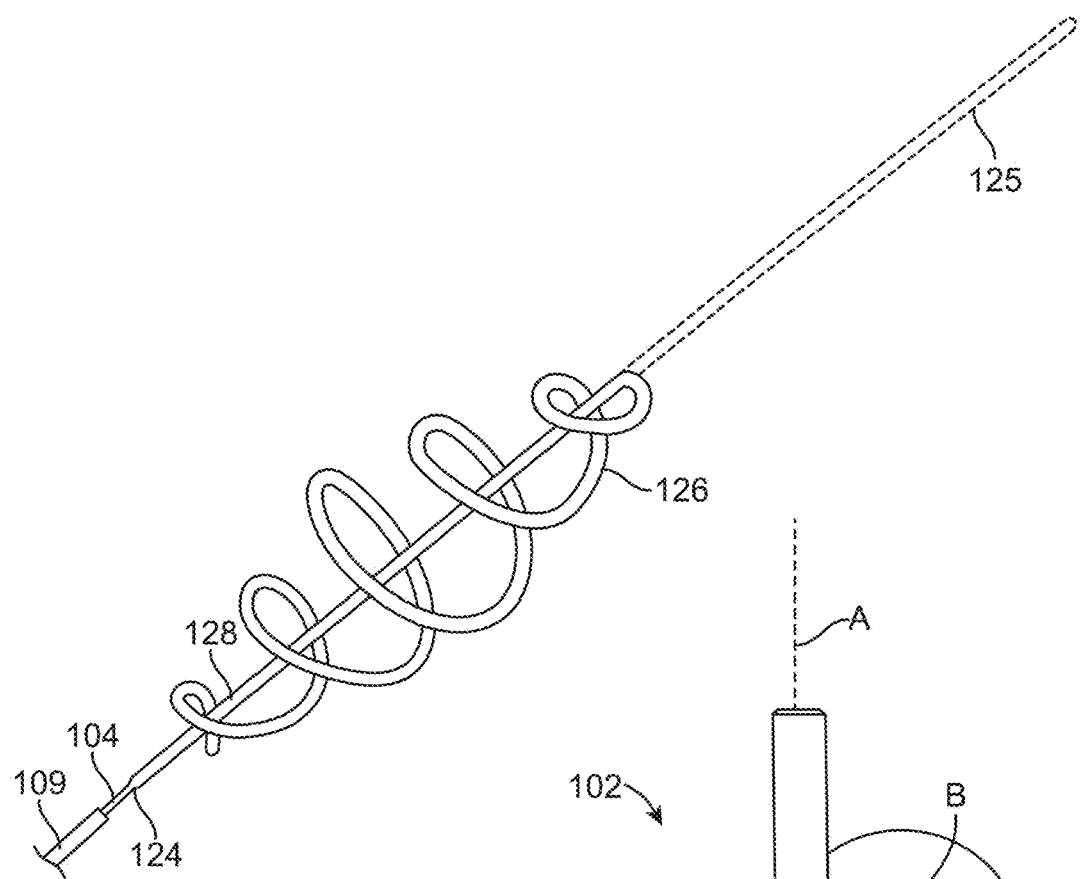
FIG. 5I illustrates a detail view, taken from Detail A of FIG. 4, of a distal portion of a tethering device, in accordance with an interrelated implementation.

FIG. 5I, a detail view of a distal portion of a tethering device, is shown in accordance with an implementation. As described above, the tethering device 100 having a self-expanding shape memory wire design may include a pre-formed shape that incorporates one or more loops or coils 126. More particularly, the anchor 102 can include a coil 126 having one or more turns about an axis. For example, a longitudinal segment 128 of the anchor 102 may be along the central axis and the turn(s) of the coil segment 126 may extend proximally from a distal end of the longitudinal segment 128 toward a proximal end of the longitudinal segment 128. The proximal end of the longitudinal segment 128 may, for example, be at the transition point 124 between the anchor 102 and the anchor wire 111. The coil 126 can be a single loop, 1.5 loop, or a 2 loop anchor 102. Each loop of the coil 126 can be a 6 mm loop.

Figure 5J:
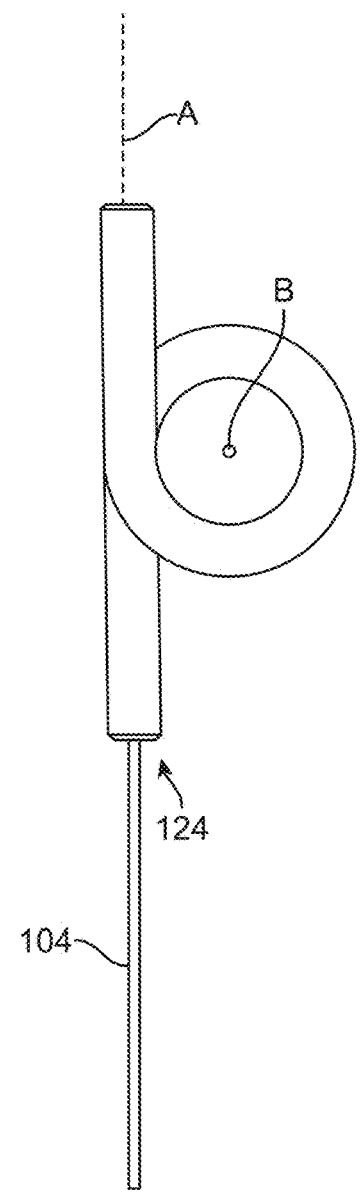
FIGS. 5J-5L illustrate detail views, taken from Detail A of FIG. 4, of a distal portion of a tethering device, in accordance with an interrelated implementation.
Figure 5K:
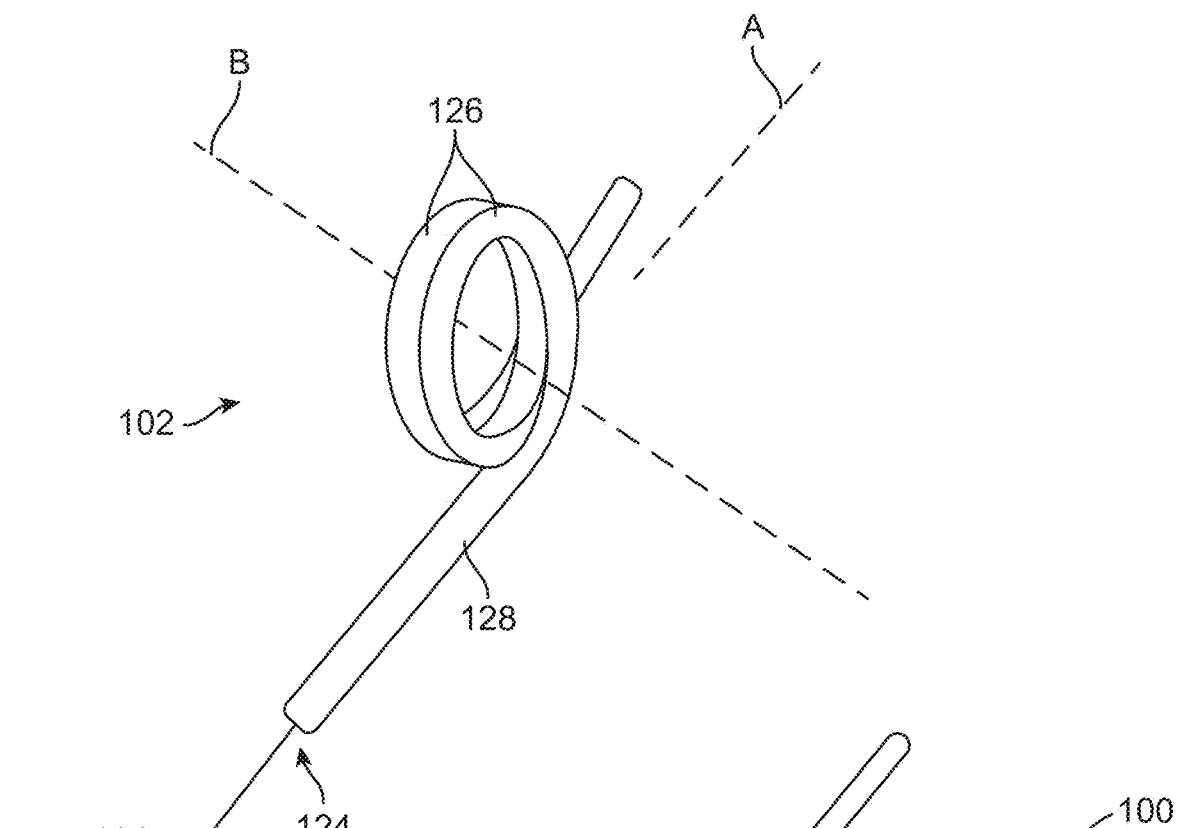
Figure 5L:
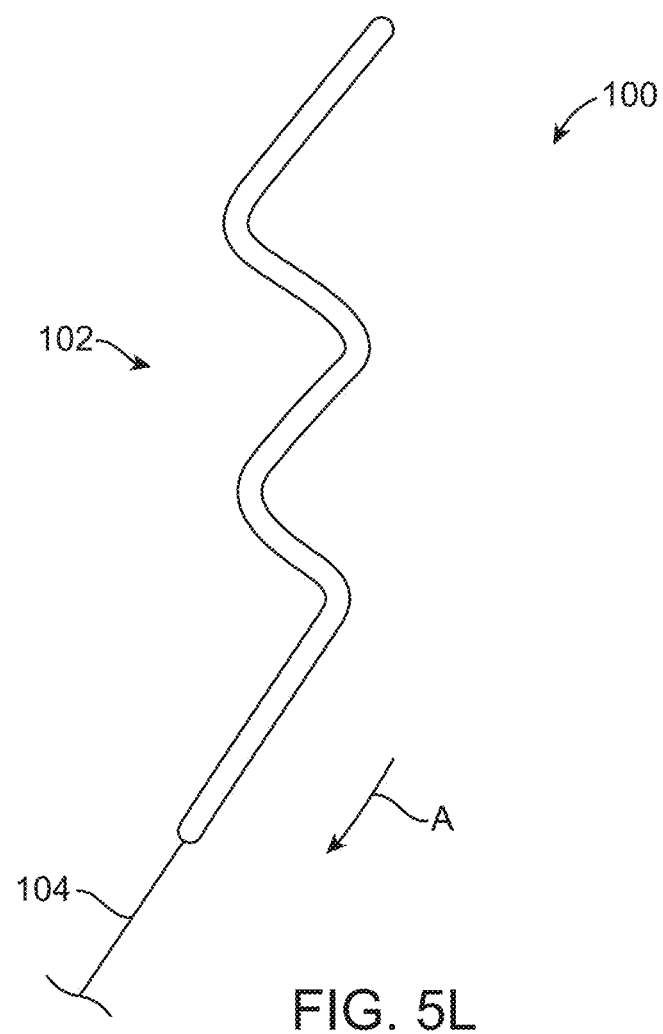

The coil segment 126 may extend out of plane with a direction of insertion or in plane with a direction of insertion. FIGS. 5J-5L show another implementation of an anchor 102 formed by an extension spring configured to coil in plane with a direction of insertion. The longitudinal segment 128 of the anchor 102 can be along the central axis A. The coil(s) 126 can loop back toward a proximal end of the longitudinal segment 128 and then back toward a distal end of the longitudinal segment 128. Rather than the coil(s) 126 being about the central axis A, the coil(s) 126 can loop around an axis B that is at an angle to, such as perpendicular or orthogonal to, the central axis A forming a pigtail type coil or spiral wire. The coils 126 in a resting state, unconstrained by either a tubular element or vessel (i.e. in the air), can touch each other or align side-by-side (see FIG. 5K). During delivery towards a vessel, the coils 126 are constrained in a substantially straightened configuration, for example, within a tubular delivery element. Withdrawal of the tubular delivery element in a proximal direction (arrow A in FIG. 5L), unsheathes the coils 126 and deploys the anchor 102 in the vessel. When deployed within a vessel, the coils 126 take on a helical, semi-helical, curved, or "wiggle" shape that can distort the vessel and fix the anchor 102 to the deployed location. As described above, the return of the coils 126 towards this shape following removal of a straightening constraint (e.g. lumen of a finder catheter through which the anchor 102 is delivered) can distort the vessel from its natural path to a path that is dictated in part by the shape the coils 126 take on upon unsheathing. For example, FIG. 5M illustrates an anchoring vessel 1904 following its natural path within the cerebral anatomy. FIG. 5N illustrates a tethering device 100 deployed within the anchoring vessel 1904 where the anchor 102 of the tethering device 100 is a stent-like vessel apposition device. The anchoring vessel 1904 generally maintains its natural path and anchoring is provided by the apposition of the anchor 102 against the vessel wall with or without the presence of additional barbs or cleats or other feature to improve fixation of the anchor 102. FIG. 5O illustrates another implementation of a tethering device 100 deployed within the anchoring vessel 1904. In this implementation, the anchor 102 takes on a substantially helical shape within the anchoring vessel 1904, which in turn, causes the anchoring vessel 1904 to distort away from its natural path and instead follow the directional turns of the anchor 102. In this implementation, engagement between the distorted vessel 1904 and the tissues of the adjacent anatomy assist in the holding force provided by the anchor 102. The distortion within the surrounding tissue allows the resistance of the surrounding tissue to these distortions to increase the hold of the anchor 102 such that the anchor 102 now engages an entire "block" of tissue rather than just the vessel wall. The holding force provided can be sufficient to prevent the anchor 102 from being dislodged from the anchoring vessel 1904 upon application of a pulling force on the tether 104 in a proximal direction even when tightly drawn and coupled to the proximal end of the guiding sheath 400 such that advancement of a working device causes a downward pulling force on the sheath 400.

The wire composition and size, as well as the coil diameter, the number of coils, and the amount of expected external force on the anchor 102 can all be considered in the design of the anchor 102. FIG. 5K shows two coil segments 126 to the anchor 102, however, the anchor 102 can include one, two, three, four, five, six, or more coil segments 126. The diameter of the coils 126 can vary depending on the vessel within which the anchor device is intended to be used. The diameter of the coils 126 can affect the holding force as the smaller the coil loop, generally the stiffer the anchor.

The tethering device 100 can include the tether 104 extending proximally from the anchor 102. In an implementation, the tether 104 may have a smaller diameter than the shape memory wire used to form the anchor 102. In some implementations, the tether 104 can be formed from a shape memory wire having a diameter between about 0.005-inch to about 0.014-inch, e.g., 0.006-inch, 0.007 inch, 0.008 inch, or 0.009-inch up to 0.016-inch. In other implementations, the tether 104 can have a diameter from about 0.005 inches to 0.025 inches, e.g., 0.008 inches, or 0.009 inches, or 0.010 inches, or 0.035 inches, depending on the degree of support that the tether 104 provides. The tether 104 can be a solid wire rod, a ribbon, or a hypotube. In some implementations, the tether 104 can be a stainless steel rod, ribbon or hypotube. In other implementations, the tether 104 can be Drawn Filled Tubing (DFT) with a radiopaque core, such as an outer sheath of a composite to provide strength and a core material to provide superelasticity, conductivity, radiopacity, resiliency, etc. In some implementations, the tether 104 can be DFT of Nickel titanium with a radiopaque core such as platinum or tantalum.

Figure 5P:
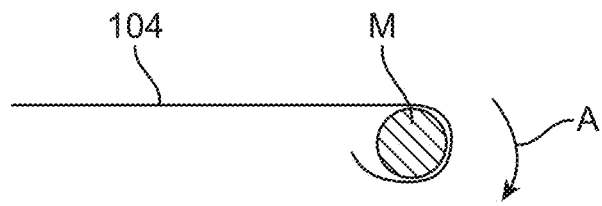
FIGS. 5P-5R illustrate schematic views of a method of manufacturing an anchor of a tethering device, in accordance with an implementation.
Figure 5Q:
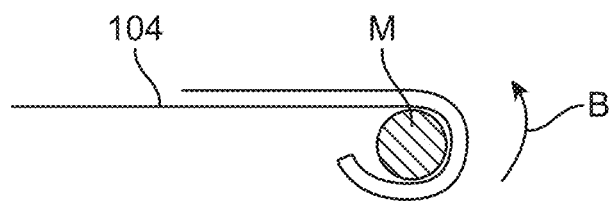
Figure 5R:
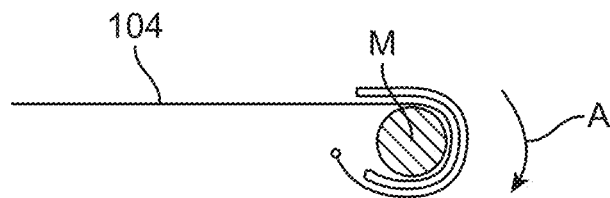

The tether 104 may be integrally formed with the anchor 102, e.g., the anchor 102 and the tether 104 may be segments of a same wire. Alternatively, the anchor 102 and the tether 104 may be different wires that are connected at a transition point 124 via a mechanical, adhesive, or welded bond. In some implementations, the wire of the tether 104 is integral with the wire of the anchor 102 and the anchor 102 created by coiling over a mandrel and/or via grinding. For example, in some implementations the anchor 102 can be formed by winding the wire around a shaft such as a mandrel. The ends of the anchor 102 can be bent into a desired shape, whether that is straight or otherwise looped, hooked, or bent. The anchor 102 can be formed by cold winding or hot winding and then hardened to relieve stress and allow resilience in the spring. The anchor 102 can be formed by coiling a length of wire around a mandrel M in a first direction (arrow A in FIG. 5P) and doubling back around the mandrel M in a second opposition direction (arrow B in FIG. 5Q) to create a first overlap section. More overlap sections can be created by once again coiling the wire about the mandrel M in the first direction (arrow A in FIG. 5R) until a coil having a particular holding strength is formed. More coils can be formed in the length of wire in a similar manner until an anchor 102 is formed having the desired number of coils having a desired overall diameter and a desired holding force. The anchor 102 can also be formed by grinding a round or flat wire using a coiling lathe to create single diameter coils or tapered coils. The anchor 102 can be formed of a plurality of materials including a core wire and an external coil laser welded to the core wire. The anchor 102 can be formed of stainless steel wire, nitinol wire, drawn filled tube (DFT) with a radiopaque core, hypotube.

One skilled in the art will appreciate that a shape memory wire may be pre-formed to have numerous larger profile configuration shapes. For example, the coil segment 126 of the anchor 102 may extend distally from the longitudinal segment 128 of the anchor 102 with turns having increasing diameters such that a conical coil shape is formed. Alternatively, the turn diameters may increase and decrease in a longitudinal direction of the coil segment 126 such that a barbell shaped coil segment is formed. Still further, the coil segments 126 may each have a diameter that are substantially the same and sized to engage the vessel within which the anchor 102 is implanted upon release from the catheter lumen. Thus, the anchor 102 may include a shape memory wire segment that may be deformed or deflected to the smaller profile configuration and then released into a heat set shape of the larger profile configuration to create friction against a vessel wall. The larger profile configuration of the anchor 102 may be wider in a transverse dimension than the smaller profile, and thus, the anchor 102 may press against a vessel wall to anchor the tethering device 100 when it emerges from the lumen of the catheter.

Figure 5U:
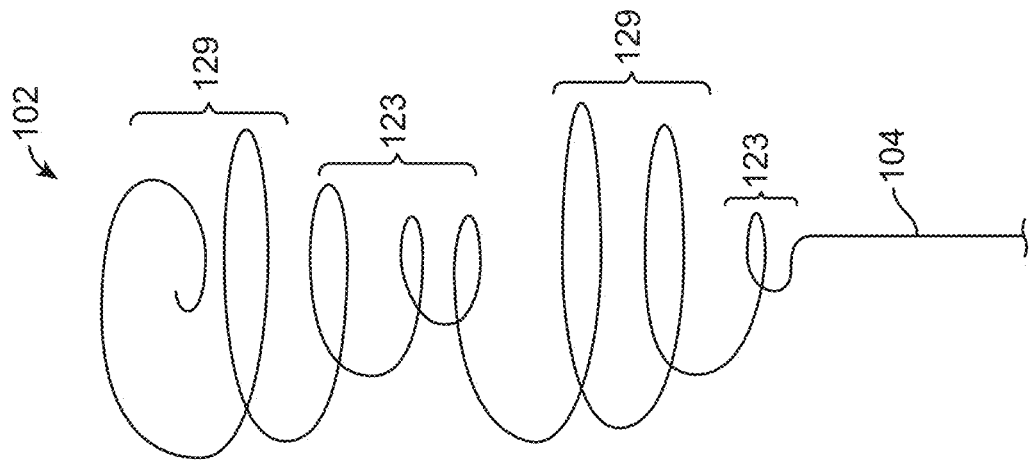
FIGS. 5S-5U illustrate schematic views of further implementations of a distal portion of a tethering device, in accordance with an interrelated implementation.
Figure 5T:
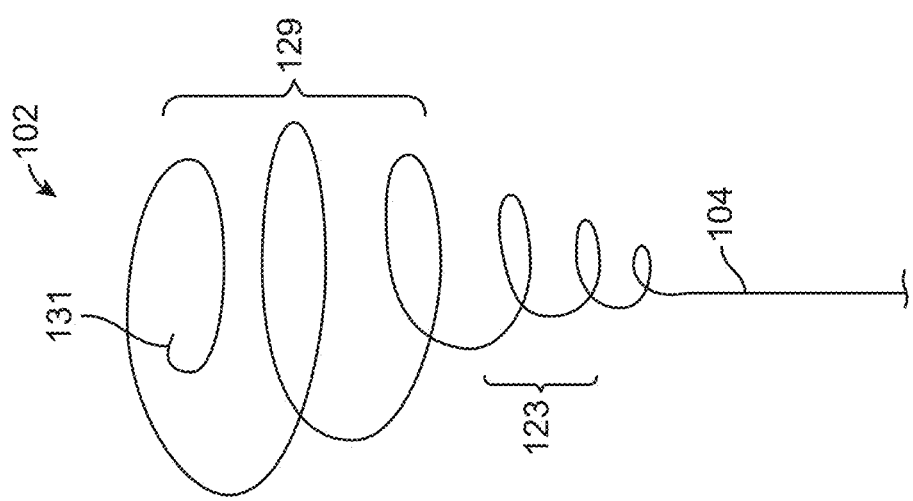
Figure 5S:
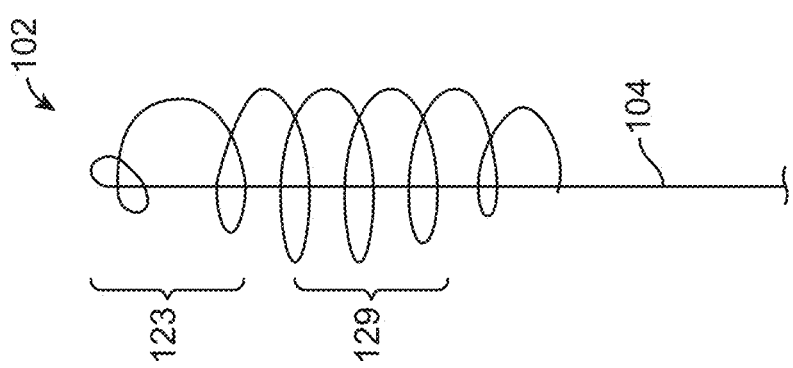

FIGS. 5S-5U illustrate various implementations of a distal end of a tethering device 100. The anchor 102 can include one or more shock absorber regions 123 and one or more anchoring loop regions 129. FIG. 5S illustrates an anchor 102 having a wire coiled into a distal shock absorber region 123 adjacent a central anchoring loop region 129 whereas FIG. 5T illustrates a distal anchoring loop region 129 having a floppy J-tip 131. FIG. 5U illustrates an anchor 102 having a wire coiled into a distal anchoring loop region 129 and a proximal anchoring loop region 129 interspersed with a first shock absorber region 123 and a second shock absorber region 123, thus creating two sets of anchoring loops 129 and two sets of absorbent loops 123.

The anchor 102, with or without additional barbed or cleat elements, can embed within the wall of the vessel and optionally can cause the vessel within which it is deployed to undergo a degree of distortion, particularly if a proximal tugging force is applied on the tether 104. Thus, the friction between the anchor 102 and the vessel aids in the retention of the tethering device in the vessel as does the distortion of the vessel within which the tethering device is anchored, and optionally engagement between barbs of the anchor and the vessel. The vessel can deform into a single or double curve under the distortion force of the anchors 102 described herein further improving their anchoring function while maintaining flow through the anchor 102 with little disturbances due to the presence of the anchor 102. Thus, a combination of forces provides an anchoring function. The combination of proficient anchoring for the delivery of large bore catheters and maintenance of blood flow in and around the anchor are beneficial to successful interventions within the neurovasculature and consistent access catheter delivery to the skull base It should be appreciated that the anchor itself need not embed within the wall of the vessel due to a shape change upon deployment. In some implementations, the anchor 102 is deployed in a more superficial anatomic location, such as within a facial artery, that allows for fixation of the anchor 102 from outside the body anatomy. For example, the tethering device 100 can include a proximal tether 104 and a distal anchor 102 deployed within a superficial vessel. The distal anchor 102 can be fastened within the superficial vessel by magnetic attraction between the distal anchor 102, formed of a magnetic material such as stainless or incorporating magnetic elements, and one or more magnets placed on a skin surface near the superficial vessel, such as on the cheek or the neck near the ear. In other implementations, at least a portion of the anchor 102 can be externalized and clamped outside the body.

It should be appreciated that various anchor implementations are described herein and the term anchor is used generally herein to refer to an element used for anchoring of the tethering device within a target anatomy. Anchors can include any of a variety of configurations as described herein including, but not limited to self-expanding or non-self-expanding devices, braids, mesh, wires, stents, coils, or other particular implementation described herein. Any of a variety of combinations of features of the anchors are considered herein. Further, although a particular anchor implementation may be shown in a particular figure for purposes of illustration, it is not intended to be limiting or to suggest that the anchor implementation shown would be the only anchor implementation useful for that particular feature.

The deployment of the various anchoring devices described herein will now be described. It should be appreciated that the anchor shown in the figure is represented in schematic for illustration purposes only to represent a change from a low profile configuration to a higher profile configuration. The actual configuration of the anchor can vary as described herein.

Figure 6A:
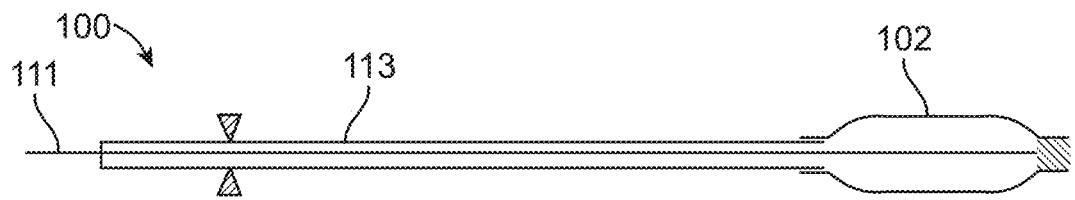
FIGS. 6A-6B illustrate schematic views of a tethering device deployment, in accordance with an implementation.
Figure 6B:
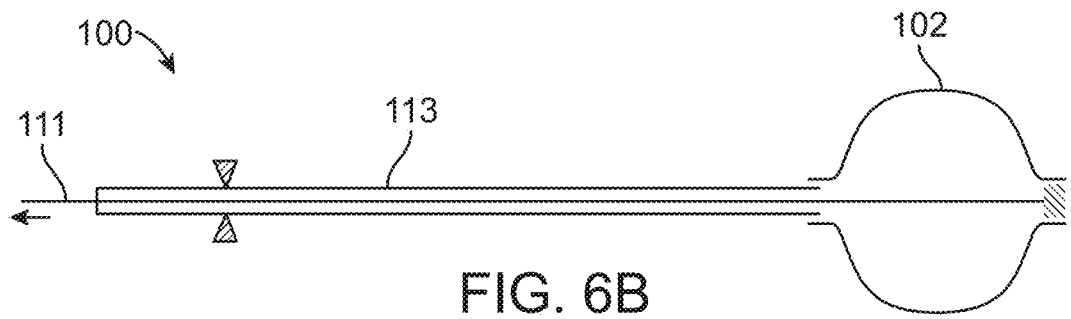

Referring to FIGS. 6A-6B, a schematic view of a tethering device deployment is illustrated in accordance with an implementation. The tethering device 100 can include a distal anchor 102, a proximal tether 104 having an inner anchor wire 111 and an outer runner tube 113. When deploying the tethering device 100, the operator may fix the runner tube 113 in place and adjust the placement of the anchor 102 in the vessel. The anchor 102 can be expanded and the anchoring can be tested by pulling the anchor wire 111 relative to the runner tube 113 and then fixing the two in relative position to each other (see FIG. 6B). The tethering device 100 can be adjustable, for example, if there is slip or an "extreme" moment during the procedure extra anchoring can be transiently applied to the anchoring vessel and released when the distension applied to the vessel is not desired. The expansion applied by pulling the anchor wire 111 can be in addition to expansion provided by self-expansion of the anchor 102 to a preformed expanded shape, for example as shown in FIGS. 2B-2D or FIGS. 5A-5B. If the runner tube 113 and anchor wire 111 interaction provides some friction the expansion of the anchor 102 can be retained from the friction between the two systems. It can provide anchoring that allows the deployment of the tetherable guide-sheath 400 over the tether 104, i.e., the runner tube 113/anchor wire 111 combination, as will be described in more detail below.

Figure 7A:
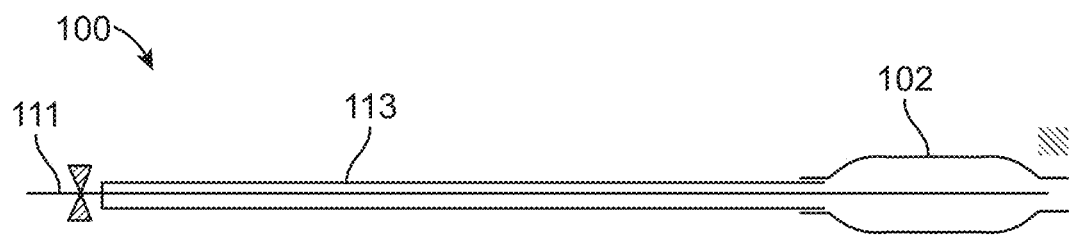
FIGS. 7A-7B illustrate schematic views of a tethering device deployment, in accordance with an implementation.
Figure 7B:
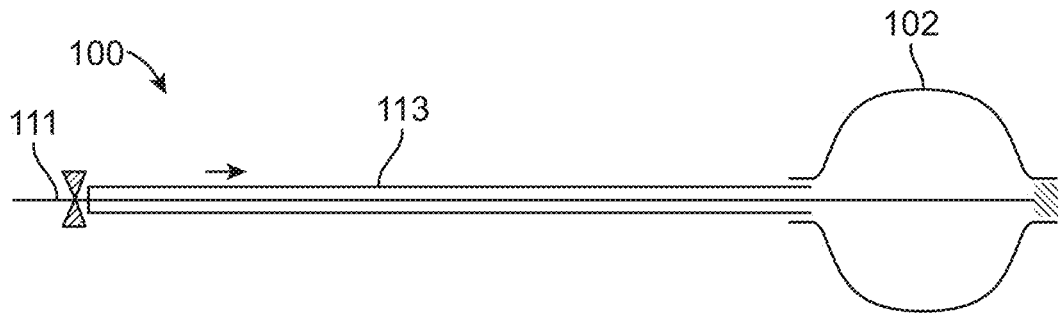

Referring to FIG. 7A, a schematic view of a tethering device deployment is illustrated in accordance with an implementation. Once tetherable guide-sheath 400 is positioned, another adjustment of the runner tube 113 relative to the anchor wire 111 can be done, and then the anchor wire 111 can be locked in place relative to the tetherable guide-sheath 400. Referring to FIG. 7B, a schematic view of a tethering device deployment is illustrated in accordance with an implementation. In an implementation, when the fixation point is applied to the anchor wire 111, downward forces on the tetherable guide-sheath will transmit directly to the anchor wire 111 and in return will expand the anchor 102 as the distal tip is pulled downward with downward force—further anchoring the system in response to downward force. It is expected that during the procedure, as long as the anchor wire 111 fixation relative to the tetherable guide-sheath 400 is constant, the anchor 102 will expand and anchor in accordance with the forces that are transmitted downward on the tetherable guide-sheath 400. Increasing or decreasing "baseline anchoring" can be dialed into the system in accordance with operator preferences and the needs of the procedure. The baseline anchoring may also be applied by self-expansion of the anchor 102 to a preformed expanded shape as shown in FIGS. 5D-5F.

Figure 8A:
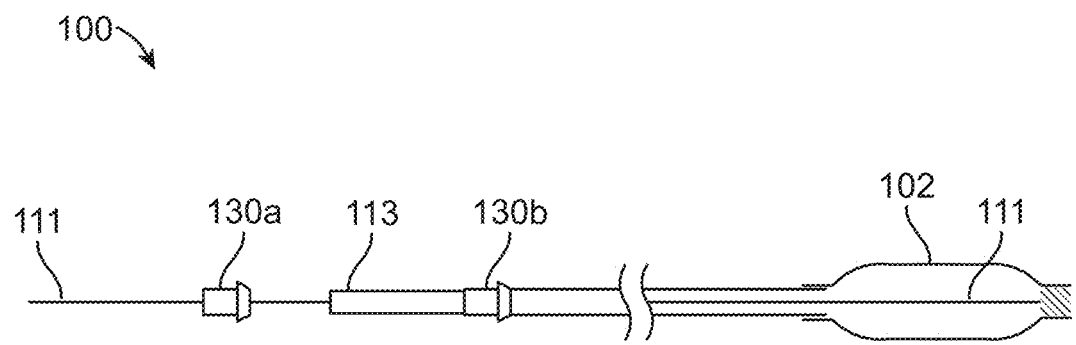
FIG. 8A illustrates a schematic view of a tethering device in an unexpanded state, in accordance with an implementation.

Referring to FIG. 8A, a schematic view of a tethering device in an unexpanded state is illustrated in accordance with an implementation. Taking this to a more mechanical level, one or more locking elements 130 may be used to "open and close" the anchor 102 at different diameters (and corresponding tensions against the vessel wall). The anchor 102 is shown in a low-profile configuration with the anchor 102 cut away so that the anchor wire 111 traversing the entire length of the assembly is visible within the anchor 102 and exiting the proximal end of the runner tube 113. Specialized locking elements 130 can be applied individually to the portions of the anchor wire 111 and the runner tube 113 that are exposed, e.g., that are situated outside of a patient anatomy and/or a rotating hemostatic valve (RHV) coupled with the tetherable guide-sheath, as described below. For example, a first locking element 130a can be coupled to the anchor wire 111 and a second locking element 130b can be coupled to runner tube 113.

Figure 8B:
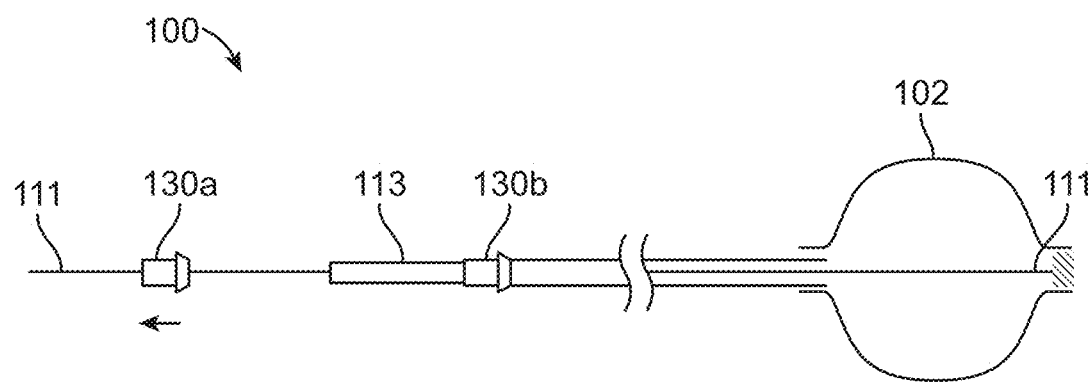
FIG. 8B illustrates a schematic view of the tethering device of FIG. 8A in an expanded state.

Referring to FIG. 8B, a schematic view of a tethering device in an expanded state is illustrated in accordance with an implementation. With tightened down locking elements 130a, 130b, the relationship of the anchor wire 111 to the runner tube 113 can be adjusted—either adjusted to tactile feedback or perhaps to fluoroscopic visualization of the expansion and contraction of the anchor. Tension can be applied by pulling the two locking elements 130a, 130b apart to expand the anchor 102. The reverse can be used to contract the anchor 102 and may even be held contracted to withdraw the device into a catheter or sheath.

Figure 8C:
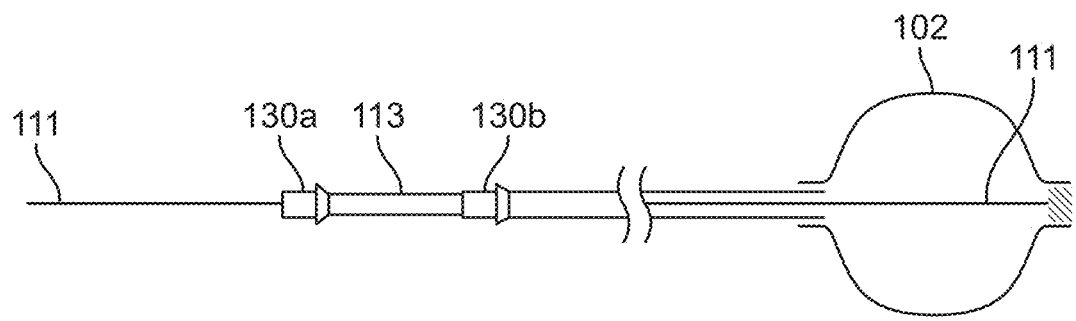
FIG. 8C illustrates a schematic view of the tethering device in an expanded state of FIG. 8B and a locked state.

Referring to FIG. 8C, a schematic view of a tethering device in an expanded state and locked state is illustrated in accordance with an implementation. Once the desired tension is applied to expand the anchor 102 to a target dimension for anchoring at an anchoring site in an anchoring vessel, the anchor wire locking element 130a can be advanced forward to abut a proximal end of the runner tube 113. Holding the anchor wire locking element 130a firm against the runner tube 113 at the anchor wire/runner tube transition and locking the anchor wire locking element 130a down at that position can lock the relationship of the anchor wire 111 and the runner tube 113 relative to each other (and lock the anchor 102 under a fixed tension). This is "locking open" the anchor 102. For added security, the runner tube locking element 130b can be loosened and advanced to the face of the RHV and/or the tetherable guide sheath, and locked down to prevent movement of the runner tube 113 relative to the RHV/tetherable guide-sheath assembly. If the RHV being used is not "specialized" to hold the runner tube 113 firmly, there can be a risk of slippage. If the runner tube 113 is of a stainless steel or nitinol or hardened material, when the operator encounters resistance on advancing interventional tools and anchoring is called for a downward force can be transmitted from the tetherable guide-sheath down the column of the tether 104, for example, formed by the anchor wire 111 extending through the runner tube 113. A standard commercial RHV can slip, and thus, a tether gripper such as a specialized RHV may be used to reinforce the relationship of the tether 104 relative to the sheath assembly and is described in more detail below (see FIGS. 25-27).

Figure 9A:
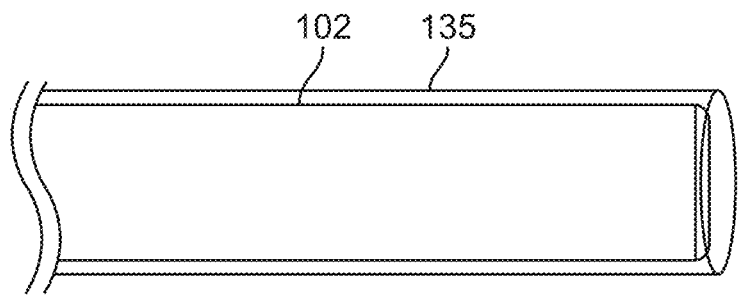
FIGS. 9A-9C illustrate schematic views of a tethering device deployment, in accordance with an implementation.
Figure 9B:
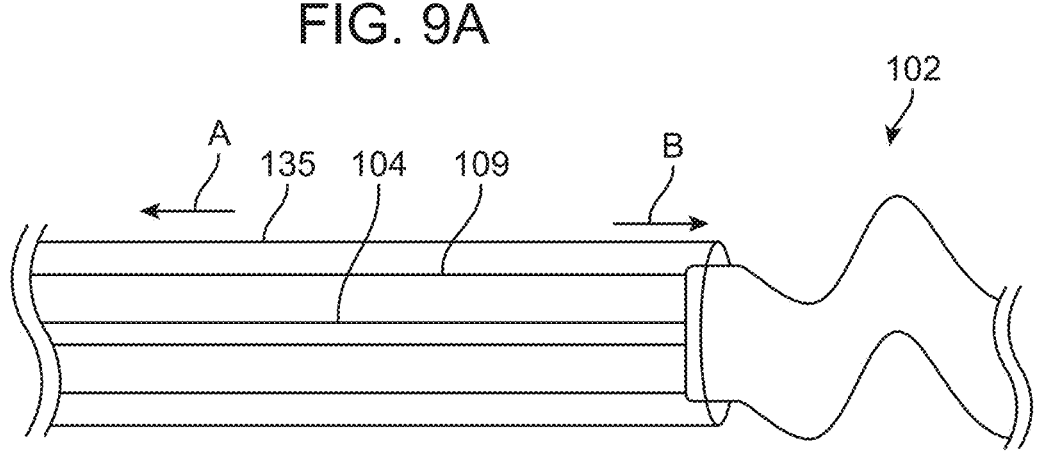
Figure 9C:
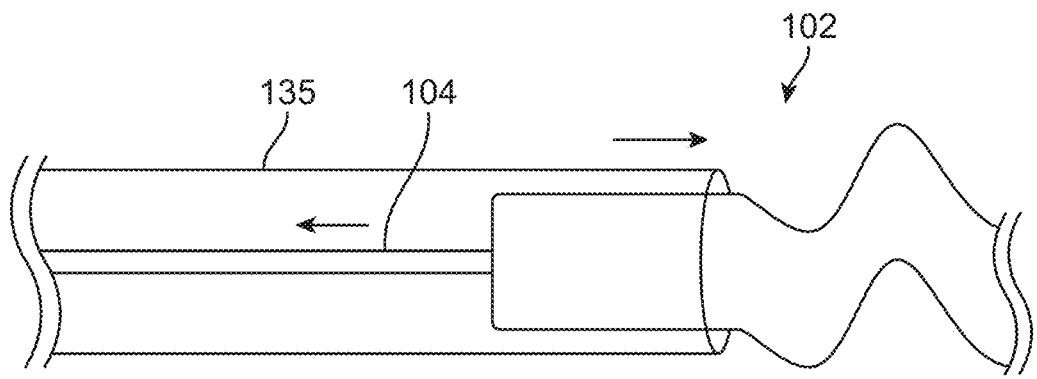

As described herein the tethering device can vary in its pushability, steerability, torque and opacity. Thus, in some implementations the tethering device 100 can have a relatively pushable tether 104 such that the tethering device 100 can be advanced through a guide catheter. In other implementations, the tethering device has a tether 104 that is less pushable to advance and steer the anchor 102 into place. Thus, a pusher tube 109 or other tubular element 135 configured to receive the tether 104 may be incorporated to aid in the delivery of the anchor 102 to the target site through a catheter lumen. FIGS. 9A-9B illustrate a schematic view of a tethering device 100 having an anchor 102 configured to be elastically deformed into a low profile configuration. In the low-profile configuration, the coil segments 126 of the anchor 102 coupled at a distal end region of the tether 104 are extended or substantially straightened into a smaller profile configuration such as those shown by dotted lines in FIGS. 5H-5I such that the anchor 102 can be positioned within a tubular element 135 (see FIG. 9A). A pusher tube 109 can be positioned over the tether 104 and within the tubular element 135 such that a distal end of the pusher tube 109 abuts a proximal end of the anchor 102 to aid in the delivery of the anchor 102 at the target location. In order to release the anchor 102 into the higher-profile configuration, the tubular element 135 can be withdrawn in a proximal direction (arrow A) and/or the pusher tube 109 advanced in a distal direction (arrow B) urging at least a portion of the anchor 102 to exit the tubular element 135 prior to unsheathing the anchor 102 from the tubular element 135 such that the anchor 102 emerges from the lumen of the tubular element 135 and self-expand or otherwise return to a larger profile configuration to anchor within a vessel (see FIG. 9B). The pusher tube 109 can have an outer diameter between that of the tether 104 and the anchor 102, for example an outer diameter of 0.006-inch to 0.038 inch, e.g. 0.021-inch. As described elsewhere herein, one or more locking elements 130 can be coupled to the tether 104, the tubular element 135, and/or a portion of the pusher tube 109 and situated outside of a patient anatomy and/or a rotating hemostatic valve (RHV) coupled with a proximal end of the tetherable guide-sheath. Further, as described elsewhere herein, the anchor 102 can be re-sheathed such as by advancing the tubular element 135 in a distal direction, pulling the tether 104 in a proximal direction, or both such that the anchor 102 abuts a distal end of the tubular element 135 and gradually straightens as the anchor 102 is pulled into the tubular element 135 (FIG. 9C).

Figure 10A:
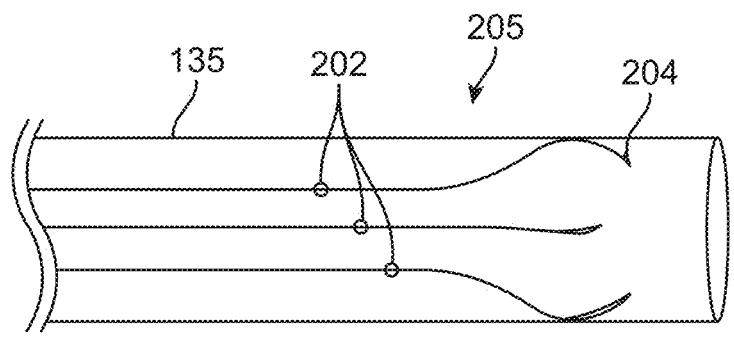
FIGS. 10A-10C illustrate schematic views of a tethering device deployment, in accordance with an implementation.
Figure 10B:
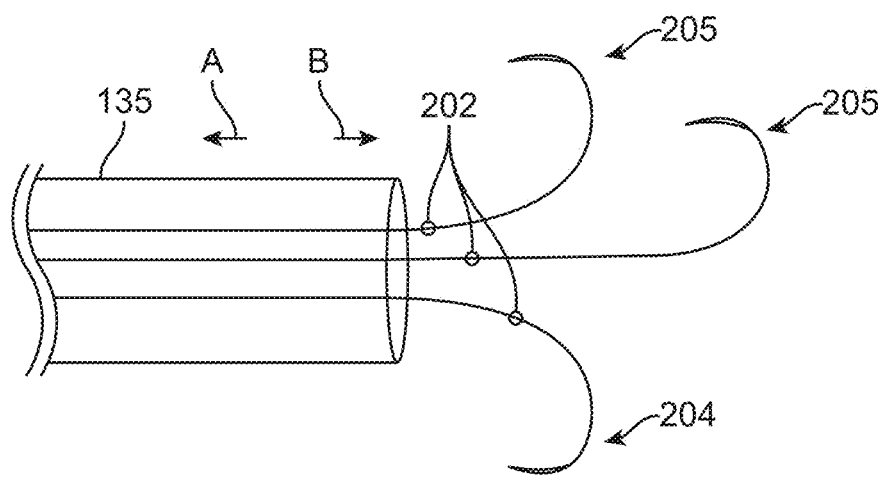
Figure 10C:
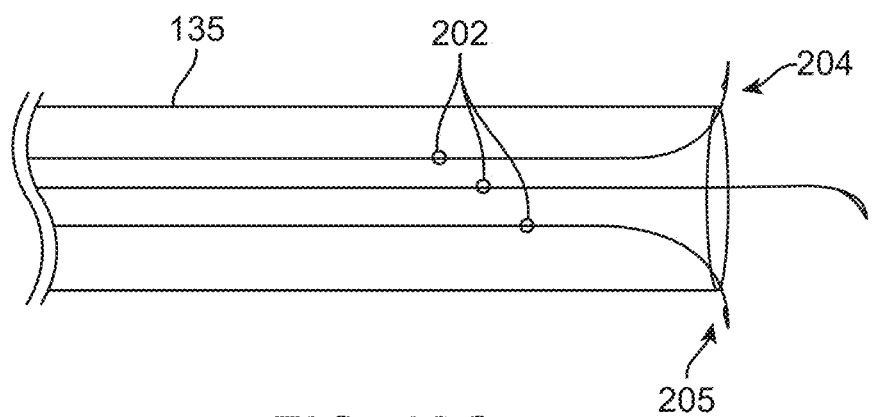

As described above, the anchor 102 can incorporate one or more struts 202 having free, distal strut ends 204. As shown in FIGS. 10A-10C, the strut ends 204 can form cleats 205 that protrude outwards upon expansion or release of the struts 202 form their constrained configuration such that the pointed ends 204 of the cleats 205 can engage with the vessel wall. The cleats 205 can undergo flexure upon sheathing and re-sheathing such that they can be removable from the vessel. FIG. 10A shows the struts 202 in a constrained configuration such that the cleats 205 and their pointed ends 204 are contained within a tubular element 135. Upon retraction of the tubular element 135 in a proximal direction (arrow A) and/or extension of the struts 202 in a distal direction (arrow B), the struts 202 and associate cleats 205 are released from constraining forces (FIG. 10B). The struts 202 can flex in a direction away from the longitudinal axis of the tubular element 135 and the associated cleats 205 can flex or bend such that their pointed ends 204 extend towards the vessel wall. In some implementations, the cleats 205 upon release from the constraint of the tubular element 135 can take on a curved shape such that their pointed ends 204 are oriented in a direction back toward a proximal direction (see FIG. 10B). As such, the cleats 205 can allow for distal movement within the vessel, but are prevented from moving proximally within the vessel due to the pointed ends 204 of the cleats 205 snagging on the vessel wall. The pointed ends 204 of the cleats 205 can be urged away from the vessel wall during re-sheathing, for example by advancing the tubular element 135 in a distal direction such that the pointed ends 204 of the cleats 205 flex back towards the longitudinal axis and the struts 202 are constrained in the lower profile configuration within the tubular element 135 (see FIG. 10C).

Figure 10D:
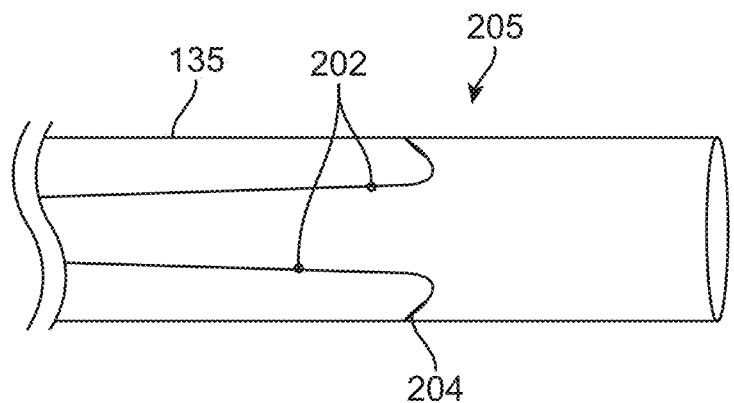
FIGS. 10D-10E illustrate schematic views of a further implementation of a tethering device deployment, in accordance with an implementation.
Figure 10E:
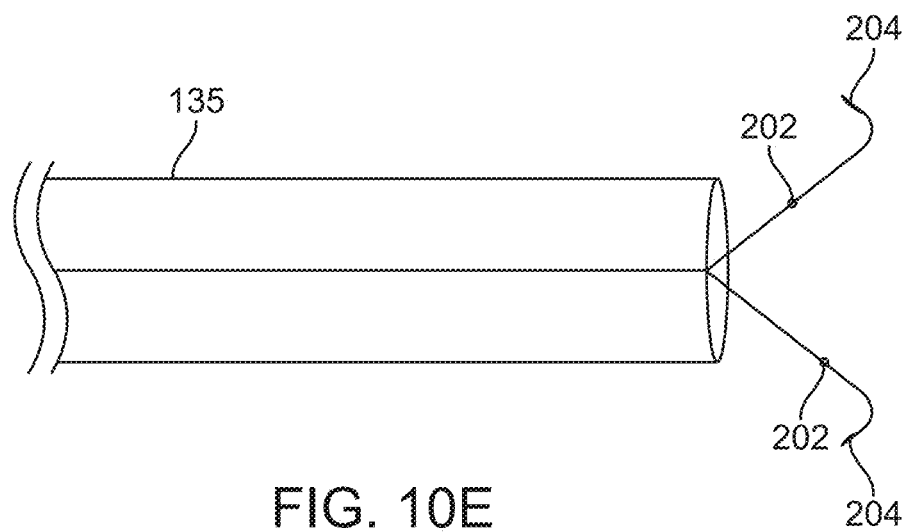

FIGS. 10D-10E illustrate another implementation of cleats 205 that can spring out upon withdrawal of or advancement from a tubular element 135.

Tetherable Guide-Sheath

Figure 11:
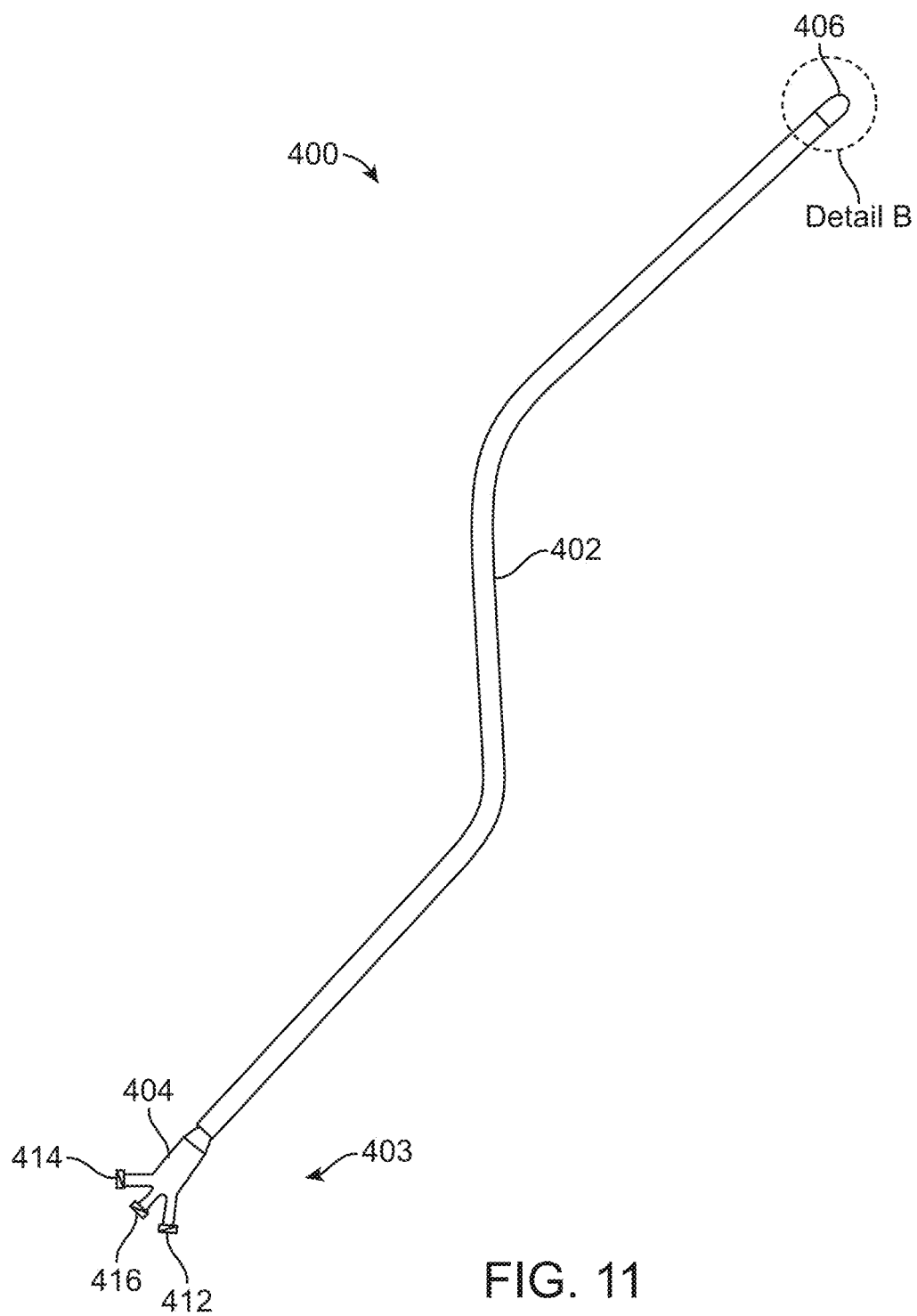
FIG. 11 illustrates a perspective view of a tetherable guide-sheath, in accordance with an implementation.

Again with respect to FIGS. 1A-1B, the anchoring delivery system 10 can include a tethering device 100 and a tetherable guide-sheath 400 to support and guide working devices 802 to a target anatomy. It should be appreciated that although the tethering devices are described herein in the context of implementations of tetherable guide-sheaths 400 that they may be used with conventional sheaths to provide the fixation and support as described elsewhere herein. FIG. 11 shows a perspective view of an implementation of a tetherable guide-sheath 400. The tetherable guide-sheath 400 can be an over-the-wire (OTW) type device and include an elongated body 402 extending from a proximal furcation 404 at a proximal end region 403 to a tip 406 at a distal end configured to bluntly dissect through and dilate narrowed sections of a diseased vessel as it is advanced. The proximal furcation 404 may include several lumens molded into a connector body to connect to corresponding lumens of the body 402 of the tetherable guide-sheath 400. For example, the body 402 and the proximal furcation 404 may include a respective tether lumen 408 and a respective working lumen 410. The proximal furcation 404 may also include additional lumens, e.g., an optional lumen 412, that can be connected to a corresponding lumen of the body 402 to serve a purpose other than receiving the tether 104 of the tethering device 100 or receiving a working device 802 to be delivered to a target anatomy. For example, the optional lumen 412 may be connected with a syringe to deliver contrast through a contrast lumen in the body 402 toward the tip 406 and into the target anatomy. A segment of the tether lumen 408 can bifurcate away from a segment of the working lumen 410. More particularly, the segment of the tether lumen 408 may extend at an angle from the segment of the working lumen 410 to create a separation between the tether proximal port 414 and the working proximal port 416. The tether lumen 408 can extend from the tether distal port 504 at a distal end to a tether proximal port 414 of the proximal portion 403 of the elongated body 402. Similarly, the working lumen 410 can extend from a distal end to a working proximal port 416 of the proximal portion 403 of the elongated body 402.

The furcation 404 can be coupled to a rotating hemostatic valve (RHV) 434. As mention above, the furcation 404 can include an optional lumen 412 that may be connected with a syringe via a connector 432 to deliver a forward drip, a flush line for contrast or saline injections through a lumen in the body 402 toward the tip 406 and into the target anatomy. The optional lumen 412 can also connect to a large-bore aspiration line and an aspiration source (not shown) such as a syringe or pump to draw suction through the working lumen 410. The furcation 404 can be constructed of thick-walled polymer tubing or reinforced polymer tubing. The RHV 434 allows for the introduction of devices through the guide-sheath 400 into the vasculature, while preventing or minimizing blood loss and preventing air introduction into the guide-sheath 400. The RHV 434 can include a flush line or connection to a flush line so that the guide-sheath 400 can be flushed with saline or radiopaque contrast during a procedure. The flush line can also be used as a second point of aspiration. The RHV 434 can be integral to the guide-sheath 400 or the guide-sheath 400 can terminate on a proximal end in a female Luer adaptor to which a separate hemostasis valve component, such as a passive seal valve, a Tuohy-Borst valve or rotating hemostasis valve may be attached. The valve 434 can have an adjustable opening that is open large enough to allow removal of devices that have adherent clot on the tip without causing the clot to dislodge at the valve 434 during removal. Alternately, the valve 434 can be removable and is removed when a device is being removed from the sheath 400 to prevent clot dislodgement at the valve 434. The furcation 404 can include various features of the proximal components described, for example, in U.S. application Ser. No. 15/015,799, filed Feb. 4, 2016, which is incorporated herein in its entirety. The systems described herein can provide advantages from a user-standpoint over tri-axial systems in that they can be safely used by a single user. Common tri-axial systems have multiple RHV—one for each component inserted. The positional location of the various components on the table, from left to right, inform users of which component it is. For example, components positioned to a right side of the table are inserted more distally and components positioned to the left side of the operating table are inserted more proximally. The space on the table must be quite large (e.g. up to 210 cm-220 cm long). Generally all the components are arranged in this way and require an additional technician to organize and arrange the various components. The systems described herein incorporate components inserted through a single RHV. As such, rather than relying on a positional organization spread out across a table over 6 feet long, multiple components of the systems described herein extend through the same RHV such that a single user can control delivery, all the components can be shorter, and can be used with less risk of sterile field contamination.

The length of the elongated body 402 is configured to allow the distal tip 406 of the body 402 to be positioned as far distal as the bifurcation between the external carotid artery (ECA) and the internal carotid artery (ICA), for example, from a transfemoral approach with additional length providing for adjustments if needed. In some implementations, the length of the body 402 can be in the range of 80 to 90 cm or up to about 100 cm or up to about 105 cm. In implementations, the body 402 length is suitable for a transcarotid approach to the bifurcation of the carotid artery, in the range of 20-25 cm. In further implementations, the body 402 length is suitable for a transcarotid approach to the CCA or proximal ICA, in the range of 10-15 cm. The body 402 is configured to assume and navigate the bends of the vasculature without kinking, collapsing, or causing vascular trauma, even, for example, when subjected to high aspiration forces.

Figure 12A:
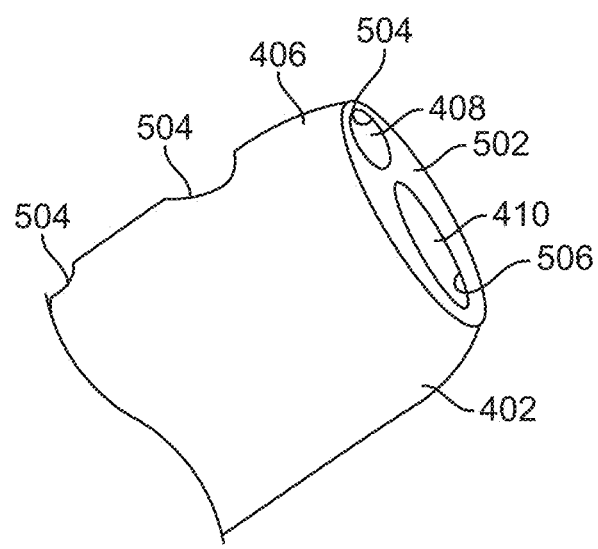
FIGS. 12A-12B illustrate detail views, taken from Detail B of FIG. 11, of a distal end of a tetherable guide-sheath.

Referring to FIG. 12A, a detail view, taken from Detail B of FIG. 11, of a distal end of a tetherable guide-sheath is illustrated in accordance with an implementation. The tip 406 of the tetherable guide-sheath 400 can have a same or similar outer diameter as a section of the body 402 leading up to the distal end. Accordingly, the tip 406 may have a distal face 502 orthogonal to a longitudinal axis passing through the body 402 and the distal face 502 may have an outer diameter substantially equal to a cross-sectional outer dimension of the body 402. In an implementation, the tip 406 includes a chamfer, fillet, or taper, making the distal face 502 diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402 (see FIGS. 12C-12D). Thus, the tip 406 can be elongated or can be more bluntly shaped. Accordingly, the tip 406 may be configured to smoothly track through a vasculature and/or to dilate vascular restrictions as it tracks through the vasculature. In an implementation, the tether lumen 408 may have a distal end forming a tether distal port 504 in the distal face 502. Similarly, the working lumen 410 may have a distal end forming a working port 506 in the distal face 502. As will be described below, the tetherable guide-sheath 400 may also include one or more tether entry ports 504 along a side of the body 402.

Figure 12B:
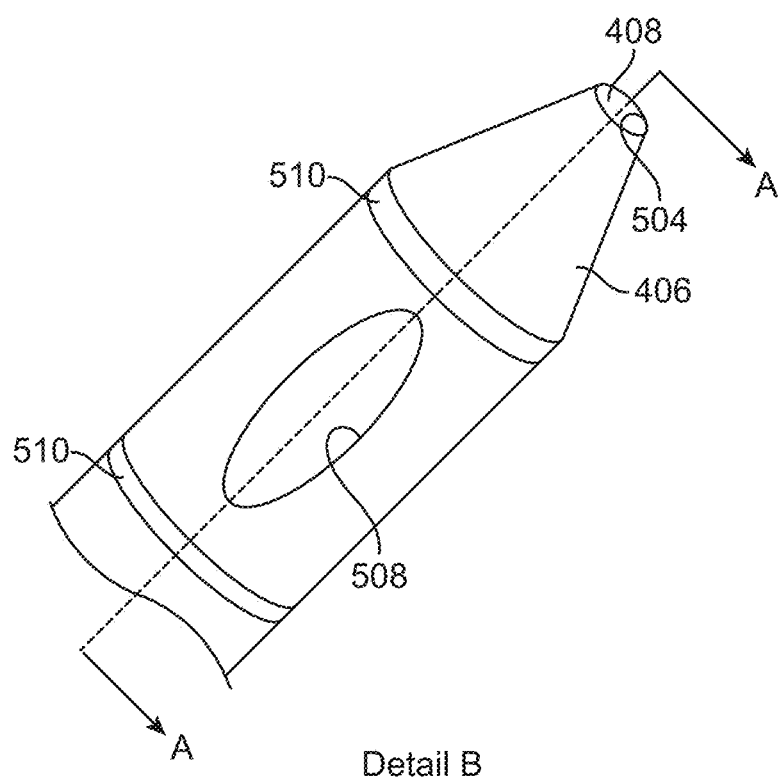

Referring to FIG. 12B, a detail view, taken from Detail B of FIG. 11, of a distal end of a tetherable guide-sheath is illustrated in accordance with an implementation. The tetherable guide-sheath 400 may include a tip 406 that tapers from a section of the body 402 leading up to the distal end. That is, an outer surface of the body 402 may have a diameter that reduces from a larger dimension to a smaller dimension at a distal end of the tether lumen 408, i.e., at the tether distal port 504. For example, the tip 406 can taper from an outer diameter of approximately 0.114" to about 0.035". The angle of the taper of the tip 406 can vary depending on the length of the tapered tip 406. For example, in some implementations, the tip 406 tapers from 0.110" to 0.035" over a length of approximately 50 mm. In an implementation, the tether distal port 504 is centered along a longitudinal axis passing through the body 402. Thus, the tapered tip 406 may be concentrically disposed around the tether distal port 504. Accordingly, the tapered tip 406 may track smoothly around bends within the targeted anatomy to avoid causing trauma to the tissue. The working lumen 410 may extend parallel to the tether lumen 408 through the body 402 to a mouth 508 located proximal to the tether distal port 504 near the distal end of the tetherable guide-sheath 400. More particularly, the working port 506 may be an elongated mouth 508 disposed in a side surface of the body 402, for example proximal to the tip taper. The mouth 508 may be formed in the side surface using manufacturing techniques such as skiving and/or drilling. Thus, the mouth 508 may have a dimension in at least one direction that is larger than a diameter of the working lumen 410. For example, the mouth 508 may have a longitudinal dimension that is larger than a cross-sectional diameter of the working lumen 410. The diameter of the mouth 508 can be at least 1.5×, 2×, 2.5×, or 3× as large as an outer diameter of a working device 802 extending therethrough. The mouth 508 can be skived such that it has a length from a proximal end to a distal end that allows for a working device 802 to exit at a range of angles, for example, very nearly parallel to the body 402 to a position that is at an angle to the body 402, for example substantially perpendicular as well as greater than a right angle to the body 402. This arrangement allows for ease of delivery of a working device 802 through the mouth 508 even in the presence of a severe angulation within the vessel being traversed or where a bifurcation is present. Often, tortuous segments in vessels and bifurcations have severe angulations to 90° or greater angle up to 180°. Classic severe angulation points in the vasculature can include the aorto-iliac junction, the left subclavian artery takeoff from the aorta, the brachiocephalic (innominate) artery takeoff from the ascending aorta as well as many other peripheral locations. A distal tip 406 can extend well beyond a distal end of the mouth 508 such that the tip 406 forms an elongate, soft tip for maneuvering through the turns of the vasculature (see, e.g., FIGS. 12C-12D). In some implementations, the mouth 508 can be located just proximal to the tip 406 or can be located at least 0.25 mm or more away from the tip 406.

In an implementation, the tetherable guide-sheath 400 includes one or more radiopaque markers 510. The radiopaque markers 510 can be disposed near the mouth 508. For example, a pair of radiopaque bands may be swaged, painted, embedded, or otherwise disposed in or on the body 402, for example on either side of the mouth 508. In some implementations, the radiopaque markers 510 include a barium polymer, tungsten polymer blend, tungsten-filled or platinum-filled marker that maintains flexibility of the distal end of the device and improves transition along the length of the guide-sheath 400 and its resistance to kinking. In some implementations, the radiopaque marker 510 is a tungsten-loaded PEBAX or polyurethane that is heat welded to the body 402. The markers 510 are shown in the figures as rings around a circumference of one or more regions of the body 402. However, the markers 510 can have other shapes or create a variety of patterns that provide orientation to an operator regarding the position of the mouth 508 within the vessel. Accordingly, an operator may visualize a location of the mouth 508 under fluoroscopy to confirm that the mouth 508 is directed toward a target anatomy where a working device 802 is to be delivered. For example, radiopaque marker(s) 510 allow an operator to rotate the body 402 of the tetherable guide-sheath 400 at an anatomical access point, e.g., a groin of a patient, such that the mouth 508 provides access to an ICA by subsequent working device(s), e.g., catheters and wires advanced to the ICA. In some implementations, the radiopaque marker(s) 510 include platinum, gold, tantalum, tungsten or any other substance visible under an x-ray fluoroscope. In various implementations, the distance from the tether distal port 504 to the mouth 508 should be in a range that facilitates maneuvering of subsequent devices advanced through mouth 508. It should be appreciated that any of the various components of the systems described herein can incorporate radiopaque markers as described above.

Figure 12C:
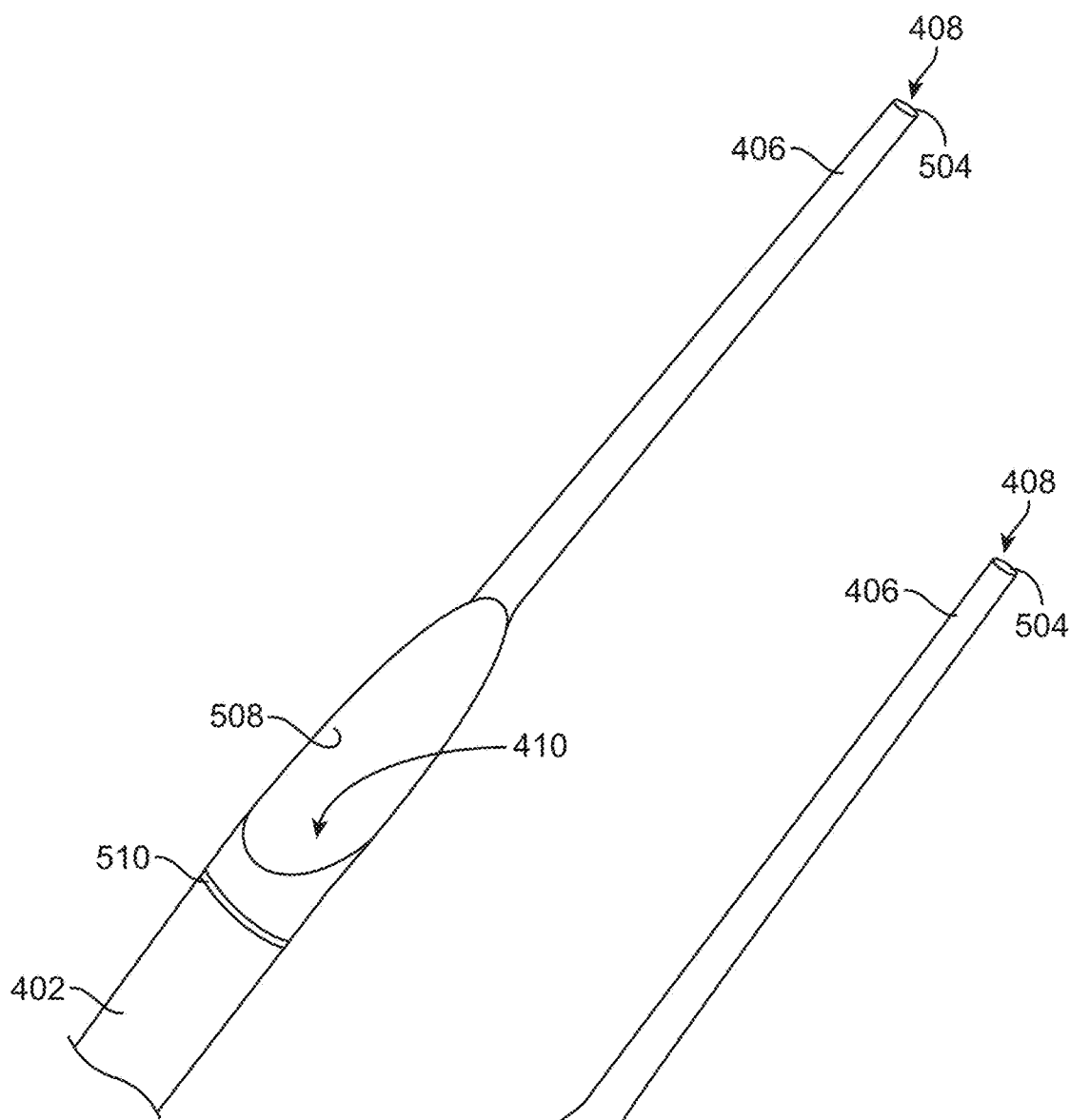
FIGS. 12C-12D illustrate detail views, taken from Detail B of FIG. 11, of a distal end of a tetherable guide-sheath.
Figure 12D:
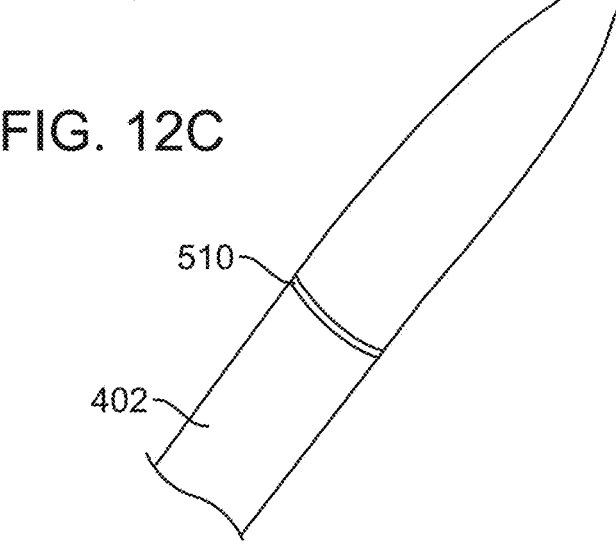
Figure 13:
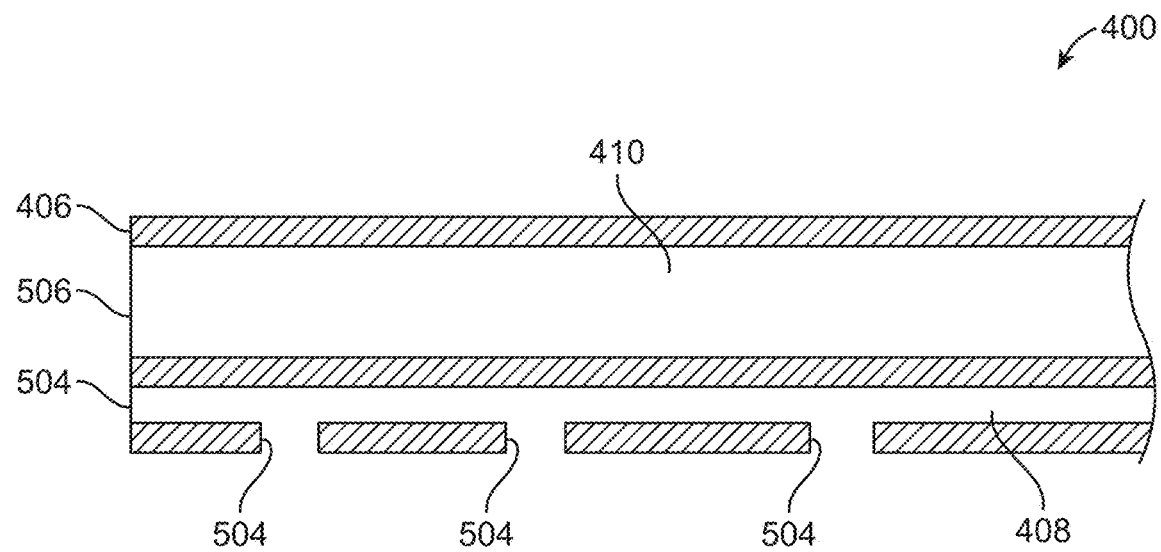
FIG. 13 illustrates a sectional view of a distal end of a tetherable guide-sheath, in accordance with an implementation.

Referring to FIG. 13, a sectional view of a distal end of a tetherable guide-sheath is illustrated in accordance with an implementation. In an implementation, the tetherable guide-sheath 400 includes the tip 406 at the distal face 502 of the body 402. Thus, FIG. 13 may be a cross-sectional view of the distal end of the tetherable guide-sheath 400 illustrated in FIG. 12A and described above. The working lumen 410 and the tether lumen 408 can extend longitudinally along respective axes between the proximal end 403 of the tetherable guide-sheath 400 and the distal tip 406. Furthermore, the tether lumen 408 may include more than one tether distal port 504. For example, a tether distal port 504 may optionally be disposed in the distal face 502 of the body 402, and one or more additional tether entry ports 504 may be disposed in a side surface of the body 402, such that the ports are in fluid communication with the tether lumen 408. More particularly, several tether entry ports 504 may be disposed in the side surface at regularly spaced intervals. The tether 104 may be inserted through any of the tether entry ports 504 into the tether lumen 408 to allow the tip 406 of the tetherable guide-sheath 400 to be advanced into a same or a different anatomy than the anatomy that the anchor 102 is deployed within. For example, the tether 104 may be disposed in an anchoring vessel and the tip 406 of the tetherable guide-sheath 400 may be advanced into a target vessel that bifurcates away from the anchoring vessel. As such, it will be recognized that depending on the tether distal port 504 through which the tether 104 is placed, a different length of the tetherable guide-sheath 400 may be advanced into the target anatomy. For example, when the tether 104 is placed in the most distal tether distal port 504 in the side surface, a distal segment of the tetherable guide-sheath 400 between the utilized tether distal port 504 and the tip 406 may be advanced into the target anatomy. When the tether 104 is placed in the most proximal port in the side surface, however, the distal segment of the tetherable guide-sheath 400 between the utilized tether distal port 504 and the tip 406 may be longer. Accordingly, a stump tip of the tetherable guide-sheath 400 as that shown in FIG. 12A or a long tip of the tetherable guide-sheath 400 as shown in FIGS. 12C-12D may be advanced into the target anatomy.

Figure 14:
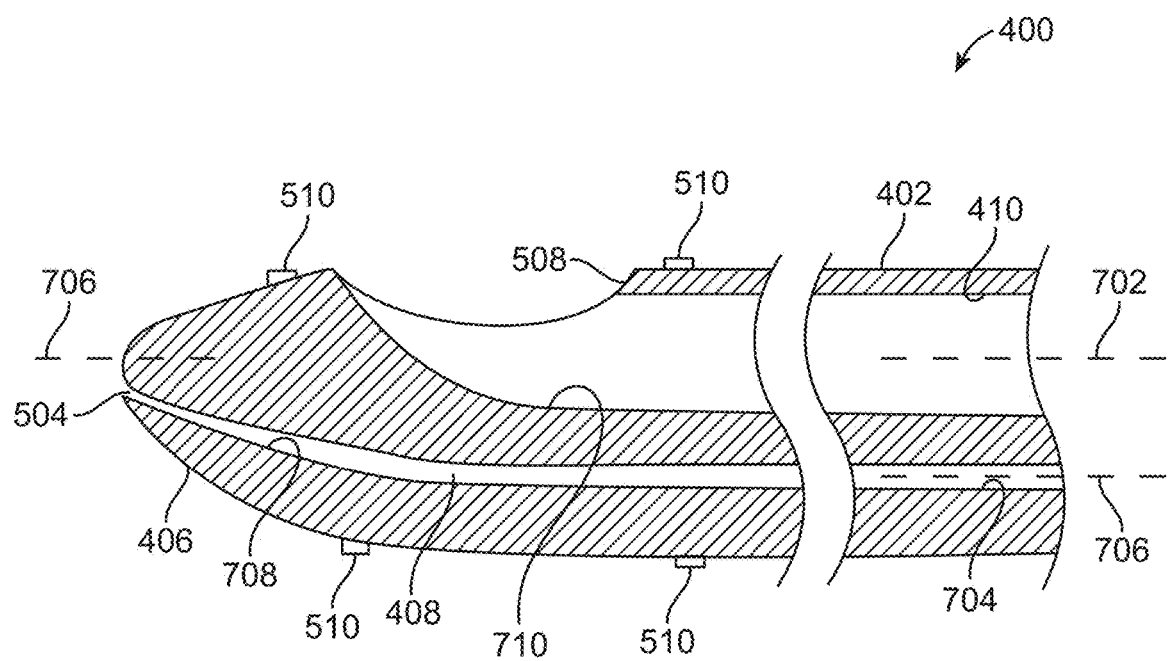
FIG. 14 illustrates a sectional view, taken about line A-A of FIG. 12B, of a distal end of a tetherable guide-sheath.

Referring to FIG. 14, a sectional view, taken about line A-A of FIG. 12B, of a distal end of a tetherable guide-sheath is illustrated in accordance with an implementation. In an implementation, the tetherable guide-sheath 400 includes the mouth 508 on a side surface of the body 402. The working lumen 410 and the tether lumen 408 may extend in a longitudinal direction through at least a portion of the tetherable guide-sheath 400. For example, the working lumen 410 may extend along a longitudinal working axis 702 between the proximal furcation 404 and the mouth 508. Similarly, a proximal tether lumen 704 having a segment extending proximal to the mouth 508 may extend along a longitudinal tether axis 706 from the proximal furcation 404 (in the case of an OTW tetherable guide-sheath 400) and/or an exit port (in the case of a rapid-exchange (RX) type of tetherable guide-sheath 400 as described below). The lumens need not, however, extend longitudinally over the entire length of the tetherable guide-sheath 400. For example, a distal tether lumen 708 segment may be directed radially inward from the proximal tether lumen 704 over a portion of the tetherable guide-sheath 400 distal to the mouth 508. More particularly, the tether lumen 408 may diverge from the longitudinal direction toward the tether distal port 504, which may be centrally located relative to a cross-section of the body 402. Thus, the tether axis 706 passing through the tether distal port 504 may be radially offset from the tether axis 706 passing through the proximal tether lumen 704. The tether axis 706 passing through the tether distal port 504 may pass through the working lumen 410 at a location proximal to the mouth 508, i.e., the tether distal port 504 may be longitudinally aligned with the working lumen 410. In an implementation, the tether axis 706 passing through the tether distal port 504 may be coaxial with the working axis 702, or may be closer to the working axis 702 then to the tether axis 706 extending through the proximal tether lumen 704.

In an implementation, the working lumen 410 extends along a deflecting surface 710 that directs a working device 802 passing distally through the body 402 outward through the mouth 508. More particularly, the working lumen 410 may extend from the mouth 508 at the tip 406 of the tetherable guide-sheath 400 to a proximal end 403 of the tetherable guide-sheath 400, and the tetherable guide-sheath 400 may include a deflecting surface 710 between the working lumen 410 and the tether lumen 408. The deflecting surface 710 may be oblique to the working lumen 410. That is, the deflecting surface 710 may include a ramp having a radius that provides a smooth distal transition from the working axis 702 to an exit axis extending radially outward through the mouth 508. The exit axis may be at an angle to the working axis 702, for example, a 10, 15, 20, 25, 30, 35, 40, or 45 degree angle. In some implementations the exit axis is at a 30° angle.

As described above, the body 402 of the tetherable guide-sheath 400 may include at least one lumen, and may include several lumens. More particularly, the implementations depicted in FIGS. 12-14 are dual-lumen catheters having a working lumen 410 accompanied by a tether lumen 408 along a majority of a length of tetherable guide-sheath 400. A diameter of tether lumen 408 may be less than a diameter of working lumen 410. Furthermore, the diameter of tether lumen 408 may vary. For example, the tether lumen 408 may have a diameter large enough to receive the tether 104, but not large enough to receive the anchor 102 of the tethering device 100. Alternatively, the tether lumen 408 may have a diameter large enough to receive the anchor 102 over at least a portion of a length of the tether lumen 408, e.g., to allow the anchor 102 to be pushed or pulled through the tether lumen 408. The tether lumen 408 may also have a diameter large enough to receive the anchor 102 when the anchor 102 is urged into a lower profile configuration such that it can be received within at least a portion of the tether lumen 408.

According to some implementations, the tether lumen 408 is independent of the working lumen 410, and the working lumen 410 runs the entire length of tetherable guide-sheath 400. In some implementations, the tetherable guide-sheath 400 will have performance characteristics similar to other sheaths used in carotid access and AIS procedures in terms of kinkability, radiopacity, column strength, and flexibility. The working lumen 410 may deliver a working device toward the anchor 102, and the working device may be directed to the deflecting surface 710 to smoothly exit at an angle to the longitudinal axis of the working lumen 410. Furthermore, the mouth 508 of the tetherable guide-sheath 400 may be wider than the internal diameter of the working lumen 410 so as to allow a wide range of exit angles of a working device exiting the tetherable guide-sheath 400. According to some implementations, the exiting working device can run almost parallel with the tetherable guide-sheath 400 to greater than 90 degrees, which severely angulated arteries may require. Exit angles from the mouth 508 of the tetherable guide-sheath 400 should consider the variety of angles that the anatomy may require.

Figure 15A:
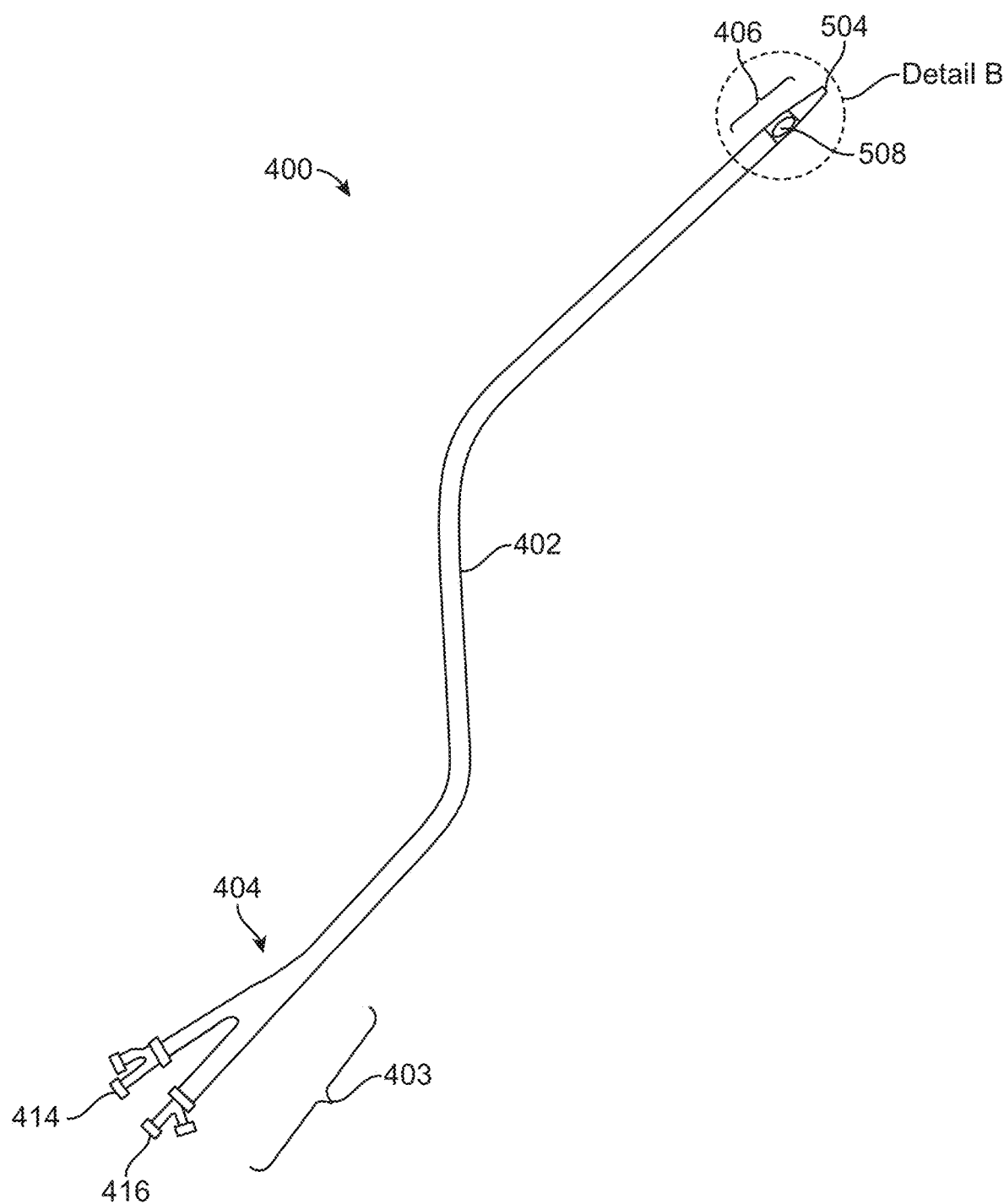
FIG. 15A illustrates a perspective view of a tetherable guide-sheath, in accordance with an implementation.

FIG. 15A illustrates a perspective view of an implementation of a tetherable guide-sheath 400. As with other implementations, the tetherable guide-sheath 400 can include an elongated body 402 containing one or more lumens extending from a distal end to a proximal portion. For example, a tether lumen 408 may extend from a tether distal port 504 at a tip 406 of the tetherable guide-sheath 400 to a tether proximal port 414 of the proximal portion 403. Similarly, a working lumen 410 may extend from a mouth 508 of the tip 406 to a working proximal port 416 of the proximal portion 403. The tetherable guide-sheath 400 may include a proximal furcation 404 in the proximal portion 403 where a segment of the tether lumen 408 bifurcates away from a segment of the working lumen 410. More particularly, the segment of the tether lumen 408 may extend at an angle from the segment of the working lumen 410 to create a separation between the tether proximal port 414 and the working proximal port 416. One or more of the tether proximal port 414 or the working proximal port 416 may incorporate a tether gripper 1502 (see FIGS. 25-27).

Figure 15B:
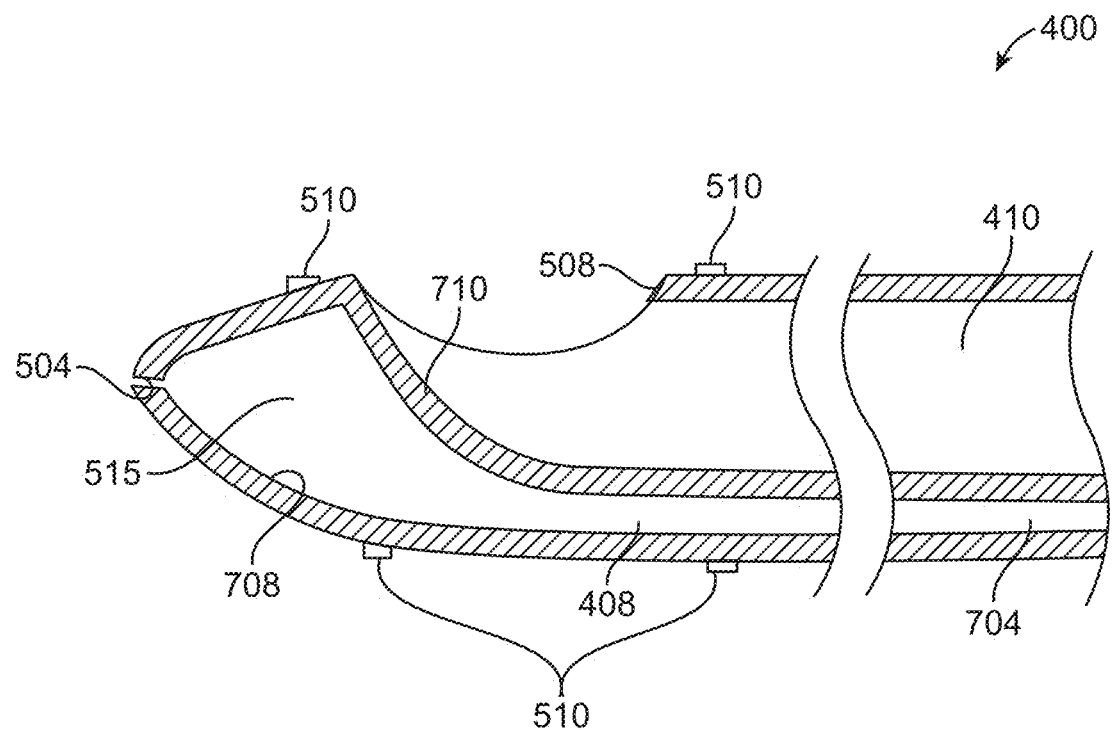
FIG. 15B illustrates a detailed sectional view, taken from Detail B of FIG. 15A, of a distal portion of a tetherable guide-sheath, in accordance with an implementation.

Referring to FIG. 15B, a detailed sectional view taken from Detail B of FIG. 15A, of a distal portion of a tetherable guide-sheath is illustrated in accordance with an implementation. In an implementation, the tetherable guide-sheath 400 may include a chamber 515 located proximal to the tether distal port 504 in the tip 406. The chamber 515 may be sized to receive the anchor 102 of the tethering device 100. For example, the tether distal port 504 may be chamfered, i.e., having a distal port diameter that is larger than a proximal port diameter, such that the proximal joint 108 of the tethering device 100 moves smoothly into the tether distal port 504 when the tetherable guide-sheath 400 is advanced over the anchor 102. The tether distal port 504 may expand slightly to receive the anchor 102. Furthermore, the anchor

102 may be retracted into the chamber 515 to store the anchor 102. Thus, in an implementation, the chamber 515 within the tip 406 of the tetherable guide-sheath 400 may have a chamber volume that is at least as large as a volume occupied by the anchor 102 when the anchor 102 is in the unexpanded, lower profile state. The chamber 515 may also have a variable chamber volume as described in more detail below with respect to FIGS. 17A-17B.

Figure 15C:
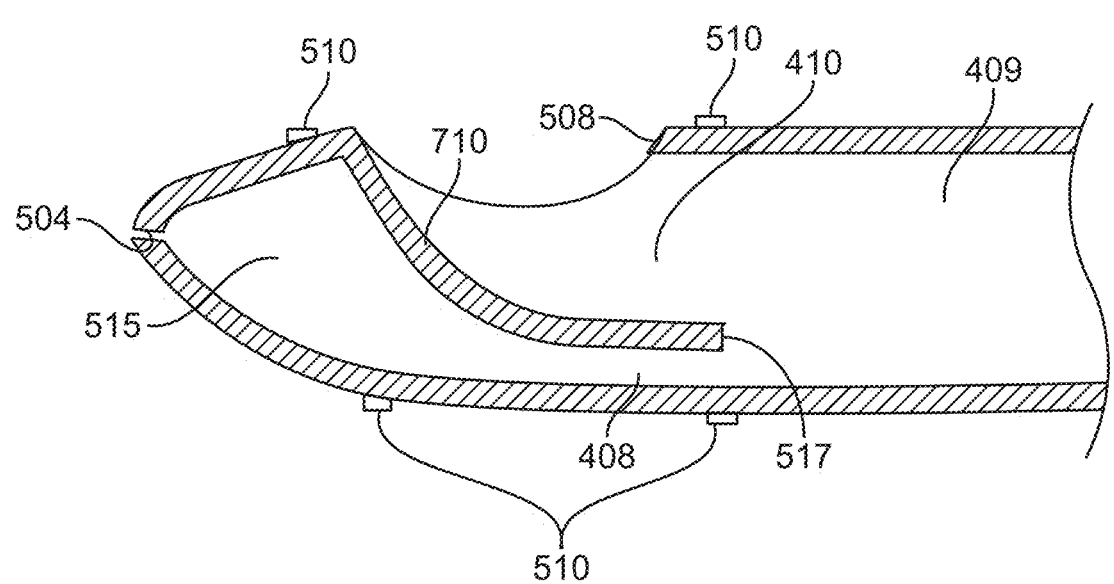
FIG. 15C illustrates a detailed sectional view, taken from Detail B of FIG. 15A, of a distal portion of a tetherable guide-sheath, in accordance with an implementation.

Referring to FIG. 15C, a detailed sectional view, taken from Detail B of FIG. 15A, of a distal portion of a tetherable guide-sheath is illustrated in accordance with an implementation. In an implementation, the separation between the working lumen 410 and the tether lumen 408 proximal to the mouth 508 may have a termination point distal to the tether gripper and/or the exit port of the tetherable guide-sheath 400. For example, the wall 517 dividing the working lumen 410 and the tether lumen 408, which the ramp 710 makes up a portion of, may end proximal to the mouth 508. This may allow the anchor 102 to remain separated from a working device in the working lumen 410 in the distal region of the tetherable guide-sheath 400. However, separation between the tether 104 and the working device at a location proximal to the mouth 508 may be less critical, and thus, the separating barrier or wall 517 may terminate near this region in order to maximize the cross-sectional area of a proximal portion of the tetherable guide-sheath 400. It will be appreciated that when there is no separating barrier between the working lumen 410 and the tether lumen 408 the lumens merge into a common lumen 409 and the tether 104 and the working device exit through a single proximal port, e.g., in the tether gripper 1502. Furthermore, it will be appreciated that a proximal edge of the separating barrier 517 may include a tapered wall thickness to ease the distal joint 108 of the working device as it is advanced from the common lumen 409 into the working lumen 410 and through the mouth 508.

Figure 16A:
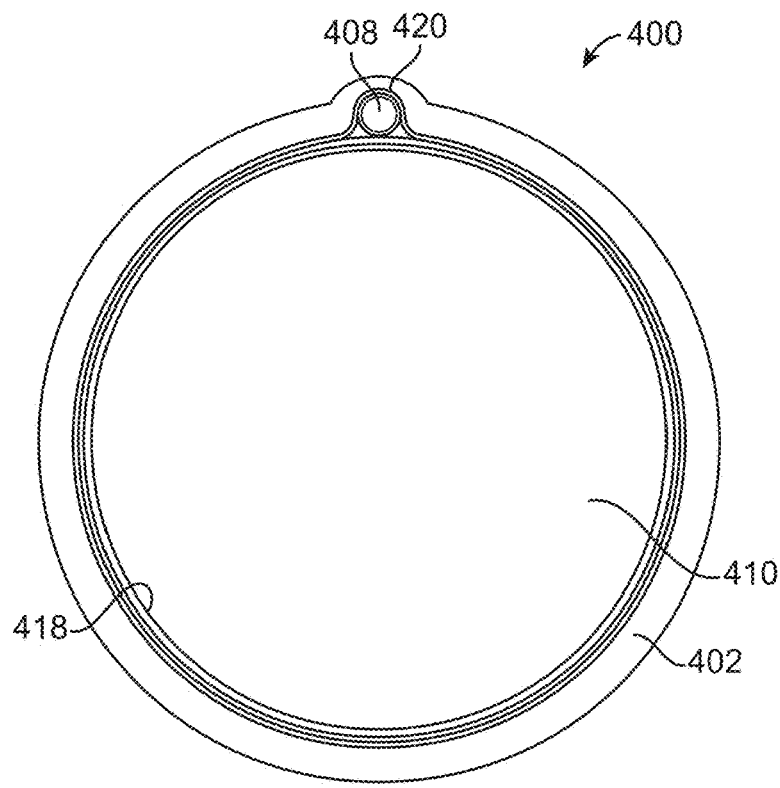
FIGS. 16A-16B illustrate sectional views of a tetherable guide-sheath, in accordance with an implementation.

Referring to FIG. 16A, a sectional view of a tetherable guide-sheath is illustrated in accordance with an implementation. The available cross-sectional area of the tetherable guide-sheath 400 may be used to maximize the working lumen 410 and to minimize the tether lumen 408. For example, the body 402 of the tetherable guide-sheath 400 may surround the working lumen 410 defined by an inner diameter of a working lumen liner 418, and the tether lumen 408 may be defined by an inner diameter of a tether lumen liner 420. The lumen liners 418, 420 may be, for example, non-concentric tubes that are laterally spaced and positioned adjacent to one another. In an implementation, a dimension of the tether lumen 408 is large enough to allow a slip fit between the tether lumen liner 420 of the tetherable guide-sheath 400 and the runner tube 113 of the tethering device 100. The dimension, however, may not be large enough to allow a slip fit between the tether lumen liner 420 and the pusher tube 109 of the tethering device 100. More particularly, the tether lumen 408 may be configured to advance over the tether 104 only after the pusher tube 109 has been removed. Accordingly, cross-sectional area that would otherwise be required to receive the runner tube 113 may instead be dedicated to the working lumen 410, and thus, the working lumen 410 may be maximized within the available cross-sectional area of the tetherable guide-sheath 400.

The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. A third layer can be incorporated that can provide reinforcement between the inner liner and the outer jacket. The reinforcement layer can prevent flattening or kinking of the inner lumens of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like. The outer jacket of the body 402 can be formed of increasingly softer materials towards the distal end. For example, proximal region of the body 402 can be formed of a material such as Nylon, a region of the body 402 distal to the proximal region of the body 402 can have a hardness of 72D whereas areas more distal can be increasingly more flexible and formed of materials having a hardness of 55D, 45D, 35D extending towards the distal tip 406, which can be formed of a material having a hardness of 35D, for example. The body 402 can include a hydrophilic coating.

Figure 16B:
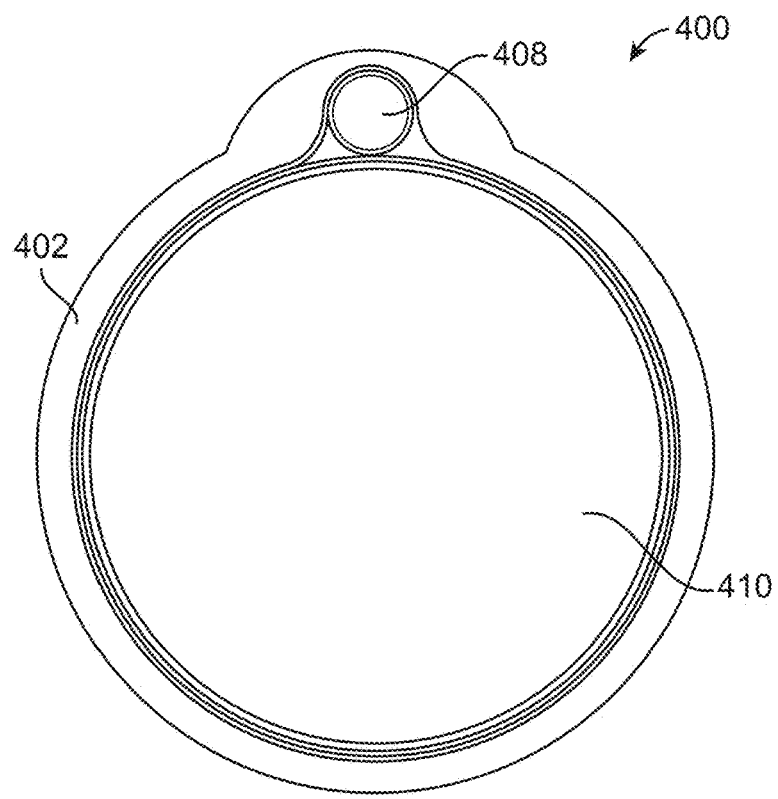

Referring to FIG. 16B, a sectional view of a tetherable guide-sheath is illustrated in accordance with an implementation. Dimensions of the tether lumen 408 and a working lumen 410 of the tetherable guide-sheath 400 may be varied in accordance with the principle described above. More particularly, although the size of the tetherable guide-sheath 400 may be changed to accommodate a particular anatomy and/or intended working device, the tether lumen 408 may be sized to receive the runner tube 113 of a corresponding tethering device 100 in the anchoring delivery system, but may not be large enough to receive the pusher tube 113 of the corresponding tethering device 100.

The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide-sheath compared to other sections of the guide-sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the elongate body 402. In another implementation, there is a transition section between the distal-most flexible section and the proximal section, with one or more sections of varying flexibilities between the distal-most section and the remainder of the elongate body 402. In this implementation, the distal-most section is about 2 cm to about 5 cm, the transition section is about 2 cm to about 10 cm and the proximal section takes up the remainder of the sheath length.

Figure 17A:
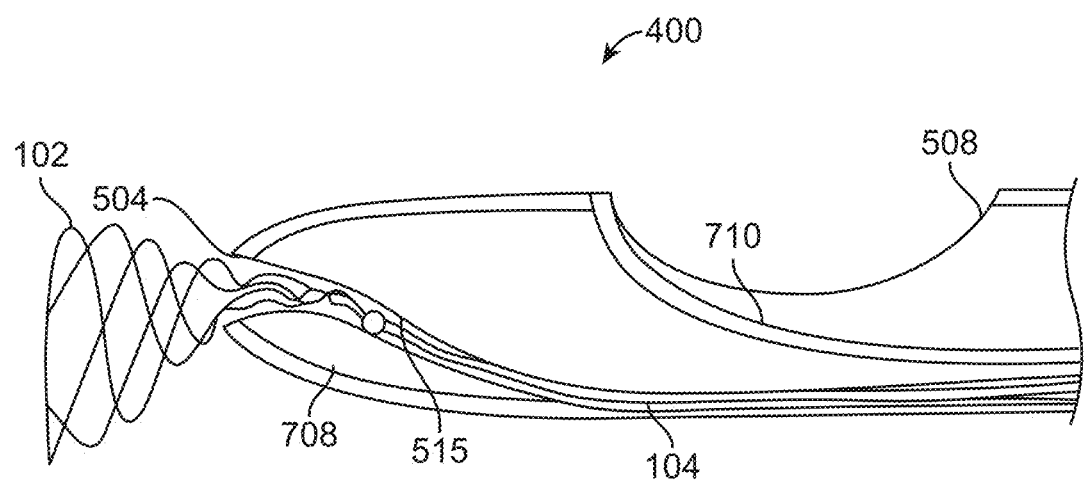
FIG. 17A illustrates a support guide during retrieval of an anchoring structure.
Figure 17B:
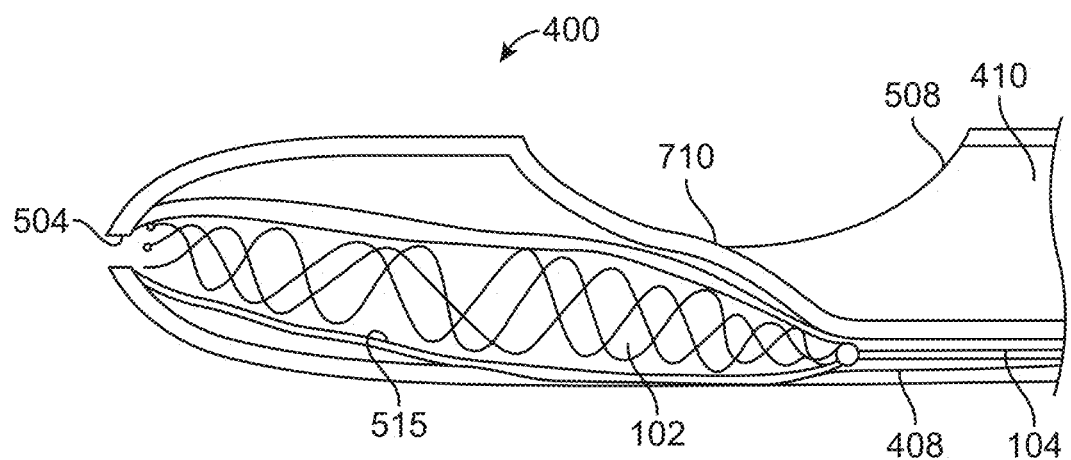
FIG. 17B illustrates the retrieved anchoring structure in a tip of the support guide of FIG. 17A.

FIGS. 17A-17B illustrate an implementation of a distal end of a tetherable guide-sheath 400 including a variable volume chamber 515. As mentioned above, the ramped deflecting surface 710 can deflect working devices from the working lumen 410 out through the mouth 508 as the working device exits the guide-sheath 400. The ramped deflecting surface 710 may be formed from a flexible membrane that is able to move, for example, toward the mouth 508 or toward an interior of the chamber 515. Thus, the ramp 710 may flex toward the chamber when a working device is being delivered through the mouth 508 of the working lumen 410. Similarly, after the working device is removed from the working lumen 410, the ramp 710 may flex toward the mouth 508 to capture the anchor 102 within the chamber 515.

As mentioned, the tetherable guide-sheath 400 may capture the anchor 102 of the tethering device 100 in one of the lumens of the tetherable guide-sheath 400. The ramp 710 not only can deflect working devices as the devices exit the tetherable guide-sheath 400, but also can deflect the anchor 102 of the tethering device 100 as it is withdrawn into the chamber 515. As an anchor 102 of a tethering device 100 is withdrawn in a proximal direction through the tether distal port 504 into chamber 515, the anchor 102 can be deflected from the expanded state towards the unexpanded state as a reaction to a relative lack of expansion of the tether distal port 504 as compared to the anchor 102 of the tethering device 100 (see FIG. 17A) as the anchor 102 is withdrawn into the tether lumen 408. More particularly, as described below, the distal tip of the tetherable guide-sheath 400 may be advanced over the tether 104 to the anchor 102 of the tethering device 100 in the anchoring vessel, and the design of the anchor 102 may allow the anchor 102 to collapse as the distal tip of the tetherable guide-sheath 400 swallows the anchor 102 and the anchor 102 is pulled into the distal tether lumen 708 segment. In some implementations, the tether distal port 504 can have a large diameter at the tip where the anchor 102 is withdrawn to avoid additional friction. The retrieval of the anchor 102 of tethering device 100 may therefore be a smooth interaction having a reduced likelihood that the anchor 102 will catch on the distal tip or fracture on an edge of the distal tip of the tetherable guide-sheath 400. Traction can be applied to the tether 104 simultaneously as the tetherable guide-sheath 400 is advanced forward so that the tethering device 100 causes minimal trauma to the vessel. Once the tip of the tetherable-guide sheath 400 is advanced over guide tether 104 and reaching the anchor 102 in the ECA, the design of the tethering device 100 can allow the anchor 102 to collapse as the distal tip of the guide-sheath 400 swallows the anchor 102. In some implementations, the withdrawal of the anchor 102 can cause expansion of deflecting surface into the working lumen 410. At the end of the procedure, such reduction in working lumen diameter 410 can be acceptable. In some implementations, an outer diameter of the tetherable guide-sheath 400 minimally increases with the capture of the anchor 102 of the tethering device 100. For example, the distal region of the tetherable guide-sheath 400 can have an inner diameter of about 0.087" to 0.088" and can be enlarged to a diameter of about 0.100" to 0.120" although the size can vary and/or can be flared.

FIGS. 18-20 illustrate different configurations of an anchoring delivery system 10 having a tethering device 100 and a tetherable guide-sheath 400 configured to receive a working device 802 therethrough. FIG. 18 shows a tethering device 100 extending through a tether lumen 408 of a tetherable guide-sheath 400 and a working device 802 extending through a working lumen 410 of the tetherable guide-sheath 400. The anchoring delivery system 10 may include a combination of the tethering device 100 and the tetherable guide-sheath 400. For example, the anchoring delivery system 10 may be manufactured as a kit including at least the tethering device 100 and the tetherable guide-sheath 400. The kit can include one or more tethering devices 100 and one or more tetherable guide-sheaths 400, such as a first tetherable guide-sheath 400 having a first inner diameter and a second tetherable guide-sheath 400 having a second, larger inner diameter. In some implementations, the kit can include the tethering device 100 pre-assembled with one or more of a hypotube positioned over the tether 104 and the anchor 102 in a low profile configuration within a delivery tool. It should be appreciated that the tethering device 100 can be provided separately from the tetherable guide-sheath 400 such that it can be used with another appropriately sized commercial guiding sheath as described elsewhere herein. The different inner diameters of the tetherable guide-sheaths 400 can be used to receive different outer diameter working devices 802. In some implementations, the working lumen 410 of a first tetherable guide-sheath 400 can have an inner diameter that is 6F and the working lumen 410 of a second tetherable guide-sheath 400 can have an inner diameter that is 8F. The 6F has an inner diameter of 0.071" and the 8F has an inner diameter of 0.088". Thus, the tetherable guide-sheaths 400 can receive working devices having an outer diameter that is snug to these dimensions. It should be appreciated that the tetherable guide-sheath 400 can be OTW or RX, which will be described in more detail below.

During use, the tethering device 100 may be physically coupled with the tetherable guide-sheath 400, e.g., by tracking the tetherable guide-sheath 400 over the tethering device 100 and/or by locking the components together, as described below. When the tetherable guide-sheath 400 includes a centrally located tether distal port 504 distal to the mouth 508, the tether 104 of the tethering device 100 may extend distally from the tether distal port 504 to the deployed anchor 102 along the longitudinal axis passing through the body 402 of the tetherable guide-sheath 400. Furthermore, the anchoring delivery system 10 can include a working device 802, which may be packaged as part of the same kit or provided separately as its own kit, to be delivered to a target anatomy. During use, the working device 802 can be tracked through the tetherable guide-sheath 400 to exit the tetherable guide-sheath 400 through the mouth 508, the mouth 508 optionally located between the radiopaque markers 510, into the target anatomy. The target anatomy can bifurcate away from the anchoring anatomy. It should be appreciated that the anchoring delivery system 10 shown in FIG. 18 can include any of a variety of tethering devices described herein including a tethering device 100 incorporating an anchor 102 configured to take on a higher profile configuration.

Referring to FIG. 19, a distal end of an anchoring delivery system having a tethering device 100 in a tether lumen 408 of a tetherable guide-sheath 400 and a working device 802 in a working lumen 410 of the tetherable guide-sheath 400 is illustrated in accordance with an implementation. The tethering device 100 can include an anchor 102 configured to be released from constraint and expanded in the anchoring anatomy at a location distal to the tetherable guide-sheath 400. More particularly, the tether 104 can extend proximally from the deployed anchor 102 through the tether distal port 504 and within the tether lumen 408 to an exit port in the tetherable guide-sheath 400. Similarly, the working device 802 being delivered to the target anatomy can pass through the working port 506 and the working lumen 410 to a proximal exit point, e.g., at the proximal furcation 404. As shown, when the tether distal port 504 and the working port 506 are formed in a distal face 502 of the body 402, the tether 104 and the working device 802 can exit the tetherable guide-sheath 400 generally parallel to each other. The components may, however, diverge along different paths. For example, the tether 104 may extend distally into the anchoring anatomy and the working device 802 may extend distally into the target anatomy, which may bifurcate away from the anchoring anatomy. It should be appreciated that the anchoring delivery system shown in FIG. 19 can include any of a variety of tethering devices described herein including a tethering device incorporating an anchor configured to take on a higher profile configuration.

Referring to FIG. 20, a distal end of an anchoring delivery system having a tethering device 100 and a working device 802 in a same lumen of a tetherable guide-sheath 400 is illustrated in accordance with an implementation. When the tetherable guide-sheath 400 includes a working port 506 in the distal face 502 of the body 402 and one or more tether entry ports 504 in the side surface of the body 402, the tethering device 100 may extend laterally through the tether entry ports 504 into the anchoring anatomy and the working device 802 to be delivered to the target anatomy can extend distally from the distal face 502 along a longitudinal axis of the body 402. As described above, depending upon the tether distal port 504 through which the tether 104 is inserted, a different length of the tetherable guide-sheath 400 may be tracked into the target anatomy. For example, a segment of the tetherable guide-sheath 400 distal to the tether distal port 504 holding the tether 104 may be advanced into the target anatomy that bifurcates from the anchoring anatomy. Accordingly, the tether 104 and the segment of the tetherable guide-sheath 400 distal to the utilized tether distal port 504 may be pressed against the carina at which the anchoring anatomy and the target anatomy bifurcate. It should be appreciated that the anchoring delivery system shown in FIG. 20 can include any of a variety of tethering devices described herein including a tethering device incorporating an anchor configured to take on a higher profile configuration.

As shown in FIG. 20, tetherable guide-sheath 400 can include a single lumen in which at least one elongated structure can be received. For example, the tether lumen 408 and the working lumen 410 can be a same lumen running longitudinally through tetherable guide-sheath 400 from proximal furcation 404 to tether distal port 504 and working port 506. Thus, the tether 104 may enter a same lumen of tetherable guide-sheath 400 through the tether distal port 504 as the working device 802 enters through the working port 506, rather than being received by separate lumens of tetherable guide-sheath 400. Thus, working port 506 shown in FIG. 20 can also be the tether distal port 504.

According to some implementations, the length of the tetherable guide-sheath 400 is long enough to access the target anatomy and exit the arterial access site with extra length outside of a patient's body for adjustments. For example, the tetherable guide-sheath 400 can be long enough to access the petrous ICA from the femoral artery such that an extra length is still available for adjustment. The tetherable guide-sheath 400 can be a variety of sizes to accept various working devices 802 and can be accommodated to the operator's preference. For example, current MAT and SMAT techniques describe delivering aspiration catheters having inside diameters of 0.071-0.072 inches to an embolus during AIS. Accordingly, the working lumen 410 of the tetherable guide-sheath 400 can be configured to receive such aspiration catheters as the working device 802. For example, the working lumen 410 can have an inner diameter of at least 6 French, or preferably at least 6.3 French to accommodate such working devices 802. The inner diameter of the tetherable guide-sheath 400, however, may be smaller or larger. In some implementations, the working lumen 410 can have an inner diameter of 7 French or 8 French to accommodate even larger working devices 802. In some implementations, the working lumen 410 can having an inner diameter of 0.088" or 0.071" and thus, are configured to receive a working device 802 having an outer diameter that fits snug with these dimensions. In alternative implementations, the distal tip of the tetherable guide-sheath 400 may be balloon-tipped to provide anchoring and/or flow arrest (see FIGS. 39A-39B, as will be described in more detail below). Regardless of the length and inner diameter, the tetherable guide-sheath 400 is resistant to kinking during distal advancement through the vasculature.

Referring to FIG. 21, a perspective view of a tetherable guide-sheath is illustrated in accordance with an implementation. The tetherable guide-sheath 400 can be a rapid exchange (RX) type device. Accordingly, the tetherable guide-sheath 400 can include a hypotube 1102 extending distally from a connector 1104 at a proximal end 403. The hypotube 1102 can be coupled with the body 402 of the tetherable guide-sheath 400 at a joint between the connector 1104 and the tip 406. Furthermore, an exit port 1106 can be positioned distal from the joint. The exit port 1106 can connect with the tether lumen 408 in the body 402. Furthermore, the connector 1104 can connect with the working lumen 410 in the body 402.

Referring to FIG. 22, a sectional view, taken about line B-B of FIG. 20, of a tetherable guide-sheath is illustrated in accordance with an implementation. The body 402 of the tetherable guide-sheath 400 can include one or more lumens extending longitudinally toward the tip 406. For example, the body 402 can include the tether lumen 408 to receive the tether 104 of the tethering device 100. Furthermore, the body 402 can include the working lumen 410 to receive the working device 802 to be delivered through tetherable guide-sheath 400 to a target anatomy. The lumens 408, 410 can be sized to receive their respective working devices in a sliding fit. For example, the tether 104 can have an outer diameter of 0.014 inch and the tether lumen 408 can have an inner diameter in a range of 0.015-0.020 inch sufficient to receive the outer diameter of the tether 104. Similarly, the tether 104 can have an outer diameter of 0.035 inch and the tether lumen 408 can have an inner diameter in a range of 0.036-0.041 inch. The working lumen 410 may be similarly sized according to the working device 802 that will be delivered through it to the target anatomy. More particularly, the working lumen 410 may have an inner diameter that is at least 0.001 inch larger than an outer diameter of any working device 802 it is intended to receive, particularly if the working device 802 is to be used for aspiration as will be described in more detail below.

Referring to FIG. 23, a sectional view, taken about line C-C of FIG. 20, of a tetherable guide-sheath is illustrated in accordance with an implementation. When tetherable guide-sheath 400 is an RX-type working device, the hypotube 1102 may have an inner diameter that is at least as large as the working lumen 410 in the body 402. For example, the working lumen 410 in the hypotube 1102 may have a diameter that is at least 0.001 inch larger than any working device 802 that it is intended to receive.

Figure 24:
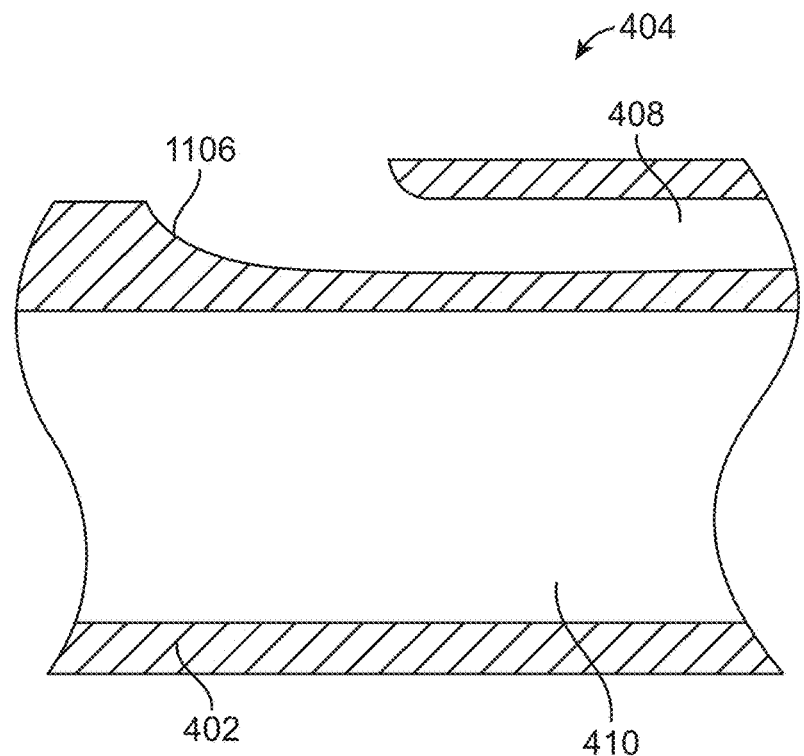
FIG. 24 illustrates a sectional view of a proximal end of the tether lumen of a tetherable guide-sheath, in accordance with an implementation.

Referring to FIG. 24, a sectional view of a proximal end of the tether lumen of a tetherable guide-sheath is illustrated in accordance with an implementation. When the tetherable guide-sheath 400 is an RX type device, the tether 104 of the tethering device 100 can exit the exit port 1106 in the body 402 distal to the hypotube 1102, which contains the working lumen 410 of the tetherable guide-sheath 400. Accordingly, the exit port 1106 may be considered to be the proximal furcation 404 in the tetherable guide-sheath 400, as it represents a location where the tether 104 and the working device 802 diverge from each other at a proximal location in the system. In practice, the exit port 1106 can be located within the patient, and thus, the tether 104 and the hypotube 1102 can emerge from the access site in a side-by-side manner. The tether lumen 408 and the working lumen 410 can extend along respective longitudinal axes that are parallel to each other near the exit port 1106. However, like the mouth 508 of the tetherable guide-sheath 400, the tether lumen 408 may be directed toward the exit port 1106 formed in the side surface of the body 402 such that the tether 104 exits the body 402 at an angle to the longitudinal axis of the tether lumen 408. This exit angle may be controlled by a radius used to form the exit port 1106.

Figure 25:
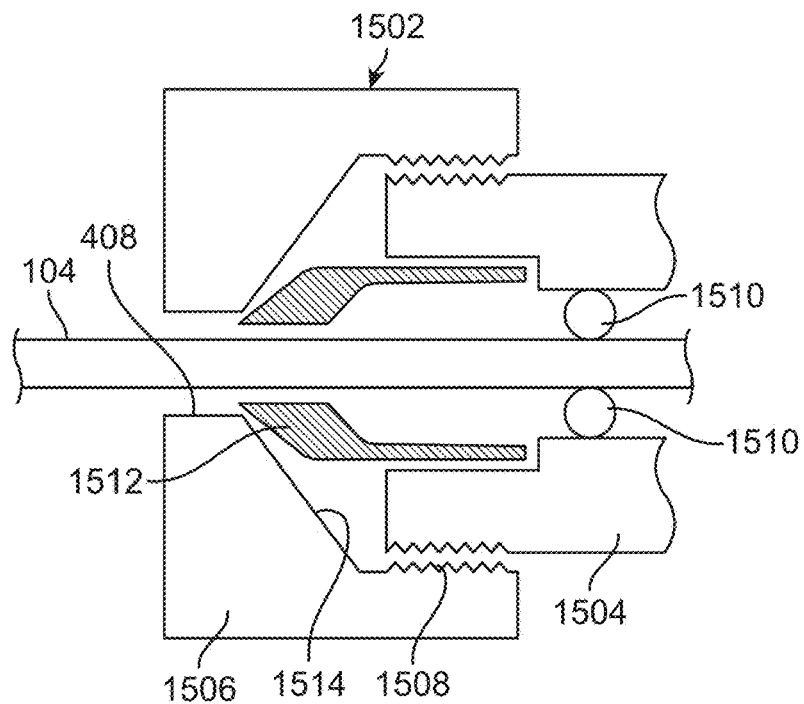
FIG. 25 illustrates a tether gripper of a tetherable guide-sheath, in accordance with an implementation.

As mentioned above, the anchoring delivery systems described herein can include a tether gripper 1502 to fasten the tether 104 of the tethering device 100 to the tetherable guide-sheath 400. FIG. 25 shows a tether gripper 1502 in accordance with an implementation. More particularly, one or more of the tethering device 100 or the tetherable guide-sheath 400 can include the tether gripper 1502 at a point of fixation between the components to attach the tetherable guide-sheath 400 to the tether 104 of the tethering device 100. Thus, the tetherable guide-sheath 400 can be reversibly attachable to the tether 104 at the point of fixation, which can be located proximal to the anchoring site at which the anchor 102 of the tethering device 100 is deployed within the anchoring anatomy. Accordingly, when the anchor 102 is deployed at the anchoring site and the tetherable guide-sheath 400 is attached to the tether 104 at the point of fixation, any proximal loading applied to the tetherable guide-sheath 400 distal to the fixation point can tension the tether 104 between the anchoring site and the point of fixation. Furthermore, this tension can have a straightening effect on the tetherable guide-sheath 400 to increase the column strength of the tetherable guide-sheath 400 and buttress the tetherable guide-sheath 400 against buckling or prolapse. Proximal loading on the tetherable guide-sheath 400 may result from, e.g., delivery or advancement of the working device 802 through the working lumen 410 of the tetherable guide-sheath 400 toward the target anatomy. Thus, the support provided by fixing the tether 104 to the tetherable guide-sheath 400 in combination with anchoring within the anatomy by the anchor 102 can prevent buckling of the tetherable guide-sheath 400 during working device 802 delivery, which can improve the ease and success of any interventional procedure performed through the tetherable guide-sheath 300.

In an implementation, the tether gripper 1502 is incorporated in the tetherable guide-sheath 400. One or both of the tether proximal port 414 or the working proximal port 416 can incorporate a tether gripper 1502. The tether gripper 1502 can include a clamping or clipping mechanism, such as a cleat, clamp, clip, etc., to fix the respective proximal port to a separate device passing through the port. The tether gripper 1502 can also include tape or suture to fix the respective proximal port to a separate device passing through the port. By way of example, the tether proximal port 414 can include an RHV capable of being tightened onto the runner tube 113 of the tethering device 100 when the runner tube 113 extends through the tether lumen 408 of the tetherable guide-sheath 400. As such, a fixation point may be formed between the tethering device 100 and the tetherable guide-sheath 400 at the tether gripper 1502 at some point proximal to the tether distal port 504. Again with respect to FIG. 25, the tether gripper 1502 can include a fixation mechanism having a gripper body 1504 that includes the tether lumen 408 and a cap 1506 that screws onto the gripper body 1504 via fastening threads 1508. Furthermore, the tether gripper 1502 can include one or more seals 1510 that surround the tether 104 when it is passed through the gripper body 1504, and thus, prevent fluid leakage through the tether gripper 1502. It will be appreciated that the seal 1510 is illustrated here without a backing surface, but in an implementation, the tether gripper 1502 can be designed such that the seal 1510 is squeezed when the cap 1506 is screwed onto the gripper body 1504. The seal 1510 can squeeze the tether 104 with enough force to fasten the tether 104 within the tether gripper 1502. In an implementation, the tether gripper 1502 can include a rotating hemostatic valve (RHV) that is configured to fix the tether 104 to the tetherable guide-sheath 400 without additional clamping features. For example, the RHV can be connected to the proximal furcation 404 and can be actuated to compress the seal 1510 that grips the tether 104.

In an implementation, the tether gripper 1502 can incorporate additional clamping features to grip the tether 104. For example, a collet 1512 component can be incorporated in the tether gripper 1502 such that the tether 104 passes through a central opening of the collet 1512 between the collet 1512 teeth. When the cap 1506 is screwed onto the gripper body 1504, a taper 1514 in the cap 1506 can press against the collet 1512 teeth forcing them against the tether 104. Accordingly, the tether 104 can be gripped with greater force than can be achieved using, e.g., an elastomeric seal 1510, and the tether gripper 1502 of the tetherable guide-sheath 400 can be used to fix the tetherable guide-sheath 400 to the tether 104.

Figure 26:
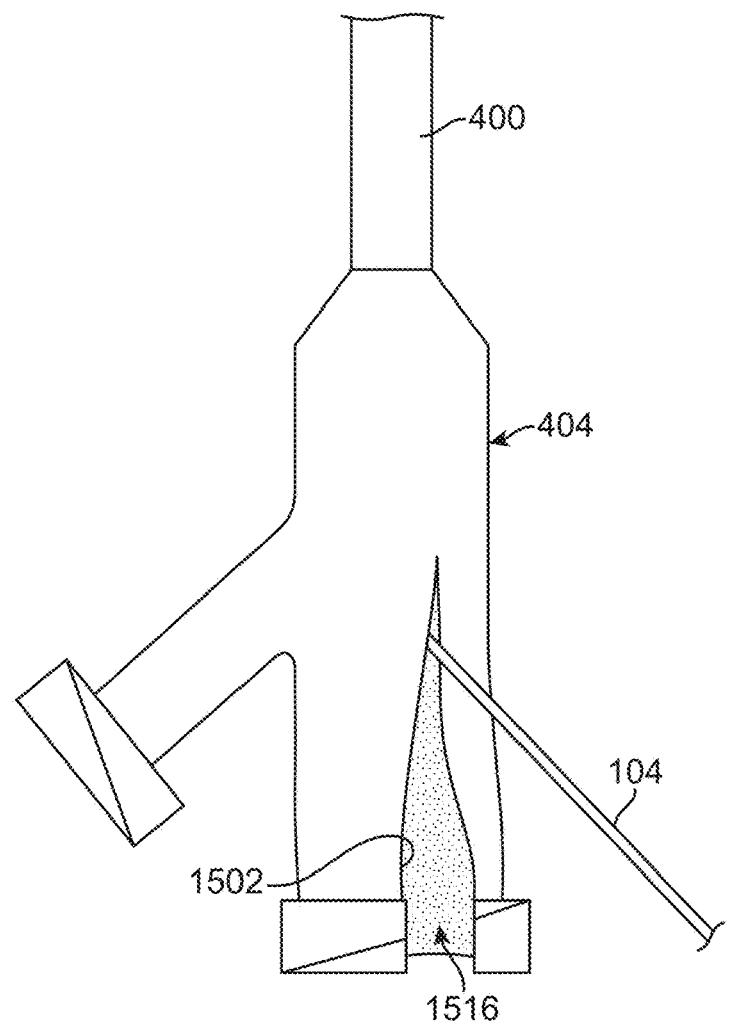
FIG. 26 illustrates a tether gripper of a tetherable guide-sheath, in accordance with an implementation.

FIG. 26 shows a further implementation of a tether gripper of a tetherable guide-sheath. The tether gripper 1502 of the tetherable guide-sheath 400 can be incorporated in the proximal furcation 404 of the tetherable guide-sheath 400. For example, the proximal furcation 404 can include a gripping feature to clamp the tether 104. For example, the tether gripper 1502 can include a slot 1516 formed through a sidewall of the proximal furcation 404 such that the tether 104 can be pulled laterally outward through the proximal furcation 404. Furthermore, by pulling the tether 104 out and upward through the slot 1516 with sufficient force, the tether 104 can be wedged toward a distal portion of the slot 1516. Accordingly, the tether gripper 1502 can pinch the tether 104 and prevent movement between the tether 104 and the tether gripper 1502. More particularly, the tether gripper 1502 can fix the tether 104 to the tetherable guide-sheath 400.

In the tether gripper 1502 implementations described above with respect to FIGS. 25-26, the tether lumen 408 may extend from the tether distal port 504 at the tip 406 of the tetherable guide-sheath 400 to the tether gripper 1502 connected to or incorporated in the tetherable guide-sheath 400.

Figure 27:
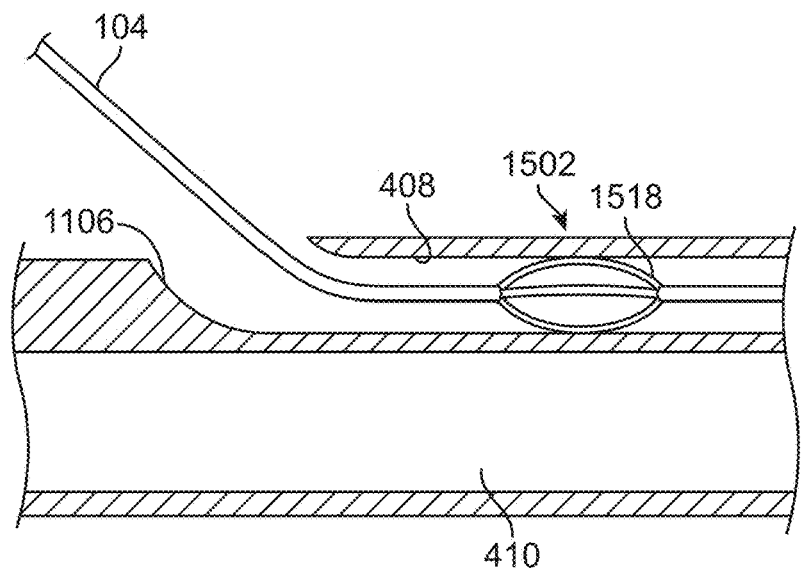
FIG. 27 illustrates a tether gripper of a tethering device, in accordance with an implementation.

As described above, the tetherable guide-sheath 400 can also be an RX type device such that the tether 104 can exit the tetherable guide-sheath 400 through the exit port 1106 within the patient anatomy as shown in FIG. 21. Thus, the exit port 1106 may not be reachable to fix the tether 104 to the tetherable guide-sheath 400 at the exit port 1106. FIG. 27 shows an implementation of a tether gripper 1502 of a tethering device 100 for use with an RX type guide-sheath. The tether 104 can be attached to the tetherable guide-sheath 400 proximal to the exit port 1106, e.g., using a clamp, clip, etc., to fasten the tether 104 to the body 402 of the tetherable guide-sheath 400. The distance between the fixation point and the exit port 1106 in such a case, however, may allow the tether 104 to bend relative to the tetherable guide-sheath 400 such that the tetherable guide-sheath 400 is not adequately buttressed against buckling. Accordingly, the tether gripper 1502 can be incorporated in the tether 104 to fix the tether 104 to the tetherable guide-sheath 400 within the tether lumen 408. For example, the tether gripper 1502 can be integrated in the tether 104 at a location distal to the exit port 1106. In an implementation, the tether gripper 1502 can include an expandable structure 1518 that can expand radially within the tether lumen 408 to press against an inner surface of the tether lumen 408 and lock the tether 104 to the tetherable guide-sheath 400 from moving slideably within the lumen 408. The expandable structure 1518 can be a self-expanding structure that is captured by a thin tubular sheath disposed over a proximal segment of the tether 104. More particularly, the thin tubular sheath can be retracted to expose the expandable structure 1518 and allow it to expand against the tether lumen 408 surface to lock the tether 104 to the tetherable guide-sheath 400. Furthermore, the thin tubular sheath can be advanced to capture the expandable structure 1518 and allow the tetherable guide-sheath 400 to be tracked over the tether 104 again.

The expandable structure 1518 of the tether gripper 1502 can be an inflatable member, such as a balloon, that is not self-expandable so-to-speak. More particularly, the tether 104 can have a tubular structure along a proximal segment. The tubular structure can have a proximal end 106 in fluid communication with the tether gripper 1502. The tether gripper 1502 can be connected to a syringe for inserting an inflation fluid into the tubular structure. Thus, the inflation fluid can be delivered into an inner volume of the expandable structure 1518 located at a distal joint of the tubular structure, causing the balloon to be inflated to press against the tether lumen 408 surface. The tubular structure can have a distal joint connected with a proximal end of a core wire. More particularly, the tether 104 can include a distal segment having a core wire extending from the distal joint of the tubular structure to the anchor 102. Accordingly, the tethering device 100 can include an anchor 102 at a distal joint 108, a core wire portion of the tether 104 extending proximally from the anchor 102, and a tether gripper 1502 portion extending proximally from the core wire portion. The tether gripper 1502 implementations described above are not intended to be limiting, but rather, illustrate that the tether gripper 1502 can be incorporated in one or both of the tethering device 100 or the tetherable guide-sheath 400 to fix the components of the anchoring delivery system 10 to each other during use.

Anchoring Delivery System Methods of Use

Figure 28:
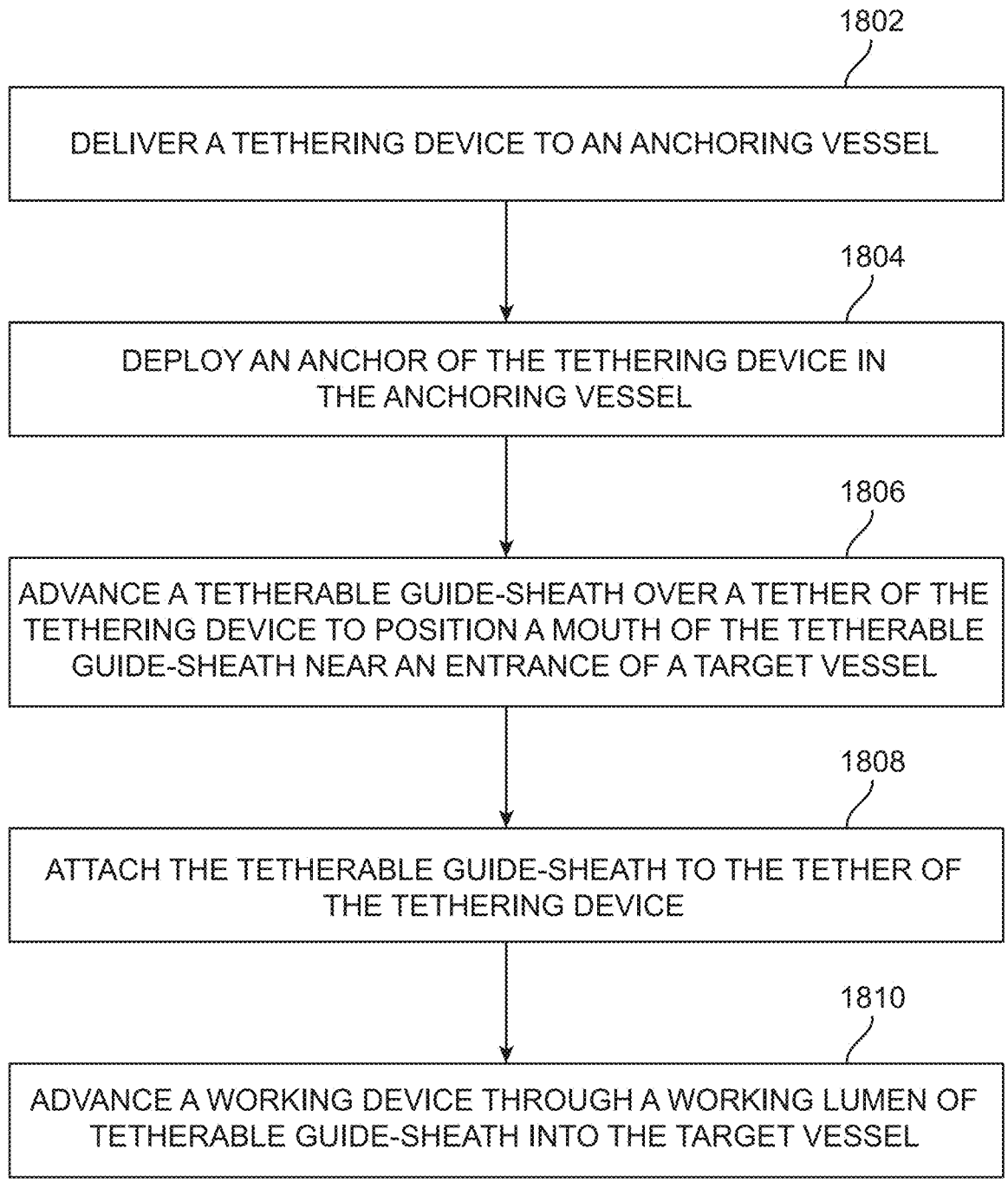
FIG. 28 illustrates a method of using an anchoring delivery system to deliver a working device, in accordance with an implementation.

Referring to FIG. 28, a method of using an anchoring delivery system to deliver a working device is illustrated in accordance with an implementation. FIGS. 29A-29F illustrate operations of the method illustrated in FIG. 28. Accordingly, FIGS. 28-29 are described in combination below.

Figure 29B:
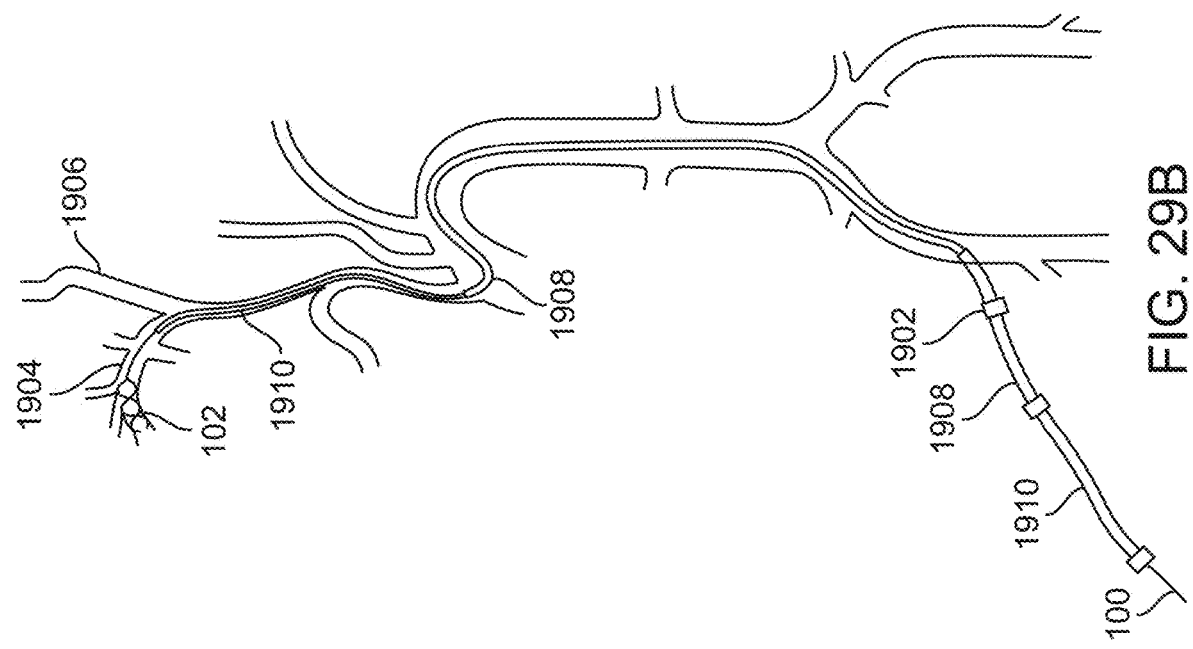
FIGS. 29A-29F illustrate operations of a method of using an anchoring delivery system to deliver a working device, in accordance with an implementation.
Figure 29A:
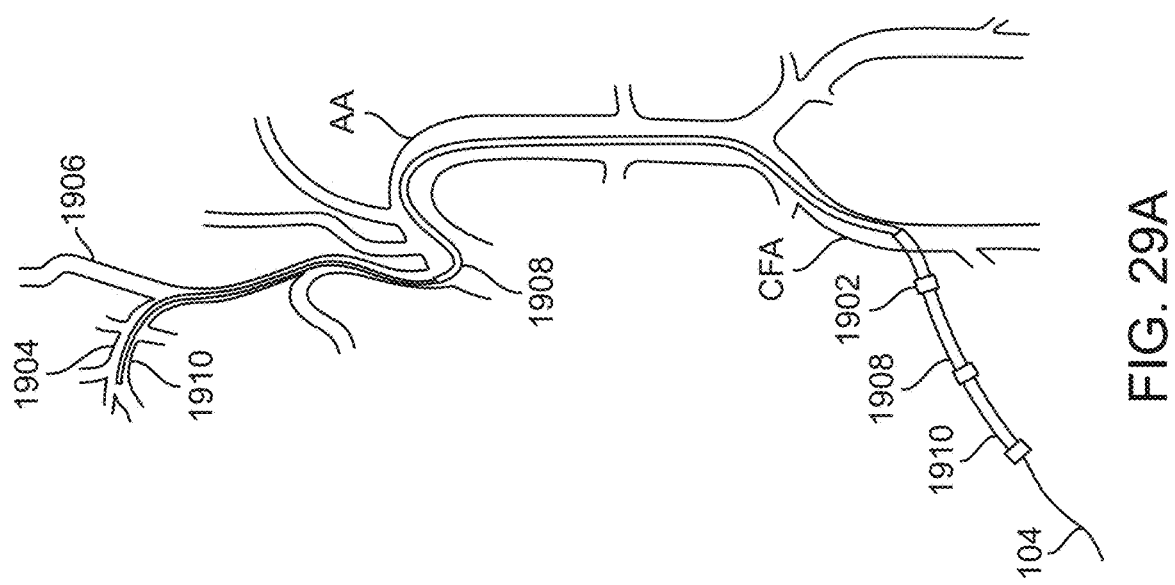

An arterial access device 1902, such as a standard transfemoral sheath, can be inserted into an arterial access point such as the femoral artery. Referring to FIG. 29A, the arterial access device 1902 is shown inserted via a percutaneous puncture into the common femoral artery (CFA), such as near the groin. In alternate implementations, other access points can be used such as radial artery access, brachial artery access, transcervical or transcarotid access to the CCA or proximal internal carotid artery (ICA), or any other access point. In some implementations, arterial access device 1902 has an inside diameter range of 3 to 10 French. For example, the transfemoral sheath illustrated in FIG. 21A can be a standard 7 French sheath size.

After inserting the arterial access device 1902, a finder tool set, which can include a guidewire (not shown), a microcatheter 1910, and/or a finder catheter 1908, can be inserted individually or in combination into the transfemoral sheath and advanced to an anchoring vessel 1904, e.g., an ECA, ICA, CCA, etc. For example, a guidewire can be advanced to the distal ECA, ipsilateral to a target vessel 1906, which may be the ICA, using conventional techniques known to persons having ordinary skill in the art. For example, the guidewire can be preloaded into a finder catheter 1908 and advanced to the aortic arch (AA). In some implementations, the finder catheter 1908 includes a hook-shaped distal section, such as in the case of a Vertebral, Hockey Stick, VTK shape, or LIMA pre-shaped catheter or the like. A distal end of the finder catheter 1908 can be manipulated and positioned at the brachiocephalic artery or right CCA. The guidewire can then be pushed up as far as possible to the anchoring vessel 1904, e.g., the distal ipsilateral ECA. A microcatheter 1910 can be advanced over the guidewire. Optionally, the finder catheter 1908 can be advanced over the guidewire and the microcatheter 1910 to an anchoring site of the anchoring vessel 1904, e.g., the ECA distal to a takeoff of the target vessel 1906. It should be appreciated that the anchoring vessel can include other vessels that those shown and described herein. Typically, an operator will use the ipsilateral ECA or ICA above the bifurcation of the CCA as this is the target of stiff wire placement for delivery of standard sheaths. An anchoring artery will preferentially not be in the path to the cerebral target, thus, anchoring target arteries include external carotid artery (ECA) or subclavian artery (SA) to access the internal carotid artery (ICA) or common carotid artery (CCA), respectively. The choice of ipsilateral SA or ECA as the anchoring target can depend on anatomy and clinical indication. For instance, it may be more challenging for certain anatomies to easily reach the ECA or anchoring in the SA may give the operator guide support to access most any ICA through the generally non-tortuous thoracic CCA.

At operation 1802, the tethering device 100 can be delivered to the anchoring vessel 1904. For example, still referring to FIG. 29A, the guidewire can be removed from the microcatheter 1910 and the tethering device 100 can be inserted into and advanced through a lumen of the microcatheter 1910 and the finder catheter 1908 until the anchor 102 is near the anchoring vessel 1904. As described above, the tethering device 100 can include an anchor 102, such as an expandable element that can anchor and/or fix into an artery with or without scaffolding the artery, and the anchor 102 can be connected to the tether 104, which includes an elongated member. The anchor 102 is not shown in FIG. 29A, since it is hidden within a distal region of the microcatheter 1910 placed in the anchoring vessel 1904. Thus, delivery of the tethering device 100 to the anchoring vessel 1904 can include advancement of the anchor 102 connected to the distal end of the tether 104 through the vasculature, and not necessarily deployment of the anchor 102 from the unexpanded state to the expanded state. The tethering device 100 can include a pusher tube, such as a hypotube, extending over the tether 104 such that a distal end of the pusher tube is positioned adjacent a proximal end of the anchor 102. The pusher tube can provide "pushability" to an otherwise floppy tether 104 such that the anchor 102 can be advanced through the microcatheter 1910. A distal end of the pusher tube 109 can abut against the anchor 102 and urge it forward through a lumen of the microcatheter 1910. The tethering device 100 and the pusher tube 109 can be preloaded or otherwise assembled with a delivery tool configured to maintain the anchor 102 in a low profile configuration such that the anchor 102 can be inserted into a proximal end of the microcatheter 1910 and advanced to the distal anchoring vessel 1904 through the microcatheter 1910 lumen.

At operation 1804, the anchor 102 of the tethering device 100 can be deployed in the anchoring vessel 1904. Referring to FIG. 29B, the microcatheter 1910 can be retracted over the tethering device 100 to unsleeve and expose the anchor 102 of the tethering device 100. In the case of a self-expanding anchor 102 structure (see, e.g., FIG. 2B or 5J), the anchor 102 of the tethering device 100 can automatically deploy into the anchoring vessel 1904. Alternatively, in the case of an inflatable anchor 102 structure (see, e.g., FIG. 2C), the anchor 102 can be manipulated to deploy into the anchoring vessel 1904. More particularly, the anchor 102 can transition from the low profile, unexpanded state to the higher profile, expanded state to contact and anchor 102 at an anchoring site within the anchoring vessel 1904, e.g., distal to an entrance of the target vessel 1906.

Figure 29D:
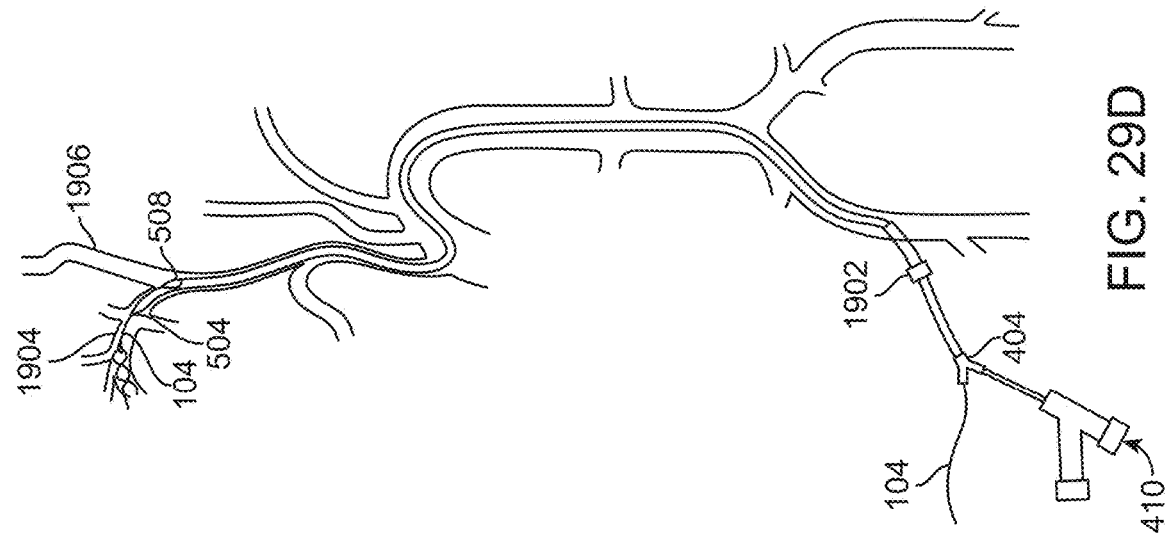
Figure 29C:
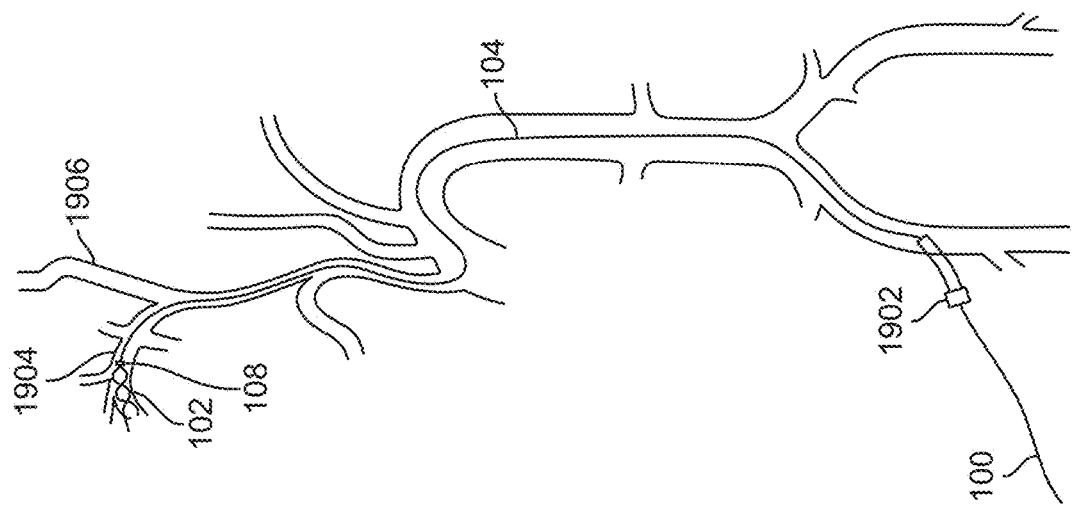

Referring to FIG. 29C, the microcatheter 1910 and/or the finder catheter 1908 can be removed through the arterial access device 1902 such that the tethering device 100 is anchored within the anchoring vessel 1904 and a proximal end of the tether 104 extends from the distal joint 108 through the arterial access device 1902. In some implementations, deployment of the anchor 102 and/or the deployed anchor 102 of the tethering device 100, e.g., expansion of a cage structure or inflation of a balloon anchor, or release of a wire device, may cause endothelial injury. Accordingly, application of tension to the tether 104 when the anchor 102 is deployed may create shear stress on the vascular tissue and/or distortion of the vascular anatomy at a location of the anchor deployment. However, minor vascular trauma in the anchoring vessel 1904 may be an acceptable tradeoff to get a supportive system in place when AIS is the clinical indication for the target vessel 1906. It is also comprehended that the anchoring delivery system presented herein may also be used where the clinical syndrome is severe and the "cost" of trauma at an endothelial cell layer level in the anchoring vessel 1904 is acceptable in the judgment of the operator to achieve a desired outcome in the target vessel 1906. The anchoring delivery system may also be used for cases with or without AIS where intracerebral access is needed, as compared to current transfemoral systems that simply do not allow such access.

At operation 1806, the tetherable guide-sheath 400 may be advanced over the tether 104 of the tethering device 100 to position the mouth 508 of the tetherable guide-sheath 400 near the entrance of the target vessel 1906. The tether 104 can include a length extending outside the patient. Referring to FIG. 29D, the proximal end 106 of the tether 104 (extending outside the patient) can be inserted into the tether distal port 504 of the tetherable guide-sheath 400 at a distal end of the tether lumen 408. Thus, the tether 104 can be received in the tether lumen 408. The length of the tether 104 extending outside the patient can be advanced through the tether lumen 408 until the proximal end of the tether 104 is once again available outside the proximal end of the sheath 400, for example by extending from the tether lumen 408 through the tether proximal port 414. Although the tether 104 is generally not pushable up through the vasculature without a pusher tube or some kind of delivery component, the tether 104 can have enough heft that it can be pushed through the tether lumen 408 of the sheath 400. Once the tether 104 extends out the tether proximal port of the sheath 400, the tetherable guide-sheath 400 can be advanced into the patient over the tether 104. The tethering device 100 between the anchor 102 and the proximal end of the tether 104 can be made taut such that the tether 104 of the tethering device 100 can function like a rail for advancing the tetherable guide-sheath 400 up the tether 104 until the working port 506, e.g., the mouth 508, of the tetherable guide-sheath 400 is positioned at the entrance to the target vessel 1906. The entrance to the target vessel 1906 can be, for example, a carotid bifurcation, and thus, the mouth 508 may provide access to the ICA. Thus, the tetherable guide-sheath 400 can be positioned to deliver a working device 802 toward the target vessel 1906 through the working lumen 410 in the proximal furcation 404 while the tether 104 of the tethering device 100 exits the tetherable guide-sheath 400 through the tether lumen 408 in the proximal furcation 404.

The tether 104 can provide the route for the tetherable guide-sheath 400, and the tether 104 can extend the length of the vascular path and exit near a distal end of the tetherable guide-sheath 400, e.g., through the tip 406 or a side of the tetherable guide-sheath 400 near the tip 406, leaving the working lumen 410 of the tetherable guide-sheath 400 available for petrous access. The length of the tether 104 can vary depending on the type of the tetherable guide-sheath 400. More particularly, the tetherable guide-sheath 400 can be an over-the-wire (OTW) type device as described above, having an exit port at a proximal end, or a rapid exchange (RX) type device, having the exit port 1106 at a medial location between ends. Thus, in the case of an OTW tetherable guide-sheath 400, the tether 104 runs within the tether lumen 408 extending the length of the tetherable guide-sheath 400. Alternatively, in the case of the RX tetherable guide-sheath 400, the tether 104 runs within the tether lumen 408 extending from the tip 406 of the tetherable guide-sheath 400 to an exit port 1106 where the tether lumen 408 terminates on the outside of the tetherable guide-sheath 400. Since the length of the tether lumen 408 that receives the tether 104 can be shorter in an RX type than in an OTW type of tetherable guide-sheath 400, the length of the tether 104 of the anchoring delivery system may vary. In some implementations, an extension member having an elongated body and a distal end configured to couple with a proximal end 106 of the tether 104 can be attached and detached from the tether 104 to allow for the exchange of one type of tetherable guide-sheath 400, e.g., an RX type, for another type of tetherable guide-sheath 400, e.g., an OTW type, while maintaining the position of the tethering device 100 in the target anatomy.

Advancing the tetherable guide-sheath 400 over the tether 104 of the tethering device 100 can advance the tip 406 of the tetherable guide-sheath 400 through the entrance of the target vessel 1906 into the target vessel 1906. The tetherable guide-sheath 400 can have a stump tip. More particularly, the working port 506 can be distal to one or more tether entry ports 504 (see, e.g., FIGS. 12A and 13). The tether 104 of the tethering device 100 can be inserted through a tether distal port 504 on the side of the tetherable guide-sheath 400 proximal to the tip 406. For example, the tether 104 can be inserted into a tether distal port 504 near the tip 406 such that the portion of tetherable guide-sheath 400 distal to the utilized tether distal port 504 is short enough to be able to be advanced up the tether 104 of tethering device 100 through the arteries as well as long enough such that the keel-shaped intersection of the tetherable guide-sheath 400 and the tether 104 of the tethering device 100 exerts enough force to fix the tetherable guide-sheath 400 against the carina of the anchoring vessel/target vessel bifurcation.

In another implementation, the tether 104 of the tethering device 100 is inserted into the tether distal port 504 spaced further proximally away from the working port 506 at the tip 406. Thus, a longer portion of the tetherable guide-sheath 400 can extend into the target vessel 1906. The length of the long tip can vary depending on which tether distal port 504 the tether 104 of tethering device 100 is inserted into. That is, when the tether 104 is inserted into a more proximal tether distal port 504, then the distance between the utilized tether distal port 504 and the tip 406 of the tetherable guide-sheath 400 may be longer. In various implementations, the at least one tether distal port 504 is adjacent to one or more radiopaque markers 510 (e.g., a pair of radiopaque markers 510 may flank the utilized tether distal port 504) to indicate the location of the tether distal port 504 under fluoroscopy.

Figure 29F:
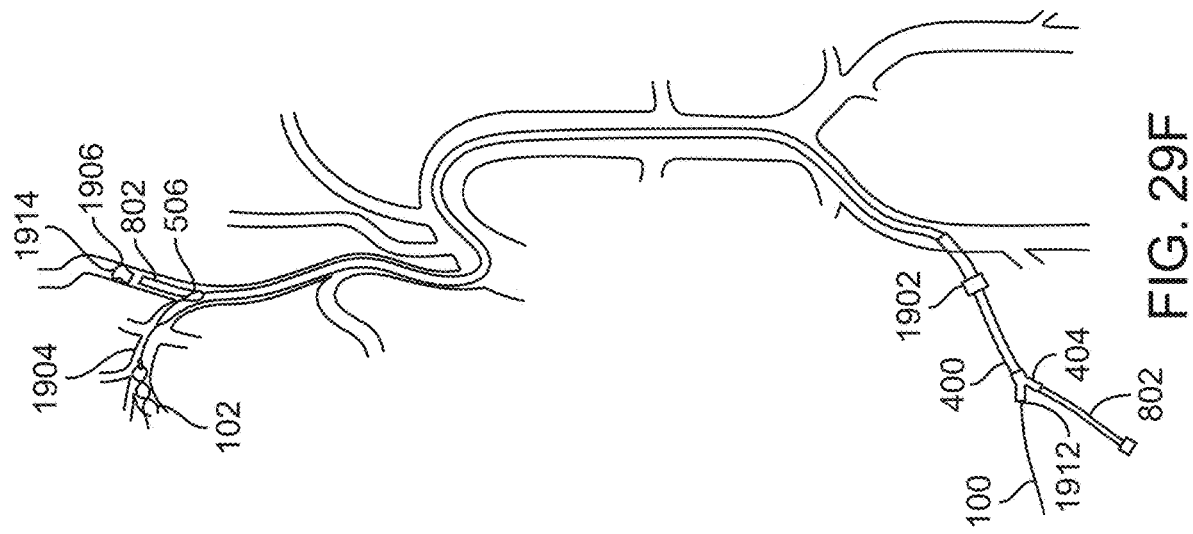
Figure 29E:
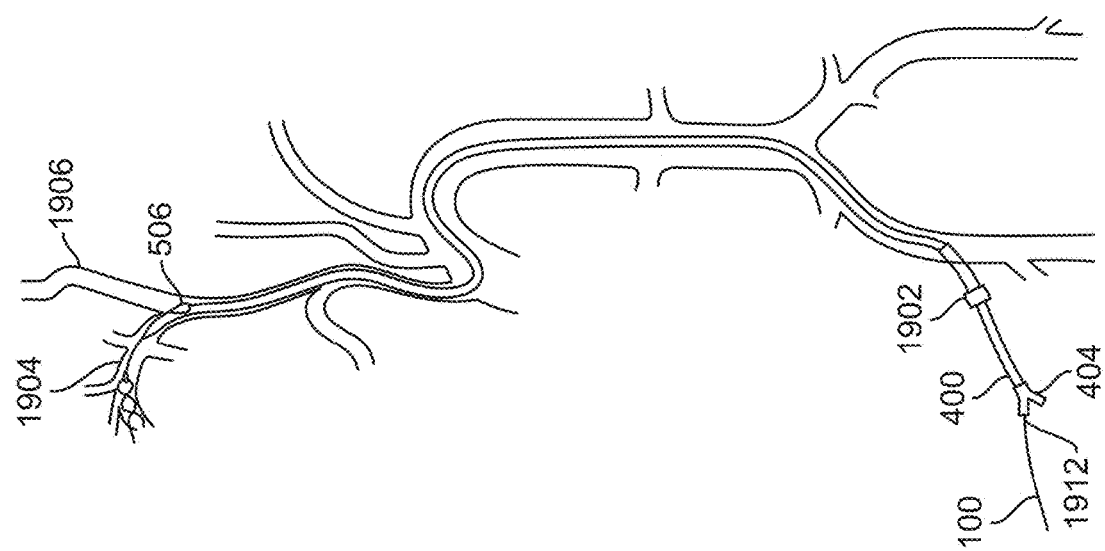

At operation 1808, the tetherable guide-sheath 400 can be attached to the tether 104 of the tethering device 100. Referring to FIG. 29E, the tether 104 can be fixed to the tetherable guide-sheath 400 at a point of fixation 1912 proximal to the entrance of the target vessel 1906. The tether 104 and the tetherable guide-sheath 400 can be fixed or locked into position relative to each other after the tetherable guide-sheath 400 is positioned at a carotid bifurcation with the mouth 508 providing access to the ICA, creating a tension in the tether 104 between the anchor 102 anchored in the target vessel 1904 distal to the target vessel 1906 takeoff and the tetherable guide-sheath 400 near the arterial access site. The tether 104 can be affixed to an outer surface or an inner surface of the tetherable guide-sheath 400 at the point of fixation 1912. The point of fixation 1912 can be outside of the patient anatomy, or in an implementation, the point of fixation 1912 can be within the patient anatomy, as may be the case when the tetherable guide-sheath 400 is an RX type device and the tether gripper 1502 is incorporated along the tethering device 100 (FIG. 19). The connection between the tetherable guide-sheath 400 and the tether 104 can be achieved using any of the fixation mechanisms described above, e.g., by the tether grippers 1502 described with respect to FIGS. 25-27. Such implementations, however, are illustrative and not limiting. For example, the tether 104 of the tethering device 100 can be attached to the tetherable guide-sheath 400 using conventional securement techniques such as by clamping, taping, or otherwise securing the tether 104 to the tetherable guide-sheath 400.

In an implementation, the tether 104 and the tetherable guide-sheath 400 are fixed by a clamp. For example, the clamp can be secured to a tab on the outside of the tetherable guide-sheath 400 or by other means of fixation. In alternative implementations, the tether 104 and the tetherable guide-sheath 400 are fixed by a hemostat, mosquito, suture, by application of a clear dressing or tape (e.g., Tegaderm™ or Opsite™), by a wire grasping element, by a closed RHV, or similar means of fixation. In additional various implementations, a non-clamping fixation technology can be used to avoid kink development of a mechanical fixation. For example, the tether 104 and the tetherable guide-sheath 400 can be fixed magnetically as described elsewhere herein. In addition, the tether 104 can be fixed within a lumen of tetherable guide-sheath 400 closer to the distal tip of tetherable guide-sheath 400 using a small interlocking detent within the tetherable guide-sheath 400. In an implementation, the tether gripper 1502 includes a balloon that is inflated within the tetherable guide-sheath 400 to pin the tether 104 within the tether lumen 408 and lock the relationship of the tether 104 to the tetherable guide-sheath 400. In some implementations, the tether 104 can be designed with at least one protrusion, e.g., a bulge formed around the tether 104, that engages with the tether lumen 408 of the tetherable guide-sheath 400. The bulge can be configured to engage the tether lumen 408 when stationary and can deflate when pushed forward. In an implementation, the tether 104 will not stretch, or may only minimally stretch, when pulled on.

At operation 1810, a working device 802 can be advanced through a working lumen 410 of the tetherable guide-sheath 400 toward the target anatomy. As described elsewhere herein, the working devices delivered through the guide sheaths described herein can vary and are not intended to be limiting. For example, the working device 802 can include a guidewire, balloon, embolectomy device like a Stentriever or aspiration catheter. After the tetherable guide-sheath 400 is delivered to the anchoring vessel/target vessel junction, e.g., the ECA/ICA bifurcation, angiography can be performed through the tetherable guide-sheath 400 to allow full opacification of the cerebral vasculature. Referring to FIG. 29F, the operator can then deliver the working device 802 into the entrance of the target vessel 1906 and proceed with a preferred AIS treatment approach aided by the anchoring provided by the fixed tethering device 100 and tetherable guide-sheath 400, i.e., the anchoring delivery system. The support provided by the anchoring delivery system 10 can allow some AIS approaches to be performed when they otherwise could not have been possible because of tortuous anatomy either at the great vessels and/or at the intracranial vasculature that tend to result in kinking and prolapse of typical sheaths as the working device is advanced distally. Moreover, the additional guide support can allow procedures to be completed more quickly and simply than routine interventional approaches. For example, some operators prefer to use a retrievable structure technique by delivering a retrievable structure via a balloon-tipped guide catheter or a non-balloon large bore catheter to the ICA. The support of the anchoring delivery system 10 can allow those operators to deliver their catheter systems to the petrous carotid or to a target embolus consistently. In contrast, such delivery is a challenge with current guide catheter technology.

For operators who prefer to use SMAT where the working device 802 includes a large bore catheter (e.g., Covidien Navien™ A+ Intracranial Support Catheter, Stryker/Concentric Distal Access Catheter™, Penumbra Benchmark™ 071, Penumbra Neuron™ 070, etc.) that needs to be delivered, and the largest possible catheter yields the best aspiration result, the anchoring delivery system can aid in the delivery of large catheters during SMAT or in any other procedure. For example, using a SMAT approach to treat an M1 occlusion (an occlusion in a main stem of middle cerebral artery) with anterior circulation AIS, the working device 802 can be a large bore catheter delivered through the working lumen 410 of the tetherable guide-sheath 400 to an embolus 1914 in the target vessel 1906. Delivery can be facilitated by the anchoring of the tethering device 100 and tethering of the tetherable guide-sheath 400, which tensions the tether 104 between the anchoring site and the point of fixation 1912 as the working device 802 advances through the mouth 508 into the distal target vessel 1906. Accordingly, commercially available 6 French intracranial catheter families which have up to 0.072 inch inner diameters for maximum diameter and aspiration capability would be compatible with a 7 or 8 French tetherable guide-sheath 400.

In various implementations, once the working device 802, e.g., a large bore catheter, exits the mouth 508 of tetherable guide-sheath 400 and is in the ICA, the fixation of the tether 104 to the tetherable guide-sheath 400 can be relaxed. The carina formed between the working device 802 and the tetherable guide-sheath 400 can be advanced against the carina of the anchoring vessel/target vessel junction, e.g., the carotid bifurcation, to provide an additional point of securement at the bifurcation. This carina-to-carina cinching between the device junction and the anatomical junction can reestablish the fixation of the tethering device 100 and the tetherable guide-sheath 400, eliminating the possibility of both upward motion of the system and downward buckling or prolapsing of the tetherable guide-sheath 400 within the CCA or brachiocephalic artery. If a subsequent device, e.g., a balloon angioplasty device or another tethering device 100, is advanced out of the working device 802, e.g., the large bore catheter, a reaction force can be created when that device meets resistance. The reaction force can act on the working device 802 and may press against the tetherable guide-sheath 400. In the present system, however, the force should not reach the area of the aortic arch where prolapse is typical in standard systems because of the anchoring of the tethering device 100 and the fixation of the tether 104 to the tetherable guide-sheath 400 as well as the carina-to-carina cinching. The opposite reaction force can be counteracted. For example, when a Stentriever or aspiration catheter engages an embolus lodge in a cerebral vessel, the pull on the embolus could cause the tetherable guide-sheath 400 to ride upward in the vessel. The carina-to-carina cinching can prevent this upward motion. In essence, the tetherable guide-sheath 400 is locked into its relative position in the vasculature and provides a fulcrum for advancing subsequent devices, e.g., catheter systems and interventional devices, into the distal vessels of the neurovasculature.

In an implementation, after the AIS embolus 1914 has been successfully treated, e.g., by aspirating and/or removing the embolus 1914, all wires, retrievable structures, and catheters can be removed from the tetherable guide-sheath 400, leaving the anchoring delivery system (the tethering device 100 and the tetherable guide-sheath 400). The fixation between the tethering device 100 and the tetherable guide-sheath 400 can be removed. For example, the tether 104 can be disengaged from the tether gripper 1502. Thus, the tetherable guide-sheath 400 can be advanced over the tether 104 to the anchor 102 deployed in the anchoring vessel 1904, e.g., the ECA. In some implementations, traction on the tether 104 can be applied to keep the tethering device 100 in position and to minimize trauma to the anchoring vessel as the tetherable guide-sheath 400 is advanced. The tetherable guide-sheath 400 can be advanced over the tether 104 to capture the anchor 102. That is, the tetherable guide-sheath 400 can be advanced to capture the anchor 102 within the tether lumen 408. Accordingly, the anchor 102 can be collapsed towards its lower profile configuration and the anchor 102 can be disengaged from the anchoring vessel 1904. The anchoring delivery system can then be retracted from the patient anatomy through the arterial access by removing tetherable guide-sheath 400 and the captured anchor 102 from the target anatomy. In an implementation, the tetherable guide-sheath 400 can be removed from the patient, leaving the deployed tethering device 100 in place, and a separate catheter, e.g., a microcatheter, can be advanced over the tether 104 to capture the anchor 102 and retrieve the tethering device 100 from the patient.

The method described with respect to FIG. 28 is illustrative, and one skilled in the art may extrapolate from this description other methods of using the anchoring delivery system to effectively deliver working device(s) to distal regions of tortuous and complex anatomies. Several such methods are described in the implementations below.

Figure 30:
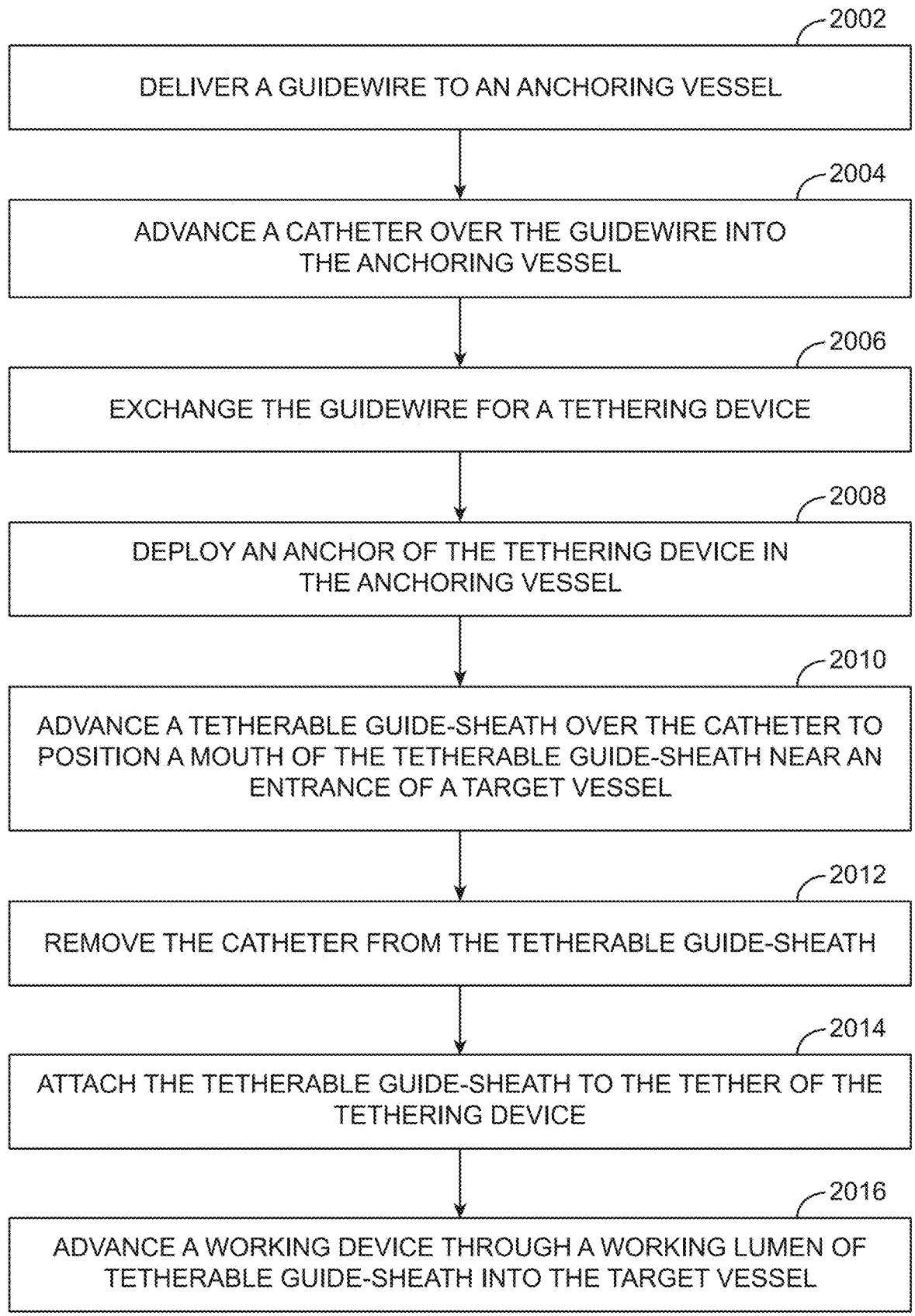
FIG. 30 illustrates a method of using an anchoring delivery system to deliver a working device, in accordance with an implementation.

Referring now to FIG. 30, a method of using an anchoring delivery system to deliver a working device is illustrated in accordance with an implementation. FIGS. 31A-31D illustrate operations of the method illustrated in FIG. 30. Accordingly, FIGS. 30-31 are described in combination below.

Figure 31B:
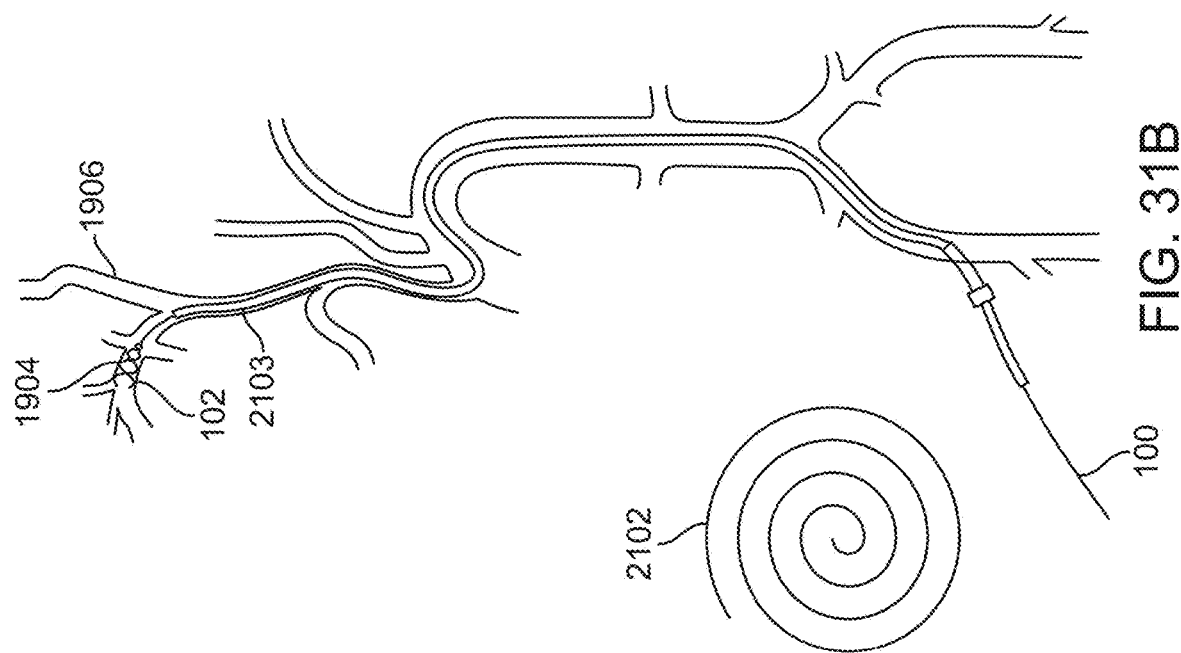
FIGS. 31A-31D illustrate operations of a method of using an anchoring delivery system to deliver a working device, in accordance with an implementation.
Figure 31A:
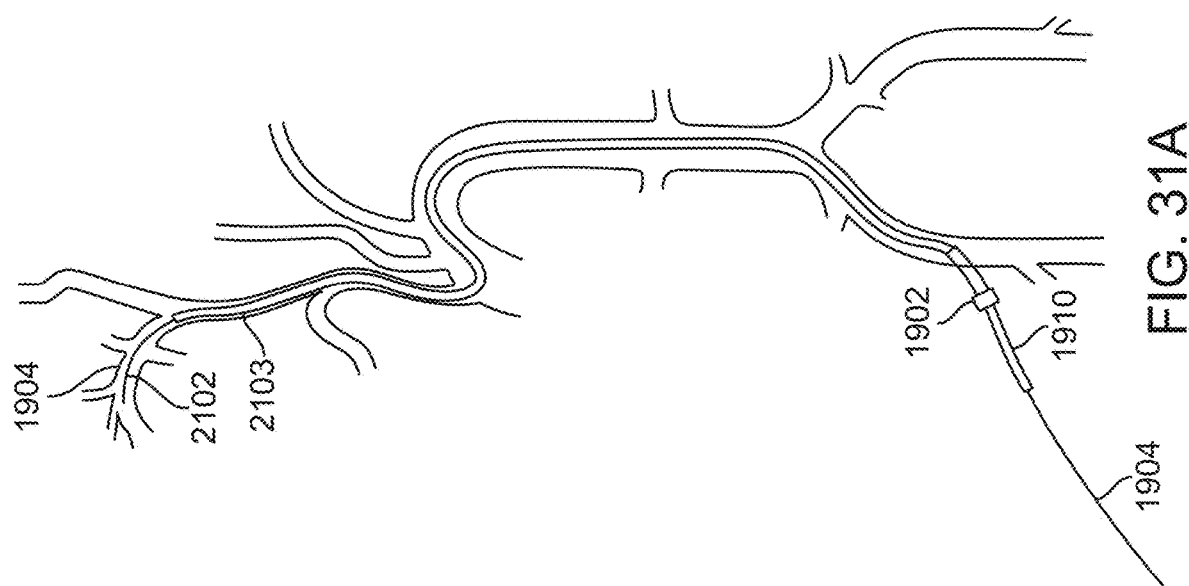

Referring to FIG. 31A, preparation of a patient may be similar to that described above. For example, an arterial access device 1902, such as a standard transfemoral sheath, can be inserted into an arterial access point such as the femoral artery. At operation 2002, a guidewire 2102 can be delivered through the arterial access device 1902 to the anchoring vessel 1904. Subsequently, at operation 2004, a catheter 2103, such as a microcatheter 1910 or a finder catheter 1908, can be delivered over the guidewire 2102 into an anchoring vessel 1904 of a target anatomy. In an implementation, the catheter 2103 can be preloaded with the guidewire 2102, and thus, the guidewire 2102 and the catheter 2103 can be advanced simultaneously. The guidewire 2102 can extend at least the length of the catheter 2103 and can be independently maneuverable within the catheter 2103 to lead the guidewire/catheter system to the anchoring vessel 1904. The coaxial system can be moved as a unit and each part can be manipulated independently depending on anatomical requirements and operator preferences. In particular implementations, a finder catheter 1908 (not shown) can also be positioned as part of the guidewire/catheter system. Thus, a route for the tethering device 100 can be established by the guidewire 2102 and one or more catheters 2103.

Referring to FIG. 31B, at operation 2006, the guidewire 2102 is exchanged for the tethering device 100. The guidewire 2102 can be removed from a lumen of the catheter 2103 and the tethering device 100 can be inserted into the catheter 2103 outside of the body 402 using an insertion tool. Insertion tools are known, for example, to insert a retrievable structure into a patient anatomy during a SMAT procedure. It is also possible that the tethering device 100 is already preloaded in the catheter system and the entire catheter 2103 with the tethering device 100 is inserted into the catheter 2103 instead of loading the tethering device 100 into the catheter 2103 without an outer sheath.

At operation 2008, the anchor 102 of the tethering device 100 can be deployed in the anchoring vessel 1904, e.g., the ECA. That is, the anchor 102 can be deployed at an anchoring site in the anchoring vessel 1904 distal to the entrance of the target vessel 1906. Deployment of the anchor 102 can include a standard "pin and pull" technique to keep the anchor 102 in a fixed position and prevent jumping of the device while the catheter 2103 is pulled back to unsleeve the anchor 102.

Figure 31D:
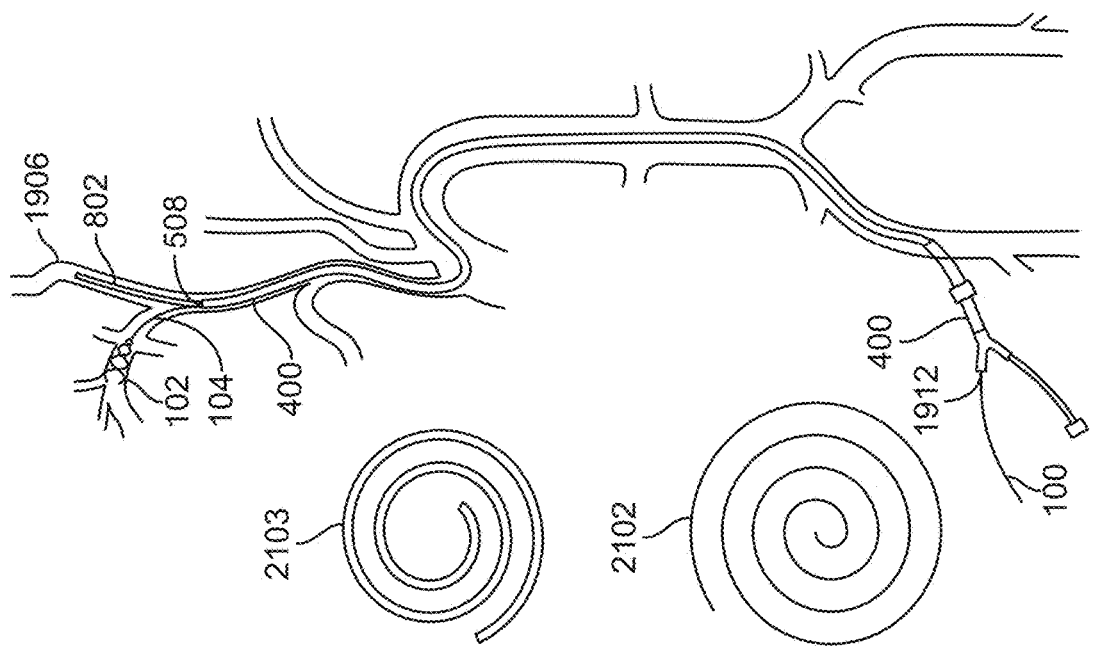
Figure 31C:
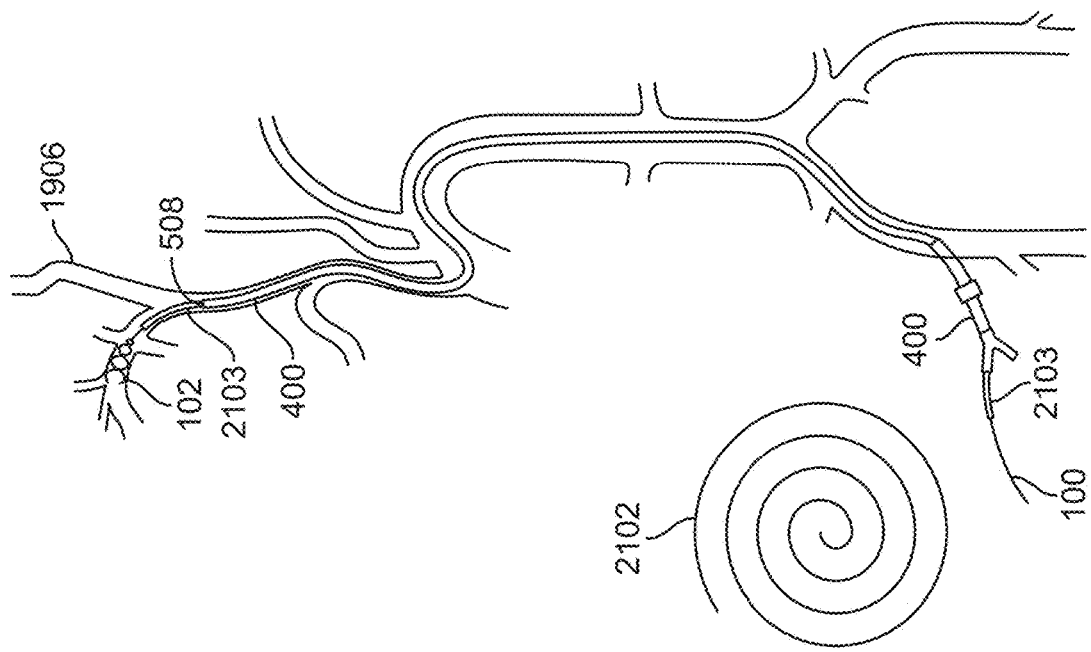

Referring to FIG. 31C, at operation 2010, the tetherable guide-sheath 400 is advanced over the catheter 2103 to position the mouth 508 of the tetherable guide-sheath 400 near an entrance of a target vessel 1906. That is, the tetherable guide-sheath 400 may include a tether lumen 408 to receive both the catheter 2103 and the tether 104 to allow the tetherable guide-sheath 400 to be tracked over an outside of the catheter 2103. Using the tethering device 100 and the catheter 2103 as support, the tetherable guide-sheath 400 can be advanced into the CCA up to the ECA/ICA bifurcation. Advancement of the tetherable guide-sheath 400 leverages the support of the tandem tether 104 and catheter 2103 combination, as well as the pulling force that the anchor 102 of the tethering device 100 provides when fully deployed in the ECA. The tetherable guide-sheath 400 can be advanced to the ECA/ICA bifurcation and a mouth 508 of the tetherable guide-sheath 400 may be directed towards the targeted vessel 1906, e.g., the ICA. The combination of the catheter 2103 and the tether 104 may provide sufficient column strength to reduce the likelihood of prolapse of the tetherable guide-sheath 400 into the ascending aorta, and to direct the tetherable guide-sheath 400 into the brachiocephalic as described in more detail above.

Referring to FIG. 31D, at operation 2012, the catheter 2103 can be removed from the tetherable guide-sheath 400. The tether 104 of the tethering device 100 can allow the catheter 2103 to be removed by pulling the catheter 2103 proximally. This differs from other techniques that require long wires and long wire exchanges. After the catheter 2103 is removed, the tetherable guide-sheath 400 can be coaxially located over the tethering device 100. The mouth 508 of the tetherable guide-sheath 400 can be adjusted, e.g., the tetherable guide-sheath 400 may be torqued, to direct the mouth 508 toward the entrance of the target vessel 1906, e.g., the ICA or another target vessel 1906.

At operation 2014, the tetherable guide-sheath 400 can be attached to the tether 104 of the tethering device 100 at a point of fixation 1912 proximal to the entrance of the target vessel 1906. For example, an RHV (not shown) connected to a connector of the proximal furcation 404 of the tetherable guide-sheath 400 can be tightened to lock the tether 104 of the tethering device 100 to the tetherable guide-sheath 400. Optionally, another securement device, e.g., a tether gripper 1502 incorporated in the tetherable guide-sheath 400 and/or the tethering device 100, a locking element, a clamp, or another clamping device, can be actuated to grip the tether 104 and lock the tether 104 to the tetherable guide-sheath 400. Thus, the tetherable guide-sheath 400 can become tethered to the deployed anchor 102 of the tethering device 100 by the tether 104.

At operation 2016, a working device 802 can be advanced through a working lumen 410 of the tetherable guide-sheath 400. For example, a large bore catheter can be advanced into the entrance of the target vessel 1906 as described above. Delivery of the working device 802 can cause a reaction force to be applied to the tetherable guide-sheath 400 between the anchoring site and the point of fixation 1912, and the reaction force may thus tension the tether 104 between the anchoring site and the point of fixation 1912. Accordingly, the anchoring delivery system can buttress the working device 802 against back-out and/or prolapse to facilitate delivery to a distal portion of the target vessel 1906. The anchoring delivery system can provide dual anchoring points, for example, at the ECA and the petrous carotid, that allows the guide-sheath to be pulled into position rather than "pushed" upstream. Further, the anchoring delivery system can allow for single operator ease of use in a rapid exchange fashion.

Figure 32:
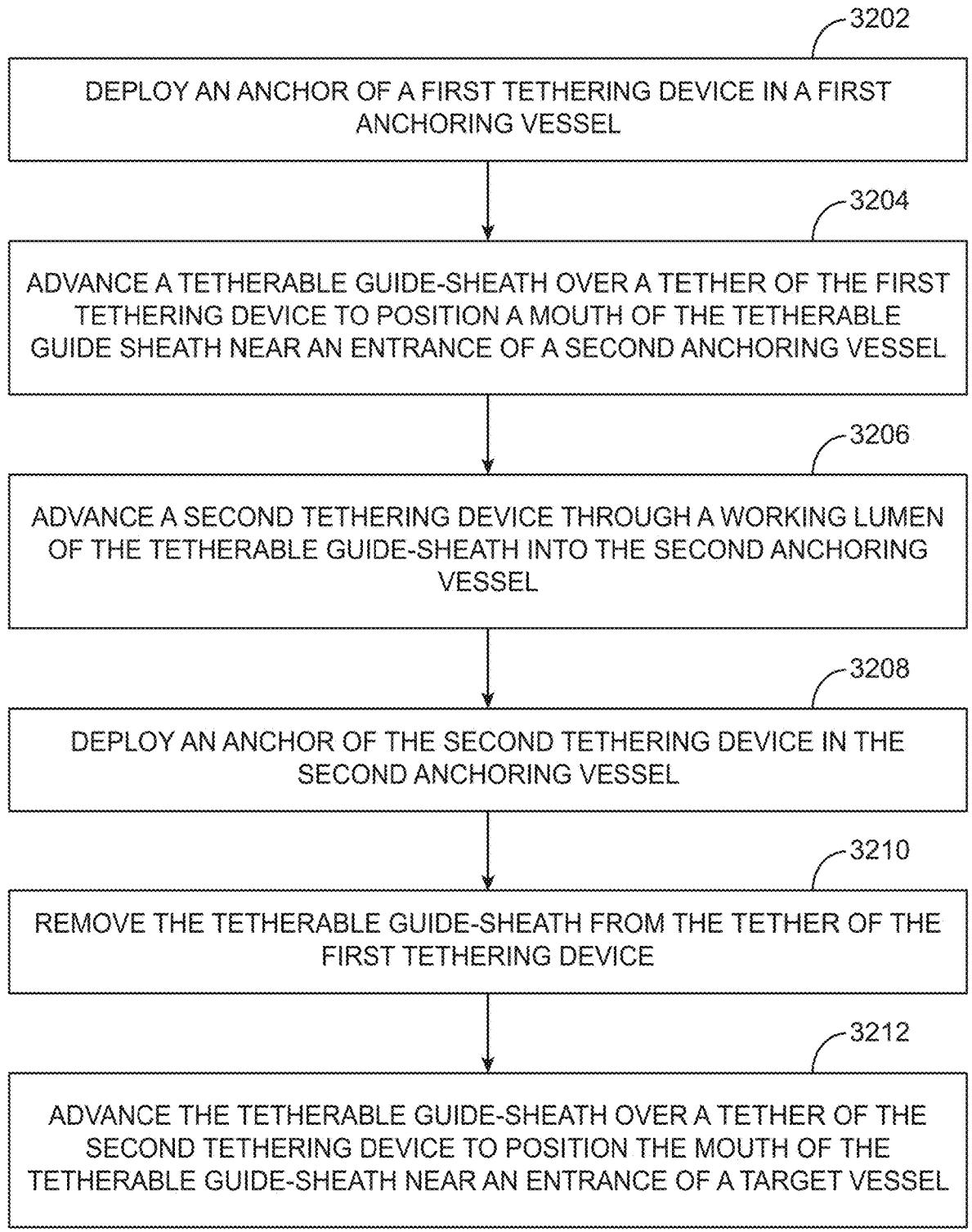
FIG. 32 illustrates a method of using several anchoring delivery systems to gain access to a target vessel, in accordance with an implementation.
Figure 33B:
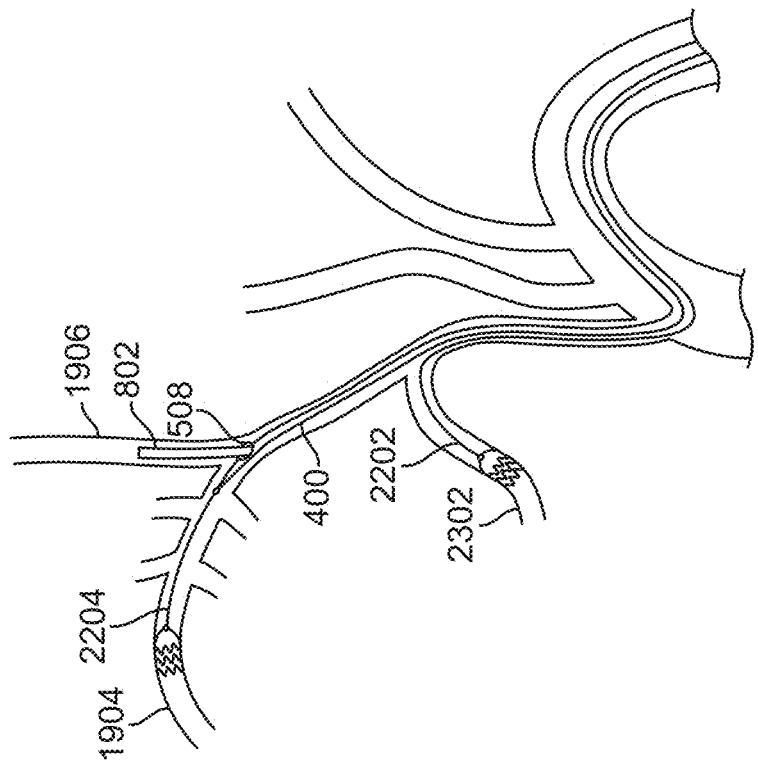
FIGS. 33A-33B illustrate operations of a method of using several anchoring delivery systems to gain access to a target vessel, in accordance with an implementation.
Figure 33A:
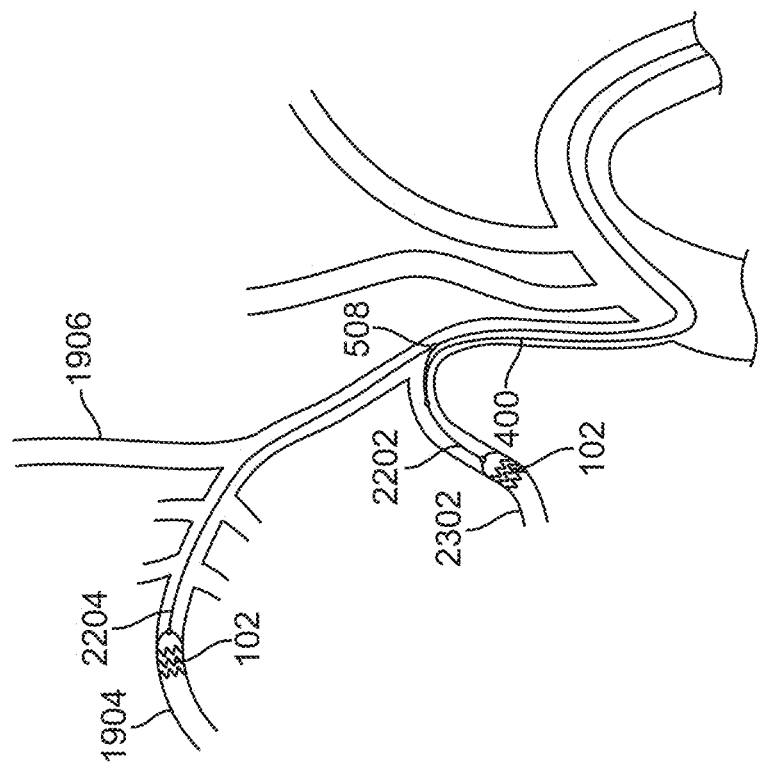

Referring to FIG. 32, a method of using multiple anchoring delivery systems to gain access to a target vessel is illustrated in accordance with an implementation. FIGS. 33A-33B illustrate operations of the method illustrated in FIG. 32. Accordingly, FIGS. 32-33 are described in combination below.

The method of FIG. 32 can include operations similar to those described above. For example, at operation 3202, an anchor 102 of a first tethering device 2202 can be deployed in a first anchoring vessel 2302. Referring to FIG. 33A, the first tethering device 2202 can be comparable to the tethering device 100 described above. Thus, the operations leading up to and including operation 3202 can be similar to those leading up to and including operation 1802 of FIG. 28, or those leading up to and including operation 2008 of FIG. 30. In an implementation, the first anchoring vessel 2302 is a vessel proximal to the anchoring vessel 1904 used to reach a target vessel 1906. For example, the first anchoring vessel 2302 can be an ipsilateral subclavian and can be used as a stepping stone when an operator encounters challenging anatomies and is unable to reach the preferred anchoring vessel 1904, e.g., the ECA, with a preferred guidewire/catheter system "finder set". In the event that the operator cannot advance the finder set to the preferred anchoring vessel 1904, the finder set may instead be advanced into the first anchoring vessel 2302, where the anchor 102 of first tethering device 2202 can be deployed to provide an anchor point for the tetherable guide-sheath 400.

At operation 3204, a tetherable guide-sheath 400 can be advanced over a tether 104 of the first tethering device 2202 to position a mouth 508 of the tetherable guide-sheath 400 near an entrance of the a second anchoring vessel 1904. Thus, the operations leading up to and including operation 3204 can be similar to those leading up to and including operation 1806 of FIG. 28, or leading up to and including operation 2010 of FIG. 30.

At operation 3206, a second tethering device 2204 can be advanced through a working lumen 410 of the tetherable guide-sheath 400 into the second anchoring vessel 1904. That is, using the anchoring support of the first tethering device 2202 and the tetherable guide-sheath 400, the second tethering device 2204 can be advanced through a working lumen 410 of the tetherable guide-sheath 400 into the second anchoring vessel 1904, e.g., the ECA. The second tethering device 2204 can include a second anchor 102 attached to a second distal end of a second tether 104, and thus, can be similar in some or all respects to the first tethering device 2202. That is, the first and second tethering devices 2202, 2204 can be duplicates of the tethering device 100 described above. The second anchoring vessel 1904 can be similar to the target vessel 1906 described above, in that the second anchoring vessel 1904 can branch away from the first anchoring vessel 2302 (or vice versa) like the target vessel 1906 branches from the anchoring vessel 1904 in the above description. At operation 3208, the second anchor 102 of the second tethering device 2204 can be deployed in the second anchoring vessel 1904.

Referring to FIG. 33B, the tetherable guide-sheath 400 can be relocated to facilitate delivery of a working device 802 into a target vessel 1906. At operation 3210, the tetherable guide-sheath 400 can be removed from the tether 104 of the first tethering device 2202. At operation 3212, the tetherable guide-sheath 400 can be advanced over the second tether 104 of the second tethering device 2204 to position the mouth 508 of the tetherable guide-sheath 400 near a second entrance of a second target vessel 1906. For example, the mouth 508 can be positioned toward a target ICA branching from the second anchoring vessel 1904, e.g., the ECA. Thus, the tetherable guide-sheath 400 can be fixed to the second tether 104 of the second tethering device 2204 to provide support to the working device 802 as it is advanced into the target vessel 1906 in a manner similar to that described above. Accordingly, it is contemplated that one or more tethering devices 100 can be used to allow an operator to make his or her way up to the target anatomy in an operation using any anatomy proximal to the target anatomy as a preliminary anchoring site to advance toward a preferred anchoring site nearer to the target artery.

In some cases, the tetherable guide-sheath 400 may not be able to advance to retrieve the anchor 102 of the tethering device 100. For example, after the anchor 102 of second tethering device 2204 is anchored in the second anchoring vessel 1904, the tetherable guide-sheath 400 may be unable to advance over the tether 104 of the first tethering device 2202 to capture the first anchor 102 in the first anchoring vessel 2302. In this event, the anchor 102 of the first tethering device 2202 can be detached, as described above, and the detached anchor 102 can remain in the patient and the detached tether 104 can be pulled out of the great vessels, aorta, and out of the access sheath and/or the arteriotomy of the access site. Alternatively, a separate catheter can be advanced over the tether 104 of the first tethering device 2202 after the tetherable guide-sheath 400 is removed from the tether 104, and the separate catheter can capture and retrieve the anchor 102.

Figure 34:
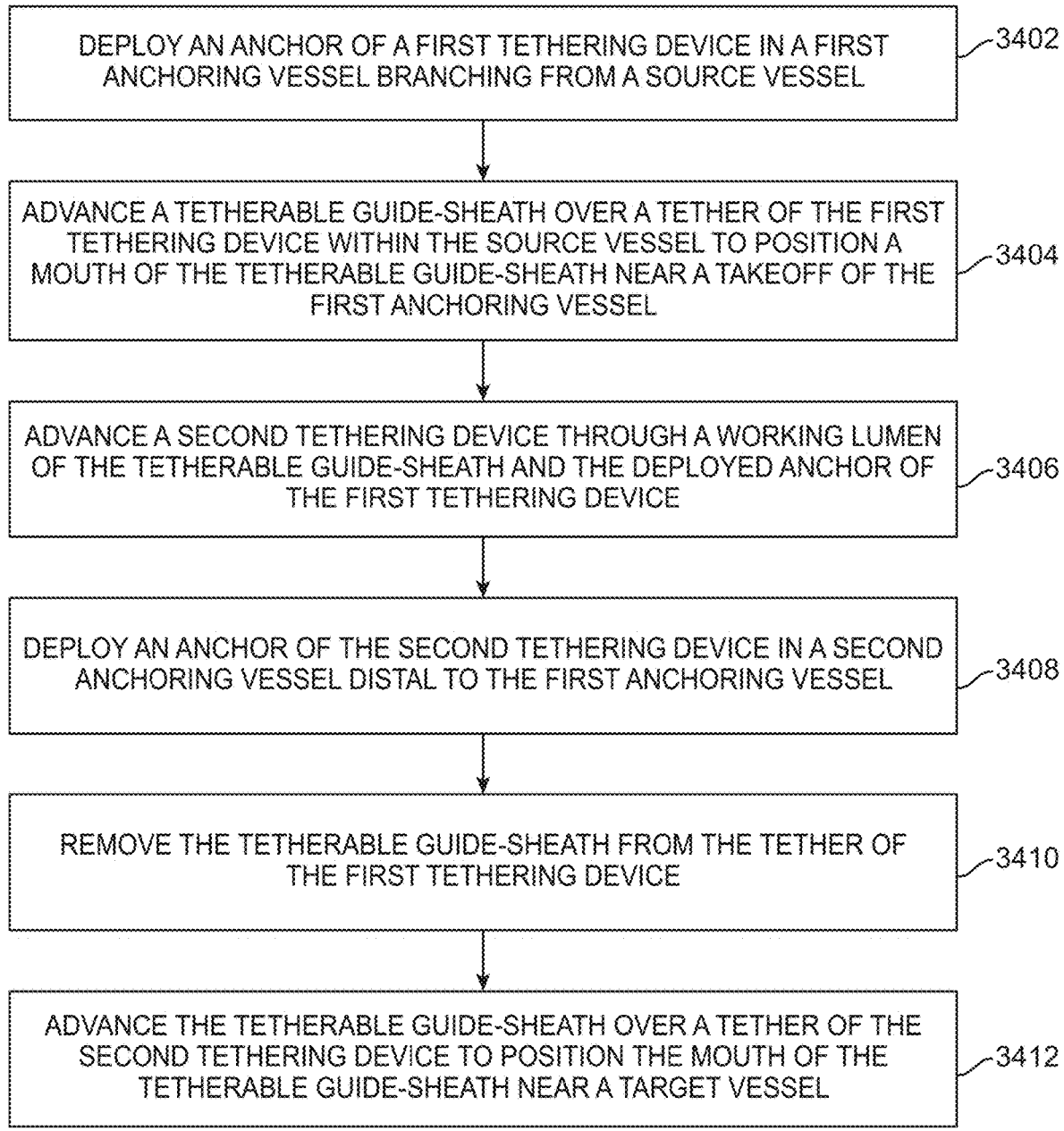
FIG. 34 illustrates a method of using several anchoring delivery systems to gain access to a target vessel, in accordance with an implementation.
Figure 35C:
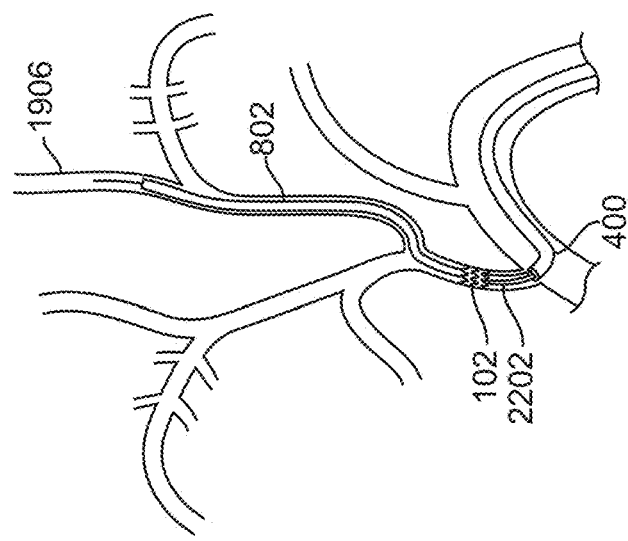
FIGS. 35A-35C illustrate operations of a method of using several anchoring delivery systems to gain access to a target vessel, in accordance with an implementation.
Figure 35B:
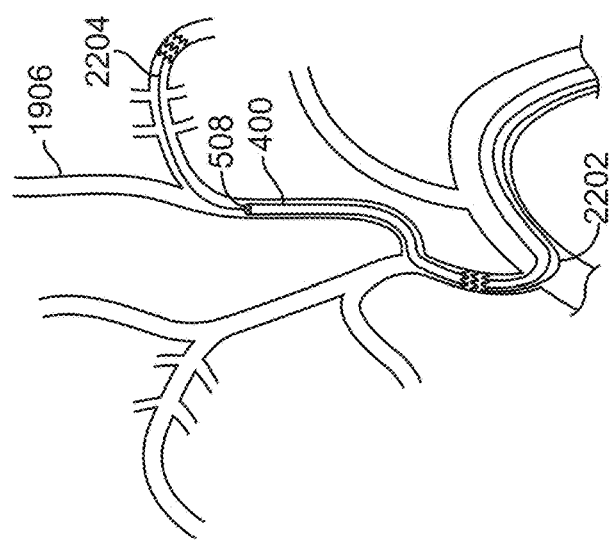
Figure 35A:
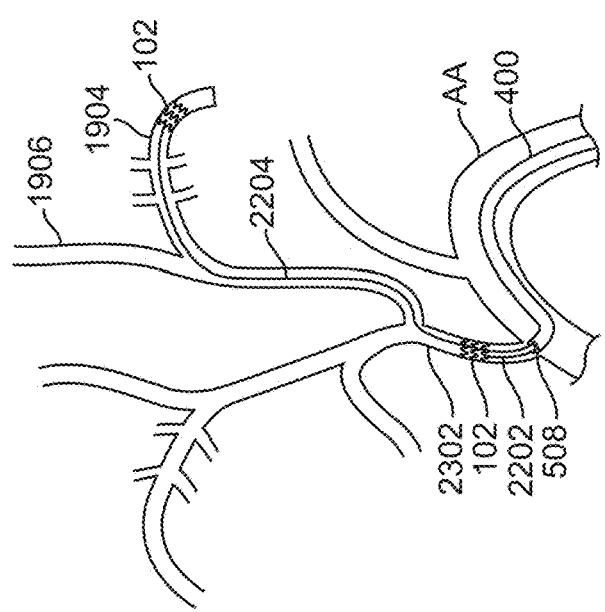

Referring to FIG. 34, a method of using several anchoring delivery systems to gain access to a target vessel is illustrated in accordance with an implementation. FIGS. 35A-35C illustrate operations of the method illustrated in FIG. 34. Accordingly, FIGS. 34-35 are described in combination below.

In some anatomies, a "through-the-anchor" approach may be used to access a target vessel 1906. For example, referring to FIG. 35A, a complex anatomy includes a "bovine" arch where the left CCA takes off from the brachiocephalic artery instead of the aorta. At operation 3402, an anchor 102 of a first tethering device 2202 can be deployed in a first anchoring vessel 2302, e.g., a brachiocephalic artery proximal to a left CCA takeoff, branching from a source vessel, e.g., the AA. At operation 3404, a tetherable guide-sheath 400 can be advanced over a tether 104 of the first tethering device 2202 within the source vessel to position a mouth 508 of the tetherable guide-sheath 400 near a takeoff of the first anchoring vessel 2302. For example, the mouth 508 can be located adjacent to the takeoff of the brachiocephalic artery from the AA. At operation 3406, a second tethering device 2204 can be advanced through a working lumen 410 of the tetherable guide-sheath 400 and the deployed anchor 102 of the first tethering device 2202. For example, the anchor 102 of the first tethering device 2202 can have a central lumen, as in the case of an expandable cage, or expand in a manner that allows a second tethering device 2204 to be advanced through or along the deployed anchor 102 of the first tethering device 2202 toward a target vessel 1906. At operation 3408, an anchor 102 of the second tethering device 2204 can be deployed in a second anchoring vessel 1904 distal to the first anchoring vessel 2302. Thus, the tethers 104 of the first tethering device 2202 and the second tethering device 2204 may remain within the tetherable guide-sheath 400, e.g., in respective lumens or in a same lumen.

Referring to FIG. 35B, at operation 3410, the tetherable guide-sheath 400 can be removed from the tether 104 of the first tethering device 2202. Subsequently, at operation 3412, the tetherable guide-sheath 400 can be advanced over the tether 104 of the second tethering device 2204 to position the mouth 508 of the tetherable guide-sheath 400 near a target vessel 1906. The tetherable guide-sheath 400 can be advanced up the tether 104 of second tethering device 2204 to the anchoring vessel/target vessel junction, e.g., the carotid bifurcation. The mouth 508 of the tetherable guide-sheath 400 can be positioned to face the target vessel 1906, e.g., the ICA.

Referring to FIG. 35C, if the target vessel 1906 cannot be reached, the CCA can be used as an anchor point for the second tethering device 2204 to be deployed. Thus, the anchor 102 of the first tethering device 2202 can be anchored in the brachiocephalic artery, and a working device 802, such as a large bore catheter, can be delivered through a working lumen 410 of the tetherable guide-sheath 400 to traverse through the anchor 102 of the first tethering device 2202.

Figure 36:
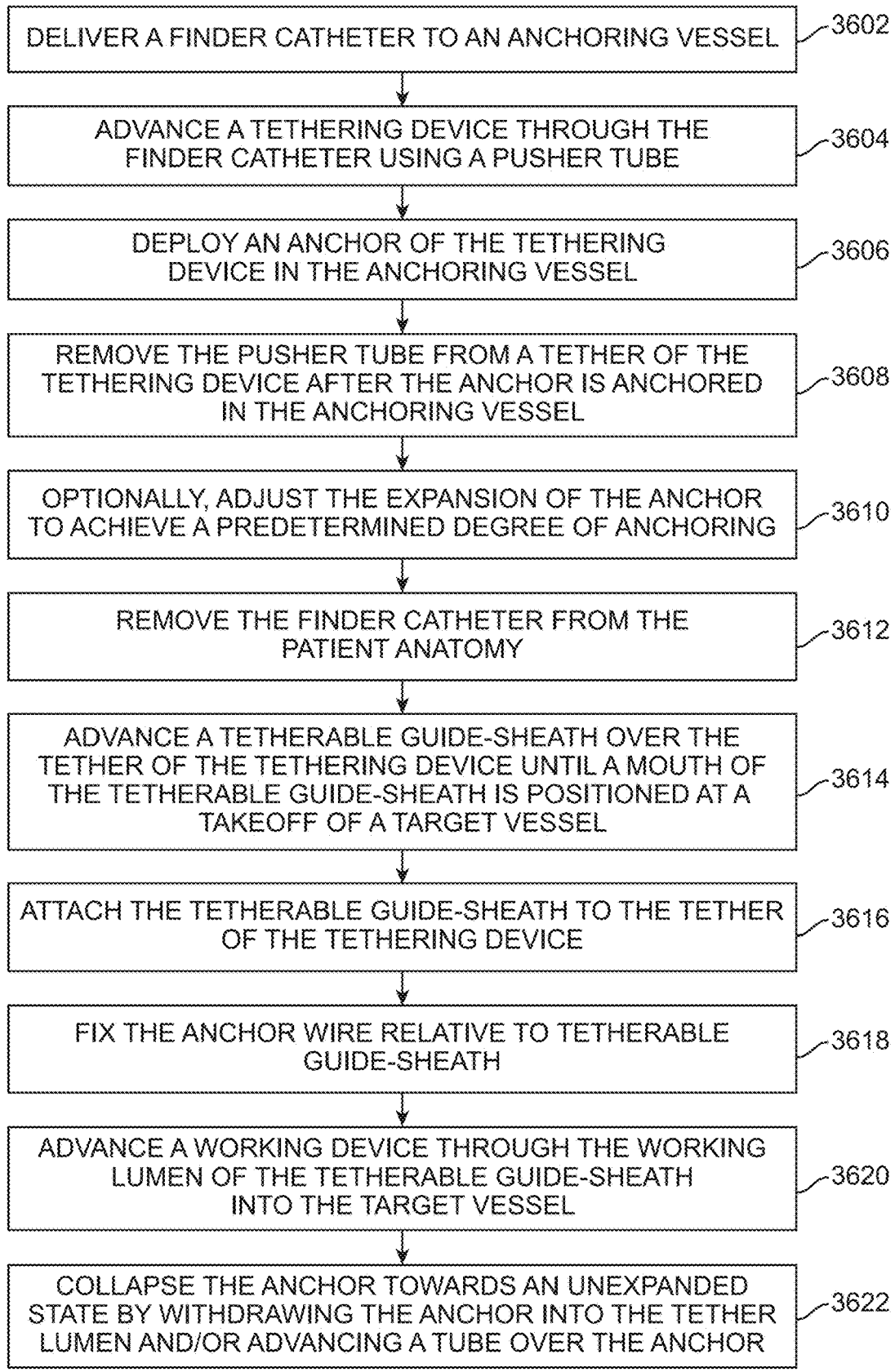
FIG. 36 illustrates a flowchart of a method of deploying an anchoring delivery system, in accordance with an implementation.

Referring to FIG. 36, a method of deploying an anchoring delivery system to gain access to a target vessel is illustrated in accordance with an implementation. At operation 3602, an operator can deliver a finder catheter (typically a 5F guide or diagnostic catheter) to an anchoring vessel in a patient anatomy, e.g., an external carotid artery (ECA). At operation 3604, the tethering device can be advanced through the finder catheter. The tethering device 100 can have a pusher tube 109 preloaded over a runner tube 113 of the tether 104. As the tethering device 100 is advanced, the anchor 102 can slide through the finder catheter in an unexpanded state, constrained by the finder catheter. The tethering device 100 can be advanced until the anchor 102 is near a distal end of the finder catheter, and near an anchoring site in the anchoring vessel 1904. In some implementations, the distal joint 108 of the anchor 102 can move relative to the proximal joint 108 of the anchor 102, i.e., the anchoring wire can slide within the runner tube, may allow the anchor 102 to be easily loaded into a sheath or a catheter by simply pushing the anchor 102 into the sheath. More particularly, by pushing the anchor 102 into the sheath using the tether 104, the push force can be transmitted through the anchor 102 to cause the anchor 102 to elongate and/or contract such that the procedure effectively "pulls" the anchor 102 into the sheath, which may significantly simplify loading.

At operation 3606, the anchor 102 can be deployed at the anchoring site by advancing the anchor 102 out of the finder catheter, or by retracting the finder catheter over the tethering device 100 to unsleeve the anchor 102. The anchor 102 can therefore self-expand to the expanded state to press against, and anchor, within the anchoring vessel 1904. In an implementation, the anchor 102 includes a closed-cell structure, and thus, the anchor 102 can remain constricted in an unexpanded diameter as long as the anchor 102 is not full released. This may simplify the release of the anchor 102 into the anchoring anatomy.

Still with respect to FIG. 36, at operation 3608, after the anchor 102 is anchored at the anchoring site, the pusher tube 109 can be removed from the tether 104. More particularly, the pusher tube 109 can be pulled proximally to slide over the runner tube 113 and to be removed from the patient anatomy.

At operation 3610, the operator may optionally adjust the anchor 102 to achieve a predetermined degree of anchoring. For example, the anchor wire 111 can be pulled relative to the runner tube 113 to cause a desired degree of expansion of the anchor 102. It will be noted that this may cause the anchor 102 to expand from a first expanded state, e.g., a self-expanded state, to a second expanded state, e.g., an actuated state. Accordingly, the second expanded state may be greater than the first expanded state to seat the anchor 102 in the anchoring vessel 1904. The opposite can be true, and the anchor wire 102 can be advanced relative to the runner tube 113 to reduce the degree of expansion from the self-expanded state to the actuated state, e.g., if the operator assesses that the anchor 102 is oversized for the anchoring vessel 1904 and that a reduced expansion diameter will reduce the likelihood of vascular trauma while still achieving effective seating of the anchor at the anchoring site.

At operation 3612, the finder catheter can be removed from the patient anatomy with a pulling motion. In an implementation, the anchor 102 provides a resistive anchoring force greater than the friction force applied to the tether 104 by the finder catheter, and thus, the tethering device 100 remains in place during retraction of the finder catheter.

At operation 3614, the operator can advance the tetherable guide-sheath 400 over the tether 104 of the tethering device 100. For example, the anchor wire 111 can be loaded into the tether distal port 504 of the tetherable guide-sheath 400 and the tetherable guide-sheath 400 can be advanced over the runner tube 109 through the anatomy toward the target vessel 1904. More particularly, the tetherable guide-sheath 400 can be advanced until the mouth 508 is positioned at a takeoff of a target vessel 1906, e.g., an internal carotid artery (ICA) leading to a targeted embolus. The tetherable guide-sheath 400 can be torqued to rotate the mouth 508 such that a working device delivered through the working lumen will be directed into an entrance of the target vessel 1906 at the anchoring vessel/target vessel junction by the deflecting surface in the working channel of the tetherable guide-sheath 400.

At operation 3616, the tetherable guide-sheath 400 can be attached to the tether 104 of the tethering device 100. For example, the tether gripper 1502, e.g., an RHV or another gripping technology (see "Dedicated Exit Lumen" and "Multi-headed RHV" implementations) can be used to affix the tetherable guide-sheath 400 to the tethering device 100 at a point of fixation 1912 proximal to the anchoring site 1904 and/or the entrance to the target vessel 1906.

At operation 3618, the anchor wire 111 of the tether 104 can be fixed by releasing an RHV 434 connected to the tether proximal port 414 and pulling relative to the tetherable guide-sheath 400 and then fixing it again in position. A locking element 130 may be added to additionally fix the anchoring wire 111 as well as given the operator an easy "handle" with which to apply push/pull on the distal anchor 102 via the anchor wire 111.

At operation 3620, a working device, e.g., a large bore catheter, may be advanced through the working lumen into the target vessel 1906 to perform a preferred AIS treatment. As the working device is advanced into the target vessel 1906, any reaction force applied by the distal anatomy may be transmitted by the working device to the tetherable guide-sheath 400 and the tethering device 100, placing the tether 104 in tension between the anchoring site 1904 and the point of fixation 1912. Whereas such reaction force may ordinarily cause buckling of the working device, the tetherable guide-sheath 400 may be buttressed by the tensioned tether 104, and thus, may effectively support the working device to allow it to be advanced without buckling or prolapse. Once the working device is in place, e.g., at the embolus, the preferred AIS treatment, e.g., aspiration of the embolus, can be performed. The working device can then be removed from the anchoring delivery system and the patient anatomy.

At operation 3622, the tetherable guide-sheath 400 has a detachment point 1916 that allows the operator to manually grasp the runner tube 113 or apply a locking element 130 to the runner tube 113. Force may be applied to the runner tube 113 to move the runner tube 113 relative to the anchor wire 111 to collapse the anchor 102 from the expanded state to or towards an unexpanded state, or from the actuated state to the self-expanded state. The anchor 102 can thus be withdrawn into the tether lumen 408 and/or chamber 515 of the tetherable guide-sheath 400, or the tetherable guide-sheath 400 can be exchanged with a separate catheter, such as a guide or diagnostic catheter, that can be advanced over the anchor 102 to capture the anchor 102. The tetherable guide-sheath 400 and/or tethering device 100 can then be removed from the patient anatomy to complete the use of the anchoring delivery system and finish the AIS intervention.

Figure 37B:
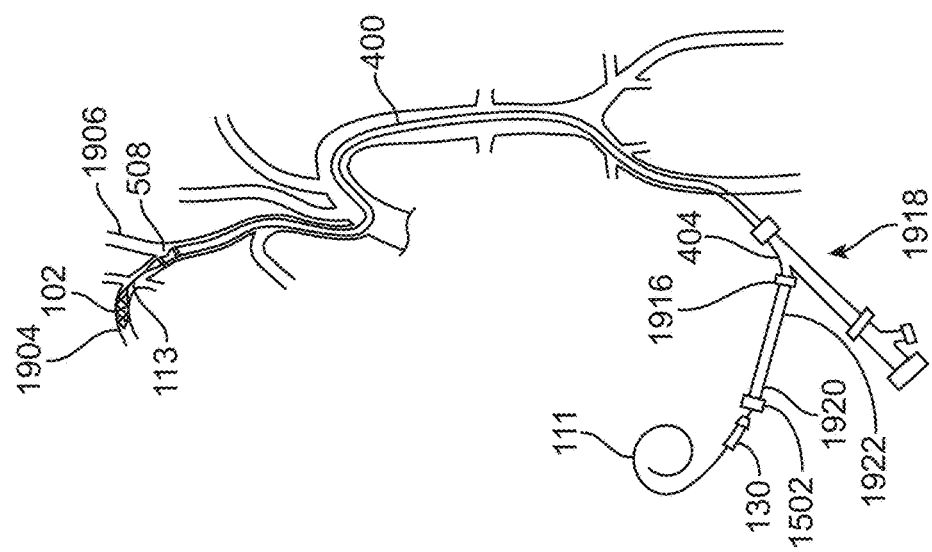
FIG. 37A-37B illustrate schematic views of an anchoring delivery system deployed in a target anatomy, in accordance with an implementation.
Figure 37A:
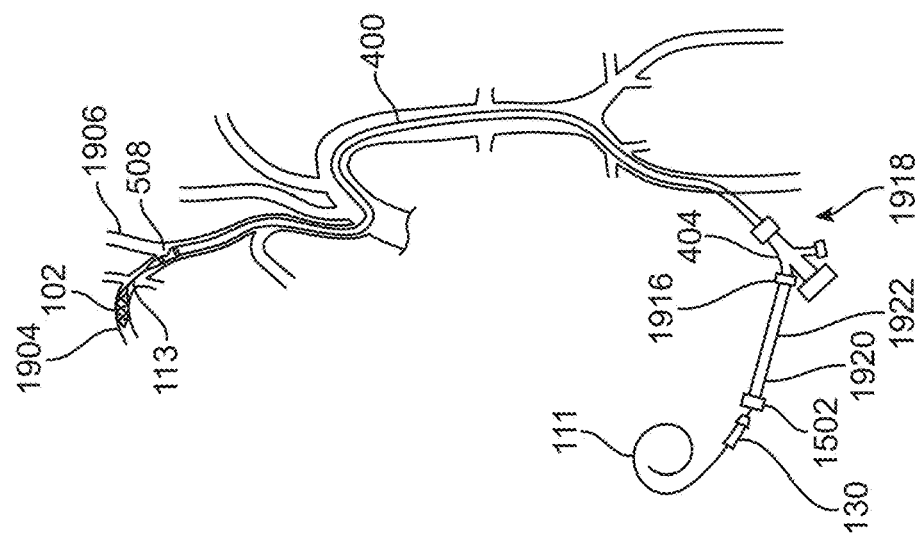

Referring to FIG. 37A, a schematic view of an anchoring delivery system deployed in a target anatomy is illustrated in accordance with an implementation. The proximal portion of the tetherable guide-sheath 400 can incorporate a multi-headed RHV 1918. The multiheaded RHV 1918 can include an elongated arm 1920 having a detachment point 1916 to expose the runner tube 113 for operator access. The elongated arm 1920 may provide an extension leading to the tether gripper 1502, which may include an anchoring RHV. For example, the anchoring RHV may include a collet, such as a brass or metal insert in the diaphragm which allows it to grasp and hold the anchoring wire, as described in more detail above.

The detachment point 1916 can include a detachable coupling, which may be formed by numerous mechanisms. For example, the elongated arm 1920 can include an external O-ring that fits within an internal groove formed in the multi-headed RHV. The elongated arm 1920 can include a rigid or semi-rigid clear extender that is of sufficient distance to reach and surpass the end of the runner tube 113. More particularly, a transition point 1922 between the anchor wire 111 and the runner tube 113, i.e., a proximal end of the runner tube 113, may occur within the elongated arm 1920 when the elongated arm 1920 is attached to the multi-headed RHV body. Accordingly, the runner tube 113 and the anchor wire 111 may be visualized, e.g., if they are of different colors or sufficient contrast to each other, in the extension tube. In an implementation, the elongated arm includes demarcations that may be used to estimate a tension applied to the tethering device 100. For example, a first distance between a point on the anchoring wire 111 and the proximal end of the transition tube may be measured when the anchor 102 is in the self-expanded state, and a second distance between those points may be measured upon actuation of the anchor wire 111. A difference in the distances may correspond to a degree of tension or an amount of anchoring provided by the tethering device 100.

The detachment point 1916 may or may not have an ability to restrain or fix the runner tube 113. In an implementation, an "in-line" RHV can be used to fix the runner tube 113 at the detachment point 1916. Alternatively, a transient fixation can be achieved using a push button, a lever, or another mechanism that can be actuated by an operator to temporarily apply pressure to the runner tube 113 when desired. Transient fixation can allow withdrawal of the anchor wire 111 relative to the runner tube 113 for adjustments during a procedure, and such adjustments may be followed by fixation of the anchor wire 111 with a separate anchoring RHV. If prolonged fixation is provided on the runner tube 113 and the anchor wire 111 simultaneously, the relative size of the anchor 102 can remain fixed by the relative positions of the tether components, and the transient increase and decrease of anchoring by loads applied to the tether 104 by the tetherable guide-sheath 400, e.g., during working device advancement, may not occur.

Reiterating the steps above with the system illustrated in FIG. 37A-37B, after the tetherable guide-sheath 400 is positioned, the tether 104 can be fed through the elongated arm 1920 of the multiheaded RHV 1918 and the anchoring RHV 1502 can fix the anchor wire 111 as it is tightened. A locking element 130, i.e., a torque device as is known in the art, can also be added to provide security of the hold on the system. If the runner tube 113 has an independent fixating technology applied to it (it is not "non-restraining"), then the relationship of the runner tube 113 and the anchor wire 111 can be stabilized to fix the tension applied to the anchor 102.

Referring to FIG. 37B, a schematic view of an anchoring delivery system deployed in a target anatomy is illustrated in accordance with an implementation. The proximal portion of the tetherable guide-sheath 400 can include a dedicated bifurcation having the multi-headed RHV 1918. For example, the working lumen may pass through an arm of the dedicated bifurcation having length of 10 to 20 mm between the working proximal port and the bifurcation point. Accordingly, standard RHVs may be connected to the tetherable guide-sheath 400. This "dedicated exit" version of the tetherable guide-sheath system may include the working lumen and the tether lumen, and the tether lumen may extend through the elongated arm and the tether gripper. More particularly, each end of the dedicated bifurcation may include a "single-headed" RHV. The arm sections of the dedicated bifurcation may be separated, e.g., by 10 to 20 mm, to avoid operator confusion during use. The working lumen portion of the dedicated bifurcation, i.e., the working lumen and RHV connected to the working lumen, may operate similar to typical neurovascular access systems. The tether lumen portion of the dedicated bifurcation may include a clear semi-rigid or rigid segment, i.e., the elongated arm, to allow visualization of the runner tube and anchoring wire for refined adjustment of the expansion of the anchor, as described above. The anchor wire may also be anchored outside the locking RHV with an anchoring locking element or other clamping device. Furthermore, the detachment point may or may not have an ability to restrain or fix the runner tube in place, as described above.

Figure 38:
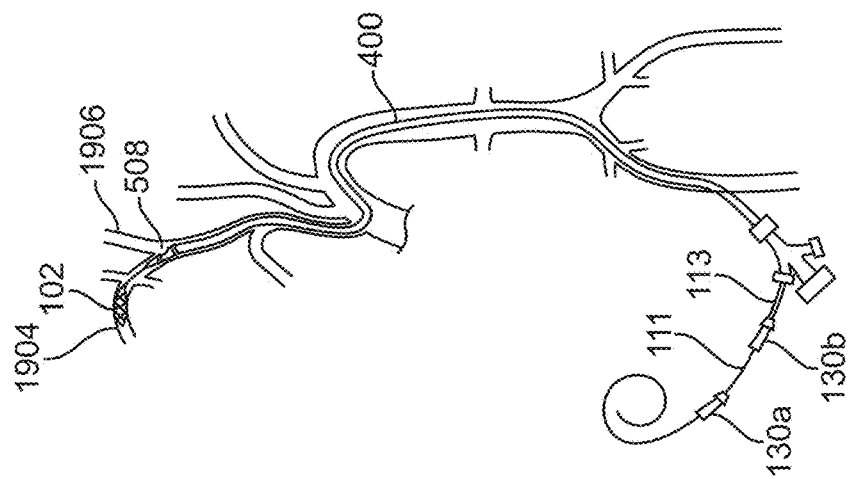
FIG. 38 illustrates a schematic view of an anchoring delivery system deployed in a target anatomy, in accordance with an implementation.

Referring to FIG. 38, a schematic view of an anchoring delivery system deployed in a target anatomy is illustrated in accordance with an implementation. The anchor 102 can be configured anchor within a vessel 1904. As previously described, anchoring can be controlled by adjusting a relative position of the anchoring wire 111 relative to the runner tube 113. In an implementation, the tethering device 100 can include a locking mechanism to fix the relative position between the anchoring wire 111 and the runner tube 113 after the desired anchor dimension or tension is achieved.

In an implementation, the locking mechanism includes a pair of clamping mechanism or devices, such as a pair of locking elements 130. Each locking element 130 can have a fitting adapted to grip one or more of the tether components (the runner tube 113 or the anchoring wire 111) securely. Thus, a predetermined tension can be applied by gripping and moving the tether components by a respective locking element 130. The pair of clamping devices can be referred to as an anchor wire locking element 130a (connected to the anchor wire 111) and the runner tube locking element 130b (connected to the runner tube 113). In an implementation, the anchor wire locking element 130a is sized to accept the anchor wire 111 diameter, but not to accept the larger diameter of the runner tube 113. For example, the anchor wire locking element 130a can incorporate a collet having a relaxed inner diameter smaller than the outer diameter of the runner tube 113. By contrast, the runner tube locking element 130b can be sized to receive the runner tube 113 in the unclamped state, but to lock down firmly on the runner tube 113 in a locked state, e.g., when the torque device is actuated by rotation of a cap component on a body component, as is known in the art.

The paradigm of a pair of locking element devices 130 to control the tethering device anchor 102 expansion can be incorporated in a "dedicated bifurcation" version of a tetherable guide-sheath 400 or in a "multiheaded RHV" version of a tetherable guide-sheath 400. In either case, respective locking elements 130 can be tightened down on a corresponding anchor wire 111 and a corresponding runner tube 113 to apply tension to expand or contract the anchor 102, e.g., between an unexpanded state and an expanded state. Furthermore, the locking element devices 130 can be gripped to advance or withdraw the tethering device 100 within the tetherable guide-sheath 400, or to advance or withdraw the combined anchoring delivery system.

In an implementation, the locking elements 130 can be used to lock the anchor 102 in position. For example, after pulling on the anchoring wire 111 relative to the runner tube 113 to expand the anchor 102, the anchoring wire locking element 130a can be repositioned to abut a proximal end of the runner tube 113. The anchoring wire locking element 130a can then be tightened and released, such that spring force retained within the anchor 102 can tension the anchoring wire 111 and the proximal end of the runner tube 113 can press against (but not move) the anchoring wire locking element 130a. The tethering device 100 can therefore be locked into position to maintain a constant size of the expanded anchor 102. Similarly, the runner tube locking element 130b, after being used to apply desired pressure and expansion to the anchor 102, can be loosened and advanced against the proximal furcation 404 or an RHV connected to the proximal furcation 404 so as to not allow any motion of the runner tube 113 relative to the tetherable guide-sheath 400.

Figure 39A:
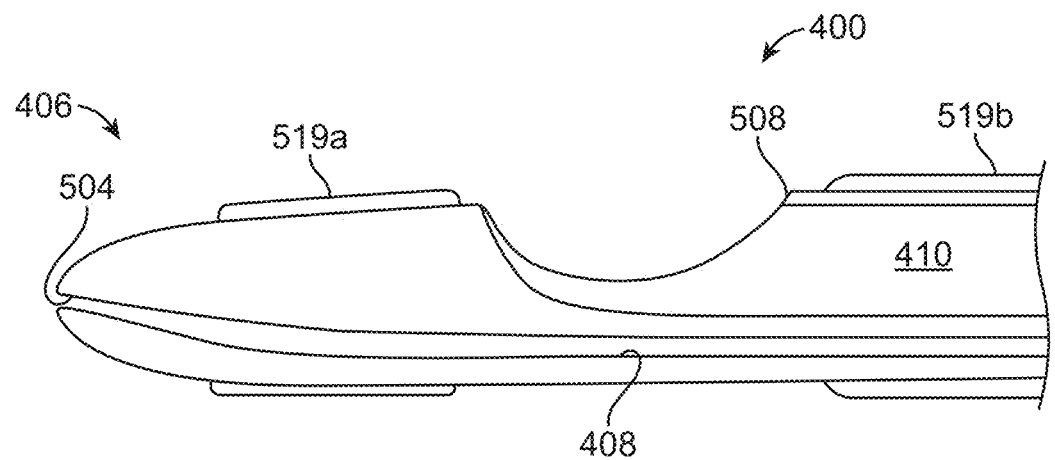
FIG. 39A-39B illustrate detailed sectional views, taken from Detail B of FIG. 9, of a distal portion of a tetherable guide-sheath, in accordance with an implementation.
Figure 39B:
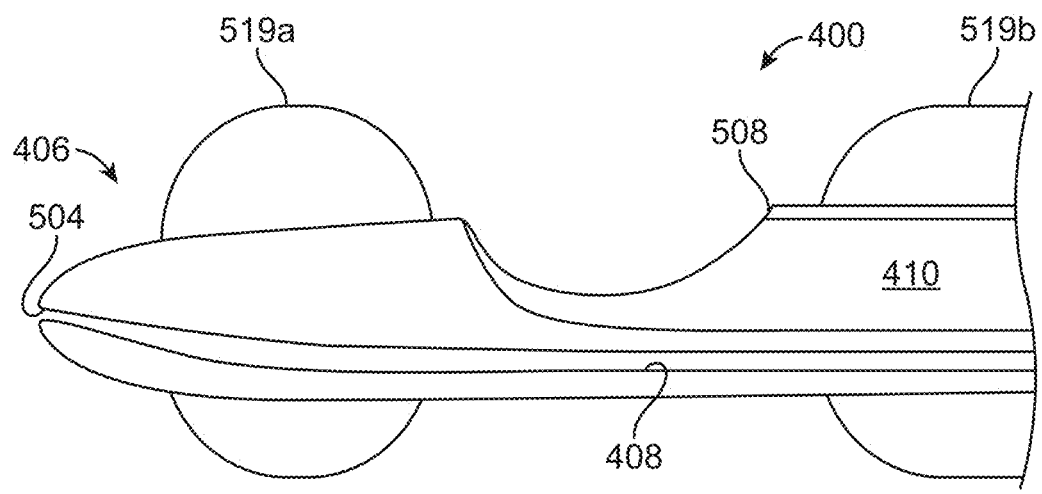

Referring to FIG. 39A, a detailed sectional view, taken from Detail B of FIG. 15A, of a distal portion of a tetherable guide-sheath is illustrated in accordance with an implementation. Many stroke interventionists prefer the use of balloon guide catheters to create flow cessation and reduce the risk of fragmentation and distal embolization due to the constant current of antegrade flow in the Circle of Willis and internal carotid artery during Stentriever use or MAT/ADAPT/SMAT/Solumbra. Balloon guides are typically placed in the cervical ICA and single balloon inflation creates cessation of flow in the ICA to the ICA terminus. A system is illustrated, which may be used with an anchoring delivery system to provide similar flow cessation.

In an implementation, a tetherable guide-sheath 400 incorporates one or more balloons 519 near the tip to isolate the mouth from blood flow within a target anatomy. For example, a distal balloon 519a and a proximal balloon 519b positioned relative to the mouth 508 can be inflated, for example simultaneously, to transition from the state shown in FIG. 39A to the state shown in FIG. 39B. Inflation of the balloons 519 of the tetherable guide-sheath 400 can be performed by delivering an inflation fluid, e.g., $CO_2$, contrast, contrast/saline mix, or another inflation fluid, through one or more inflation lumens to a respective balloon.

Figure 40B:
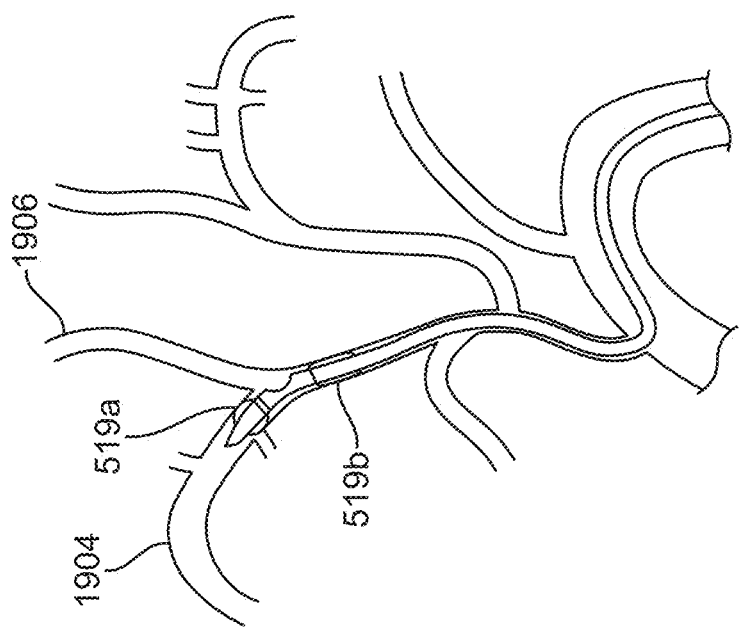
FIG. 40A-40B illustrate operations of a method of deploying an anchoring delivery system deployed in a target anatomy, in accordance with an implementation.
Figure 40A:
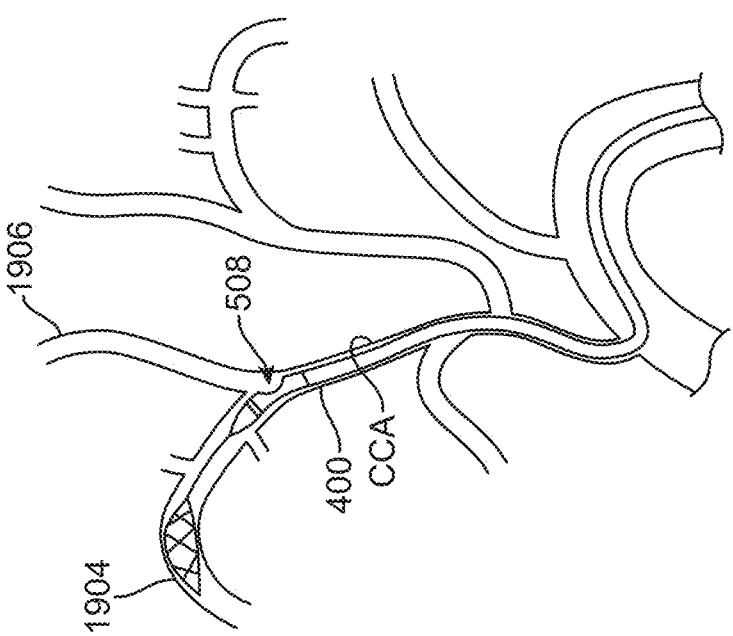

Referring to FIG. 40A, an operation of a method of deploying an anchoring delivery system deployed in a target anatomy is illustrated in accordance with an implementation. The balloons 519 can expand to create independent occlusive events in the anchoring vessel 1904, e.g., in a proximal portion of the ECA, and in the distal CCA, creating an effect similar to the ICA occlusion favored by current balloon guide usage. When in use, the tetherable guide-sheath 400 having dual balloons 519 can be positioned as before with the anchoring delivery system securing the mouth 508 to direct a working device toward the target vessel 1906, e.g., the ICA. Referring to FIG. 40B, inflation of the proximal balloon 519b and/or the distal balloon 519a can create an occlusion at the ECA and CCA level and antegrade flow up ICA may cease. If the ECA has an early branch point (often the superior thyroid artery or the like), there may be some "leak" from this ECA branch that will create a small, but present antegrade flow in the ICA. Care may be taken to position the distal balloon 519a in such a way that it occludes and covers the first branch of the ECA, if possible. As the ICA is a conduit vessel, it has no branch points while it is in the cervical segment and even into the bony petrous. Near the Circle of Willis, small collateral branches to the ICA may be present which is where the column of stagnant flow will end. It is contemplated that usage patterns of the tetherable guide-sheath may be similar with or without the balloon occlusion capability provided by the dual balloon system, i.e., a method of using the anchoring delivery system may be similar to that described with respect to FIG. 36 above, perhaps with an added operation for inflating the proximal balloon 519b and/or distal balloon 519a after advancing the tetherable guide-sheath toward the target vessel.

Figure 41:
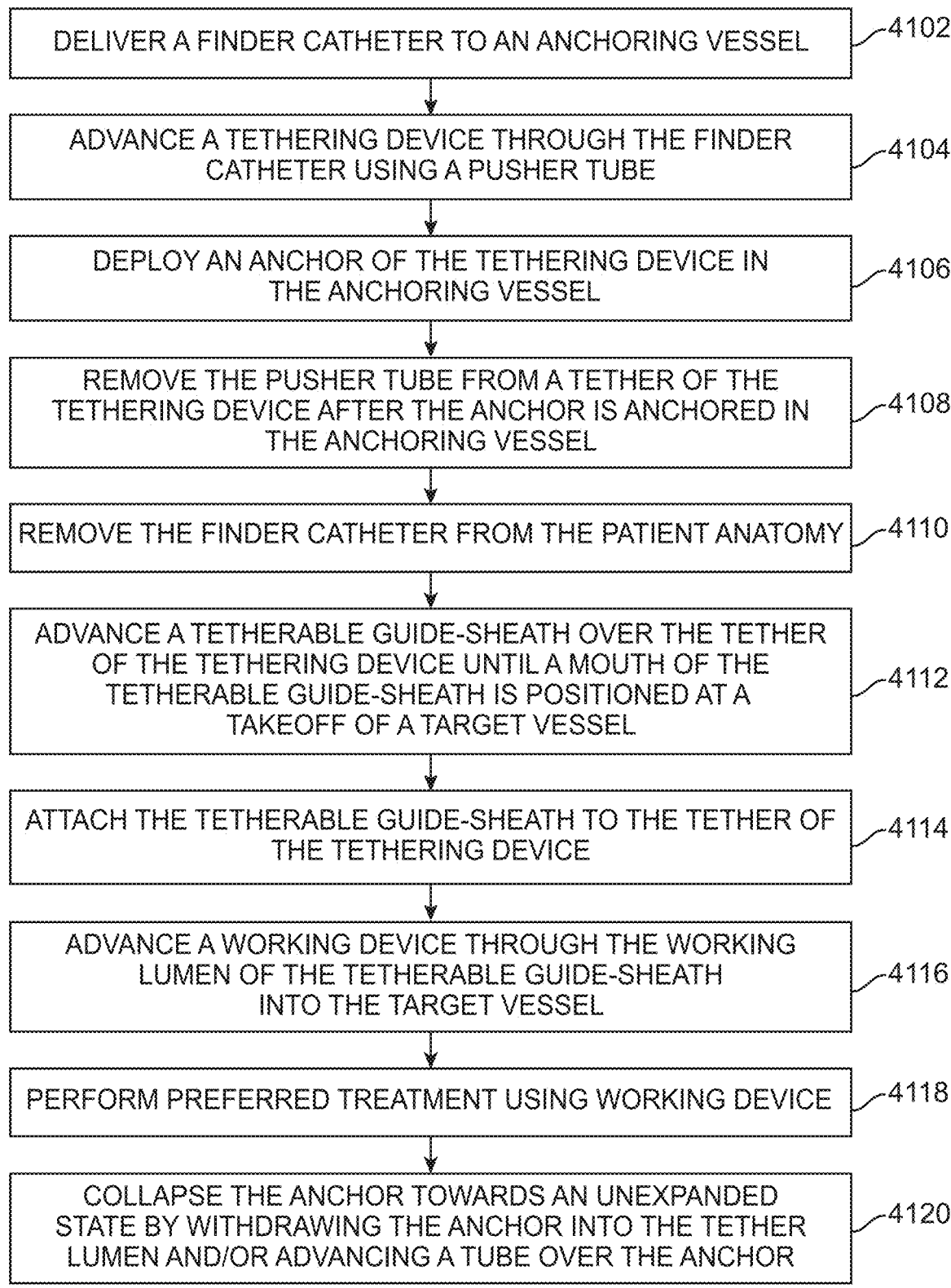
FIG. 41 illustrates a flowchart of a method of deploying an anchoring delivery system, in accordance with an implementation.

Referring to FIG. 41, a flowchart of a method of deploying an anchoring delivery system is illustrated in accordance with an implementation. The method shall be described below with reference to FIGS. 42A-42D, which illustrate schematic views of an anchoring delivery system deployed in a target anatomy, in accordance with an implementation.

Figure 42D:
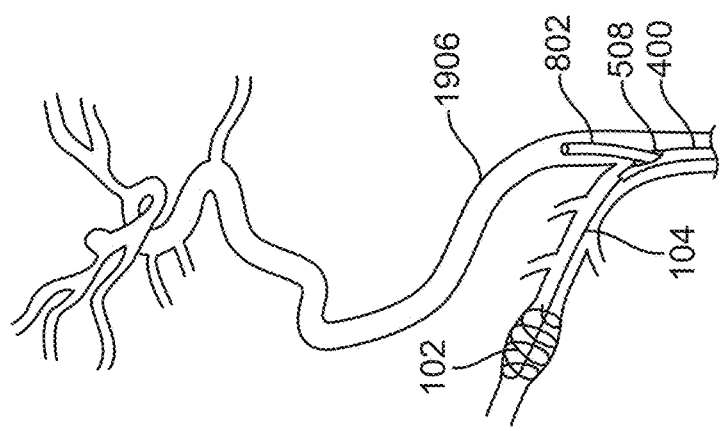
FIG. 42A-42D illustrate schematic views of an anchoring delivery system deployed in a target anatomy, in accordance with an implementation.
Figure 42C:
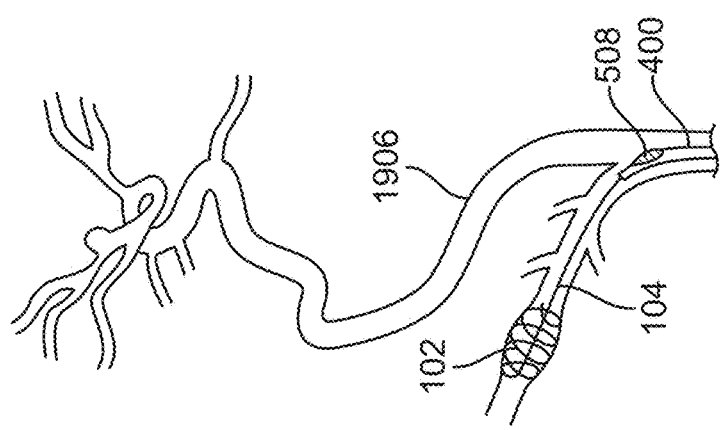
Figure 42B:
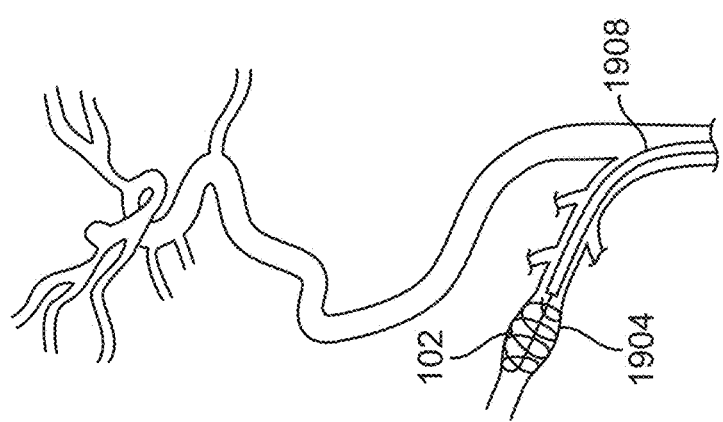
Figure 42A:
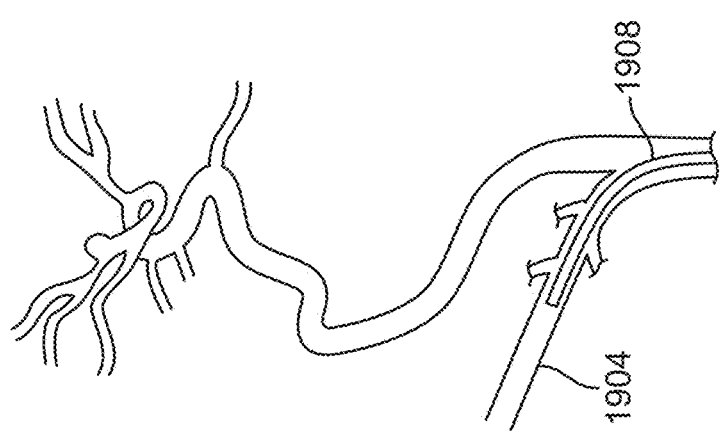

At operation 4102, referring to FIG. 42A, an operator can deliver a finder catheter 1908 (typically a 5F guide or diagnostic catheter) to an anchoring vessel in a patient anatomy, e.g., an external carotid artery (ECA). At operation 4104, the tethering device 100 can be advanced through the finder catheter 1908. The tethering device 100 can include an anchor 102 having a pre-shaped element like a wire that can pass through the finder catheter as described elsewhere herein. As the tethering device 100 is advanced, the anchor 102 can slide through the finder catheter 1908 in an unexpanded state, e.g., the lower profile configuration shown in FIGS. 5H-5L. The tethering device 100 can be advanced until the anchor 102 is near a distal end of the finder catheter 1908, and near an anchoring site in the anchoring vessel 1904. The anchor 102 can be pushed through the finder catheter 1908 by the pusher tube 109.

At operation 4106, referring to FIG. 42B, the anchor 102 can be deployed at the anchoring site by advancing the anchor 102 out of the finder catheter 1908, by retracting a constraining element positioned over the tethering device 100 to unsleeve the anchor 102, or otherwise deploying the anchor 102 at the anchoring site. The anchor 102 can therefore self-expand, e.g., to the preformed larger profile configuration shown in FIGS. 5H-5L. In the expanded state, the anchor 102 can press against, distort, and/or anchor, within the anchoring vessel 1904. In an implementation, the anchor 102 includes a coil segment having a bulbous profile, although the anchor 102 can also include other shapes, e.g., pigtail, bulbous, hook-shaped, conical, etc., as described herein.

At operation 4108, after the anchor 102 is anchored at the anchoring site, the pusher tube 109 can be removed from the tether 104. For example, the pusher tube 109 can be retrieved from the finder catheter 1908. More particularly, the pusher tube 109 can be pulled proximally to slide over the tether 104 and to be removed from the patient anatomy.

At operation 4110, the finder catheter 1908 can be removed from the patient anatomy with a pulling motion. In an implementation, the anchor 102 can provide a resistive anchoring force greater than the friction force applied to the tether 104 by the finder catheter 1908, and thus, the tethering device 100 remains in place during retraction of the finder catheter 1908.

At operation 4112, referring to FIG. 42C, the operator can advance a tetherable guide-sheath 400 over the tether 104 of the tethering device 100. For example, the anchor wire 111 can be loaded into a tether distal port 504 of the tetherable guide-sheath 400 and the tetherable guide-sheath 400 can be advanced over the tether 104 through the anatomy toward the target vessel 1906. More particularly, the tetherable guide-sheath 400 can be advanced until a mouth 508 is positioned at or near a takeoff of a target vessel 1906, e.g., an internal carotid artery (ICA) leading to a targeted embolus. The tetherable guide-sheath 400 can be torqued to rotate the mouth 508 such that a working device 802 delivered through the working lumen will be directed into an entrance of the target vessel 1906 at the anchoring vessel/target vessel junction. It should be appreciated, however, that the mouth 508 need not be aligned with or rotated towards the entrance of the target vessel 1906 for the working device 802 to be delivered into the target vessel 1906.

At operation 4114, the tetherable guide-sheath 400 can be attached to the tether 104 of the tethering device 100. For example, a tether gripper, e.g., an RHV or another gripping technology, (not shown) can be used to affix the tetherable guide-sheath 400 to the tethering device 100 at a point of fixation 1912 proximal to the anchoring site and/or the entrance to the target vessel 1906.

At operation 4116, referring to FIG. 42D, a working device 802, e.g., a large bore catheter, can be advanced through the working lumen into the target vessel 1906 to perform a preferred AIS treatment. As the working device 802 is advanced into the target vessel 1906, any reaction force applied by the distal anatomy may be transmitted by the working device 802 to the tetherable guide-sheath 400 and the tethering device 100, placing the tether 104 in tension between the anchoring site and the point of fixation 1912. Whereas such reaction force may ordinarily cause buckling of the working device 802, the tetherable guide-sheath 400 can be buttressed by the tensioned tether 104, and thus, may effectively support the working device 802 to allow it to be advanced without buckling or prolapse. At operation 4118, once the working device 802 is in place, e.g., at an embolus, the preferred AIS treatment, e.g., aspiration of the embolus, can be performed. The working device 802 can then be removed from the anchoring delivery system and the patient anatomy.

At operation 4120, the tether 104 can be pulled to withdraw the anchor 102 into the tether lumen 408 of the tetherable guide-sheath 400, or the tetherable guide-sheath 400 can be exchanged with a separate catheter, such as a guide or diagnostic catheter, that can be advanced over the anchor 102 to capture the anchor 102. The tetherable guide-sheath 400 and/or tethering device 100 can then be removed from the patient anatomy to complete the use of the anchoring delivery system and finish the AIS intervention.

Working Devices

The anchoring delivery systems described herein can be used to deliver one or more working devices through the working lumen to the distal target anatomy. It should be appreciated that the working device delivered through the anchoring delivery systems can vary. The working devices described herein can include a large-bore catheter, an advanced catheter, nesting catheters, wire, or balloon. The anchoring delivery systems described herein can be used with a variety of working devices and reference to one particular working device is not intended to be limiting. The tension and support provided by the tethering device 100 and the tetherable guide-sheath 400 allow for improved access to the particularly tortuous anatomy of the cerebral vasculature without concomitant prolapse of the tetherable guide-sheath 400 or the working device being delivered when the device is advanced more distally. The anchoring delivery systems described herein provide stability for procedures such as AIS approaches to be performed accurately, simply and safely in what would otherwise be prevented due to tortuosity or angulation at the great vessels and/or at the intracranial vasculature.

Again with respect to FIGS. 1A-1B, the anchoring delivery system 10 is shown as having a tethering device 100 and a tetherable guide-sheath 400. As described throughout the specification, the tetherable guide-sheath 400 is configured to receive and support advancement of a working device 802 and can be a commercially available guiding sheath. In some implementations, the working device 802 can include the rapid aspiration thrombectomy systems having a spined catheter as described, for example, in U.S. application Ser. No. 15/015,799, filed Feb. 4, 2016, which is incorporated by reference herein in its entirety.

As best shown in FIG. 1B, the working device 802 can include a spined catheter 320 used with or without a catheter advancement element 340. It should be appreciated that although the spined catheter 320 is described herein as being advanced with a catheter advancement element 340 that other advancement tools are considered herein, such as a microcatheter and/or guidewire as are known in the art. The spined catheter 320 can have a relatively flexible, distal luminal portion 322 coupled to a more rigid, kink-resistant proximal spine 330. The luminal portion 322 can have an inner lumen 323 extending between a proximal end and a distal end of the luminal portion 322. The spine 330 is configured to move the luminal portion 322 in a bi-directional manner through the working lumen 410 of the tetherable guide-sheath 400 such that the luminal portion 322 can be advanced out of the working lumen 410 into a target location for treatment within the target vessel. The length of the luminal portion 322 can be shorter than a length of the working lumen 410 of the tetherable guide-sheath 400 such that upon advancement of the luminal portion 322 towards the target location only a short overlap region 348 between the luminal portion 322 and the working lumen 410 remains, which will be described in more detail below.

The lumen 323 of the catheter 320 can have a first inner diameter and the working lumen 410 of the tetherable guide-sheath 400 can have a second, larger inner diameter. The lumens 323, 410 are configured to be fluidly connected and contiguous such that fluid flow into and/or out of the system 10 is possible, such as by applying suction from an aspiration source coupled to the system 10 at a proximal end. As mentioned above, the length of the luminal portion 322 is shorter than a length of the working lumen 410 of the tetherable guide-sheath 400 such that upon advancement of the luminal portion 322 towards the target location using the spine 330 only the short overlap region 348 between the luminal portion 322 and the working lumen 410 remains and the smaller diameter spine 330 extends within the working lumen 410. This allows for the larger diameter working lumen 410 to maintain greater aspiration forces than would otherwise be provided by the smaller diameter luminal portion 322 of the catheter 320. The markedly shorter length of the luminal portion 322 results in a step up in luminal diameter between the luminal portion 322 contiguous with the working lumen 410 providing a markedly increased radius and luminal area for aspiration of the clot, particularly in comparison to other systems where the aspiration lumen runs along the entire inner diameter of the aspiration catheter. More particularly, the combined volume of the luminal area of the spined catheter 320 and the luminal area of the working lumen 410 proximal to the distal luminal portion 322 is greater than the luminal area of the large bore catheter along the entire length of the system. Thus, the likelihood of removing the embolus in a single aspiration attempt may be increased. More particularly, the stepped up luminal diameter along the spine 330 may enable a greater aspiration force to be achieved resulting in improved aspiration of the embolus. Further, this configuration of the catheter 320 and spine 330 greatly speeds up the time required to retract and re-advance the catheter 320 through the working lumen 410. The proximal spine 330 of the catheter 320 has a length and structure that extends through the working lumen 410 of the tetherable sheath-guide 400 to a proximal end of the system 10 such that the spine 330 can be used to advance and retract the catheter 320 through the working lumen 410. The spine 330 of the catheter 320, however, takes up only a fraction of the luminal space of the system 10 resulting in increased luminal area for aspiration. In some implementations, for example, in an OTW version of the catheter 320, the spine 330 can be a hypotube having a lumen extending through the spine 330. The spine 330 can also be formed of a solid metal rod or a flat ribbon. In some implementations, the spine 330 is a ribbon of stainless steel having dimensions of 0.012"× 0.020". In other implementations, the spine 330 can have a cross-sectional area along an arc, such as a quarter circle or a c-shape.

Generally, the outer diameter of the spine 330 is substantially smaller than the outer diameter of the distal luminal portion 322 allowing for an increased luminal area for aspiration through the working lumen 410 of the tetherable guide-sheath 400. This decreases the time it takes to aspirate the occlusion and increases the possibility of removing the occlusion in a single aspiration attempt. The stepped up luminal diameter also increases the annular area available for forward flushing of contrast, saline, or other solutions while devices such as microcatheters or other devices may be coaxially positioned in the luminal portion 322 of the catheter 320 and/or the working lumen 410. This can increase the ease and ability to perform angiograms during device navigation.

The outer diameter of the tetherable guide-sheath 400 can be suitable for insertion into at least the carotid artery, with a working lumen 410 suitably sized for providing a passageway for a working device 802 to treat an occlusion distal to the carotid artery towards the brain. In some implementations, the inner diameter of the working lumen 410 can be about 0.074" and the outer diameter of the body of the tetherable guide-sheath 400 can be about 0.090", corresponding to a 5 French sheath size. In some implementations, the inner diameter of the working lumen 410 can be about 0.087" and the outer diameter of the body of the tetherable guide-sheath 400 can be about 0.104", corresponding to a 6 French sheath size. In some implementations, the inner diameter of the working lumen 410 can be about 0.100" and the outer diameter of the body of the tetherable guide-sheath 400 can be about 0.177", corresponding to a 7 French sheath size. However, it should be appreciated that smaller or larger sheath sizes are considered herein. In some implementations, the working device has an OD configured to fit through a 6F introducer sheath (0.071") and an inner diameter that is sized to receive a 0.054" working device. In some implementations, the working device has an OD configured to fit through an 8F introducer sheath (0.088") and an inner diameter that is sized to receive the 0.071" working device.

As mentioned above, the length of the body 402 and thus, the length of the working lumen 410 can be in the range of 80 to 90 cm or up to about 100 cm or up to about 105 cm. In comparison, the length of the luminal portion 322 of the catheter 320 fed through the working lumen 410 can be shorter than the length of the body 402. In some implementations, the length of the luminal portion 322 extends from a region near the distal end of the body 402 to a site of the occlusion, forming a proximal overlap region 348 with the distal end. Taking into account the variation in occlusion sites and sites where the tetherable guide-sheath 400 distal tip 406 may be positioned, the length of the luminal portion 322 may range from about 10 cm to about 25 cm. The length of the luminal portion 322 is less than the length of the body 402 of the tetherable guide-sheath 400 such that as the spined catheter 320 is retracted into the working lumen 410 there remains a seal between the overlap region 348 of the catheter 320 and the inner diameter of the working lumen 410. In some implementations, the length of the luminal portion 322 is sufficient to reach a region of the M1 segment of the middle cerebral artery (MCA) and other major vessels from a region of the internal carotid artery such that the proximal end region of the luminal portion 322 of the catheter 320 avoids extending within the aortic arch. This limits the number of severe angulations the luminal portion 322 of the catheter 320 must navigate while still reaching target sites in the more distal cerebral anatomy. Used in conjunction with a tetherable guide-sheath 400 having a sheath body 402 and a working lumen 410, in an implementation where the spined catheter 320 reaches the ICA and the distance to embolus can be less than 20 cm. The distal luminal portion 322 having a length of approximately 25 cm can allow for an overlap region 348 with the body 402 to create a seal. The overlap region 348 can have a length of a few centimeters and may vary depending on the distance from the embolus E to the distal end of the distal luminal portion 322, e.g., depending on how far the spined catheter 320 is advanced relative to the guide-sheath 400.

In an implementation, the distal luminal portion 322 of the catheter 320 is constructed to be flexible and lubricious, so as to be able to safely navigate to the target location. The distal luminal portion 322 can be kink resistant and collapse resistant when subjected to high aspiration forces so as to be able to effectively aspirate a clot. The luminal portion 322 can have increasing flexibility towards the distal end with smooth material transitions along its length to prevent any kinks, angulations or sharp bends in its structure, for example, during navigation of severe angulations such as those having 90° or greater to 180° turns, for example at the aorto-iliac junction, the left subclavian take-off from the aorta, the takeoff of the brachiocephalic (innominate) artery from the ascending aorta and many other peripheral locations just as in the carotid siphon. For example, a first portion of the distal luminal portion 322 can be formed of a material having a hardness of 72D along a first length, a second portion can be formed of a material having a hardness of 55D along a second length, a third portion can be formed of a material such as Pebax MX1205 (40D) along a third length, a fourth portion can be formed of a material having a hardness of 35D along a fourth length, a fifth portion can be formed of a material having a hardness of 25D along a fifth length, a sixth portion can be formed of a material such as Tecoflex having a hardness of 85A along a sixth length, and a final distal portion of the catheter can be formed of a material such as Tecoflex having a hardness of 80A. Thus, the distal luminal portion 322 transition from being less flexible near its junction with the stainless steel spine 330 to being more flexible at the distal-most end where the distal tip 346 of the catheter advancement element 340 extends therefrom.

In some implementations, the distal luminal portion 322 includes two or more layers. In some implementations, the distal luminal portion 322 includes an inner lubricious liner, a reinforcement layer, and an outer jacket layer. The outer jacket layer may be composed of discreet sections of polymer with different durometers, composition, and/or thickness to vary the flexibility along the length of the distal luminal portion 322. In an implementation, the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 322. In an implementation, the outer surface of the catheter 320 is coated with a lubricious coating such as a hydrophilic coating. In some implementations the coating may be on an inner surface and/or an outer surface to reduce friction during tracking. The coating may include a variety of materials as is known in the art. The spine portion 330 may also be coated to improve tracking through the working lumen 410. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinyl alcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It is desirable to have a catheter 320 having an inner diameter that is as large as possible that can be navigated safely to the site of the occlusion, in order to optimize the aspiration force. A suitable size for the inner diameter of the distal luminal portion 322 may range between 0.040" and 0.100", depending on the patient anatomy and the clot size and composition. The outer diameter of the distal luminal portion 322 can be sized for navigation into cerebral arteries, for example, at the level of the M1 segment or M2 segment of the cerebral vessels. The outer diameter (OD) should be as small as possible while still maintaining the mechanical integrity of the catheter 320. In an implementation, the difference between the OD of distal luminal portion 322 of the catheter 320 and the inner diameter of the working lumen 410 of the tetherable guide-sheath 400 is between 0.001" and 0.002". In another implementation, the difference is between 0.001" and 0.004". In some implementations, the guide-sheath 400 ID is between 0.087" and 0.088" and the OD of the distal luminal portion 322 of the catheter 320 is approximately 0.082" and 0.086" such that the difference in diameters is between 0.001" and 0.005". In an implementation, the luminal portion 322 of the catheter 320 has a uniform diameter from a proximal end to a distal end. In an implementation, the luminal portion 322 of the catheter 320 is tapered towards the distal end of the distal luminal portion 322 such that the distal-most end of the catheter has a smaller outer diameter compared to a more proximal region of the catheter near where it seals with the tetherable guide-sheath 400. In another implementation, the luminal portion 322 of the catheter OD steps up at an overlap portion to more closely match the sheath inner diameter. This implementation is especially useful in a system with more than one catheter suitable for use with a single access sheath size.

The overlap region 348 can be maintained between the working lumen 410 of the tetherable guide-sheath 400 near a distal end region of the sheath body 402 and the luminal portion 322 of the catheter 320 upon extension of the luminal portion 322 into the target anatomy. It should be appreciated where the catheter OD of the spined catheter 320 matches the inner diameter of the tetherable guide-sheath 400 or the difference is between 0.001"-0.002", a seal to fluid being injected or aspirated can be achieved by the overlap region 348 such that no increase in catheter OD is necessary. The difference between the catheter OD and the inner diameter of the tetherable guide-sheath 400 can vary, for example, between 1-2 thousandths of an inch, or between 1-4 thousandths of an inch, or between 1-12 thousandths of an inch. A seal to fluid being injected or aspirated between the catheter and the sheath can be achieved by the overlap 348 between their substantially similar dimensions without incorporating any separate sealing structure or seal feature.

The overlap region 348 is sized and configured to create a seal that allows for a continuous aspiration lumen from the distal tip region of the catheter 320 to the proximal end 403 of the tetherable guide-sheath 400 where it is connected to an aspiration source. The strength of the seal achieved can be a function of the difference between the outer diameter of the catheter 320 and the inner diameter of the working lumen 410 as well as the length of the overlap region 348, the force of the suction applied, and the materials of the components. For example, the sealing can be improved by increasing the length of the overlap region 348. However, increasing the length of the overlap region 348 can result in a greater length through which aspiration is pulled through the smaller diameter of the luminal portion 322 rather than the larger diameter of the working lumen 410. As another example, higher suction forces applied by the aspiration source can create a stronger seal between the luminal portion 322 and the working lumen 410 even in the presence of a shorter overlap region 348. Further, a relatively softer material forming the luminal portion and/or the body 402 can still provide a sufficient seal even if the suction forces are less and the overlap region 348 is shorter. In an implementation, the overlap region 348 is configured to enable sealing against a vacuum of up to 25 inHg, or up to 28 inHg. In an implementation, the overlap region 348 is configured to enable sealing against a pressure of up to 300 mmHg or up to 600 mmHg or up to 700 mmHg with minimal to no leakage.

The distal luminal portion 322 of the catheter 320 can have a radiopaque marker 324a at the distal tip region to aid in navigation and proper positioning of the tip under fluoroscopy (see FIG. 1B). Additionally, a proximal region of the catheter 320 may have one or more proximal radiopaque markers 324b so that the overlap region 348 can be visualized as the relationship between a radiopaque marker 510 on the tetherable guide-sheath 400 and the radiopaque marker 324b on the catheter 320. In an implementation, the two radiopaque markers (marker 324a at distal tip and a more proximal marker 324b) are distinct so as to minimize confusion of the fluoroscopic image, for example the catheter proximal marker 324b may be a single band and the marker 510 on the tetherable guide-sheath 400 may be a double band. The radiopaque markers 324 of the distal luminal portion 322, particularly those near the distal tip region navigating extremely tortuous anatomy, can be relatively flexible such that they do not affect the overall flexibility of the distal luminal portion 322 near the distal tip region. The radiopaque markers 324 can be tungsten-loaded or platinum-loaded markers that are relatively flexible compared to other types of radiopaque markers used in devices where flexibility is not paramount.

As mentioned previously, the spine 330 is configured to allow distal advancement and proximal retraction of the catheter 320 through the working lumen 410 of the tetherable guide-sheath 400. In an implementation, the length of the spine 330 is longer than the entire length of the tetherable guide-sheath 400 (from distal tip to proximal valve), such as by about 5 cm to 15 cm. As shown in FIG. 1B, the spine 330 can include a mark 332 to indicate the overlap between the distal luminal portion 322 of the catheter 320 and the sheath body 402. The mark 332 can be positioned so that when the mark 332 is aligned with the sheath proximal valve 434 during insertion of the catheter 320 through the tetherable guide-sheath 400, the spined catheter 320 is positioned at the distal-most position with the minimal overlap length needed to create the seal between the spined aspiration catheter 320 and the working lumen 410.

The spine 330 can include a gripping feature such as a tab 334 on the proximal end to make the spine 330 easy to grasp and advance or retract. The tab 334 can couple with one or more other components of the system as will be described in more detail below. The proximal tab 334 can be designed to be easily identifiable amongst the other devices existing in the sheath proximal valve 434, such as guidewires or retrievable stent device wires. In an implementation, at least a portion of the spine 330 and/or tab 334 is colored a bright color, or marked with a bright color, to make it easily distinguishable from guidewire, retrievable stent tethers, or the like. In the implementation in which multiple spined catheters 320 are used in a nesting fashion to reach more distal locations within the brain, each spine 330 and/or tab 334 can be color-coded or otherwise labeled to clearly show to an operator which spine 330 of which catheter 320 it is coupled to.

The spine 330 can be configured with sufficient stiffness to allow advancement and retraction of the distal luminal portion 322 of the spined aspiration catheter 320, yet also be flexible enough to navigate through the cerebral anatomy as needed without kinking. Further, the outer diameter of the spine 330 is sized to avoid taking up too much luminal area in the lumen 410 of the tetherable guide-sheath 400. In an implementation, the spine 330 is a round wire, with dimensions from 0.014" to 0.018". In another implementation, the spine 330 is a ribbon with dimensions ranging from 0.010" to 0.015" thick, and 0.015" thick to 0.025" thick. The ribbon can have a variety of cross-sectional shapes such as a flat ribbon or curved ribbon forming a c-shape or other shape along an arc. In another implementation, the spine 330 is a hypotube formed from a flattened ribbon of stiff material rolled into a tubular shape. In an implementation, the spine 330 material is a metal such as a stainless steel or nitinol as well as a plastic such as any of a variety of polymers.

The spine 330 can be coupled to a proximal end region of the catheter 320 and/or may extend along at least a portion of the distal luminal portion 322 such that the spine 330 couples to the distal luminal portion 322 a distance away from the proximal end. The spine 330 can be coupled to the portion 322 by a variety of mechanisms including bonding, welding, gluing, sandwiching, stringing, tethering, or tying one or more components making up the spine 330 and/or portion 322. In some implementations, the spine 330 and luminal portion 322 are coupled together by sandwiching the spine 330 between layers of the distal luminal portion 322. For example, the spine 330 can be a hypotube or rod having a distal end that is skived, ground or cut such that the distal end can be laminated or otherwise attached to the layers of the catheter portion 322 near a proximal end region. The region of overlap between the distal end of the spine 330 and the portion 322 can be at least about 1 cm. This type of coupling allows for a smooth and even transition from the spine 330 to the luminal portion 322.

The junction between the distal luminal portion 322 of the catheter 320 and the proximal spine 330 can be configured to allow a smooth transition of flexibility between the two portions so as not to create a kink or weak point, and also allow smooth passage of devices through the contiguous inner lumen created by the working lumen 410 of the tetherable guide-sheath 400 and the lumen 323 of the luminal portion 322 of the catheter 320. In an implementation, the distal luminal portion 322 has a transition section 326 near where the luminal portion 322 couples to the spine 330. The transition section 326 can have an angled cut such that there is no abrupt step transition from the working lumen 410 of the tetherable guide-sheath 400 to the catheter 320 inner lumen 323. The angled cut can be generally planer. In an alternate implementation, the angled cut is curved or stepped to provide a more gradual transition zone. It should be appreciated that the proximal end region of the distal luminal portion 322 can be angled in an oblique manner relative to a longitudinal axis of the catheter 320 such that the proximal end and proximal opening into the lumen are at an angle other than 90° to the longitudinal axis of the catheter 320, for example between approximately 0°, 5°, 10°, 15°, 20°, 25°, 30°, 35°, 40°, or 45° up to less than 90°. The proximal end region of the distal luminal portion 322 can also be aligned substantially perpendicular to the longitudinal axis of the catheter 320 such that the proximal end and proximal opening into the lumen are substantially 90° to the longitudinal axis of the catheter 320. Similarly, the distal end region of the distal luminal portion 322 can be angled in an oblique manner relative to a longitudinal axis of the catheter 320 such that the distal end and distal opening from the lumen are at an angle other than 90° to the longitudinal axis of the catheter 320, for example between approximately 0°, 5°, 10°, 15°, 20°, 25°, 30°, 35°, 40°, or 45° up to less than 90°. The distal end region of the distal luminal portion 322 can also be aligned substantially perpendicular to the longitudinal axis of the catheter 320 such that the distal end and distal opening into the lumen are substantially 90° to the longitudinal axis of the catheter 320.

The distal luminal portion 322 and the spine 330 may be joined by a weld bond, a mechanical bond, an adhesive bond, or some combination thereof. The distal end of the spine 330 may have features that facilitate a mechanical joint during a weld, such as a textured surface, protruding features, or cut-out features. During a heat weld process, the features would facilitate a mechanical bond between the polymer distal luminal portion 322 and the spine 330.

As mentioned above, an implementation of the working device 802 can include the spined catheter 320 supplied with a catheter advancement element 340. The catheter advancement element 340 can include a non-expandable, flexible elongate body 360 coupled to a proximal portion 366. The elongate body 360 can be received within and extended through an internal lumen 323 of the distal luminal portion 322 of the catheter 320 (see FIGS. 1A-1B). In some implementations, the distal luminal portion 322 has a single internal lumen 323 extending between proximal and distal ends. The proximal portion 366 of the catheter advancement element 340 is coupled to a proximal end region of the elongate body 360 and extends proximally therefrom. The proximal portion 366 can be less flexible than the elongate body 360 and configured for bi-directional movement of the elongate body 360 of the catheter advancement element 340 within the luminal portion 322 of the catheter 320, as well as for movement of the catheter system as a whole. The elongate body 360 can be inserted in a coaxial fashion through the internal lumen 323 of the luminal portion 322. The outer diameter of at least a region of the elongate body 360 can be sized to substantially fill the internal lumen 323 of the luminal portion 322. The elongate body 360 can have a length that is at least as long as the luminal portion 322 of the catheter although it should be appreciated the elongate body 360 can be shorter than the luminal portion 322 so long as at least a length remains inside the luminal portion 322 when a distal portion of the elongate body 360 is extended distal to the distal end of the luminal portion 322. The distal portion extending distal to the distal end of the luminal portion 322 can include distal tip 346 that protrudes a length beyond the distal end of the luminal portion 322 during use of the catheter advancement element 340. The distal tip 346 of the elongate body 360 that is configured to protrude distally from the distal end of the luminal portion 322 aids in the navigation of the catheter system through the tortuous anatomy of the cerebral vessels, as will be described in more detail below. The proximal portion 366 coupled to and extending proximally from the elongate body 360 can align generally side-by-side with the proximal spine 330 of the catheter 320. The arrangement between the elongate body 360 and the luminal portion 322 can be maintained during advancement of the catheter 320 through the tortuous anatomy to reach the target location for treatment in the distal vessels and aids in preventing the distal end of the catheter 320 from catching on tortuous branching vessels, as will be described in more detail below.

In some implementations, the elongate body 360 can have a region of relatively uniform outer diameter extending along at least a portion of its length and the distal tip 346 tapers down from the uniform outer diameter. When the catheter advancement element 340 is inserted through the catheter 320, this tapered distal tip 346 is configured to extend beyond and protrude out through the distal end of the luminal portion 322 whereas the more proximal region of the body 360 having a uniform diameter remains within the luminal portion 322. As mentioned, the distal end of the luminal portion 322 can be blunt and the distal tip 346 can be tapered providing an overall elongated tapered geometry of the catheter system. The outer diameter of the elongate body 360 also approaches the inner diameter of the luminal portion 322 such that the step up from the elongate body 360 to the outer diameter of the luminal portion 322 is minimized and the lip formed by the distal end of the luminal portion 322 is minimized preventing the lip of the luminal portion 322 from catching on the tortuous neurovasculature, such as around the carotid siphon near the ophthalmic artery branch. In some implementations, the inner diameter of the luminal portion 322 can be 0.072" and the outer diameter of the elongate body 360 is 0.070" such that the difference between them is only 2 thousandths of an inch. In other implementations, the outer diameter of the elongate body 360 is 0.062". Despite this, the luminal portion 322 and the elongate body 360 extending through it in co-axial fashion are flexible enough to navigate the tortuous anatomy leading to the level of M1 or M2 arteries without kinking and without damaging the vessel. The length of the distal tip 346 can vary. In some implementations, the length of the distal tip 346 can be in a range of between about 1.5 cm and about 3.0 cm from the distal-most terminus of the elongate body 360. In other implementations, the length of the distal tip 346 is between 2.0 cm to about 2.5 cm. The distal tip 346 can be a constant taper from the outer diameter of the elongate body 360 down to a second smaller outer diameter at the distal-most tip. The constant taper of the distal tip 346 can be from 0.062" outer diameter to about 0.031" outer diameter. The length of the constant taper of the distal tip 346 can vary, for example, between 1 cm and 3 cm, or between 2.0 cm and 2.5 cm. It should be appreciated that the distal tip 346 need not taper and can achieve its soft, atraumatic and flexible characteristic due to a material property other than change in outer dimension to facilitate endovascular navigation to an embolus in tortuous anatomy. For example, the distal tip 346 can be formed of a material having a hardness of 35D and transitions proximally towards increasingly harder materials having a hardness of 55D and 72D up to the proximal portion 366, which can be a stainless steel hypotube, or a combination of a material property and tapered shape. The materials used to form the regions of the elongate body 360 can include Pebax (such as Pebax 25D, 35D, 55D, 72D) with a lubricious additive compound, such as Mobilize (Compounding Solutions, Lewiston, Maine). Incorporation of a lubricious additive directly into the polymer elongate body means incorporation of a separate lubricious liner, such as a Teflon liner, is unnecessary. This allows for a more flexible element that can navigate the distal cerebral anatomy and is less likely to kink. Similar materials can be used for forming the distal luminal portion 322 of the catheter 320 providing similar advantages. It should also be appreciated that the flexibility of the distal tip 346 can be achieved by a combination of flexible lubricious materials and tapered shapes. For example, the length of the tip 346 can be kept shorter than 2-3 cm, but maintain optimum deliverability due to a change in flexible material from distal-most tip towards a more proximal region a distance away from the distal-most tip. In an implementation, the elongate body 360 is formed of PEBAX (polyether block amide) embedded silicone designed to maintain the highest degree of flexibility. It should be appreciated that the wall thickness of the distal end of the luminal portion 322 can also be made thin enough such that the lip formed by the distal end of the luminal portion 322 relative to the elongate body 360 is minimized.

As mentioned above, the elongate body 360 can be constructed to have variable stiffness between the distal and proximal ends of the elongate body 360. The flexibility of the elongate body 360 is highest at the distal-most terminus of the distal tip 346 and can gradually transition in flexibility to approach the flexibility of the distal end of the luminal portion 322. Upon coupling the catheter advancement element 340 and the catheter 320, the region of the elongate body 360 extending beyond the distal end of the luminal portion 322 can be the most flexible and the region of the elongate body 360 configured to be aligned with the distal end of the luminal portion 322 during advancement in the vessel can have a substantially identical flexibility as the distal end of the luminal portion 322 itself. As such, the flexibility of the distal end of the luminal portion 322 and the flexibility of the body 360 just proximal to the extended portion (whether tapered or having no taper) can be substantially the same. This provides a smooth transition in material properties to improve tracking of the catheter system through tortuous anatomy. Further, the more proximal sections of the elongate body 360 can be even less flexible and increasingly stiffer. It should be appreciated that the change in flexibility of the elongate body 360 can be a function of a material difference, a dimensional change such as through tapering, or a combination of the two. The elongate body 360 has a benefit over a microcatheter in that it can have a relatively large outer diameter that is just 0.003"-0.010" smaller than the inner diameter of the spined catheter 320 and still maintain a high degree of flexibility for navigating tortuous anatomy.

The elongate body 360 can be formed of various materials that provide a suitable flexibility and lubricity. Example materials include high density polyethylene, 72D PEBAX, 90D PEBAX, or equivalent stiffness and lubricity material. The flexibility of the elongate body 360 can increase towards the distal tip such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking.

In some implementations, the elongate body 360 can be generally tubular along at least a portion of its length such that it has a lumen extending parallel to a longitudinal axis of the catheter advancement element 340. In an implementation, the lumen of the elongate body 360 is sized to accommodate a guidewire. The guidewire can extend through the lumen from a proximal opening to a distal opening through which the guidewire can extend. In some implementations, the proximal opening is configured for rapid exchange rather than over-the-wire such that the proximal opening is located a distance away from a proximal tab 364 and distal to the proximal portion 366. The lumen of the elongate body 360 can be configured to receive a guidewire in the range of 0.014" and 0.018" diameter, or in the range of between 0.014" and 0.022". In this implementation, the inner luminal diameter of the elongate body 360 can be between 0.020" and 0.024". The guidewire, the catheter advancement element 340, and the spined catheter 320 can all be assembled co-axially for insertion through the working lumen 410 of the tetherable guide-sheath 400.

Figure 1D:
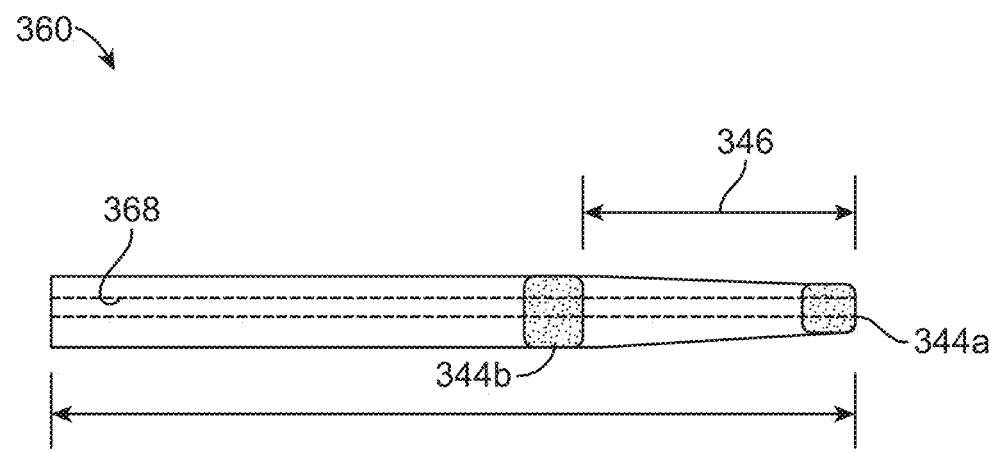
FIG. 1D illustrates a detail view of a distal end of a catheter advancement element shown in FIG. 1A taken along circle D-D.

In other implementations, the entire catheter advancement element 340 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 1D). In some implementations, the proximal portion 366 can be a skived hypotube of stainless steel coated with PTFE having an outer diameter of 0.026". In some implementations, such as an over-the-wire version, the proximal portion 366 can be a skived hypotube coupled to a proximal hub. The proximal portion 366 can extend eccentric or concentric to the distal luminal portion 322. In still further implementations, the elongate body 360 can be a solid element coupled to the proximal portion 366 having no guidewire lumen. At least a portion of the solid elongate body 360, such as the elongate distal tip 346, can be formed of or embedded with or attached to a malleable material that skives down to a smaller dimension at a distal end. The distal tip 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. The shape change can be a function of a user manually shaping the malleable length prior to insertion. Alternatively, the shape change can be a reversible and actuatable shape change such that the tip forms the shape upon activation by a user such that the tip can be used in a straight format until a shape change is desired by the user.

It should be appreciated that the elongate body 360 can extend along the entire length of the catheter 320, including the distal luminal portion 322 and the spine 330 or the elongate body 360 can incorporate the proximal portion 366 that aligns generally side-by-side with the spine 330 of the catheter 320, as described above. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Like the distal luminal portion 322 of the catheter 320, the elongate body 360 can have one or more radiopaque markers 344 along its length. In some implementations, a distal end region can have a first radiopaque marker 344a and a second radiopaque marker 344b can be located to indicate the border between the tapering of the distal tip 346 and the more proximal region of the elongate body 360 having a uniform or maximum outer diameter. This provides a user with information regarding an optimal extension of the distal tip 346 relative to the distal end of the luminal portion 322 to minimize the lip at this distal end of the luminal portion 322 for advancement through tortuous anatomy. In other implementations, for example where the distal tip 346 is not necessarily tapered, but instead has a change in overall flexibility along its length, the second radiopaque marker 344b can be located to indicate the region where the relative flexibilities of the elongate body 360 (or the distal tip 346 of the elongate body 360) and the distal end of the luminal portion 322 are substantially the same. The marker material may be a platinum/iridium band, a tungsten, platinum, or tantalum-impregnated polymer, or other radiopaque marker that does not impact the flexibility of the distal tip 346 and elongate body 360. In some implementations, the radiopaque markers are extruded Pebax loaded with tungsten for radiopacity.

As mentioned above, the spine 330 of the catheter 320 can include a proximal tab 334 on the proximal end of the spine 330. Similarly, the proximal portion 366 coupled to the elongate body 360 can include a tab 364. The tabs 334, 364 can be configured to removably and adjustable connect to one another and/or connect to their corresponding spines. The coupling allows the catheter advancement element 340 to reversibly couple with the catheter 320 to lock (and unlock) the relative extension of the distal luminal portion 322 and the elongate body 360. This allows the spined catheter 320 and the catheter advancement element 340 to be advanced as a single unit. In the locked configuration, the tab 364 can be engaged with the catheter tab 334. In the unlocked configuration, the tab 364 may be disengaged from the catheter tab 334. The tab 364 may attach, e.g., click or lock into, the catheter tab 334 in a fashion as to maintain the relationships of corresponding section of the elongate body 360 and the spined catheter 320 in the locked configuration.

Such locking may be achieved by, e.g., using a detent on the tab 364 that snaps into place within a recess formed in the catheter tab 334, or vice versa. For example, the tab 334 of the catheter 320 can form a ring having a central opening extending therethrough. The tab 364 of the body 360 can have an annular detent with a central post sized to insert through the central opening of the tab 334 such that such that the ring of the tab 334 is received within the annular detent of tab 364 forming a singular grasping element for a user to advance and/or withdraw the catheter system through the access sheath. The tabs 334, 364 may be affixed or may be slideable to accommodate different relative positions between the elongate body 360 and the luminal portion 322 of the spined catheter 320. In some implementations, a proximal end of the spine 330 of the catheter 320 can include a coupling feature 335, such as clip, clamp, c-shaped element or other connector configured to receive the proximal portion 366 of the catheter advancement element 340 (see FIG. 1A). The coupling feature 335 can be configured to snap together with the proximal portion 366 through an interference fit such that a first level of force is needed in order to insert the proximal portion 366 into the clip of the tab 334 and a second, greater level of force is needed to remove the proximal portion 366 from the clip of the tab 334. However, upon inserting the proximal portion 366 into the coupling feature 335 the catheter advancement element 340 and the catheter 320 can still be slideably adjusted relative to one another along a longitudinal axis of the system. The amount of force needed to slideably adjust the relative position of the two components can be such that inadvertent adjustment is avoided and the relative position can be maintained during use, but can be adjusted upon conscious modification. It should be appreciated that the configuration of the coupling between the proximal portion 366 of the catheter advancement element 340 and the spine 360 of the catheter 320 can vary. Generally, however, the coupling is configured to be reversible and adjustable while still providing adequate holding power between the two elements in a manner that is relatively user-friendly (e.g. allows for one-handed use) and organizes the proximal ends of the components (e.g. prevents the spine 360 and proximal portion 366 from becoming twisted and entangled with one another). It should also be appreciated that the coupling feature 335 configured to prevent entanglement and aid in the organization of the proximal spines can be integrated with the tabs or can be a separate feature located along a proximal end region of the spines.

The catheter advancement element 340 is shown in FIG. 1A in a locked configuration with the catheter 320 configured for improved tracking through a tortuous and often diseased vasculature in acute ischemic stroke. Other configurations are considered herein. For example, the elongate body 360 can include one or more detents on an outer surface. The detents can be located near a proximal end region and/or a distal end region of the elongate body 360. The detents are configured to lock with correspondingly-shaped surface features on the inner surface of the luminal portion 322 through which the elongate body 360 extends. The catheter advancement element 340 and the catheter 320 can have incorporate more than a single point of locking connection between them. For example, a coupling feature 335, such as clip, clamp, c-shaped element or other connector configured to hold together the catheter advancement element 340 and spine 360 or tab of the catheter 320 as described elsewhere herein.

In some implementations, the spine 330 of the spined catheter 320 can run alongside or within a specialized channel of the proximal portion 366. The channel can be located along a length of the proximal portion 366 and have a cross-sectional shape that matches a cross-sectional shape of the catheter spine 330 such that the spine 330 of the catheter 320 can be received within the channel and slide smoothly along the channel bi-directionally. Once the spined catheter 320 and elongate body 360 are fixed, the combined system, i.e., the spined catheter 320-catheter advancement element 340 may be delivered to a target site, for example through the working lumen 410 of the tetherable guide-sheath 400 described elsewhere herein.

Anchoring Delivery System and Spined Catheter Methods of Use

As mentioned above, the luminal portion 322 has a flexibility and lubricity that when paired with the rigid spine 330 and the catheter advancement element 340 allow for the spined catheter 320 to navigate to the site of occlusions in the cerebral vasculature better when compared to other systems configured to navigate the cardiac vasculature. The systems described herein can reach occlusions in a region of the anatomy that has a long, tortuous access route. The route may contain stenosis plaque material in the aortic arch and carotid and brachiocephalic vessel origins, presenting a risk of embolic complications. Further, cerebral vessels are usually more delicate and prone to perforation than coronary or other peripheral vasculature. The catheter systems described herein can provide for neurovascular interventional procedures more easily due to its ability to overcome these access challenges. The catheter systems described herein are designed for navigating tortuosity rather than pushing through it. U.S. patent application Ser. No. 15/015,799, filed Feb. 4, 2016, U.S. Patent Publication Number 2015/0174368, filed on Dec. 12, 2014, and U.S. Patent Publication Number 2015/0173782, filed on Dec. 19, 2014, which are incorporated herein by reference, describe features of catheter devices that can navigate the tortuous anatomy of the cerebral arteries.

Figure 43:
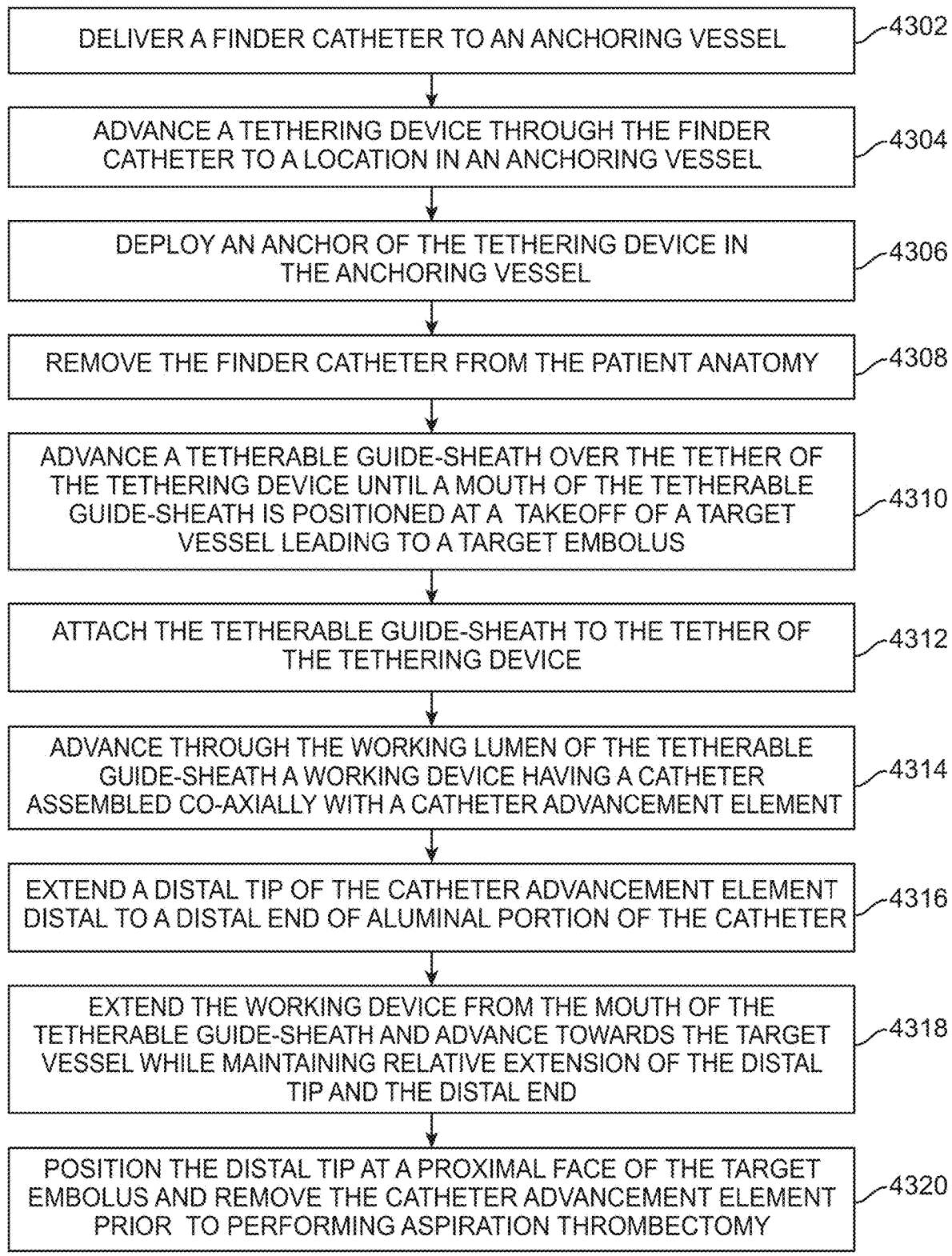
FIG. 43 illustrates a flowchart of a method of deploying and using an anchoring delivery system for aspiration thrombectomy through a catheter system, in accordance with an implementation.

FIG. 43 is a method of using an anchoring delivery system 10 to deliver a working device 802 that includes a spined aspiration catheter in accordance with an implementation.

At operation 4302, a finder catheter 1908 can be delivered to an anchoring vessel 1904, e.g., an ECA, ICA, CCA, etc. in a patient anatomy. The finder catheter 1908 can be a 5F guide catheter or a diagnostic catheter known in the art. The finder catheter 1908 can be delivered using a guidewire such as an Amplatz or other guidewire positioned in the ECA. At operation 4304, a tethering device 100 can be advanced through the finder catheter 1908. The tethering device 100 can be loaded into a dual lumen catheter having a first lumen to house the tethering device 100 and a second lumen configured to receive a guidewire and a pusher tube 109 positioned inside of the catheter to advance the anchor 102 as described elsewhere herein. The catheter holding the tethering device 100 can be inserted through a diagnostic catheter. As such, the 5Fr guide or diagnostic catheter can be inserted and then a 5Fr angiographic catheter advanced over an Amplatz or other guidewire. The guidewire can be removed and then the tethering device 100 can be advanced. The tethering device 100 is advanced and an anchor 102 at a distal end of the tethering device 100 is constrained in a low profile, constrained configuration such that it can slide through the finder catheter 1908. The tethering device 100 can be advanced until the anchor 102 is positioned near a distal end of the finder catheter 1908 and near an anchoring site in the anchoring vessel 1904.

At operation 4306, the anchor 102 can be deployed at the anchoring site by advancing the anchor 102 distally and/or by retracting a constraining element positioned over the anchor 102 of the tethering device 100 to unsleeve the anchor 102 from its constrained configuration. The anchor 102 can be self-expanding, e.g., to the preformed larger profile configuration upon release of the constraint. In the unconstrained state, the anchor 102 can press against and optionally distort the anchoring vessel 1904 within which it anchors.

After the anchor 102 is anchored at the anchoring site, if a pusher tube 109 was used to advance the anchor 102, the pusher tube 109 can be removed from the tether 104 of the tethering device 100. For example, the pusher tube 109 can be retrieved from the finder catheter 1908. More particularly, the pusher tube 109 can be pulled proximally to slide over the tether 104 and to be removed from the patient anatomy.

At operation 4308, the finder catheter 1908 can be removed from the patient anatomy with a pulling motion. In an implementation, the anchor 102 can provide a resistive anchoring force greater than the friction force applied to the tether 104 by the finder catheter 1908, and thus, the tethering device 100 remains in place during retraction of the finder catheter 1908.

At operation 4310, a tetherable guide-sheath 400 can be advanced over the tether 104 of the tethering device 100. For example, an anchor wire 111 can be loaded into a tether distal port 504 of the tetherable guide-sheath 400 and the tetherable guide-sheath 400 can be advanced over the tether 104 through the anatomy toward the target vessel 1906. More particularly, the tetherable guide-sheath 400 can be advanced until a mouth 508 is positioned at a takeoff of a target vessel 1906, e.g., an internal carotid artery (ICA) leading to a targeted embolus. The tetherable guide-sheath 400 can be torqued to rotate the mouth 508 such that a working device 802 delivered through the working lumen will be directed into an entrance of the target vessel 1906 at the anchoring vessel/target vessel junction. The tetherable guide-sheath 400 can be advanced until the mouth 508 is positioned at the desired location.

At operation 4312, the tetherable guide-sheath 400 can be attached to the tether 104 of the tethering device 100. For example, a tether gripper, e.g., an RHV or another gripping technology, (not shown) can be used to affix the tetherable guide-sheath 400 to the tethering device 100 at a point of fixation 1912 proximal to the anchoring site and/or the entrance to the target vessel 1906. The sheath aspiration line 430 can be connected to an aspiration source such as a syringe or aspiration pump. The sheath aspiration line 430 can also be connected via a stopcock or stopcock manifold to a forward flush line (such as a pressurized saline bag).

At operation 4314, a catheter 320 assembled co-axially with a catheter advancement element 340 is advanced through the working lumen of the tetherable guide-sheath 400. A guidewire may be optionally advanced through a guidewire lumen of the catheter advancement element 340. The spined catheter 320, the catheter advancement element 340, and optionally the guidewire can be introduced together as a co-axial catheter assembly 802 through the sheath proximal hemostasis valve 434. The catheter assembly 802 can be advanced through the working lumen 410 of the tethered guide-sheath 400 until the catheter assembly 802 exits the working lumen 410 at the mouth 508. At operation 4316, the distal tip of the catheter advancement element 340 can be extended relative to the distal end of the luminal portion of the catheter 320 until the distal tip 346 extends distal to the blunt distal end of the luminal portion 322. At operation 4318, the relative extension between the distal tip 346 and the distal end of the luminal portion 322 of the catheter 320 can be maintained while the working device is advanced out from the mouth 508 of the tetherable guide-sheath 400 and distally towards the embolus E in the target vessel 1906. In some implementations, the embolus E can be located in a middle or anterior cerebral artery and the mouth 508 of the tetherable guide-sheath 400 can be located within the petrous segment of the ICA. As an example, the catheter assembly 802 can be advanced beyond the mouth 508 positioned through the cavernous segment and the supraclinoid segment of the ICA towards the anterior cerebral artery or middle cerebral artery. Because the vessels in this region of the brain follow such a tortuous path, the distal end of the luminal portion 322 of the catheter 320 can get caught on branching vessels near severe angulation points, for example, around the carotid siphon near the ophthalmic artery branch. However, as described elsewhere herein the catheter advancement element 340 extending through the luminal portion 322 of the catheter 320 minimizes the lip that would otherwise be formed at the distal end of the luminal portion 322. Thus, the catheter 320 having the catheter advancement element 340 positioned therein is less likely to hang up on these severe angulation points in the vasculature as the catheter assembly 802 is advanced distally into the cerebral vessels. As described elsewhere herein, the flexural modulus of the material forming the distal tip of the catheter advancement element 340 can transition from being most floppy and flexible to approaching the flexural modulus of the material forming the distal end of the catheter 320 such that the transition from one component to the other is minimized. The transition between the distal tip 346 of the elongate body 360 can be created due to a material change of this component towards the distal end of the luminal portion 322. The transition can also incorporate a shape change such as the distal taper of the distal tip 346 approaching the uniform outer diameter of the elongate body 360 having a substantially similar outer diameter to the luminal portion 322 of the catheter 320. The smooth transition can also be a combination of the material change and outer diameter change between the two components.

The catheter assembly 802 including the spined aspiration catheter 320 and catheter advancement element 340 is advanced until the distal tip is positioned at the treatment site. As the catheter assembly 802 is advanced into the target vessel 1906, any reaction force applied by the distal anatomy may be transmitted by the catheter assembly 802 to the tetherable guide-sheath 400 and the tethering device 100, placing the tether 104 in tension between the anchoring site and the point of fixation 1912. Whereas such reaction force may ordinarily cause buckling of the catheter assembly 802, the tetherable guide-sheath 400 can be buttressed by the tensioned tether 104, and thus, may effectively support the catheter assembly to allow it to be advanced without buckling of the assembly and/or prolapse of the catheter assembly 802 or the tetherable guide-sheath 400.

At operation 4320, the distal tip 436 is positioned at a proximal face of the occlusion, e.g., at an embolus E, and the catheter advancement element 340 is withdrawn from the working lumen 410 prior to performing the preferred AIS treatment, e.g. aspiration of the embolus E, can be performed using the catheter 320 of the catheter assembly 802. A mark 332 on the spine 330 of the catheter 320 ensures that there is still an overlap region 348 between the distal luminal portion 322 and the sheath body 402. The catheter advancement element 340 (and the guidewire, if present) can be removed from the luminal portion 322 and the working lumen 410 of the tetherable guide-sheath 400. A forward flush can be opened to the aspiration lumen 430 to keep the lumen clear before or between periods of aspiration. At any point during device navigation, aspiration may be initiated from the aspiration source 600 at a level suitable for distal embolic protection, for example, during crossing of the occlusion.

Once the distal tip of the aspiration catheter 320 is positioned at a face of the embolus E, aspiration can be initiated at a level suitable for aspiration thrombectomy, which can be higher than a level used for distal embolic protection. The catheter 320 can remain in aspiration mode against the embolus E for some period of time, as deemed suitable by the user. The luminal portion 322 of the catheter 320 and the working lumen 410 of the tetherable guide-sheath 400 are contiguous and form a stepped up diameter for aspiration as described elsewhere herein. The overlap region 348 is maintained between the catheter 320 extending distally from the lumen 410 of the guide-sheath 400. The overlap region 348 can create a seal and allow for full transmission of aspirating force through the contiguous lumen formed by the luminal portion 322 and the working lumen 410 of the guide-sheath 400, as well as providing a seal for delivery of fluids to the target vessel such as angiographic contrast injection, saline, one or more drugs, or other materials directly into the neuroanatomy.

The spined aspiration catheter 320 can create a more powerful aspiration force by allowing for the working lumen 410 of the guide-sheath 400 to provide a majority of the aspiration column. As described elsewhere herein, the dimension of the lumen of the distal luminal portion 322 of the aspiration catheter 320 may be less than the diameter of the working lumen 410 of the guide-sheath 400, which is reduced only by a diameter of the spine 330 extending therethrough. The increased diameter of the lumen 410 can create a larger aspiration column than, e.g., an aspiration column of a large bore catheter having a similar overall length. The spined aspiration catheter 320 may also be used as a supportive delivery catheter, for example, where the operator wants to reach the petrous carotid or other hard to reach landmarks within the cerebral vasculature. More particularly, after delivering the spined aspiration catheter 320 into the target vessel through the working lumen 410 of the guide-sheath 400, a secondary working device such as a guidewire, microcatheter, stent retriever, etc. may be delivered through the lumen of the luminal portion 322 into a more distal anatomy to perform other procedural operations as described elsewhere herein.

Depending on the results of the aspiration thrombectomy maneuver (as observed by flow though the aspiration line 430 and/or resistance to backwards force on the spine 330 of the catheter 320), the user may determine that the embolus E has been completely aspirated, or if not, the user may choose to move the catheter 320 back and forth to aspirate the clot in situ, or to slowly retract the catheter 320 into the mouth 508 of the tetherable guide-sheath 400. If flow is restored to the target artery via aspiration of the clot through the catheter 320 and tetherable guide-sheath 400, a final angiogram may be performed and the catheter 320 can be retracted. If, however, thrombus occludes the catheter tip and cannot be removed, the catheter 320 is pulled back, with some or all of the occlusion attached through suction force to the tip of the catheter 320.

In the latter scenario, aspiration can be maintained at the tip of the catheter 320 the entire time the catheter 320 is being pulled into the tetherable guide-sheath 400. Once the catheter 320 has been completely retracted into the tetherable guide-sheath 400, the catheter 320 can be quickly removed from the sheath body 402 while aspiration is maintained on the tetherable guide-sheath 400. At some time during catheter retraction, depending on if the catheter 320 is clogged with occlusive material, the aspiration level may be changed from a high level desirable for aspiration thrombectomy to a lower level desirable for distal embolic protection. By providing the ability to maintain aspiration continuously from either the catheter tip or the sheath tip or the sheath distal region, and providing the means to change aspiration levels and maintain aspiration, the procedure optimizes the ability to aspiration clot while minimizing distal emboli and minimizing blood loss from aspiration. If desired, aspiration may also be initiated at the flush line of the proximal valve to reduce chance of distal embolization during removal of the catheter tip with possibly adhered clot through the proximal valve.

The spined aspiration catheter 320 may be removed completely from the proximal hemostasis valve 434 of the sheath 400. Alternately, if the access sheath 400 has a proximal extension (not shown), the distal luminal portion 322 may be pulled into the proximal extension portion such that the catheter 320 and sheath 220 may be flushed to remove potential embolic material without removing the catheter 320 completely from the sheath 400. A vigorous flush from the proximal valve flush line simultaneous with aspiration from the aspiration line 430 creates a flush environment for the catheter 320 and sheath 400. If desired, a catheter clearing tool may be inserted into the sheath proximal valve 434 and used at this time to clear the inner lumen of the catheter 320. If the access sheath 400 has a connector valve, the proximal portion may be closed off from the sheath body 402 during this stage, so that there is no risk of flushing embolic material into the sheath body 402 and thence into the artery.

Alternately, the valve may be closed off and aspiration paused while the proximal valve is opened or removed and the catheter 320 is completely removed from the sheath 400. Closing the valve limits the blood loss from the sheath 400 as the catheter 320 is removed. The catheter 320 may then be flushed onto the table or into a bowl or other receptacle, using the cleaning tool. The proximal extension portion may also be flushed by providing a flush source from the proximal valve flush line simultaneous with aspiration from the aspiration line 430, or by opening a side port on the aspiration line 430 to flush to the table or into a bowl or other receptacle. If desired, an angiogram may be performed to assess flow through the treated artery. If the procedure dictates, the catheter 320 or another catheter may be re-advanced as described above to the site of the occlusion to attempt another aspiration thrombectomy step. The flushing of the catheters and proximal extension portion of the access sheath minimizing the risk of distal emboli during these subsequent steps.

Upon successful aspiration procedure, the anchored delivery system can be removed. The tether 104 can be pulled to withdraw the anchor 102 into the tether lumen 408 of the tetherable guide-sheath 400, or the tetherable guide-sheath 400 can be exchanged with a separate catheter, such as a guide or diagnostic catheter, that can be advanced over the anchor 102 to capture the anchor 102. The tetherable guide-sheath 400 and/or tethering device 100 can then be removed from the patient anatomy to complete the use of the anchoring delivery system and finish the AIS intervention.

As mentioned above, if after treatment of the embolus E in the first treatment vessel 1906 shows via angiogram that another occlusion exists distal to the first treatment vessel, at least a second aspiration catheter can be advanced through the lumen of the first aspiration catheter 320 already positioned in the first treatment vessel 1906. In this implementation, the working device can include multiple spined catheters that are nested inside one another to allow for an extended or telescoping reach into the tortuous anatomy. For example, a first catheter having a largest OD can be inserted through an introducer sheath, such as an 8F having an ID snug of 0.071". The second catheter can have an ID of 0.054" snug to a third catheter having a corresponding OD. Each sequentially smaller catheter can extend through its respective catheter to reach an ever deeper location within the brain such that the overlapping segments seal forming a contiguous lumen for aspiration that steps up to a larger diameter thereby maximizing aspiration force. The catheter having an OD configured to extend through an ID of 0.071" can reach, for example, up to the M1 level whereas the smaller catheter having an OD configured to extend through an ID of 0.054" can reach, for example, up to the M2 level and the larger catheter having an OD configured to extend through an ID of 0.088" can be used for high volume lesions, for example in the carotid terminus or basilar artery. The smallest catheter can serve as a clean-up device following a first pass with a 0.071" ID. Further, aspiration through the system can be at a single point with the RHV closed and still with single-operator use.

Figure 44:
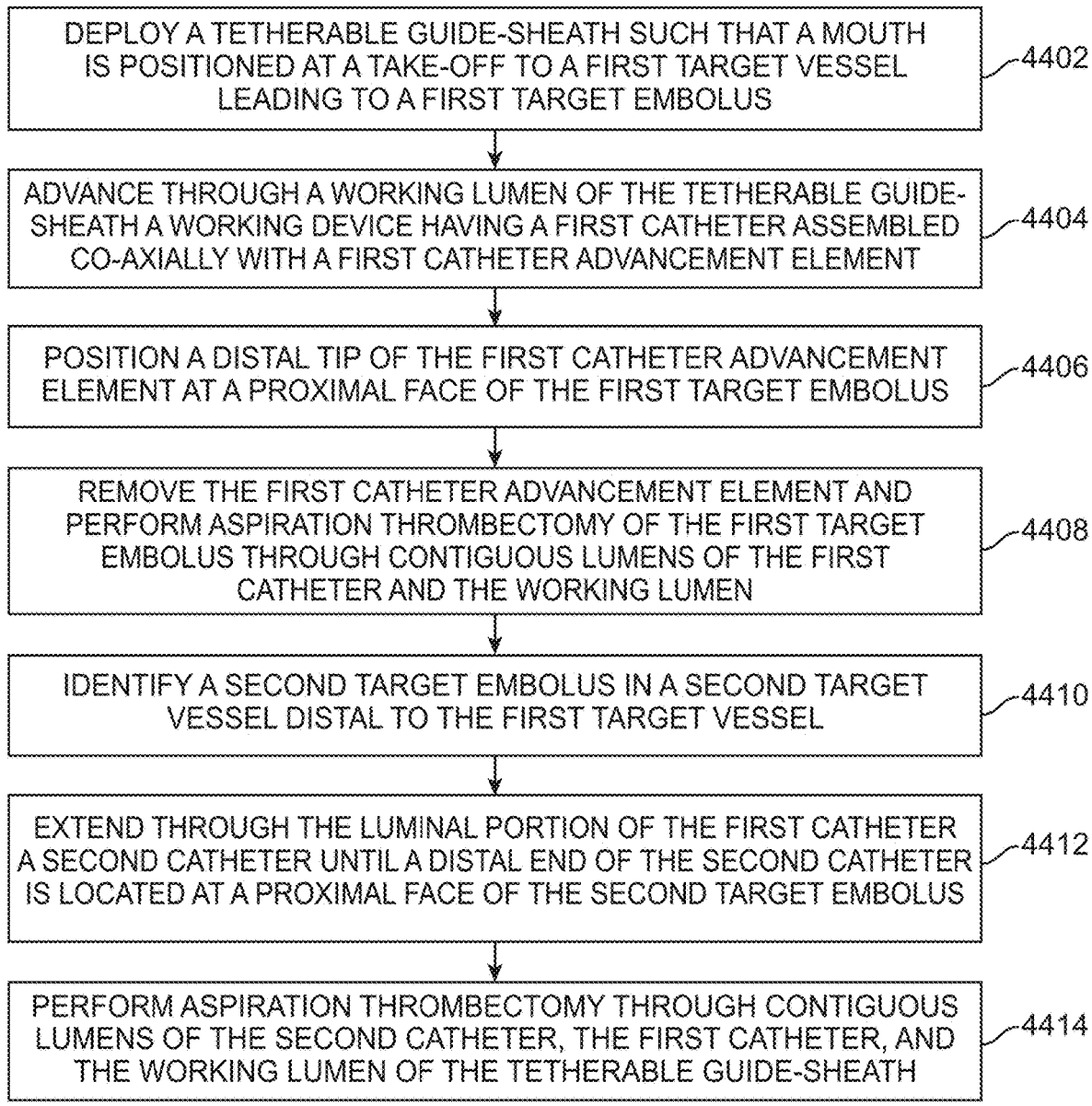
FIG. 44 illustrates a flowchart of a method of using an anchoring delivery system for aspiration thrombectomy through a nested catheter system, in accordance with an implementation.
Figure 45:
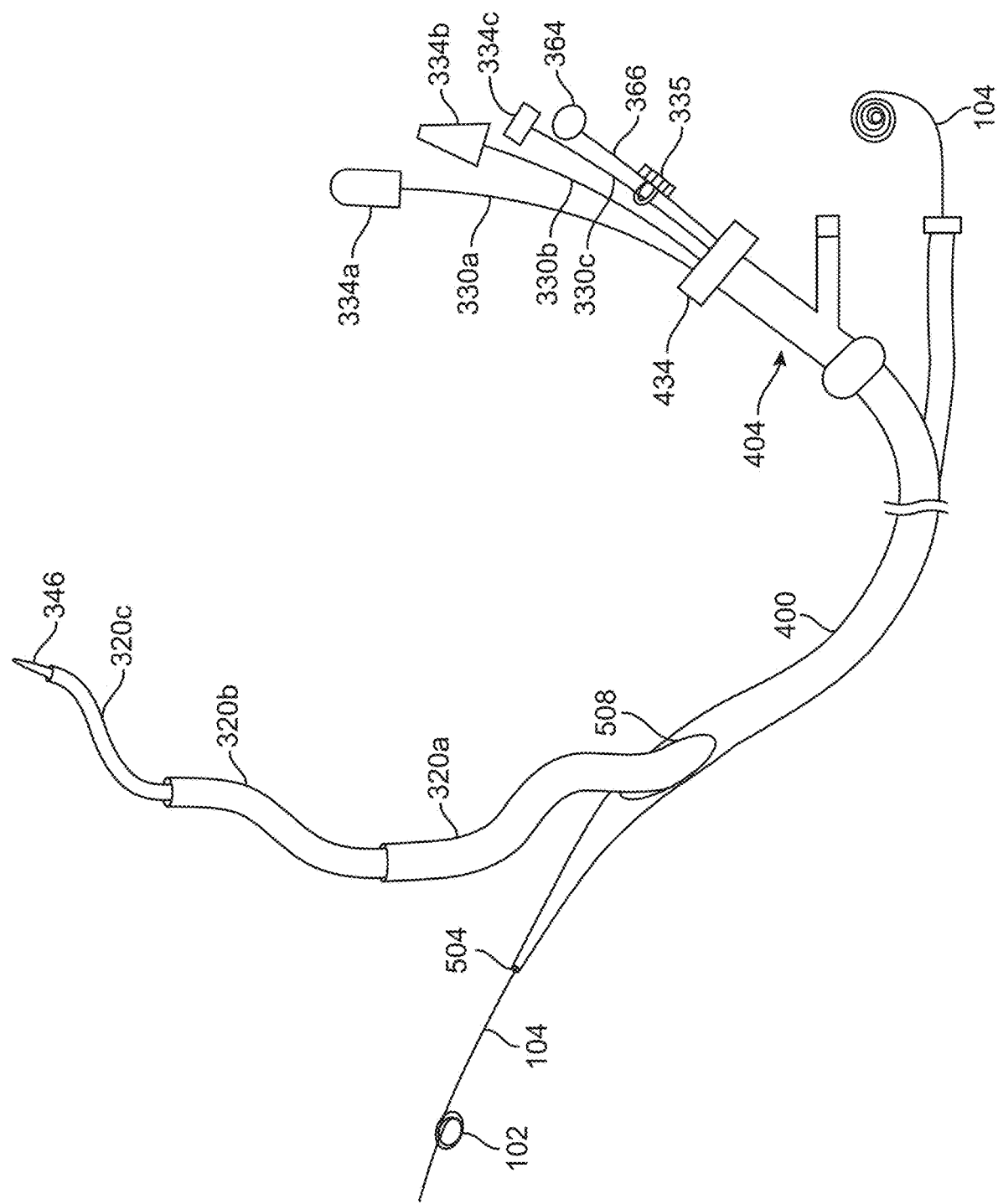
FIG. 45 illustrates an implementation of a nested catheter system, in accordance with an implementation.

Referring to FIG. 44, a method of using an anchoring delivery system to deliver a working device is illustrated in accordance with an implementation. FIG. 45 illustrates an implementation of a working device used in the method illustrated in FIG. 44. Accordingly, FIGS. 44-45 are described in combination below.

At operation 4402, referring to FIG. 45, an access device such as a tetherable guide-sheath 400 can be deployed as described elsewhere herein such that the mouth 508 is positioned at a take-off to a first target vessel leading to a first target embolus. It should be appreciated, however, than any access device or guide sheath known in the art can be used in place of a tetherable guide-sheath to perform the method of FIG. 44 and is not intended to be limiting in this way. At operation 4404, a working device can be advanced through a working lumen 410 of the tetherable guide-sheath 400. The working device can be a first spined catheter 320*a* having an outer diameter sized to be received within the working lumen 410 of the tetherable guide-sheath 400 as described elsewhere herein. The first spined catheter 320*a* can have a luminal portion 322 having an elongate body 360 of a catheter advancement element 340 extending therethrough as described elsewhere herein. A distal tip 356 of the elongate body 360 can extend distal to the luminal portion 322 to aid in the advancement of the catheter 320*a* through the vessel without hanging up on a severe angulation and/or a branching vessel. At operation 4406, the first spined catheter 320*a* is advanced through the first target vessel until the distal tip 346 is located at a proximal face of the first target embolus. At operation 4408, the first catheter advancement element (not shown) is removed from the luminal portion 322 of the first catheter 320*a* and aspiration thrombectomy is performed on the first target embolus through the first catheter 320*a*. An angiogram can be performed to assess the success of aspiration thrombectomy and to identify whether a second target embolus is present (operation 4410), for example in a target vessel distal to the first target vessel. At operation 4412, a second spined catheter 320*b* having a second catheter advancement element positioned therethrough can be extended through the luminal portion 322 of the first spined catheter 320*b*. The second spined catheter 320*b* can be extended using its proximal spine 330*b* beyond a distal end of the first spined catheter 320*a* such that the smaller diameter second spined catheter 320*b* can reach the second target embolus that may be located distal to the first target embolus and in particular within a distal vessel having a narrower dimension. In this implementation, the first spined catheter 320*a* can act as a support catheter for the second spined catheter 320b. The inner lumen of the second spined catheter 320b can fluidly communicate with the inner lumen of the first spined catheter 320a that fluidly communicates with the working lumen 410 of the tetherable guide-sheath 400 forming a contiguous aspiration lumen formed of three sections of increasingly larger dimensions (operation 4414). It should be appreciated that additional spined catheters 320c can then be inserted through the luminal portion of the second spine catheter 320b and so forth. The contiguous aspiration lumens can seal against one another such that the appropriate pressure can be applied through the nested catheters to accomplish aspiration force sufficient for aspiration thrombectomy of distant clots. It should also be appreciated that each additional spined catheter can be advanced with the use of its own catheter advancement element having appropriate corresponding outer diameter to the inner diameter of the lumen within which it is intended to be inserted.

The proximal end of the nested catheter system can incorporate various gripping, organizing, and attachment features as described elsewhere herein. For example, the guide-sheath 400 can include a proximal furcation 404 at a proximal end coupled to a rotating hemostatic valve (RHV) 434 that provides access to the working lumen 410 through which the components of the catheter system are inserted. Each of the components of the catheter system can extend proximally out from the valve 434. For example, spined catheters 320a, 320b, and 320c nested within one another can have a respective proximal spine 330a, 330b, and 330c extending through the valve 434. Similarly, the proximal spine 360 of the catheter advancement element 340 can also extend proximally through the valve 434. Each of these components in the nesting or telescoping catheter set can incorporate identifying features at their proximal end regions that distinguish them from one another. For example, each proximal spine 330 can include a tab 334 having a distinguishing shape, color, or other visual characteristic that is unique to that particular catheter 320. Further, each proximal spine 330 of the nesting catheters can incorporate a coupling feature 335, such as a clip or other connector, that organizes the various spines 330 and prevents entanglement. Similarly, the proximal portion 366 of the catheter advancement element 340 can also include a unique tab 364 that identifies it from the spines of the various catheters, for example, by shape, color, or other identifying feature. It should be appreciated that the coupling features 335 configured to prevent entanglement and aid in the organization of the proximal spines can be integrated with the tabs or can be a separate feature located along a proximal end region of the spines as shown in FIG. 45.

The nesting catheters and their respective catheter advancement elements can be incorporated within a kit.

One or more components of the working devices and anchoring delivery systems described herein may be made from a metal, metal alloy, polymer, a metal-polymer composite, ceramics, combinations thereof, and the like, or other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

It should be appreciated that the methods described above may be adapted to different anatomies. For example, the ipsilateral subclavian could be a point of anchoring in order to target the ipsilateral vertebral artery. Vertebral arteries are often very tortuous and benefit from support to push interventional systems through them to target anatomies at which interventions are to be performed. For example, a tethering device can be positioned distal to the takeoff of the vertebral artery with the mouth of the tetherable guide-sheath positioned at the vertebral ostium. In instances when the vertebral arteries are very tortuous, i.e., weaving in and out of the bony openings of the vertebral column, the large bore catheter can provide "push" to get across these turns, which is particularly beneficial for rapid access to the site of AIS embolization. According to various implementations, the anchoring delivery system may facilitate access to all four vessels of the carotid/vertebral arterial circulation as well as anatomic variants such as the "bovine" arch discussed above.

Implementations describe anchoring delivery systems and methods of using anchoring delivery system to deliver working devices to target anatomies. However, while some implementations are described with specific regard to delivering working devices to a target vessel of a neurovascular anatomy such as a cerebral vessel, the implementations are not so limited and certain implementations may also be applicable to other uses. For example, an anchoring delivery system as described above may be used to deliver working devices to a target vessel of a coronary anatomy, to name only one possible application. It should also be appreciated that although the systems described herein are described as being useful for treating a particular condition or pathology, that the condition or pathology being treated may vary and are not intended to be limiting. Use of the terms "embolus," "embolic," "emboli," "thrombus," "occlusion," etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method of performing a medical procedure at a treatment site in a cerebral vessel of a patient, the method comprising:
   delivering a neurovascular catheter through a working lumen of a sheath to a treatment location distal to a petrous portion of an internal carotid artery, the neurovascular catheter comprising:
      an elongate control element configured to advance the neurovascular catheter comprising a flat ribbon; and
      a distal luminal portion extending along a longitudinal axis having a proximal end region coupled to the control element, wherein the distal luminal portion has a side wall defining a single, inner lumen, the side wall comprising:
         a tubular inner liner;
         a reinforcement structure wound around and bonded to the tubular inner liner; and
         an outer jacket surrounding the reinforcement structure,
      wherein a distal end of the elongate control element is coupled to the proximal end region of the distal luminal portion sandwiched between layers of the side wall, and
      wherein the proximal end region of the distal luminal portion includes a step-up in outer diameter to form a seal with the working lumen of the sheath; and
   applying suction through the working lumen of the sheath and the single, inner lumen of the neurovascular catheter to the treatment location from a single source of suction.

2. The method of claim 1, wherein the distal luminal portion has a transition section near where the distal luminal portion couples to the elongate control element.

3. The method of claim 2, wherein the transition section has an angled cut.

4. The method of claim 3, wherein the proximal opening is formed within the transition section and the proximal end region of the distal luminal portion is coupled to the distal end region of the control element adjacent the transition section.

5. The method of claim 1, wherein a proximal end of the elongate flexible control element is coupled to a tab.

6. The method of claim 1, further comprising organizing the control element of the neurovascular catheter and a component used with the catheter by engaging a reversible coupling feature on the control element to the component.

7. The method of claim 1, wherein the flat ribbon has a rectangular cross-sectional dimension that is wider than it is thick.

8. The method of claim 1, wherein a maximum cross-sectional dimension of the flat ribbon is 0.025".

9. The method of claim 1, advancing the neurovascular catheter through the sheath from a transfemoral access site to a middle cerebral artery so that the proximal end region of the distal luminal portion remains outside the aortic arch.

10. The method of claim 9, further comprising the steps of:
   inserting the sheath into a blood vessel from the transfemoral access site, wherein the working lumen of the sheath extends between a proximal end region and a distal end region of the sheath, the distal end region having at least one opening in communication with the working lumen; and
   advancing the sheath toward a treatment location.

11. The method of claim 10, further comprising advancing the sheath over a tethering device anchored at an anchoring site proximal of the treatment site.

12. The method of claim 10, wherein the sheath is advanced to a location within the petrous segment of the internal carotid artery.

13. The method of claim 1, wherein delivering the neurovascular catheter to a treatment location distal to the petrous portion comprises advancing a catheter system comprising the neurovascular catheter and a catheter advancement element positioned within the inner lumen of the catheter, wherein a tapered distal tip of the catheter advancement element extends distal to a distal end of the neurovascular catheter during the delivering.

14. The method of claim 13, further comprising withdrawing the catheter advancement element from the single, inner lumen.

15. The method of claim 14, further comprising placing the distal end of the neurovascular catheter on or near a proximal face of an occlusion at the treatment location.

16. The method of claim 15, further comprising removing occlusive material while applying suction capturing the occlusive material at, within, or through the distal end of the neurovascular catheter.

17. The method of claim 16, wherein applying suction through the sheath and the inner lumen of the neurovascular catheter comprises initiating aspiration from the single source of suction at a level suitable for distal embolic protection.

18. The method of claim 16, wherein applying suction through the sheath and the inner lumen of the neurovascular catheter comprises initiating aspiration from the single source of suction at a level suitable for aspiration thrombectomy.

19. The method of claim 1, wherein applying suction through the sheath and the inner lumen of the neurovascular catheter comprises applying suction through a contiguous lumen formed by the single, inner lumen of the distal luminal portion and the working lumen of the sheath to remove occlusive material through the contiguous lumen.

20. The method of claim 19, further comprising delivering a fluid through the working lumen of the sheath.

21. The method of claim 20, wherein the fluid comprises angiographic contrast, saline, or at least one drug.

22. The method of claim 19, wherein applying suction through the contiguous lumen comprises applying suction to a distal end of the neurovascular catheter as the neurovascular catheter is retracted inside of the sheath.

23. The method of claim 19, further comprising advancing a second catheter through the neurovascular catheter to a second treatment location, the second treatment location distal to the first treatment location.

24. The method of claim 23, wherein the second catheter, the neurovascular catheter, and the sheath form an extended contiguous lumen.

25. The method of claim 24, wherein applying suction from the single source of suction delivers suction to a distal end of the second catheter through the extended contiguous lumen.

26. A neurovascular catheter, comprising:
an elongate control element configured to advance the catheter, the control element comprising a flat ribbon, a proximal end region, and a distal end region; and
a distal luminal portion extending along a longitudinal axis having a proximal end region coupled to the distal end region of the control element,
wherein the distal luminal portion has a side wall defining a single, inner lumen extending between a proximal opening into the inner lumen at the proximal end region and a distal opening from the central lumen at the distal end region, the side wall comprising:
a tubular inner liner having an outer surface coated with a compound suitable for bonding;
a reinforcement structure that is a helical coil bonded to the coated outer surface of the tubular inner liner; and
an outer jacket surrounding the helical coil,
wherein the distal end region of the elongate control element is coupled to the proximal end region of the distal luminal portion sandwiched between layers of the side wall,
wherein the proximal end region of the distal luminal portion where the distal end region of the elongate control element is coupled has a step-up in outer diameter compared to an outer diameter of the distal luminal portion distal to the proximal end region of the distal luminal portion.

27. A neurovascular catheter as in claim 26, wherein a distal end of the flat ribbon has a feature that facilitates a mechanical joint during a weld.

28. A neurovascular catheter as in claim 27, wherein the feature comprises a textured surface, protruding feature, or cut-out feature.

29. Neurovascular catheter as in claim 26, wherein the distal luminal portion and the flat ribbon are joined by a weld bond, a mechanical bond, or an adhesive bond.

30. A neurovascular catheter as in claim 26, wherein a distal end of the flat ribbon is skived, ground or cut.

31. A neurovascular catheter as in claim 26, wherein a region of overlap between a distal end of the ribbon and the proximal end region of the distal luminal portion is at least about 1 cm.

32. A neurovascular catheter as in claim 26, wherein the distal luminal portion has a transition section near where the distal luminal portion couples to the elongate control element.

33. A neurovascular catheter as in claim 32, wherein the transition section has an angled cut.

34. A neurovascular catheter as in claim 33, wherein the proximal opening is formed within the transition section and the proximal end region of the distal luminal portion is coupled to the distal end region of the control element adjacent the transition section.

35. A neurovascular catheter as in claim 26, wherein a proximal end of the distal luminal portion is angled in an oblique manner relative to a longitudinal axis of the catheter.

36. A neurovascular catheter as in claim 35, wherein the proximal end and the proximal opening into the lumen are at an angle other than 90 degrees to the longitudinal axis of the catheter.

37. A neurovascular catheter as in claim 26, wherein the outer jacket is formed from a plurality of tubular segments positioned coaxially about the helical coil.

38. A neurovascular catheter as in claim 37, wherein a proximal one of the plurality of tubular segments has a durometer of at least about 60D and a distal one of the plurality of tubular segments has a durometer of no more than about 35D.

39. A neurovascular catheter as in claim 26, wherein the tubular liner comprises polytetrafluoroethylene.

40. A neurovascular catheter as in claim 26, wherein the helical coil comprises a shape memory material.

41. A neurovascular catheter as in claim 40, wherein the helical coil comprises Nitinol.

42. A neurovascular catheter as in claim 37, wherein the outer jacket is formed from at least five discrete tubular segments.

43. A neurovascular catheter as in claim 37, wherein the outer jacket is formed from more than five discrete tubular segments.

44. A neurovascular catheter as in claim 43, wherein a difference in durometer between a proximal one of the tubular segments and a distal one of the tubular segments is at least about 20D.

45. A neurovascular catheter as in claim 44, wherein the difference is at least about 30D.

46. A neurovascular catheter as in claim 26, wherein the distal luminal portion is non-expandable.

47. A neurovascular catheter as in claim 26, wherein a proximal end of the elongate flexible control element is coupled to a tab.

48. A neurovascular catheter as in claim 26, wherein the control element further comprises a reversible coupling feature configured to engage with a component used with the catheter to aid in organization of the catheter and the component.

49. A neurovascular catheter as in claim 26, wherein a distal end of the tubular segment is angled in an oblique manner relative to the longitudinal axis.

50. A neurovascular catheter as in claim 26, wherein the flat ribbon has a rectangular cross-sectional dimension that is wider than it is thick.

51. A neurovascular catheter as in claim 26, wherein a maximum cross-sectional dimension of the flat ribbon is 0.025".

52. A neurovascular catheter as in claim 26, wherein a length of the distal luminal portion is sufficient to reach from a transfemoral access site to a middle cerebral artery so that the proximal end region of the distal luminal portion remains outside the aortic arch.

* * * * *